US012643884B2

(12) United States Patent
Fuhrmann et al.

(10) Patent No.: US 12,643,884 B2
(45) Date of Patent: Jun. 2, 2026

(54) 1-(2-(4-CYCLOPROPYL-1H-1,2,3-TRIAZOL-1-YL)ACETYL)-4-HYDROXYPYRROLIDINE-2-CARBOXAIMIDE DERIVATIVES AS VHL INHIBITORS FOR THE TREATMENT OF ANEMIA

(71) Applicant: Genentech, Inc., South San Francisco, CA (US)

(72) Inventors: Jakob Fuhrmann, Foster City, CA (US); Hao Wu, Brisbane, CA (US); Wayne J. Fairbrother, Burlingame, CA (US)

(73) Assignee: Genentech, Inc., South San Francisco, CA (US)

(*) Notice: Subject to any disclaimer, the term of this patent is extended or adjusted under 35 U.S.C. 154(b) by 435 days.

(21) Appl. No.: 18/195,141

(22) Filed: May 9, 2023

(65) Prior Publication Data

US 2023/0271944 A1 Aug. 31, 2023

Related U.S. Application Data

(63) Continuation of application No. PCT/US2021/072338, filed on Nov. 10, 2021.

(60) Provisional application No. 63/119,586, filed on Nov. 30, 2020, provisional application No. 63/112,611, filed on Nov. 11, 2020.

(51) Int. Cl.

| | |
|---|---|
| ***C07D 403/06*** | (2006.01) |
| ***C07D 401/14*** | (2006.01) |
| ***C07D 403/14*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |

(52) U.S. Cl.

CPC ......... *C07D 403/06* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01)

(58) Field of Classification Search

CPC .. C07D 403/06; C07D 401/14; C07D 403/13; C07D 405/14; C07D 409/14; C07D 413/14; C07D 417/14

See application file for complete search history.

(56) References Cited

U.S. PATENT DOCUMENTS

| | | | |
|---|---|---|---|
| 4,522,811 | A | 6/1985 | Eppstein et al. |
| 11,242,344 | B2 | 2/2022 | Blaquiere et al. |
| 2014/0356322 | A1 | 12/2014 | Crews et al. |
| 2020/0282068 | A1 | 9/2020 | Desantis et al. |
| 2023/0295145 | A1 | 9/2023 | Fuhrmann et al. |
| 2023/0391766 | A1 | 12/2023 | Fuhrmann |
| 2025/0129063 | A1 | 4/2025 | Fuhrmann et al. |

FOREIGN PATENT DOCUMENTS

| | | | |
|---|---|---|---|
| JP | 2005526091 | A | 9/2005 |
| JP | 2018515555 | A | 6/2018 |
| JP | 2019535728 | A | 12/2019 |
| WO | 2013106643 | A2 | 7/2013 |
| WO | WO2013/106646 | A2 * | 7/2013 |
| WO | 2018051107 | A1 | 3/2018 |
| WO | 2018189554 | A1 | 10/2018 |
| WO | 2019084026 | A1 | 5/2019 |
| WO | 2019084030 | A1 | 5/2019 |
| WO | 2019224773 | A1 | 11/2019 |
| WO | 2021262731 | A2 | 12/2021 |
| WO | 2022103411 | A1 | 5/2022 |
| WO | 2022115879 | A1 | 6/2022 |
| WO | 2022173032 | A1 | 8/2022 |
| WO | 2023099620 | A1 | 6/2023 |
| WO | 2023119677 | A1 | 6/2023 |
| WO | 2023120742 | A1 | 6/2023 |
| WO | 2023138524 | A1 | 7/2023 |
| WO | 2023220237 | A1 | 11/2023 |

OTHER PUBLICATIONS

Buckley, D.L. et al. (Nov. 12, 2012-2013). "Small Molecule Inhibitors of the Interaction Between the E3 Ligase VHL and HIF1α," Angew Chem Int Ed Engl.51(46):11463-11467, 15 pages.

International Preliminary Report on Patentability for PCT Application No. PCT/US2021/072644, issued on May 30, 2023, filed on Nov. 30, 2021, 6 pages.

International Preliminary Report on Patentability, issued May 16, 2023, for PCT Application No. PCT/US2020/062627, filed Nov. 30, 2021, 8 pages.

International Preliminary Report on Patentability, issued May 16, 2023, for PCT Application No. PCT/US2021/072338, filed Nov. 10, 2021, 7 pages.

International Search Report and Written Opinion for PCT Application No. PCT/US2021/072644, mailed on Mar. 2, 2022, filed on Nov. 30, 2021, 14 pages.

(Continued)

*Primary Examiner* — Brandon J Fetterolf

(74) *Attorney, Agent, or Firm* — Morrison & Foerster LLP

(57) ABSTRACT

The present disclosure relates to compounds comprising a VHL ligand moiety and to methods of using such compounds as ligands of VHL. The present disclosure further relates to the use of the compounds described herein, or pharmaceutical compositions thereof, to prevent and/or treat a range of diseases, disorders, and conditions.

21 Claims, No Drawings

(56) References Cited

OTHER PUBLICATIONS

International Search Report and Written Opinion, mailed Feb. 22, 2022, for PCT Application No. PCT/US2021/072338, filed Nov. 10, 2021, 14 pages.
International Search Report and Written Opinion, mailed Jul. 13, 2021, for PCT Application No. PCT/US2020/062626, filed Nov. 30, 2020, 15 pages.
International Search Report and Written Opinion, mailed Jul. 13, 2021, for PCT Application No. PCT/US2020/062627, filed Nov. 30, 2020, 16 pages.
Li, Z. et al. (Jan. 25, 2019, e-pub. Feb. 8, 2019). "Small-Molecule Modulators of the Hypoxia-Inducible Factor Pathway: Development and Therapeutic Applications," J. Med. Chem. 62(12):5725-5749.
Nicolaou, K.C. et al. (1994). "Calicheamicin ⊖1[1]: A Rationally Designed Molecule with Extremely Potent and Selective DNA Cleaving Properties and Apoptosis Inducing Activity," Angew. Chem. Intl. Ed. Engl. 33(2):183-186.
Goracci, L. et al. (Oct. 7, 2020). "Understanding the Metabolism of Proteolysis Targeting Chimeras (PROTACs): The Next Step Toward Pharmaceutical Applications," J. Med. Chem. 63:11615-11638.
International Preliminary Report on Patentability for PCT Application No. PCT/US2023/021832, issued on Nov. 7, 2024, filed on May 11, 2023, 7 pages.
Van Molle, I. et al. (Oct. 26, 2012). "Dissecting Fragment-Based Lead Discovery at the Von Hippel-Lindau Protein: Hypoxia Inducible Factor 1a Protein-Protein Interface," Chemistry & Biology 79:1300-1322.
International Search Report and Written Opinion, for PCT Application No. PCT/US2023/021832, mailed Aug. 18, 2023, filed on May 11, 2023, 11 pages.

* cited by examiner

1-(2-(4-CYCLOPROPYL-1H-1,2,3-TRIAZOL-1-YL)ACETYL)-4-HYDROXYPYRROLIDINE-2-CARBOXAIMIDE DERIVATIVES AS VHL INHIBITORS FOR THE TREATMENT OF ANEMIA

CROSS-REFERENCE TO RELATED APPLICATIONS

This application is a continuation of International Application No. PCT/2021/072338, filed Nov. 10, 2021, which claims priority to and benefit of U.S. Provisional Patent Application No. 63/112,611, filed Nov. 11, 2020, and U.S. Provisional Patent Application No. 63/119,586, filed Nov. 30, 2020, the disclosures of which are hereby incorporated herein by reference in their entireties.

FIELD OF THE DISCLOSURE

The present disclosure relates to compounds comprising a VHL ligand moiety and to methods of using such compounds as ligands of VHL. The present disclosure further relates to the use of the compounds described herein, or pharmaceutical compositions thereof, to prevent and/or treat a range of diseases, disorders, and conditions.

BACKGROUND OF THE DISCLOSURE

E3 ubiquitin ligases (of which over 600 are known in humans) confer substrate specificity for ubiquitination. There are known ligands which bind to these ligases. An E3 ubiquitin ligase binding group (E3LB) is a peptide or small molecule that can bind an E3 ubiquitin ligase.

A particular E3 ubiquitin ligase is von Hippel-Lindau (VHL) tumor suppressor, the substrate recognition subunit of the E3 ligase complex VCB (an important target in cancer, chronic anemia, and ischemia), which also consists of elongins B and C, Cul2, and Rbxl. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. While HIF-1α is constitutively expressed, its intracellular levels are kept very low under normoxic conditions via its hydroxylation by prolyl hydroxylase domain (PHD) proteins and subsequent VHL-mediated ubiquitination.

The crystal structure of VHL with ligands has been obtained, confirming that a compound can mimic the binding mode of the transcription factor HIF-1α, the major substrate of VHL. These compounds bind VHL competing with the HIF-1α substrate, thereby reducing or blocking the activity of the VHL protein. There exists an ongoing need in the art for small molecule VHL ligands that are effective across a broad range of disease indications.

BRIEF DESCRIPTION OF THE DISCLOSURE

The present disclosure is directed to VHL ligands and, specifically, to VHL ligands that bind to a VHL E3 ubiquitin ligase.

In one aspect, the present disclosure is directed to a compound of formula (I):

(I)

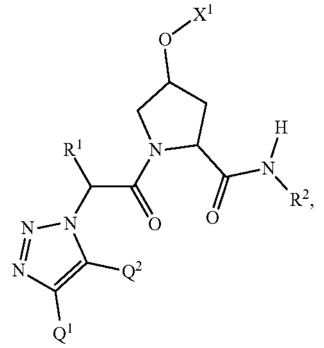

or a stereoisomer or tautomer thereof, or a pharmaceutically acceptable salt of any of the foregoing, wherein:

$X^1$ is, independently at each occurrence, H, $C_{1-12}$alkyl, or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-6}$cycloalkyl, wherein the $C_{1-12}$alkyl or $C_{3-6}$cycloalkyl of $R^2$ is independently optionally substituted with one or more halo or —CN; and $Q^1$ and $Q^2$ are, independently of each other and independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^1$ or $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

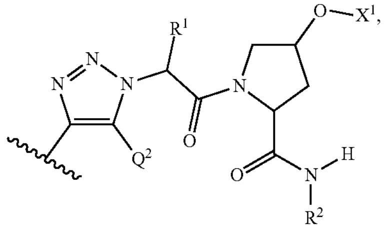

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, or $C_{1-12}$alkyl, wherein the $C_{1-12}$alkyl of $R^s$ is independently further optionally substituted with one or more halo, cyano, or OH.

In another aspect, the present disclosure is directed to a compound of formula (I):

(I)

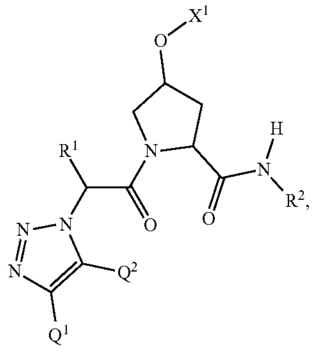

or a stereoisomer or tautomer thereof, or a pharmaceutically acceptable salt of any of the foregoing, wherein:

$X^1$ is, independently at each occurrence, H or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; and $Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

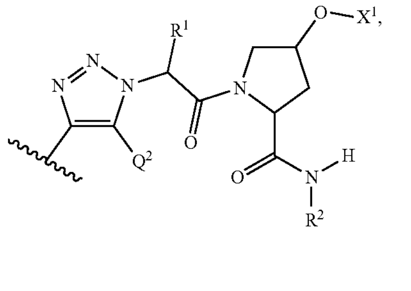

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

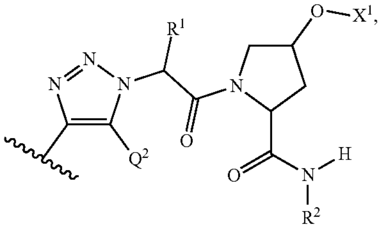

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN, or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

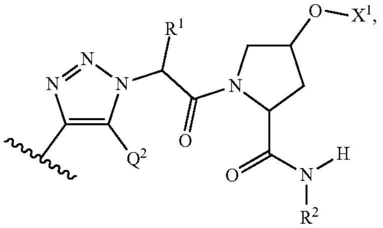

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH;

with the proviso that when $Q^1$ is cyclohexyl, biphenyl, or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In some embodiments, the compound of formula (I), or a pharmaceutically acceptable salt thereof, is a compound of formula (I'):

(I')

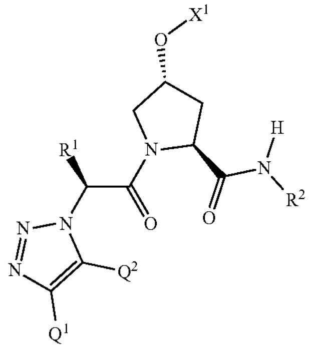

or a pharmaceutically acceptable salt thereof, wherein $X^1$, $R^1$, $R^2$, $Q^1$, and $Q^2$ are as defined in formula (I). It is understood that $X^1$, $R^1$, $R^2$, $Q^1$, and $Q^2$ of such embodiments of compounds of formula (I') may include $X^1$, $R^1$, $R^2$, $Q^1$, and $Q^2$ as described for formula (I)

In some embodiments, the compound of formula (I), or a stereoisomer or tautomer thereof, or a pharmaceutically acceptable salt of any of the foregoing, is a compound of formula (IA):

(IA)

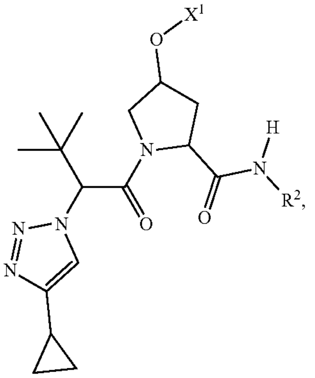

or a stereoisomer or tautomer thereof, or a pharmaceutically acceptable salt of any of the foregoing, wherein $X^1$ and $R^2$ are as defined in formula (I). It is understood that $X^1$ and $R^2$ of such embodiments of compounds of formula (IA) may include $X^1$ and $R^2$ as described for formula (I).

In some embodiments, the compound of formula (I), or a stereoisomer or tautomer thereof, or a pharmaceutically acceptable salt of any of the foregoing, is a compound of formula (IB):

(IB)

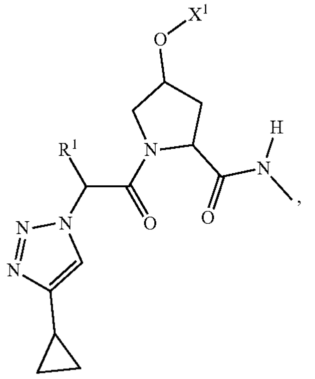

or a stereoisomer or tautomer thereof, or a pharmaceutically acceptable salt of any of the foregoing, wherein $X^1$ and $R^1$ are as defined in formula (I). It is understood that $X^1$ and $R^1$ of such embodiments of compounds of formula (IB) may include $X^1$ and $R^1$ as described for formula (I).

In some embodiments, the compound of formula (I), or a stereoisomer or tautomer thereof, or a pharmaceutically acceptable salt of any of the foregoing, is a compound of formula (IC):

(IC)

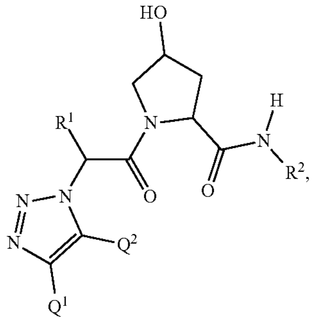

wherein:

$R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl;

$R^2$ is H or $C_{1-12}$alkyl;

$Q^1$ is H or $C_{3-15}$cycloalkyl; and $Q^2$ is, independently at each occurrence, H or $C_{3-15}$cycloalkyl.

In some embodiments, the compound of formula (I), or a stereoisomer or tautomer thereof, or a pharmaceutically acceptable salt of any of the foregoing, is a compound of formula (ID):

(ID)

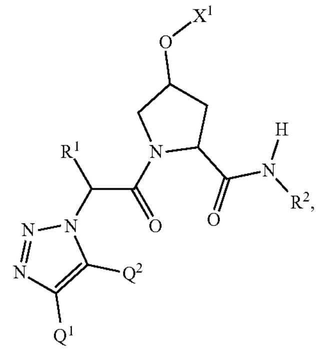

wherein:

$X^1$ is, independently at each occurrence, H or —C(O)—$C_{1-12}$alkyl;

$R^1$ is, independently at each occurrence, $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo;

$Q^1$ is H, $C_{6-20}$aryl, 5-6 membered heteroaryl, or $C_{3-5}$cycloalkyl, wherein the 5-6 membered heteroaryl of $Q^1$ is independently optionally substituted with one or more $R^q$, wherein each $R^q$ is independently halo;

$Q^2$ is, independently at each occurrence, H or $C_{3-5}$cycloalkyl;

or $Q^1$ and $Q^2$ are taken, together with the atoms to which they are attached, to form a $C_{6-20}$aryl, wherein the $C_{6-20}$aryl formed by $Q^1$ and $Q^2$ is independently optionally substituted with one or more $R^s$, wherein $R^s$ is, independently at each occurrence, halo or $C_{1-6}$alkoxy;

with the proviso that when $Q^1$ is $C_{6-20}$aryl or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —S(O)$_2$—$C_{1-12}$alkyl, or —C(O)—$C_{1-12}$alkyl.

In some embodiments, the compound of formula (I), or a stereoisomer or tautomer thereof, or a pharmaceutically acceptable salt of any of the foregoing, is a compound of formula (IE):

(IE)

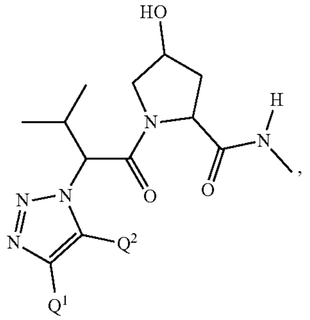

or a stereoisomer or tautomer thereof, or a pharmaceutically acceptable salt of any of the foregoing, wherein $Q^1$ and $Q^2$ are as defined in formula (I). It is understood that $Q^1$ and $Q^2$ of such embodiments of compounds of formula (IE) may include $Q^1$ and $Q^2$ as described for formula (I).

In some embodiments, the compound of formula (I), or a stereoisomer or tautomer thereof, or a pharmaceutically acceptable salt of any of the foregoing, is a compound of formula (IF):

(IF)

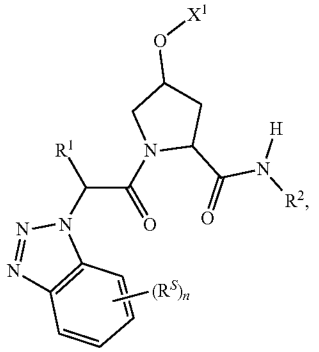

or a stereoisomer or tautomer thereof, or a pharmaceutically acceptable salt of any of the foregoing, wherein n is 0, 1, 2, 3, or 4; $R^s$ is independently OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH; and wherein $X^1$, $R^1$, and $R^2$ are as defined in formula (I). It is understood that $X^1$, $R^1$, and $R^2$ of such embodiments of compounds of formula (IF) may include $X^1$, $R^1$, and $R^2$ as described for formula (I).

In another aspect, the present disclosure is related to pharmaceutical compositions comprising one or more of the compounds described herein, or a stereoisomer or tautomer thereof, or a pharmaceutically acceptable salt of any of the foregoing, and one or more pharmaceutically acceptable excipients.

In another aspect, the present disclosure is directed to methods of binding or inhibiting VHL using one or more of the compounds described herein, or a stereoisomer or tautomer thereof, or a pharmaceutically acceptable salt of any of the foregoing, or one or more of the pharmaceutical compositions described herein.

In another aspect, the present disclosure is directed to processes for preparing one or more of the compounds described herein, or a stereoisomer or tautomer thereof, or a pharmaceutically acceptable salt of any of the foregoing, or one or more of the pharmaceutical compositions described herein.

In another aspect, the present disclosure is directed to a heterobifunctional compound of formula (II):

[A]-[B]—[C] (II), wherein:

[A] is a moiety of a VHL ligand of formula (I);

[B] is a linker moiety; and

[C] is a protein-binding moiety.

In a further aspect, the present disclosure is directed to methods of preventing or treating a disease, disorder, or condition by administering to a subject in need thereof one or more of the compounds described herein, or a stereoisomer or tautomer thereof, or a pharmaceutically acceptable salt of any of the foregoing, or one or more of the pharmaceutical compositions described herein.

DETAILED DESCRIPTION OF THE DISCLOSURE

The present disclosure is directed to compounds that bind an E3 ubiquitin ligase protein complex. In particular, compounds are described that bind to Von Hippel-Lindau (VHL), the substrate recognition subunit of the E3 ligase complex VCB.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers alternatives, modifications, and equivalents. In the event that one or more of the incorporated literature, patents, and similar materials differs from or contradicts this application, including but not limited to defined terms, term usage, described techniques, or the like, this application controls. Unless otherwise defined, technical and scientific terms used herein have the same meaning as commonly understood by one of ordinary skill in the art to which this disclosure belongs, applying that term in context to its use in describing the present disclosure. The terminology used in the description is for describing particular embodiments only and is not intended to be limiting of the disclosure. All publications, patent applications, patents, and other references mentioned herein are incorporated by reference in their entirety.

I. DEFINITIONS

The terms "residue," "moiety," or "group" refers to a component that is covalently bound or linked to another component.

The term "covalently bound" or "covalently linked" refers to a chemical bond formed by sharing of one or more pairs of electrons.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer.

The terms "cancer" and "cancerous" refer to or describe the physiological condition in mammals that is typically characterized by unregulated cell growth/proliferation. A "tumor" comprises one or more cancerous cells. Examples of cancer are provided elsewhere herein.

A "chemotherapeutic agent" or "anti-cancer agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylomithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifamib (R11577); orafenib, ABT510; Bcl-2 inhibitor such as oblimersen sodium (GENASENSE®, an antisence oligonucleotide); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestins such as megestrol acetate and medroxyprogesterone acetate, estrogens such as diethylstilbestrol and premarin, and androgens/retinoids such as fluoxymesterone, transretinoic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration, or palliation of the disease state, and remission or improved prognosis. In some embodiments, the compounds and compositions of the subject matter described herein are used to delay development of a disease or to slow the progression of a disease. In one embodiment, treatment is performed for prophylaxis only. In another embodiment, treatment is performed during the course of clinical pathology only (i.e., not for prophylaxis). In another embodiment, treatment is performed both during the course of clinical pathology and for prophylaxis.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

The term "effective" is used to describe an amount of a compound, composition or component which, when used within the context of its intended use, achieves the desired therapeutic or prophylactic result. The term effective subsumes other effective amount or effective concentration terms, including therapeutically effective amounts, which are otherwise described or used in the present application. As used herein, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a VHL ligand of the present disclosure, as well as stereoisomers or tautomers thereof, or pharmaceutically acceptable salts of any of the foregoing, may be administered as the raw chemical. Additionally, the active ingredient may be presented as a pharmaceutical composition.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two, three, four or five. The phrase should not be interpreted as duplicative of the substitutions herein described and depicted.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

A "small molecule" or "small molecular compound" generally refers to an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. Small molecules are not proteins, polypeptides, oligopeptides, peptides, polynucleotides, oligonucleotides, polysaccharides, glycoproteins, proteoglycans, etc. A derivative of a small molecule refers to a molecule that shares the same structural core as the original small molecule, but which can be prepared by a series of chemical reactions from the original small molecule.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described herein. In another embodiment, an alkyl radical is one to eight carbon atoms ($C_1$-$C_8$), or one to six carbon atoms ($C_1$-$C_6$), or one to four carbon atoms ($C_1$-$C_4$), or one to three carbon atoms ($C_1$-$C_3$). Examples of alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, isopropyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, tert-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described herein. In another embodiment, an alkylene radical is one to eight carbon atoms ($C_1$-$C_8$), one to six carbon atoms ($C_1$—C), or one to four carbon atoms ($C_1$-$C_4$). Examples of alkylene groups include, but are not limited to, methylene ($-CH_2-$), ethylene ($-CH_2CH_2-$), propylene ($-CH_2CH_2CH_2-$), and the like.

The term "alkenyl" refers to linear or branched-chain monovalent hydrocarbon radical of any length from two to twelve carbon atoms ($C_2$-$C_{12}$) with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl ($-CH=CH_2$), allyl ($-CH_2CH=CH_2$), and the like.

The term "alkenylene" refers to linear or branched-chain divalent hydrocarbon radical of any length from two to twelve carbon atoms ($C_2$-$C_{12}$) with at least one site of unsaturation, i.e., a carbon-carbon, sp2 double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH═CH—), allyl (—$CH_2$CH═CH—), and the like.

The term "alkynyl" refers to a linear or branched monovalent hydrocarbon radical of any length from two to twelve carbon atoms ($C_2$-$C_{12}$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of any length from two to twelve carbon atoms ($C_2$-$C_{12}$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a polycyclic (e.g., bicyclic) ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo [3.2.2]nonane. Polycyclic (e.g., bicyclic) rings that are overall fully saturated or partially unsaturated are encompassed within the definition of the terms "carbocycle", "carbocyclyl", "carbocyclic ring" and "cycloalkyl," including when one or more of the fused rings in the polycyclic ring is fully unsaturated (i.e., aromatic). Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, indenyl, indanyl, 1,2-dihydronaphthalene, 1,2,3,4-tetrahydronaphthyl, and the like. Carbocyclyl groups are optionally substituted independently with one or more substituents described herein.

The term "cycloalkylene" refers to a divalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic cycloalkylenes having 7 to 12 atoms can be arranged, for example, as a bicyclo [4,5], [5,5], [5,6] or [6,6] system, and bicyclic cycloalkylenes having 9 or 10 ring atoms can be arranged as a bicyclo [5,6] or [6,6] system, or as bridged systems such as bicyclo[2.2.1]heptane, bicyclo[2.2.2]octane and bicyclo [3.2.2]nonane. Spiro moieties are also included within the scope of this definition. Examples of monocyclic cycloalkylenes include, but are not limited to, cyclopropylene, cyclobutylene, cyclopentylene, 1-cyclopent-1-enylene, 1-cyclopent-2-enylene, 1-cyclopent-3-enylene, cyclohexylene, 1-cyclohex-1-enylene, 1-cyclohex-2-enylene, 1-cyclohex-3-enylene, cyclohexadienylene, cycloheptylene, cyclooctylene, cyclononylene, cyclodecylene, cycloundecylene, cyclododecylene, and the like. Cycloalkylene groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Typical aryl groups include, but are not limited to, radicals derived from benzene (phenyl), substituted benzenes, naphthalene, anthracene, biphenyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described herein. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

The term "heterocyclylene" refers to a divalent saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described herein. A heterocyclylene may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566. "Heterocyclylene" also includes divalent radicals where heterocycle radicals are fused with a saturated, partially unsaturated ring, or aromatic carbocyclic or heterocyclic ring. Examples of heterocyclylenes include, but are not limited to, morpholin-4-ylene, piperidin-1-ylene, piperazinylene, piperazin-4-ylene-2-one, piperazin-4-ylene-3-one, pyrrolidin-1-ylene, thiomorpholin-4-ylene, S-dioxothiomorpholin-4-ylene, azocan-1-ylene, azetidin-1-ylene, octahydropyrido[1,2-a]pyrazin-2-ylene, [1,4]diazepan-1-ylene, pyrrolidinylene, tetrahydrofuranylene, dihydrofuranylene, tetrahydrothienylene, tetrahydropyranylene, dihydropyranylene, tetrahydrothiopyranylene, piperidino, morpholino, thiomorpholino, thioxanylene, piperazinylene, homopiperazinylene, azetidinylene, oxetanylene, thietanylene, homopiperidinylene, oxepanylene, thiepanylene, oxazepinylene, diazepinylene, thiazepinylene, 2-pyrrolinylene, 3-pyrrolinylene, indolinylene, 2H-pyranylene, 4H-pyranylene, dioxanylene, 1,3-dioxolanylene, pyrazolinylene, dithianylene, dithiolanylene, dihydropyranylene, dihydrothienylene, dihydrofuranylene, pyrazolidinylimidazolinylene, imidazolidinylene, 3-azabicyco[3.1.0]hexanylene, 3-azabicyclo[4.1.0]heptanylene, azabicyclo[2.2.2]hexanylene, 3H-indolyl quinolizinyl and N-pyridyl ureas. Spiro moieties are also included within the scope of this definition. Examples of a heterocyclylene group wherein 2 ring atoms are substituted with oxo (=O) moieties are pyrimidinonylene and 1,1-dioxo-thiomorpholinylene. The heterocyclylene groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroarylene" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroarylene groups are pyridinylene (including, for example, 2-hydroxypyridinylene), imidazolylene, imidazopyridinylene, 1-methyl-1H-benzo[d]imidazole, [1,2,4]triazolo[1,5-a]pyridine, pyrimidinylene (including, for example, 4-hydroxypyrimidinylene), pyrazolylene, triazolylene, pyrazinylene, tetrazolylene, furylene, thienylene, isoxazolylene, thiazolylene, oxadiazolylene, oxazolylene, isothiazolylene, pyrrolylene, quinolinylene, isoquinolinylene, tetrahydroisoquinolinylene, indolylene, benzimidazolylene, benzofuranylene, cinnolinylene, indazolylene, indolizinylene, phthalazinylene, pyridazinylene, triazinylene, isoindolylene, pteridinylene, purinylene, oxadiazolylene, thiadiazolylene, thiadiazolylene, furazanylene, benzofurazanylene, benzothiophenylene, benzothiazolylene, benzoxazolylene, quinazolinylene, quinoxalinylene, naphthyridinylene, and furopyridinylene. Heteroarylene groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example, and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "acyl" refers to both substituted and unsubstituted acyl. In certain embodiments, an "acyl" may be —C(O)—$R^{16}$, wherein $R^{16}$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, and substituted or unsubstituted heterocyclyl. In one particular embodiment, it is a substituted $C_1$-$C_3$ alkyl.

The term "oxo" refers to "=O".

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond  is shown, both a double bond and single bond are represented within the context of the compound shown. When a crossed double bond () is shown, both the E and Z configurations are represented within the context of the compound shown; and the compound may contain the E isomer or the Z isomer or a mixture of both the E and Z isomers.

The term "VCB E3 Ubiquitin Ligase," "Von Hippel-Lindau (or VHL) E3 Ubiquitin Ligase," "VHL," or "Ubiquitin Ligase," which are generally used interchangeably unless the context indicates otherwise, is used to describe a target enzyme(s) binding site of ubiquitin ligase moieties as described herein. VCB E3 is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, a moiety that binds the E3 VHL ubiquitin ligase or a component thereof, is referred to a VHL ligand.

In certain embodiments disclosed herein, certain groups (e.g., alkyl, alkenyl, alkynyl, cycloalkyl, aryl, heteroaryl or heterocyclyl) are described as "substituted". In some such embodiments, the "substituted" group may be substituted with 1, 2, 3, 4, 5, or more substituents, as indicated herein. In certain embodiments, alkyl, alkenyl, alkynyl, cycloalkyl, aryl, heteroaryl or heterocyclyl may be substituted with one or more substituents independently selected from, but not limited to, alkyl, alkenyl, alkynyl, cycloalkyl heterocyclyl, aryl, heteroaryl, halo (i.e., halogen), haloalkyl, oxo, OH, CN, —O-alkyl, S-alkyl, NH-alkyl, N(alkyl)$_2$, O-cycloalkyl, S-cycloalkyl, NH-cycloalkyl, N(cycloalkyl)$_2$, N(cycloalkyl)(alkyl), $NH_2$, SH, $SO_2$-alkyl, P(O)(O-alkyl)(alkyl), P(O)(O-alkyl)$_2$, Si(OH)$_3$, Si(alkyl)$_3$, Si(OH)(alkyl)$_2$, CO-alkyl, $CO_2H$, $NO_2$, $SF_5$, $SO_2$NH-alkyl, $SO_2$N(alkyl)$_2$, SONH-alkyl, SON(alkyl)$_2$, CONH-alkyl, CON(alkyl)$_2$, N(alkyl)CONH(alkyl), N(alkyl)CON(alkyl)$_2$, NHCONH(alkyl), NHCON(alkyl)$_2$, $NHCONH_2$, N(alkyl)$SO_2$NH(alkyl), N(alkyl)$SO_2$N(alkyl)$_2$, $NHSO_2$NH(alkyl), $NHSO_2$N(alkyl)$_2$, and $NHSO_2NH_2$.

Still additional definitions and abbreviations are provided elsewhere herein.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The articles “a” and “an” as used herein and in the appended claims are used herein to refer to one or to more than one (i.e., to at least one) of the grammatical object of the article unless the context clearly indicates otherwise. By way of example, “an element” means one element or more than one element.

In the claims, as well as in the specification above, transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

As used herein in the specification and in the claims, the phrase “at least one,” in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a nonlimiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

II. COMPOUNDS

E3 ubiquitin ligases (of which over 600 are known in humans) confer substrate specificity for ubiquitination. There are known ligands which bind to these ligases. An E3 ubiquitin ligase binding group (E3LB) is a peptide or small molecule that can bind an E3 ubiquitin ligase.

A particular E3 ubiquitin ligase is von Hippel-Lindau (VHL) tumor suppressor, the substrate recognition subunit of the E3 ligase complex VCB, which also consists of elongins B and C, Cul2, and Rbxl. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels.

In one embodiment, provided herein is a compound of formula (I):

(I)

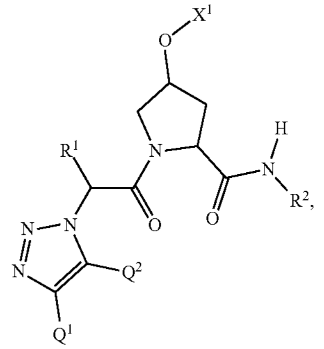

or a stereoisomer or tautomer thereof, or a pharmaceutically acceptable salt of any of the foregoing, wherein:

$X^1$ is, independently at each occurrence, H, $C_{1-12}$alkyl, or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-6}$cycloalkyl, wherein the $C_{1-12}$alkyl or $C_{3-6}$cycloalkyl of $R^2$ is independently optionally substituted with one or more halo or —CN; and $Q^1$ and $Q^2$ are, independently of each other and independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^1$ or $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

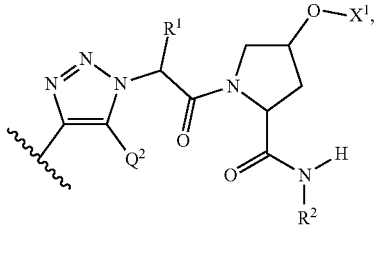

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, or $C_{1-12}$alkyl, wherein the $C_{1-12}$alkyl of $R^s$ is independently further optionally substituted with one or more halo, cyano, or OH.

In another embodiment, provided herein is a compound of formula (I):

(I)

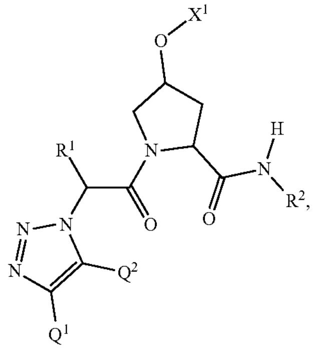

or a stereoisomer or tautomer thereof, or a pharmaceutically acceptable salt of any of the foregoing, wherein:

$X^1$ is, independently at each occurrence, H or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; and $Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$ alkoxy, or

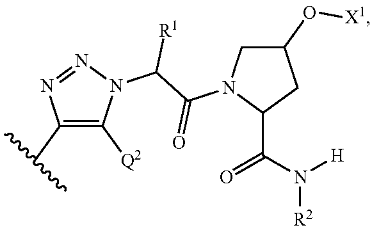

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

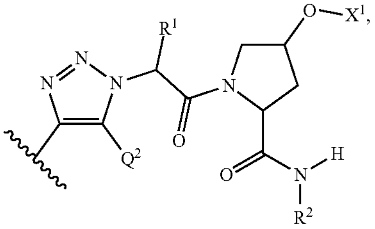

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN, or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

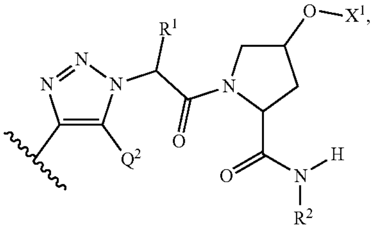

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH;

with the proviso that when $Q^1$ is cyclohexyl, biphenyl, or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In some embodiments, provided herein is a compound of formula (I), or a stereoisomer or tautomer thereof, or a pharmaceutically acceptable salt of any of the foregoing, wherein $R^2$ is, independently at each occurrence, H, $C_{1-12}$alkyl, or $C_{3-6}$cycloalkyl, wherein the $C_{1-12}$alkyl or $C_{3-6}$cycloalkyl of $R^2$ is independently optionally substituted with one or more halo or —CN. In certain embodiments, $R^2$ is, independently at each occurrence, H or $C_{1-12}$alkyl, wherein the $C_{1-12}$alkyl of $R^2$ is independently optionally substituted with one or more halo or —CN. In some embodiments, $R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN.

In some embodiments, provided herein is a compound of formula (I), or a stereoisomer or tautomer thereof, or a pharmaceutically acceptable salt of any of the foregoing, wherein $R^2$ is, independently at each occurrence, H.

In other embodiments, provided herein is a compound of formula (I), or a stereoisomer or tautomer thereof, or a pharmaceutically acceptable salt of any of the foregoing, wherein $R^2$ is, independently at each occurrence, $C_{1-12}$alkyl, wherein the $C_{1-12}$alkyl of $R^2$ is independently optionally substituted with one or more halo or —CN. In certain embodiments, $R^2$ is $C_{1-6}$alkyl, wherein the $C_{1-6}$alkyl of $R^2$ is independently optionally substituted with one or more halo or —CN. In certain embodiments, $R^2$ is $C_{1-6}$alkyl, wherein the $C_{1-6}$alkyl of $R^2$ is independently optionally substituted with one or more halo. In some embodiments, $R^2$ is $C_{1-3}$alkyl, wherein the $C_{1-3}$alkyl of $R^2$ is independently optionally substituted with one or more halo or —CN. In some embodiments, $R^2$ is $C_{1-3}$alkyl, wherein the $C_{1-3}$alkyl of $R^2$ is independently optionally substituted with one or more halo. In other embodiments, $R^2$ is unsubstituted iso-propyl. In other embodiments, $R^2$ is ethyl, wherein the ethyl of $R^2$ is independently optionally substituted with one or more halo. In certain embodiments, the one or more halo are each independently fluoro. In some embodiments, $R^2$ is —$CH_2CH_2F$. In other embodiments, $R^2$ is —$CH_2CF_3$. In certain embodiments, $R^2$ is unsubstituted ethyl. In other embodiments, $R^2$ is methyl, wherein the methyl of $R^2$ is optionally substituted with one or more halo or —CN. In certain embodiments, $R^2$ is unsubstituted methyl.

In other embodiments, provided herein is a compound of formula (I), or a stereoisomer or tautomer thereof, or a pharmaceutically acceptable salt of any of the foregoing, wherein $R^2$ is $C_{3-6}$cycloalkyl, wherein the $C_{3-6}$cycloalkyl of $R^2$ is optionally substituted with one or more halo or —CN. In other embodiments, $R^2$ is $C_{3-5}$cycloalkyl, wherein the $C_{3-5}$cycloalkyl of $R^2$ is optionally substituted with one or more halo or —CN. In other embodiments, $R^2$ is $C_{5-6}$cycloalkyl, wherein the $C_{5-6}$cycloalkyl of $R^2$ is optionally substituted with one or more halo or —CN. In certain embodiments, $R^2$ is cyclopropyl, wherein the cyclopropyl is optionally substituted with one or more halo or —CN. In some embodiments, $R^2$ is unsubstituted cyclopropyl.

In some embodiments, provided herein is a compound of formula (I), or a stereoisomer or tautomer thereof, or a pharmaceutically acceptable salt of any of the foregoing, wherein $Q^1$ and $Q^2$ are, independently at each occurrence and independently of each other, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are each independently H or $C_{1-12}$alkyl, wherein the $C_{1-12}$alkyl or $C_{3-15}$cycloalkyl of $Q^1$ or $Q^2$ is independently optionally substituted with one or more $R^q$, wherein $R^q$ is $C_{1-12}$alkyl, $C_{2-12}$ alkenyl, $C_{2-12}$alkynyl, $C_{6-20}$aryl, $C_{1-12}$alkoxy, or

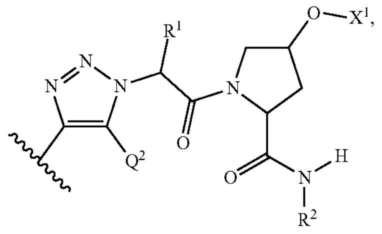

wherein the $C_{1-12}$alkyl or $C_{1-12}$alkoxy of $R^q$ is independently further optionally substituted with one or more halo or —NHC(O)—$C_{1-12}$alkyl.

In some embodiments, provided herein is a compound of formula (I), or a stereoisomer or tautomer thereof, or a pharmaceutically acceptable salt of any of the foregoing, wherein $Q^1$ and $Q^2$ are each independently H.

In certain embodiments, $Q^1$ is $C_{3-15}$cycloalkyl, wherein the $C_{3-15}$cycloalkyl of $Q^1$ is independently optionally substituted with one or more $R^q$, wherein $R^q$ is $C_{1-12}$alkyl, $C_{2-12}$alkenyl, $C_{2-12}$alkynyl, $C_{6-20}$aryl, $C_{1-12}$alkoxy, or

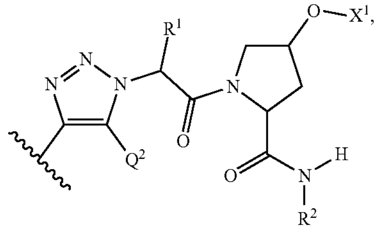

wherein the $C_{1-12}$alkyl or $C_{1-12}$alkoxy of $R^q$ is independently further optionally substituted with one or more halo or —NHC(O)—$C_{1-12}$alkyl. In certain embodiments, $Q^1$ is $C_{3-10}$cycloalkyl, wherein the $C_{3-10}$ cycloalkyl of $Q^1$ is optionally substituted with one or more $R^q$. In other embodiments, $Q^1$ is $C_{3-8}$cycloalkyl, wherein the $C_{3-8}$cycloalkyl of $Q^1$ is optionally substituted with one or more $R^q$. In still other embodiments, $Q^1$ is $C_{3-6}$cycloalkyl, wherein the $C_{3-6}$cycloalkyl of $Q^1$ is optionally substituted with one or more $R^q$. In further embodiments, $Q^1$ is $C_{3-5}$cycloalkyl, wherein the $C_{3-5}$cycloalkyl of $Q^1$ is optionally substituted with one or more $R^q$. In still other embodiments, $Q^1$ is cyclopropyl, wherein the cyclopropyl of $Q^1$ is optionally substituted with one or more $R^q$.

In some embodiments, $Q^1$ is unsubstituted $C_{3-15}$cycloalkyl. In other embodiments, $Q^1$ is unsubstituted $C_{3-10}$cycloalkyl. In further embodiments, $Q^1$ is unsubstituted $C_{3-8}$cycloalkyl. In still other embodiments, $Q^1$ is unsubstituted $C_{3-6}$cycloalkyl. In certain embodiments, $Q^1$ is unsubstituted $C_{3-5}$cycloalkyl. In further embodiments, $Q^1$ is unsubstituted cyclopropyl.

In some embodiments, when $Q^1$ is cyclohexyl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In some embodiments, $Q^1$ is unsubstituted 5-6 membered heteroaryl. In some embodiments, $Q^1$ is 5-6 membered heteroaryl substituted with one or more $R^q$. In some embodiments, each $R^q$ is independently halo, $C_{1-6}$alkoxy, —NHC(O)—$C_{1-12}$alkyl, —CN, or —$NO_2$. In some embodiments, each $R^q$ is independently halo (e.g., —Cl or —F). In some embodiments, the 5-6 membered heteroaryl of $Q^1$ has one or more annular N atom. In some embodiments, the 5-6 membered heteroaryl of $Q^1$ has one or more annular S atom. In some embodiments, the 5-6 membered heteroaryl of $Q^1$ has one or more annular 0 atom. In some embodiments, the 5-6 membered heteroaryl of $Q^1$ is selected form the group consisting of: thiophene, furan, pyrrole, oxazole, thiazole, pyridine, and pyrimidine. In some embodiments, $Q^1$ is substituted or unsubstituted 5-6 membered heteroaryl and $R^1$ is $C_{1-3}$alkyl (e.g., isopropyl). In some embodiments, $Q^1$ is substituted or unsubstituted 5-6 membered heteroaryl, $R^1$ is $C_{1-3}$alkyl (e.g., isopropyl), and $R^2$ is $C_{1-12}$alkyl (e.g., methyl).

In some embodiments, when $Q^1$ is 5-6 membered heteroaryl (e.g., substituted or unsubstituted), $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In some embodiments, when $Q^1$ is pyridine, thiazole, pyrazole, imidazole, thiophene, or oxazole, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In some embodiments, when $Q^1$ is 5-6 membered heteroaryl substituted with one or more $R^q$, wherein each $R^q$ is independently halo, $C_{1-6}$alkoxy, —NHC(O)—$C_{1-12}$alkyl, —CN, or —$NO_2$, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In any variation detailed herein where $Q^1$ is aryl, in some embodiments, the aryl is a monocyclic phenyl moiety, which is unsubstituted or substituted with one or more $R^q$.

In some embodiments, $Q^1$ is unsubstituted $C_{6-20}$aryl. In some embodiments, $Q^1$ is unsubstituted phenyl. In some embodiments, $Q^1$ is $C_{6-20}$aryl substituted with one or more $R^q$. In some embodiments, each $R^q$ is independently halo (e.g., —Cl or —F). In some embodiments, $Q^1$ is substituted or unsubstituted $C_{6-20}$aryl (e.g. phenyl) and $R^1$ is $C_{1-3}$alkyl (e.g. isopropyl). In some embodiments, $Q^1$ is substituted or unsubstituted $C_{6-20}$aryl (e.g. phenyl), $R^1$ is $C_{1-3}$alkyl (e.g. isopropyl), and $R^2$ is $C_{1-12}$alkyl (e.g., methyl).

In some embodiments, when $Q^1$ is $C_{6-20}$aryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In some embodiments, when $Q^1$ is biphenyl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In certain embodiments, provided herein is a compound of formula (I), or a stereoisomer or tautomer thereof, or a pharmaceutically acceptable salt of any of the foregoing, wherein $Q^1$ is halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are each independently H or $C_{1-12}$alkyl, wherein the $C_{1-12}$alkyl or $C_{3-15}$cycloalkyl of $Q^1$ is independently optionally substituted with one or more $R^q$, wherein $R^q$ is $C_{1-12}$alkyl, $C_{2-12}$alkenyl, $C_{2-12}$alkynyl, $C_{6-20}$aryl, $C_{1-12}$alkoxy, or

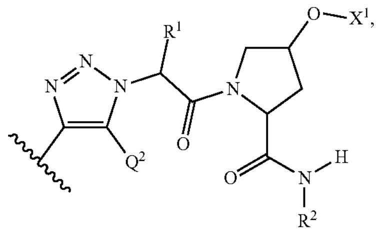

wherein the $C_{1-12}$alkyl or $C_{1-12}$alkoxy of $R^q$ is independently further optionally substituted with one or more halo or —NHC(O)—$C_{1-12}$alkyl, and $Q^2$ is H.

In certain embodiments, provided herein is a compound of formula (I), or a stereoisomer or tautomer thereof, or a pharmaceutically acceptable salt of any of the foregoing, wherein $Q^1$ is halo, $C_{1-12}$alkyl, $C_{3-15}$cycloalkyl, —C(O)—O($R^a$), or —C(O)—N($R^b$)($R^c$), wherein $R^a$, $R^b$, and $R^c$ are each independently H or $C_{1-12}$alkyl, wherein the $C_{1-12}$alkyl or $C_{3-15}$cycloalkyl of $Q^1$ is independently optionally substituted with one or more $R^q$, wherein $R^q$ is $C_{1-12}$alkyl, $C_{2-12}$alkenyl, $C_{2-12}$alkynyl, $C_{6-20}$aryl, $C_{1-12}$alkoxy, or

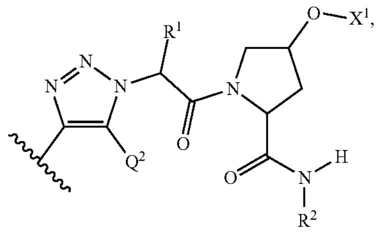

wherein the $C_{1-12}$alkyl or $C_{1-12}$alkoxy of $R^q$ is independently further optionally substituted with one or more halo or —NHC(O)—$C_{1-12}$alkyl, and $Q^2$ is H. In certain embodiments, $Q^1$ is $C_{3-15}$cycloalkyl, wherein the $C_{3-15}$cycloalkyl of $Q^1$ is independently optionally substituted with one or more $R^q$, wherein $R^q$ is $C_{1-12}$alkyl, $C_{2-12}$alkenyl, $C_{2-12}$alkynyl, $C_{6-20}$aryl, $C_{1-12}$alkoxy, or

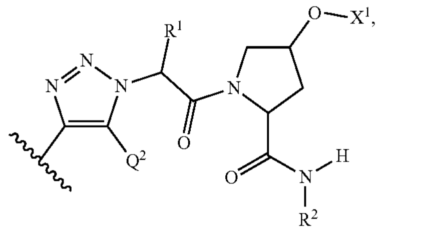

wherein the $C_{1-12}$alkyl or $C_{1-12}$alkoxy of $R^q$ is independently further optionally substituted with one or more halo or —NHC(O)—$C_{1-12}$alkyl, and $Q^2$ is H. In other embodiments, $Q^1$ is $C_{3-10}$cycloalkyl, wherein the $C_{3-10}$cycloalkyl of $Q^1$ is independently optionally substituted with one or more $R^q$, and $Q^2$ is H. In other embodiments, $Q^1$ is $C_{3-8}$cycloalkyl, wherein the $C_{3-8}$cycloalkyl of $Q^1$ is independently optionally substituted with one or more $R^q$, and $Q^2$ is H. In still other embodiments, $Q^1$ is $C_{3-6}$cycloalkyl, wherein the $C_{3-6}$cycloalkyl of $Q^1$ is optionally substituted with one or more $R^q$, and $Q^2$ is H. In further embodiments, $Q^1$ is $C_{3-5}$cycloalkyl, wherein the $C_{3-5}$cycloalkyl of $Q^1$ is independently optionally substituted with one or more $R^q$, and $Q^2$ is H. In still other embodiments, $Q^1$ is cyclopropyl, wherein the cyclopropyl of $Q^1$ is independently optionally substituted with one or more $R^q$, and $Q^2$ is H. In other embodiments, $Q^1$ is cyclopropyl, wherein the cyclopropyl of $Q^1$ is optionally substituted with one or more $R^q$, and $Q^2$ is H. In some embodiments, $Q^1$ is unsubstituted cyclopropyl and $Q^2$ is H.

In some embodiments, provided herein is a compound of formula (I), or a stereoisomer or tautomer thereof, or a pharmaceutically acceptable salt of any of the foregoing, wherein $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^S$ is OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, or $C_{1-12}$alkyl, wherein the $C_{1-12}$alkyl of $R^s$ is further optionally substituted with one or more halo, cyano, or OH. In some embodiments, $Q^1$ and $Q^2$ are taken, together with the atoms to which they are attached, to form a $C_{6-20}$aryl, wherein the $C_{6-20}$aryl formed by $Q^1$ and $Q^2$ is optionally substituted with one or more $R^s$, wherein $R^s$ is OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, or $C_{1-12}$alkyl, wherein the $C_{1-12}$alkyl of $R^s$ is further optionally substituted with one or more halo, cyano, or OH. In some embodiments, $Q^1$ and $Q^2$ are taken, together with the atoms to which they are attached, to form a $C_{6-20}$aryl, wherein the $C_{6-20}$aryl formed by $Q^1$ and $Q^2$ is optionally substituted with one or more $R^s$, wherein $R^s$ is OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is further optionally substituted with one or more halo, cyano, or OH. In some embodiments, $Q^1$ and $Q^2$ are taken, together with the atoms to which they are attached, to form a $C_{6-16}$aryl. In some embodiments, $Q^1$ and $Q^2$ are taken, together with the atoms to which they are attached, to form a $C_{6-12}$aryl. In some embodiments, $Q^1$ and $Q^2$ are taken, together with the atoms to which they are attached, to form a $C_{6-10}$aryl. In some embodiments, $Q^1$ and $Q^2$ are taken, together with the atoms to which they are attached, to form a $C_{6-8}$aryl. In some embodiments, $Q^1$ and $Q^2$ are taken, together with the atoms to which they are attached, to form a $C_{6-20}$aryl, wherein the $C_{6-20}$aryl formed by $Q^1$ and $Q^2$ is unsubstituted. In some embodiments, $Q^1$ and $Q^2$ are taken, together with the atoms to which they are attached, to form a $C_6$aryl, wherein the $C_6$aryl formed by $Q^1$ and $Q^2$ is unsubstituted. In some embodiments, $Q^1$ and $Q^2$ are taken, together with the atoms to which they are attached, to form a $C_6$aryl, wherein the $C_6$aryl formed by $Q^1$ and $Q^2$ is substituted with one or more $R^s$, wherein $R^s$ is halo or $C_{1-6}$alkoxy.

In any variation detailed herein wherein $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, in some embodiments, the $C_{3-15}$cycloalkyl, 3-15 membered heterocyclyl, $C_{6-20}$aryl, or 5-20 membered heteroaryl is fused to the triazole moiety to which $Q^1$ and $Q^2$ are attached.

In some embodiments, $R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In some embodiments, $R^1$ is, independently at each occurrence, $C_{1-12}$alkyl, wherein the $C_{1-12}$alkyl of $R^1$ is independently optionally substituted with one or more $C_{6-20}$aryl, —$S(O)_2$—$C_{1-12}$alkyl, or —C(O)—$C_{1-12}$alkyl. In some embodiments, $R^1$ is, independently at each occurrence, $C_{1-6}$alkyl, wherein the $C_{1-6}$alkyl of $R^1$ is independently optionally substituted with one or more $C_{6-20}$aryl, —$S(O)_2$—$C_{1-12}$alkyl, or —C(O)—$C_{1-12}$alkyl. In some embodiments, $R^1$ is, independently at each occurrence, $C_{1-3}$alkyl, wherein the $C_{1-3}$alkyl of $R^1$ is independently optionally substituted with one or more $C_{6-20}$aryl, —$S(O)_2$—$C_{1-12}$alkyl, or —C(O)—$C_{1-12}$alkyl. In certain embodiments, $R^1$ is, independently at each occurrence, unsubstituted $C_{1-12}$alkyl. In other embodiments, $R^1$ is, independently at each occurrence, unsubstituted $C_{1-6}$alkyl. In certain embodiments, $R^1$ is, independently at each occurrence, unsubstituted tert-butyl. In further embodiments, $R^1$ is, independently at each occurrence, unsubstituted $C_{1-3}$alkyl. In still other embodiments, $R^1$ is, independently at each occurrence, unsubstituted iso-propyl.

In some embodiments, $R^1$ is, independently at each occurrence, $C_{3-15}$cycloalkyl, wherein the $C_{3-15}$cycloalkyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In certain embodiments, $R^1$ is, independently at each occurrence, $C_{3-10}$cycloalkyl, wherein the $C_{3-10}$cycloalkyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In other embodiments, $R^1$ is, independently at each occurrence, $C_{3-8}$cycloalkyl, wherein the $C_{3-8}$cycloalkyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In other embodiments, $R^1$ is, independently at each occurrence, $C_{3-6}$cycloalkyl, wherein the $C_{3-6}$cycloalkyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In some embodiments, $R^1$ is, independently at each occurrence, cyclohexyl, wherein the cyclohexyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In other embodiments, $R^1$ is, independently at each occurrence, unsubstituted cyclohexyl. In some embodiments, $R^1$ is, independently at each occurrence, cyclohexyl, wherein the cyclohexyl of $R^1$ is independently substituted with one or more $C_{1-12}$alkyl. In certain embodiments, $R^1$ is, independently at each occurrence, cyclohexyl, wherein the cyclohexyl of $R^1$ is independently substituted with one or more methyl.

In some embodiments, $R^1$ is, independently at each occurrence, 3-15 membered heterocyclyl, wherein the 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In certain embodiments, $R^1$ is, independently at each occurrence, 3-10 membered heterocyclyl, wherein the 3-10 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In other embodiments, $R^1$ is, independently at each occurrence, 3-8 membered heterocyclyl, wherein the 3-8 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In further embodiments, $R^1$ is, independently at each occurrence, 3-6 membered heterocyclyl, wherein the 3-6 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In some embodiments, $R^1$ is, independently at each occurrence, a 6-membered heterocyclyl, wherein the 6 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl. In some embodiments, $R^1$ is, independently at each occurrence, an unsubstituted 6-membered heterocyclyl. In other embodiments, $R^1$ is, independently at each occurrence, a 6-membered heterocyclyl, wherein the 6 membered heterocyclyl of $R^1$ is independently optionally substituted with one or more $C_{1-12}$alkyl. In some embodiments, $R^1$ is, independently at each occurrence, a 6-membered heterocyclyl, wherein the 6 membered heterocyclyl of $R^1$ is independently optionally substituted with one or more —C(O)—$C_{1-12}$alkyl. In other embodiments, $R^1$ is, independently at each occurrence, a 6-membered heterocyclyl, wherein the 6-membered heterocyclyl of $R^1$ is independently optionally substituted with one or more —$S(O)_2$—$C_{1-12}$alkyl. In some embodiments, $R^1$ is, independently at each occurrence, unsubstituted piperidinyl. In other embodiments, $R^1$ is, independently at each occurrence, piperidinyl, wherein the piperidinyl of $R^1$ is independently substituted with one or more $C_{1-12}$alkyl, —C(O)—$C_{1-12}$alkyl, or —$S(O)_2$—$C_{1-12}$alkyl. In other embodiments, $R^1$ is, independently at each occurrence, unsubstituted tetrahydro-2H-pyran.

In some embodiments, provided herein is a compound of formula (I), or a stereoisomer or tautomer thereof, or a pharmaceutically acceptable salt of any of the foregoing, wherein the chiral carbon atom to which $R^1$ is attached is in the R stereochemical configuration. In other embodiments, the chiral carbon atom to which $R^1$ is attached is in the S stereochemical configuration.

In some embodiments, provided herein is a compound of formula (I), or a pharmaceutically acceptable salt of thereof, the compound of formula (I) is a compound of formula (I'):

(I')

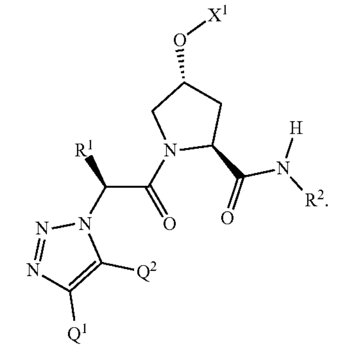

or a pharmaceutically acceptable salt of thereof, wherein $X^1$ is, independently at each occurrence, H or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; and $Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

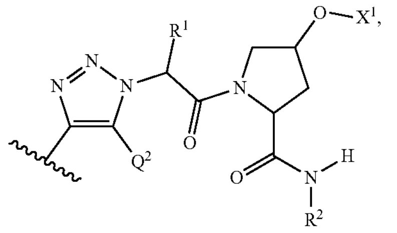

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

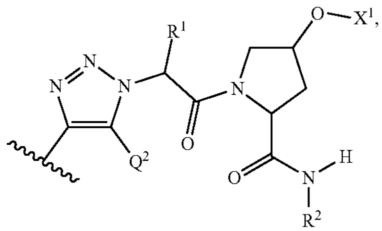

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN, or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

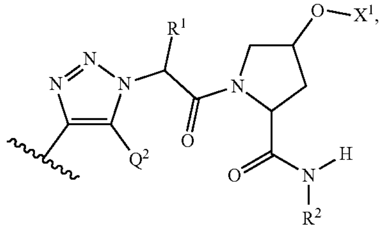

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH;

with the proviso that when $Q^1$ is cyclohexyl, biphenyl, or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

In some embodiments, $Q^1$ is $C_{3-15}$cycloalkyl, wherein the $C_{3-15}$cycloalkyl of $Q^1$ is independently optionally substituted with one or more $R^q$, wherein $R^q$ is $C_{1-12}$alkyl, $C_{2-12}$alkenyl, $C_{2-12}$alkynyl, $C_{6-20}$aryl, $C_{1-12}$alkoxy, or

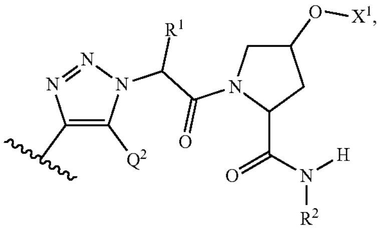

wherein the $C_{1-12}$alkyl or $C_{1-12}$alkoxy of $R^q$ is independently further independently optionally substituted with one or more halo or —NHC(O)—$C_{1-12}$alkyl, $Q^2$ is, independently at each occurrence, H, and $R^1$ is, independently at each occurrence, $C_{1-12}$alkyl, wherein the $C_{1-12}$alkyl of $R^1$ is independently optionally substituted with one or more $C_{6-20}$aryl, —$S(O)_2$—$C_{1-12}$alkyl, or —C(O)—$C_{1-12}$alkyl. In other embodiments, $Q^1$ is $C_{3-15}$cycloalkyl, $Q^2$ is, independently at each occurrence, H, and $R^1$ is, independently at each occurrence, $C_{1-6}$alkyl. In some embodiments, $Q^1$ is cyclopropyl, $Q^2$ is H, and $R^1$ is tert-butyl, such that the compound of formula (I) is a compound of formula (IA):

(IA)

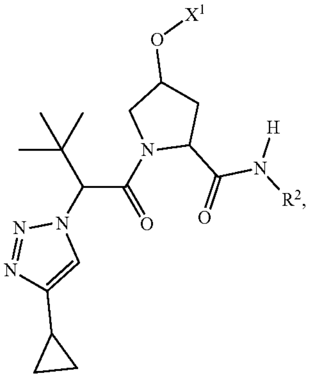

or a stereoisomer or tautomer thereof, or a pharmaceutically acceptable salt of any of the foregoing.

In some embodiments, provided herein is a compound of formula (IA), or a stereoisomer or tautomer thereof, or a pharmaceutically acceptable salt of any of the foregoing, wherein $R^2$ is $C_{1-12}$alkyl, wherein the $C_{1-12}$alkyl of $R^2$ is independently optionally substituted with one or more halo or —CN. In certain embodiments, $R^2$ is $C_{1-6}$alkyl, wherein the $C_{1-6}$alkyl of $R^2$ is independently optionally substituted with one or more halo or —CN. In some embodiments, $R^2$ is unsubstituted $C_{1-6}$alkyl. In certain embodiments, $R^2$ is methyl.

In some embodiments, provided herein is a compound of formula (I), or a stereoisomer or tautomer thereof, or a pharmaceutically acceptable salt of any of the foregoing, wherein $Q^1$ is $C_{3-15}$cycloalkyl, wherein the $C_{3-15}$cycloalkyl of $Q^1$ is optionally substituted with one or more $R^q$, wherein $R^q$ is $C_{1-12}$alkyl, $C_{2-12}$alkenyl, $C_{2-12}$alkynyl, $C_{6-20}$aryl, $C_{1-12}$alkoxy, or

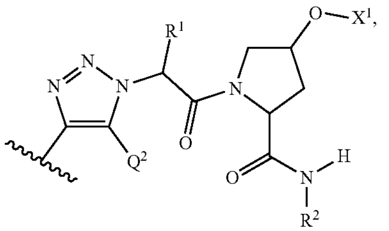

wherein the $C_{1-12}$alkyl or $C_{1-12}$alkoxy of $R^q$ is independently further optionally substituted with one or more halo or —NHC(O)—$C_{1-12}$alkyl, $Q^2$ is H, and $R^2$ is $C_{1-12}$alkyl, wherein the $C_{1-12}$alkyl of $R^2$ is optionally substituted with one or more halo or —CN. In other embodiments, $Q^1$ is $C_{3-15}$cycloalkyl, $Q^2$ is H, and $R^2$ is $C_{1-6}$alkyl, wherein the $C_{1-6}$alkyl of $R^2$ is optionally substituted with one or more halo. In some embodiments, $Q^1$ is cyclopropyl, $Q^2$ is H, and $R^2$ is $C_{1-6}$alkyl, wherein the $C_{1-6}$alkyl of $R^2$ is optionally substituted with one or more halo. In certain embodiments, the one or more halo is fluoro. In certain embodiments, $Q^1$ is cyclopropyl, $Q^2$ is H, and $R^2$ is methyl, such that the compound of formula (I) is a compound of formula (IB):

(IB)

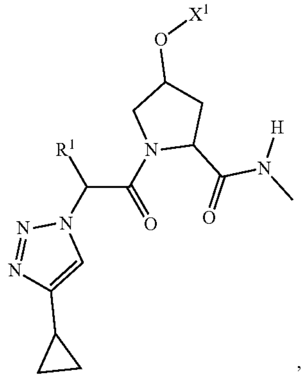

, or a stereoisomer or tautomer thereof, or a pharmaceutically acceptable salt of any of the foregoing.

In some embodiments, provided herein is a compound of formula (IB), or a stereoisomer or tautomer thereof, or a pharmaceutically acceptable salt of any of the foregoing, wherein $R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is optionally substituted with one or more $C_{1-12}$alkyl, $C_{6-20}$aryl, —$S(O)_2$—$C_{1-12}$alkyl, or —C(O)—$C_{1-12}$alkyl. In certain embodiments, $R^1$ is $C_{1-6}$alkyl. In other embodiments, $R^1$ is $C_{3-6}$cycloalkyl, wherein the $C_{3-6}$cycloalkyl is optionally substituted with one or more $C_{1-12}$alkyl. In some embodiments, $R^1$ is 3-6 membered heterocyclyl, wherein the 3-6 membered heterocyclyl of $R^1$ is optionally substituted with one or more $C_{1-12}$alkyl, $C_{6-20}$aryl, —$S(O)_2$—$C_{1-12}$alkyl, or —C(O)—$C_{1-12}$alkyl.

In some embodiments, provided herein is a compound of formula (I), such as a compound of formula (IA) or (IB), or a stereoisomer or tautomer thereof, or a pharmaceutically acceptable salt of any of the foregoing, wherein $X^1$ is H, $C_{1-12}$alkyl, or —C(O)—$C_{1-12}$alkyl. In other embodiments, $X^1$ is —C(O)—$C_{1-12}$alkyl. In some embodiments, In other embodiments, $X^1$ is —C(O)—$CH_3$. In some embodiments, $X^1$ is $C_{1-12}$alkyl. In certain embodiments, the $C_{1-12}$alkyl of $X^1$ is unsubstituted. In certain embodiments, provided herein is a compound of formula (I), such as a compound of formula (IA) or (IB), or a stereoisomer or tautomer thereof, or a pharmaceutically acceptable salt of any of the foregoing, wherein $X^1$ is H. In certain embodiments, $X^1$ is H such that the compound of formula (I) is a compound of formula (IC):

(IC)

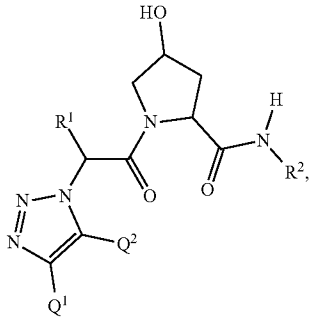

or a stereoisomer or tautomer thereof, or a pharmaceutically acceptable salt of any of the foregoing. In embodiments, $R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl; $R^2$ is, independently at each occurrence, H, $C_{1-12}$alkyl, or $C_{3-6}$cycloalkyl, wherein the $C_{1-12}$alkyl or $C_{3-6}$cycloalkyl of $R^2$ is independently optionally substituted with one or more halo or —CN; and $Q^1$ and $Q^2$ are, independently of each other and independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^1$ or $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

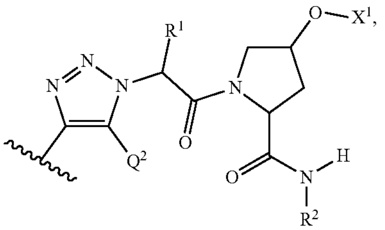

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2$ $C_{1-12}$alkyl, —$SO_2NH_2$, or $C_{1-12}$alkyl, wherein the $C_{1-12}$alkyl of $R^s$ is independently further optionally substituted with one or more halo, cyano, or OH.

In some embodiments, provided herein is a compound of formula (IC), or a stereoisomer or tautomer thereof, or a pharmaceutically acceptable salt of any of the foregoing, wherein $R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl; $R^2$ is H or $C_{1-12}$alkyl; and $Q^1$ and $Q^2$ are, independently of each other and independently at each occurrence, H or $C_{3-15}$cycloalkyl.

In embodiments, provided herein is a compound of formula (I), or a stereoisomer or tautomer thereof, or a pharmaceutically acceptable salt of any of the foregoing, wherein $X^1$ is H; $R^1$ is $C_{1-12}$alkyl, $C_{3-15}$cycloalkyl, or 3-15 membered heterocyclyl, and the chiral carbon atom to which $R^1$ is attached is in the S stereochemical configuration, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl; $R^2$ is H or $C_{1-12}$alkyl; and $Q^1$ and $Q^2$ are, independently of each other and independently at each occurrence, H or $C_{3-15}$cycloalkyl.

In embodiments, provided herein is a compound of formula (I), or a stereoisomer or tautomer thereof, or a pharmaceutically acceptable salt of any of the foregoing, wherein $X^1$ is H; $R^1$ is $C_{1-12}$alkyl, $C_{3-15}$cycloalkyl, or 3-15 membered heterocyclyl, and the chiral carbon atom to which $R^1$ is attached is in the S stereochemical configuration, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl; $R^2$ is H or $C_{1-12}$alkyl; $Q^1$ is cyclopropyl; and $Q^2$ is H.

In embodiments, provided herein is a compound of formula (I), or a stereoisomer or tautomer thereof, or a pharmaceutically acceptable salt of any of the foregoing, wherein $X^1$ is H; $R^1$ is $C_{1-12}$alkyl, $C_{3-15}$cycloalkyl, or 3-15 membered heterocyclyl, and the chiral carbon atom to which $R^1$ is attached is in the S stereochemical configuration, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl; $R^2$ is methyl; $Q^1$ is cyclopropyl; and $Q^2$ is H.

In embodiments, provided herein is a compound of formula (I), or a stereoisomer or tautomer thereof, or a pharmaceutically acceptable salt of any of the foregoing, wherein $X^1$ is H; $R^1$ is selected from the group consisting of tert-butyl, isopropyl, cyclohexyl, tetrahydropyranyl, and piperidinyl, and the chiral carbon atom to which $R^1$ is attached is in the S stereochemical configuration, wherein the cyclohexyl, pyranyl, and piperidinyl of $R^1$ are each independently optionally substituted with one or more $C_{1-12}$alkyl, —$S(O)_2$—$C_{1-12}$alkyl, or —C(O)—$C_{1-12}$alkyl; $R^2$ is H or $C_{1-12}$alkyl; and $Q^1$ and $Q^2$ are, independently of each other and independently at each occurrence, H or $C_{3-15}$cycloalkyl.

In some aspects, provided herein is a compound of formula (I), or a stereoisomer or tautomer thereof, or a pharmaceutically acceptable salt of any of the foregoing, wherein: $X^1$ is, independently at each occurrence, H or —C(O)—$C_{1-12}$alkyl; $R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl; $R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; $Q^1$ is H, halo, cyano, $C_{1-12}$alkyl, $C_{3-5}$cycloalkyl, $C_{6-20}$aryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

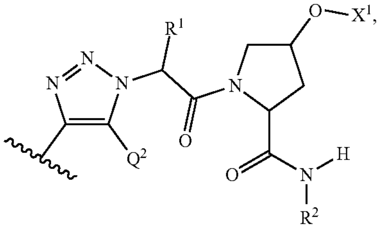

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-5}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

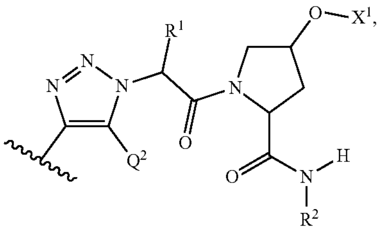

wherein the $C_{1-12}$alkyl of $R^q$ is independently further optionally substituted with one or more halo or —NHC(O)—$C_{1-12}$alkyl, and $Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

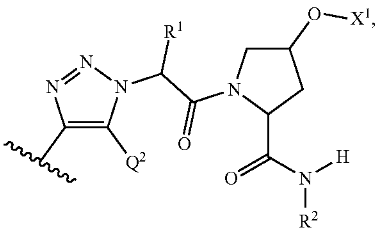

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2$ $C_{1-12}$alkyl, —$SO_2NH_2$, or $C_{1-12}$alkyl, wherein the $C_{1-12}$alkyl of $R^s$ is independently further optionally substituted with one or more halo, cyano, or OH.

In some embodiments of the foregoing, $R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN. In certain embodiments of the foregoing, $Q^1$ is H, halo, cyano, $C_{1-12}$alkyl, $C_{3-5}$cycloalkyl, $C_{6-20}$aryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

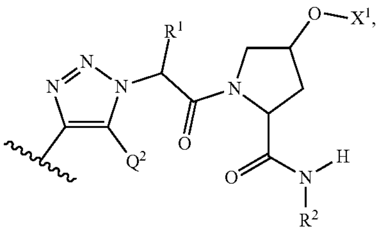

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-5}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

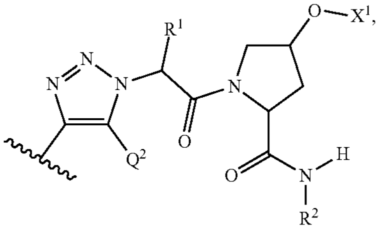

wherein the $C_{1-12}$alkyl of $R^q$ is independently further optionally substituted with one or more halo or —NHC(O)—$C_{1-12}$alkyl, and $Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

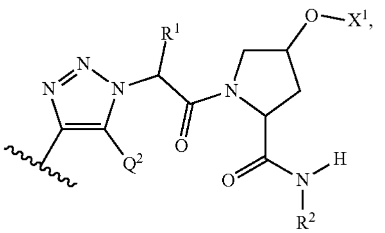

wherein the $C_{1-12}$alkyl or $C_{1-12}$alkoxy of $R^q$ is independently further optionally substituted with one or more halo or —NHC(O)—$C_{1-12}$alkyl.

In some embodiments, provided herein is a compound of formula (I), or a stereoisomer or tautomer thereof, or a pharmaceutically acceptable salt of any of the foregoing, wherein the compound of formula (I) is a compound of formula (ID):

(ID)

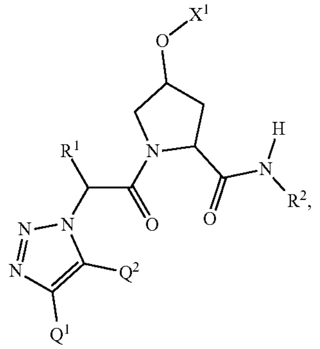

or a stereoisomer or tautomer thereof, or a pharmaceutically acceptable salt of any of the foregoing, wherein: $X^1$ is, independently at each occurrence, H or —C(O)—$C_{1-12}$alkyl; $R^1$ is, independently at each occurrence, $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl; $R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo; $Q^1$ is H, $C_{6-20}$aryl, 5-6 membered heteroaryl, or $C_{3-5}$cycloalkyl, wherein the 5-6 membered heteroaryl of $Q^1$ is independently optionally substituted with one or more $R^q$, wherein each $R^q$ is independently halo; $Q^2$ is, independently at each occurrence, H or $C_{3-5}$cycloalkyl; or $Q^1$ and $Q^2$ are taken, together with the atoms to which they are attached, to form a $C_{6-20}$aryl, wherein the $C_{6-20}$aryl formed by $Q^1$ and $Q^2$ is independently optionally substituted with one or more $R^s$, wherein $R^s$ is, independently at each occurrence, halo or $C_{1-6}$alkoxy; with the proviso that when $Q^1$ is $C_{6-20}$aryl or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —S(O)$_2$—$C_{1-12}$alkyl, or —C(O)—$C_{1-12}$alkyl.

In some embodiments, provided herein is a compound of formula (I), or a stereoisomer or tautomer thereof, or a pharmaceutically acceptable salt of any of the foregoing, wherein the compound of formula (I) is a compound of formula (ID):

(ID)

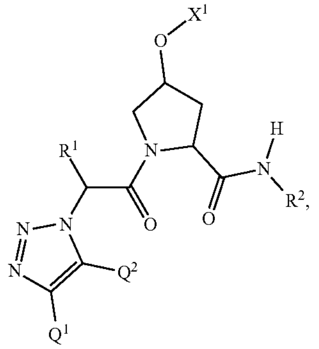

or a stereoisomer or tautomer thereof, or a pharmaceutically acceptable salt of any of the foregoing, wherein: $X^1$ is, independently at each occurrence, H or —C(O)—$C_{1-12}$alkyl; $R^1$ is, independently at each occurrence, $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl; $R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo; $Q^1$ is H or $C_{3-5}$cycloalkyl; and $Q^2$ is, independently at each occurrence, H or $C_{3-5}$cycloalkyl.

In some embodiments, provided herein is a compound of formula (ID), or a stereoisomer or tautomer thereof, or a pharmaceutically acceptable salt of any of the foregoing, wherein $X^1$ is, independently at each occurrence, H.

In some embodiments, provided herein is a compound of formula (ID), or a stereoisomer or tautomer thereof, or a pharmaceutically acceptable salt of any of the foregoing, wherein $X^1$ is H; $R^1$ is, independently at each occurrence, $C_{1-12}$alkyl, $C_{3-15}$cycloalkyl, or 3-15 membered heterocyclyl; $R^2$ is methyl; $Q^1$ is $C_{3-5}$cycloalkyl; and $Q^2$ is H. In some embodiments, provided herein is a compound of formula (ID), or a stereoisomer or tautomer thereof, or a pharmaceutically acceptable salt of any of the foregoing, wherein $X^1$ is H; $R^1$ is, independently at each occurrence, $C_{1-12}$alkyl, $C_{3-15}$cycloalkyl, or 3-15 membered heterocyclyl; $R^2$ is methyl; $Q^1$ is 5-6 membered heteroaryl; and $Q^2$ is H. In some embodiments, provided herein is a compound of formula (ID), or a stereoisomer or tautomer thereof, or a pharmaceutically acceptable salt of any of the foregoing, wherein $X^1$ is H; $R^1$ is isopropyl; $R^2$ is methyl; and $Q^2$ is H.

In some embodiments, provided herein is a compound of formula (ID), or a stereoisomer or tautomer thereof, or a pharmaceutically acceptable salt of any of the foregoing, wherein $R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl; $R^2$ is H or $C_{1-12}$alkyl; $Q^1$ is H or $C_{3-15}$cycloalkyl; and $Q^2$ is H or $C_{3-15}$cycloalkyl. In some embodiments, provided herein is a compound of formula (ID), or a stereoisomer or tautomer thereof, or a pharmaceutically acceptable salt of any of the foregoing, wherein $R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl; $R^2$ is H or methyl; $Q^1$ is H or cyclopropyl; and $Q^2$ is H.

In some embodiments, provided herein is a compound of formula (ID), or a stereoisomer or tautomer thereof, or a pharmaceutically acceptable salt of any of the foregoing, wherein $R^1$ is $C_{1-3}$alkyl, $C_{3-15}$cycloalkyl, or 3-15 membered heterocyclyl, wherein the $C_{1-3}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl; $R^2$ is H or $C_{1-12}$alkyl; $Q^1$ is $C_{6-20}$aryl or 5-6 membered heteroaryl; and $Q^2$ is H or $C_{3-15}$cycloalkyl. In some embodiments, provided herein is a compound of formula (ID), or a stereoisomer or tautomer thereof, or a pharmaceutically acceptable salt of any of the foregoing, wherein $R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl; $R^2$ is H or $C_{1-12}$alkyl; $Q^1$ and $Q^2$ are taken, together with the atoms to which they are attached, to form a $C_{6-20}$aryl.

In some embodiments, provided herein is a compound of formula (I), or a stereoisomer or tautomer thereof, or a pharmaceutically acceptable salt of any of the foregoing, wherein the compound of formula (I) is a compound of formula (IE):

(IE)

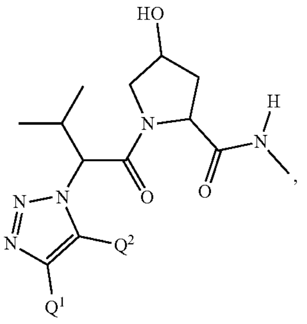

or a stereoisomer or tautomer thereof, or a pharmaceutically acceptable salt of any of the foregoing, wherein: $Q^1$ is H, halo, cyano, $C_{1-12}$alkyl, $C_{3-5}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

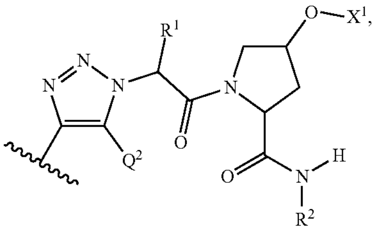

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-5}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

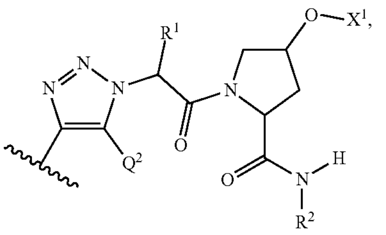

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

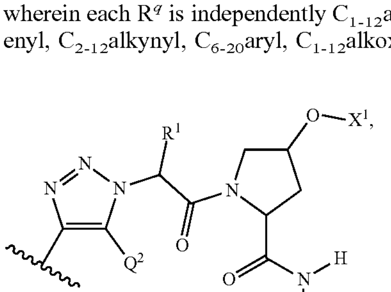

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2$ $C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH.

In some embodiments, provided herein is a compound of formula (IE), or a stereoisomer or tautomer thereof, or a pharmaceutically acceptable salt of any of the foregoing, wherein $Q^1$ is $C_{6-20}$aryl or 5-6 membered heteroaryl; and $Q^2$ is H or $C_{3-5}$cycloalkyl. In some embodiments, provided herein is a compound of formula (IE), or a stereoisomer or tautomer thereof, or a pharmaceutically acceptable salt of any of the foregoing, wherein $Q^1$ is unsubstituted 5-6 membered heteroaryl. In some embodiments, $Q^1$ is 5-6 membered heteroaryl substituted with one or more $R^q$. In some embodiments, each $R^q$ is independently halo (e.g., —Cl or —F). In some embodiments, the 5-6 membered heteroaryl of $Q^1$ has one or more annular N atom. In some embodiments, the 5-6 membered heteroaryl of $Q^1$ has one or more annular S atom. In some embodiments, the 5-6 membered heteroaryl of $Q^1$ has one or more annular O atom. In some embodiments, the 5-6 membered heteroaryl of $Q^1$ is selected form the group consisting of: thiophene, furan, pyrrole, oxazole, thiazole, pyridine, and pyrimidine.

In some embodiments, provided herein is a compound of formula (IE), or a stereoisomer or tautomer thereof, or a pharmaceutically acceptable salt of any of the foregoing, wherein $Q^1$ is unsubstituted $C_{6-20}$aryl. In some embodiments, $Q^1$ is unsubstituted phenyl. In some embodiments, $Q^1$ is $C_{6-20}$aryl (e.g., phenyl) substituted with one or more $R^q$. In some embodiments, each $R^q$ is independently halo (e.g., —Cl or —F).

In some embodiments, provided herein is a compound of formula (I), or a stereoisomer or tautomer thereof, or a pharmaceutically acceptable salt of any of the foregoing, wherein the compound of formula (I) is a compound of formula (IF):

(IF)

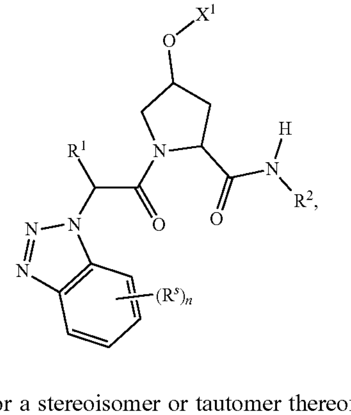

or a stereoisomer or tautomer thereof, or a pharmaceutically acceptable salt of any of the foregoing, wherein:

$X^1$ is H, $C_{1-12}$alkyl, or —C(O)—$C_{1-12}$alkyl;

$R^1$ is $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —S(O)$_2$—$C_{1-12}$alkyl, or —C(O)—$C_{1-12}$alkyl;

$R^2$ is H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN;

$R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH.

In some embodiments, provided herein is a compound of formula (IF), or a stereoisomer or tautomer thereof, or a pharmaceutically acceptable salt of any of the foregoing, wherein $X^1$ is H or $C_{1-12}$alkyl; $R^1$ is $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —S(O)$_2$—$C_{1-12}$alkyl, or —C(O)—$C_{1-12}$alkyl; $R^2$ is H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; $R^s$ is, independently at each occurrence, halogen or $C_{1-6}$alkoxy.

In some embodiments, provided herein is a compound of formula (IF), or a stereoisomer or tautomer thereof, or a pharmaceutically acceptable salt of any of the foregoing, wherein $X^1$ is H; $R^1$ is isopropyl; and $R^2$ is methyl.

In some embodiments, provided herein is a compound of formula (I), or a stereoisomer or tautomer thereof, or a pharmaceutically acceptable salt of any of the foregoing, wherein: $X^1$ is H; $R^1$ is $C_{1-12}$alkyl, $C_{3-15}$cycloalkyl, or 3-15 membered heterocyclyl, wherein the $C_{3-15}$cycloalkyl of $R^1$ is independently optionally substituted with $C_{1-12}$alkyl, or the 3-15 membered heterocyclyl of $R^1$ is independently optionally substituted with $C_{1-12}$alkyl, —S(O)$_2$—$C_{1-12}$alkyl, or —C(O)—$C_{1-12}$alkyl; $R^2$ is H or $C_{1-12}$alkyl, or $C_{3-5}$cycloalkyl, wherein the $C_{1-12}$alkyl or $C_{3-5}$cycloalkyl of $R^2$ are each independently optionally substituted with one or more halo; $Q^1$ is H, $C_{3-5}$cycloalkyl, $C_{6-20}$aryl, or 5-6 membered heteroaryl, wherein the $C_{3-5}$cycloalkyl of $Q^1$ is independently optionally substituted with one or more $R^q$, wherein each $R^q$ is independently $C_{1-12}$alkyl, and wherein the 5-6 membered heteroaryl of $Q^1$ is independently optionally substituted with one or more $R^q$, wherein each $R^q$ is independently halo; and $Q^2$ is H, with the proviso that when $Q^1$ is $C_{6-20}$aryl or 5-6 membered heteroaryl, $R^1$ is $C_{1-3}$alkyl or $C_{3-15}$cycloalkyl; or $Q^1$ and $Q^2$ are taken, together with the atoms to which they are attached, to form a $C_{6-20}$aryl, or 5-20 membered heteroaryl, wherein the 5-20 membered heteroaryl formed by $Q^1$ and $Q^2$ is optionally substituted with one or more $R^s$, wherein $R^s$ is, independently at each occurrence halogen or $C_{1-6}$alkoxy.

In some embodiments, provided herein is a compound of formula (I), or a stereoisomer or tautomer thereof, or a pharmaceutically acceptable salt of any of the foregoing, wherein: $X^1$ is H; $R^1$ is $C_{1-12}$alkyl, $C_{3-15}$cycloalkyl, or 3-15 membered heterocyclyl, wherein the $C_{3-15}$cycloalkyl of $R^1$ is independently optionally substituted with $C_{1-12}$alkyl, or the 3-15 membered heterocyclyl of $R^1$ is independently optionally substituted with $C_{1-12}$alkyl, —S(O)$_2$—$C_{1-12}$alkyl, or —C(O)—$C_{1-12}$alkyl; $R^2$ is methyl; $Q^1$ is $C_{3-5}$cycloalkyl; and $Q^2$ is H.

In some embodiments, provided herein is a compound of formula (I), or a stereoisomer or tautomer thereof, or a pharmaceutically acceptable salt of any of the foregoing, wherein: $X^1$ is H; $R^1$ is $C_{1-12}$alkyl, $C_{3-15}$cycloalkyl, or 3-15 membered heterocyclyl, wherein the $C_{3-15}$cycloalkyl of $R^1$ is independently optionally substituted with $C_{1-12}$alkyl, or the 3-15 membered heterocyclyl of $R^1$ is independently optionally substituted with $C_{1-12}$alkyl, —S(O)$_2$—$C_{1-12}$alkyl, or —C(O)—$C_{1-12}$alkyl; $R^2$ is methyl; $Q^1$ is 5-6 membered heteroaryl, wherein the 5-6 membered heteroaryl of $Q^1$ is optionally substituted with one or more halo; and $Q^2$ is H.

In some embodiments, provided herein is a compound of formula (I), or a stereoisomer or tautomer thereof, or a pharmaceutically acceptable salt of any of the foregoing, wherein: $X^1$ is H; $R^1$ is isopropyl; $R^2$ is methyl; and $Q^1$ and $Q^2$ are taken, together with the atoms to which they are attached, to form a $C_{6-20}$aryl, or 5-20 membered heteroaryl, wherein the 5-20 membered heteroaryl formed by $Q^1$ and $Q^2$ is optionally substituted with one or more $R^s$, wherein $R^s$ is, independently at each occurrence halogen or $C_{1-6}$alkoxy.

In some embodiments, provided herein is a compound of formula (I), or a stereoisomer or tautomer thereof, or a pharmaceutically acceptable salt of any of the foregoing, wherein: $X^1$ is H; $R^2$ is methyl; and $Q^2$ is H.

In some embodiments, provided herein is a compound of formula (I), or a stereoisomer or tautomer thereof, or a pharmaceutically acceptable salt of any of the foregoing, wherein: $X^1$ is H; $R^1$ is isopropyl; $R^2$ is methyl; $Q^1$ is H, $C_{3-5}$cycloalkyl, $C_{6-20}$aryl, or 5-6 membered heteroaryl, wherein the $C_{3-5}$cycloalkyl of $Q^1$ is independently optionally substituted with one or more $R^q$, wherein each $R^q$ is independently $C_{1-12}$alkyl, and wherein the 5-6 membered heteroaryl of $Q^1$ is independently optionally substituted with one or more $R^q$, wherein each $R^q$ is independently halo; and $Q^2$ is H, with the proviso that when $Q^1$ is $C_{6-20}$aryl or 5-6 membered heteroaryl, $R^1$ is $C_{1-3}$alkyl or $C_{3-15}$cycloalkyl; or $Q^1$ and $Q^2$ are taken, together with the atoms to which they are attached, to form a $C_{6-20}$aryl, or 5-20 membered heteroaryl, wherein the 5-20 membered heteroaryl formed by $Q^1$ and $Q^2$ is optionally substituted with one or more $R^s$, wherein $R^s$ is, independently at each occurrence halogen or $C_{1-6}$alkoxy.

In some embodiments, provided herein is a compound of formula (I'), or a pharmaceutically acceptable salt thereof, wherein: $X^1$ is H; $R^1$ is $C_{1-12}$alkyl, $C_{3-15}$cycloalkyl, or 3-15 membered heterocyclyl, wherein the $C_{3-15}$cycloalkyl of $R^1$ is independently optionally substituted with $C_{1-12}$alkyl, or the 3-15 membered heterocyclyl of $R^1$ is independently optionally substituted with $C_{1-12}$alkyl, —S(O)$_2$—$C_{1-12}$alkyl, or —C(O)—$C_{1-12}$alkyl; $R^2$ is H or $C_{1-12}$alkyl, or $C_{3-5}$cycloalkyl, wherein the $C_{1-12}$alkyl or $C_{3-5}$cycloalkyl of $R^2$ are each independently optionally substituted with one or more halo; $Q^1$ is H, $C_{3-5}$cycloalkyl, $C_{6-20}$aryl, or 5-6 membered heteroaryl, wherein the $C_{3-5}$cycloalkyl of $Q^1$ is independently optionally substituted with one or more $R^q$, wherein each $R^q$ is independently $C_{1-12}$alkyl, and wherein the 5-6 membered heteroaryl of $Q^1$ is independently optionally substituted with one or more $R^q$, wherein each $R^q$ is independently halo; and $Q^2$ is H, with the proviso that when $Q^1$ is $C_{6-20}$aryl or 5-6 membered heteroaryl, $R^1$ is $C_{1-3}$alkyl or $C_{3-15}$cycloalkyl; or $Q^1$ and $Q^2$ are taken, together with the atoms to which they are attached, to form a $C_{6-20}$aryl, or 5-20 membered heteroaryl, wherein the 5-20 membered heteroaryl formed by $Q^1$ and $Q^2$ is optionally substituted with one or more $R^s$, wherein $R^s$ is, independently at each occurrence halogen or $C_{1-6}$alkoxy.

In some embodiments, provided herein is a compound of formula (I'), or a pharmaceutically acceptable salt thereof, wherein: $X^1$ is H; $R^1$ is $C_{1-12}$alkyl, $C_{3-15}$cycloalkyl, or 3-15 membered heterocyclyl, wherein the $C_{3-15}$cycloalkyl of $R^1$ is independently optionally substituted with $C_{1-12}$alkyl, or the 3-15 membered heterocyclyl of $R^1$ is independently optionally substituted with $C_{1-12}$alkyl, —$S(O)_2$—$C_{1-12}$alkyl, or —C(O)—$C_{1-12}$alkyl; $R^2$ is methyl; $Q^1$ is $C_{3-5}$cycloalkyl; and $Q^2$ is H.

In some embodiments, provided herein is a compound of formula (I'), or a pharmaceutically acceptable salt thereof, wherein: $X^1$ is H; $R^1$ is $C_{1-12}$alkyl, $C_{3-15}$cycloalkyl, or 3-15 membered heterocyclyl, wherein the $C_{3-15}$cycloalkyl of $R^1$ is independently optionally substituted with $C_{1-12}$alkyl, or the 3-15 membered heterocyclyl of $R^1$ is independently optionally substituted with $C_{1-12}$alkyl, —$S(O)_2$—$C_{1-12}$alkyl, or —C(O)—$C_{1-12}$alkyl; $R^2$ is methyl; $Q^1$ is 5-6 membered heteroaryl, wherein the 5-6 membered heteroaryl of $Q^1$ is optionally substituted with one or more halo; and $Q^2$ is H.

In some embodiments, provided herein is a compound of formula (I'), or a pharmaceutically acceptable salt thereof, wherein: $X^1$ is H; $R^1$ is isopropyl; $R^2$ is methyl; and $Q^1$ and $Q^2$ are taken, together with the atoms to which they are attached, to form a $C_{6-20}$aryl, or 5-20 membered heteroaryl, wherein the 5-20 membered heteroaryl formed by $Q^1$ and $Q^2$ is optionally substituted with one or more $R^s$, wherein $R^s$ is, independently at each occurrence halogen or $C_{1-6}$alkoxy.

In some embodiments, provided herein is a compound of formula (I'), or a pharmaceutically acceptable salt thereof, wherein: $X^1$ is H; $R^2$ is methyl; and $Q^2$ is H.

In some embodiments, provided herein is a compound of formula (I'), or a pharmaceutically acceptable salt thereof, wherein: $X^1$ is H; $R^1$ is isopropyl; $R^2$ is methyl; $Q^1$ is H, $C_{3-5}$cycloalkyl, $C_{6-20}$aryl, or 5-6 membered heteroaryl, wherein the $C_{3-5}$cycloalkyl of $Q^1$ is independently optionally substituted with one or more $R^q$, wherein each $R^q$ is independently $C_{1-12}$alkyl, and wherein the 5-6 membered heteroaryl of $Q^1$ is independently optionally substituted with one or more $R^q$, wherein each $R^q$ is independently halo; and $Q^2$ is H, with the proviso that when $Q^1$ is $C_{6-20}$aryl or 5-6 membered heteroaryl, $R^1$ is $C_{1-3}$alkyl or $C_{3-15}$cycloalkyl; or $Q^1$ and $Q^2$ are taken, together with the atoms to which they are attached, to form a $C_{6-20}$aryl, or 5-20 membered heteroaryl, wherein the 5-20 membered heteroaryl formed by $Q^1$ and $Q^2$ is optionally substituted with one or more $R^s$, wherein $R^s$ is, independently at each occurrence halogen or $C_{1-6}$alkoxy.

It is to be understood that any variation or embodiment of $X^1$, $R^1$, $R^2$, $Q^1$, $Q^2$, $R^a$, $R^b$, $R^c$, $R^q$, and $R^s$ provided herein can be combined with every other variation or embodiment of $X^1$, $R^1$, $R^2$, $Q^1$, $Q^2$, $R^a$, $R^b$, $R^c$, $R^q$, and $R^s$, the same as if each and every combination had been individually and specifically described.

In some embodiments, provided herein is a compound of formula (I), such as a compound of formula (IA), (IB), (IC), or (ID), or a stereoisomer or tautomer thereof, or a pharmaceutically acceptable salt of any of the foregoing, wherein the compound has a molecular weight up to about 500 Da. In some embodiments, the compound has a molecular weight of no more than 500 Da. In some embodiments, the compound has a molecular weight between about 100 Da and about 500 Da, between about 200 Da and about 500 Da, between about 300 Da and about 500 Da, or between about 400 Da and about 500 Da. In some embodiments, the compound has a molecular weight of up to about 450 Da. In some embodiments, the compound has a molecular weight of no more than 450 Da. In some embodiments, the compound has a molecular weight between about 300 Da and about 450 Da. In some embodiments, the compound has a molecular weight of up to about 400 Da. In some embodiments, the compound has a molecular weight of no more than 400 Da. In some embodiments, the compound has a molecular weight between about 100 Da and about 400 Da, between about 200 Da and about 400 Da, or between about 300 Da and about 400 Da. In some embodiments, the compound has a molecular weight between about 300 Da and about 400 Da. In some embodiments, reference to the molecule weight of a compound herein refers to the molecular weight of the free base form of the compound. It is understood that the embodiments provided in this paragraph apply in some embodiments to a compound of formula (I), such as a compound of formula (IA), (IB), (IC), (ID), (IE), or (IF) or a stereoisomer or tautomer thereof, or a pharmaceutically acceptable salt of any of the foregoing.

In some embodiments, provided herein is a compound of formula (I), such as a compound of formula (IA), (IB), (IC), or (ID), or a stereoisomer or tautomer thereof, or a pharmaceutically acceptable salt of any of the foregoing, wherein the compound has five or fewer hydrogen bond donors (HBDs). In some embodiments, the compound has four or fewer HBDs. In some embodiments, the compound has three or fewer HBDs. In some embodiments, the compound has two or fewer HBDs. In some embodiments, provided herein is a compound of formula (I), such as a compound of formula (IA), (IB), (IC), (ID), (IE), or (IF) or a stereoisomer or tautomer thereof, or a pharmaceutically acceptable salt of any of the foregoing, wherein the compound has five or fewer (e.g., four, three, two) hydrogen bond donors (HBDs).

In some embodiments, provided herein is a compound of formula (I), such as a compound of formula (IA), (IB), (IC), or (ID), or a stereoisomer or tautomer thereof, or a pharmaceutically acceptable salt of any of the foregoing, wherein the compound has a molecular weight of up to about 500 Da and has three or fewer HBDs. In some embodiments, the compound has a molecular weight of up to about 400 Da and has two or fewer HBDs. In some embodiments, the compound has a molecular weight between about 300 Da and about 400 Da and has two or fewer HBDs. It is understood that the embodiments provided in this paragraph apply in some embodiments to a compound of formula (I), such as a compound of formula (IA), (IB), (IC), (ID), (IE), or (IF) or a stereoisomer or tautomer thereof, or a pharmaceutically acceptable salt of any of the foregoing.

In embodiments, provided herein is a compound of formula (I), such as a compound of formula (IA), (IB), (IC), (ID), (IE) or (IF), or a stereoisomer or tautomer thereof, or a pharmaceutically acceptable salt of any of the foregoing, wherein the compound is selected from the compounds in Table 1.

TABLE 1

| Compound Number | Compound Structure | Compound Name |
|---|---|---|
| 1 | 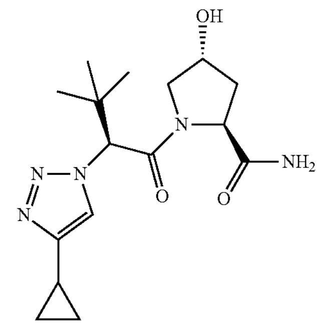 [SMILES: CC(C)(C)[C@@H](C(=O)N1C[C@H](O)C[C@H]1C(N)=O)n1cc(C2CC2)nn1] | (2S,4R)-1-((S)-2-(4-cyclopropyl-1H-1,2,3-triazol-1-yl)-3,3-dimethylbutanoyl)-4-hydroxypyrrolidine-2-carboxamide |
| 2 | 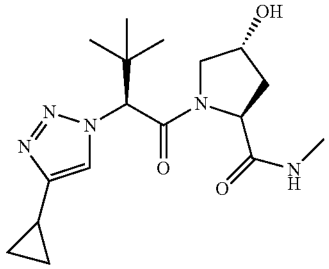 [SMILES: CNC(=O)[C@@H]1C[C@@H](O)CN1C(=O)[C@@H](n1cc(C2CC2)nn1)C(C)(C)C] | (2S,4R)-1-((S)-2-(4-cyclopropyl-1H-1,2,3-triazol-1-yl)-3,3-dimethylbutanoyl)-4-hydroxy-N-methylpyrrolidine-2-carboxamide |
| 3 | 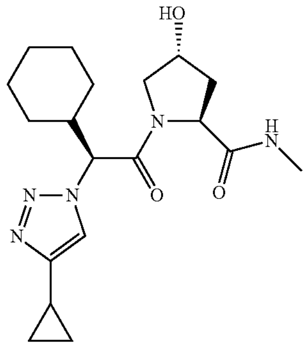 [SMILES: CNC(=O)[C@@H]1C[C@@H](O)CN1C(=O)[C@H](C1CCCCC1)n1cc(C2CC2)nn1] | (2S,4R)-1-((S)-2-cyclohexyl-2-(4-cyclopropyl-1H-1,2,3-triazol-1-yl)acetyl)-4-hydroxy-N-methylpyrrolidine-2-carboxamide |
| 4 | 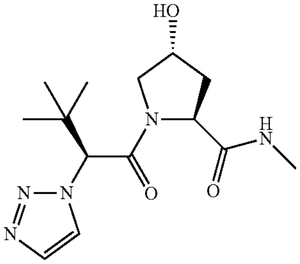 [SMILES: CNC(=O)[C@@H]1C[C@@H](O)CN1C(=O)[C@@H](n1ccnn1)C(C)(C)C] | (2S,4R)-1-((S)-3,3-dimethyl-2-(1H-1,2,3-triazol-1-yl)butanoyl)-4-hydroxy-N-methylpyrrolidine-2-carboxamide |

TABLE 1-continued

| Compound Number | Compound Structure | Compound Name |
|---|---|---|
| 5 | 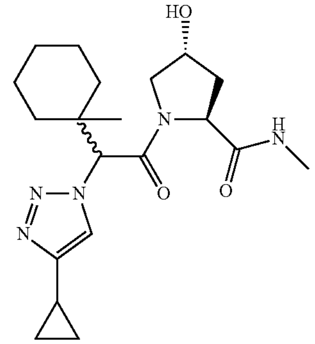 [SMILES: CNC(=O)[C@@H]1C[C@@H](O)CN1C(=O)C(n1cc(C2CC2)nn1)C1(C)CCCCC1] | (2S,4R)-1-(2-(4-cyclopropyl-1H-1,2,3-triazol-1-yl)-2-(1-methylcyclohexyl)acetyl)-4-hydroxy-N-methylpyrrolidine-2-carboxamide |
| 6 | 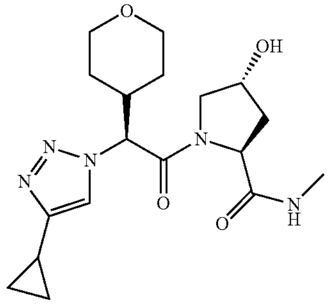 [SMILES: CNC(=O)[C@@H]1C[C@@H](O)CN1C(=O)[C@H](C1CCOCC1)n1cc(C2CC2)nn1] | (2S,4R)-1-((S)-2-(4-cyclopropyl-1H-1,2,3-triazol-1-yl)-2-(tetrahydro-2H-pyran-4-yl)acetyl)-4-hydroxy-N-methylpyrrolidine-2-carboxamide |
| 7 | 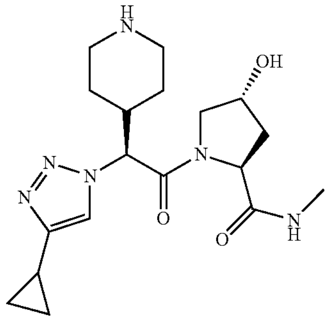 [SMILES: CNC(=O)[C@@H]1C[C@@H](O)CN1C(=O)[C@H](C1CCNCC1)n1cc(C2CC2)nn1] | (2S,4R)-1-((S)-2-(4-cyclopropyl-1H-1,2,3-triazol-1-yl)-2-(piperidin-4-yl)acetyl)-4-hydroxy-N-methylpyrrolidine-2-carboxamide |
| 8 | 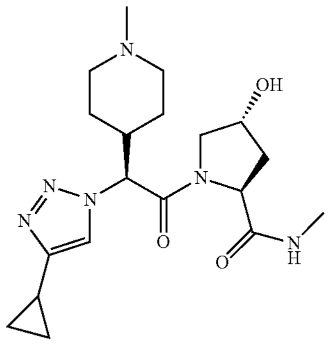 [SMILES: CNC(=O)[C@@H]1C[C@@H](O)CN1C(=O)[C@H](C1CCN(C)CC1)n1cc(C2CC2)nn1] | (2S,4R)-1-((S)-2-(4-cyclopropyl-1H-1,2,3-triazol-1-yl)-2-(1-methylpiperidin-4-yl)acetyl)-4-hydroxy-N-methylpyrrolidine-2-carboxamide |

TABLE 1-continued

| Compound Number | Compound Structure | Compound Name |
| --- | --- | --- |
| 9 | 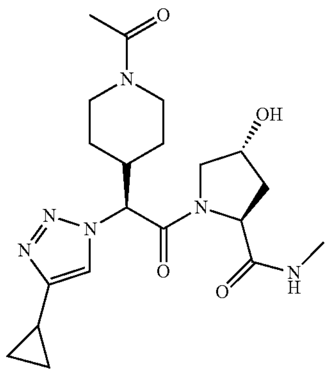 [SMILES: CNC(=O)[C@@H]1C[C@@H](O)CN1C(=O)[C@H](C1CCN(C(C)=O)CC1)n1cc(C2CC2)nn1] | (2S,4R)-1-((S)-2-(1-acetylpiperidin-4-yl)-2-(4-cyclopropyl-1H-1,2,3-triazol-1-yl)acetyl)-4-hydroxy-N-methylpyrrolidine-2-carboxamide |
| 10 | 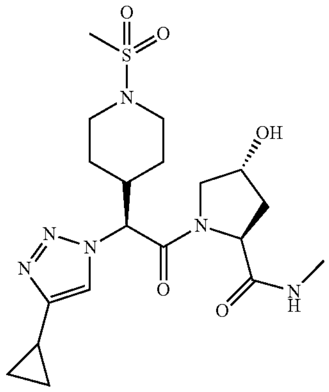 [SMILES: CNC(=O)[C@@H]1C[C@@H](O)CN1C(=O)[C@H](C1CCN(S(C)(=O)=O)CC1)n1cc(C2CC2)nn1] | (2S,4R)-1-((S)-2-(4-cyclopropyl-1H-1,2,3-triazol-1-yl)-2-(1-(methylsulfonyl)piperidin-4-yl)acetyl)-4-hydroxy-N-methylpyrrolidine-2-carboxamide |
| 11 | 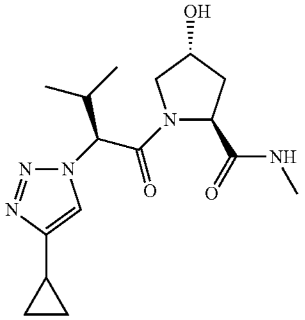 [SMILES: CNC(=O)[C@@H]1C[C@@H](O)CN1C(=O)[C@H](C(C)C)n1cc(C2CC2)nn1] | (2S,4R)-1-((S)-2-(4-cyclopropyl-1H-1,2,3-triazol-1-yl)-3-methylbutanoyl)-4-hydroxy-N-methylpyrrolidine-2-carboxamide |
| 12 | 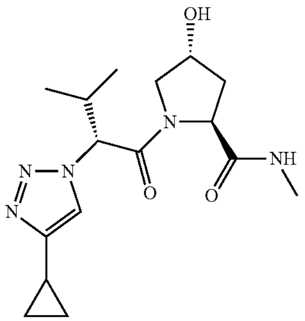 [SMILES: CNC(=O)[C@@H]1C[C@@H](O)CN1C(=O)[C@@H](C(C)C)n1cc(C2CC2)nn1] | (2S,4R)-1-((R)-2-(4-cyclopropyl-1H-1,2,3-triazol-1-yl)-3-methylbutanoyl)-4-hydroxy-N-methylpyrrolidine-2-carboxamide |

TABLE 1-continued

| Compound Number | Compound Structure | Compound Name |
| --- | --- | --- |
| 13 | 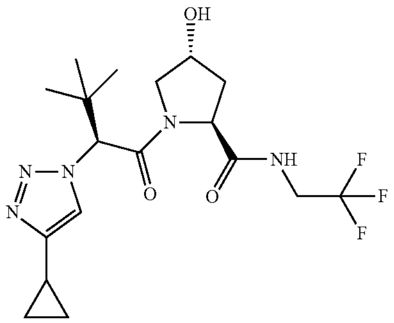 [SMILES: CC(C)(C)[C@@H](C(=O)N1C[C@H](O)C[C@H]1C(=O)NCC(F)(F)F)n1cc(C2CC2)nn1] | (2S,4R)-1-((S)-2-(4-cyclopropyl-1H-1,2,3-triazol-1-yl)-3,3-dimethylbutanoyl)-4-hydroxy-N-(2,2,2-trifluoroethyl)pyrrolidine-2-carboxamide |
| 14 | 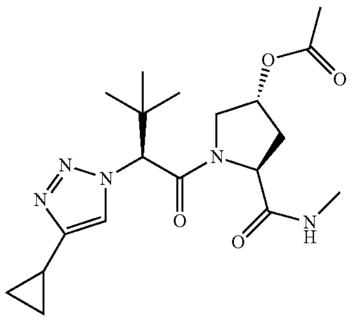 [SMILES: CNC(=O)[C@@H]1C[C@@H](OC(C)=O)CN1C(=O)[C@@H](n1cc(C2CC2)nn1)C(C)(C)C] | (3R,5S)-1-((S)-2-(4-cyclopropyl-1H-1,2,3-triazol-1-yl)-3,3-dimethylbutanoyl)-5-(methylcarbamoyl)pyrrolidin-3-yl acetate |
| 15 | 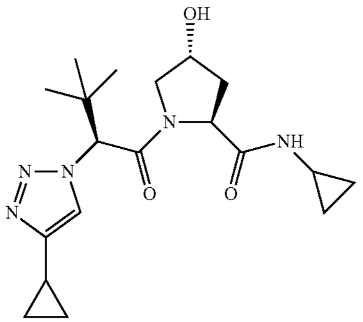 [SMILES: CC(C)(C)[C@@H](C(=O)N1C[C@H](O)C[C@H]1C(=O)NC1CC1)n1cc(C2CC2)nn1] | (2S,4R)-N-cyclopropyl-1-((S)-2-(4-cyclopropyl-1H-1,2,3-triazol-1-yl)-3,3-dimethylbutanoyl)-4-hydroxypyrrolidine-2-carboxamide |
| 16 | 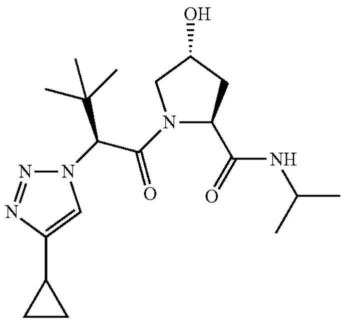 [SMILES: CC(C)NC(=O)[C@@H]1C[C@@H](O)CN1C(=O)[C@@H](n1cc(C2CC2)nn1)C(C)(C)C] | (2S,4R)-1-((S)-2-(4-cyclopropyl-1H-1,2,3-triazol-1-yl)-3,3-dimethylbutanoyl)-4-hydroxy-N-isopropylpyrrolidine-2-carboxamide |

TABLE 1-continued

| Compound Number | Compound Structure | Compound Name |
| --- | --- | --- |
| 17 | 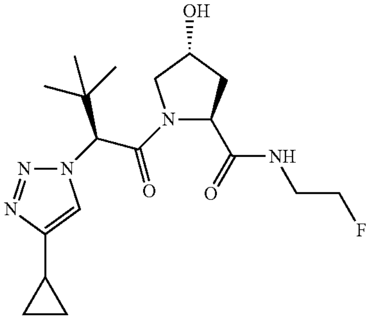 [SMILES: CC(C)(C)[C@@H](C(=O)N1C[C@H](O)C[C@H]1C(=O)NCCF)n1cc(C2CC2)nn1] | (2S,4R)-1-((S)-2-(4-cyclopropyl-1H-1,2,3-triazol-1-yl)-3,3-dimethylbutanoyl)-N-(2-fluoroethyl)-4-hydroxypyrrolidine-2-carboxamide |
| 18 | 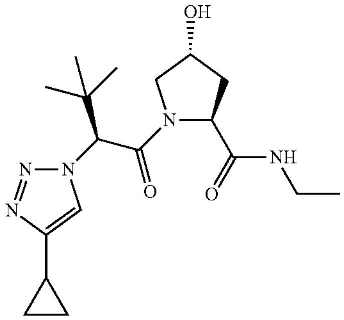 [SMILES: CCNC(=O)[C@@H]1C[C@@H](O)CN1C(=O)[C@@H](n1cc(C2CC2)nn1)C(C)(C)C] | (2S,4R)-1-((S)-2-(4-cyclopropyl-1H-1,2,3-triazol-1-yl)-3,3-dimethylbutanoyl)-N-ethyl-4-hydroxypyrrolidine-2-carboxamide |
| 20 | 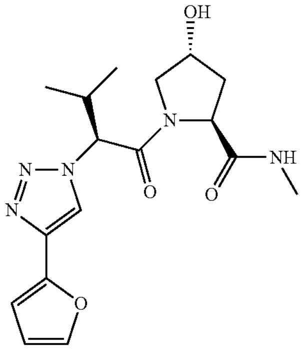 [SMILES: CNC(=O)[C@@H]1C[C@@H](O)CN1C(=O)[C@H](C(C)C)n1cc(-c2ccco2)nn1] | (2S,4R)-1-((S)-2-(4-(furan-2-yl)-1H-1,2,3-triazol-1-yl)-3-methylbutanoyl)-4-hydroxy-N-methylpyrrolidine-2-carboxamide |
| 21 | 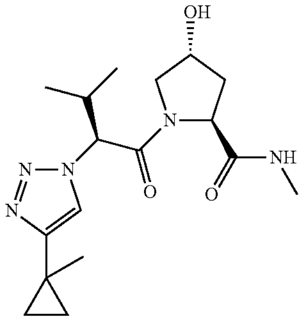 [SMILES: CNC(=O)[C@@H]1C[C@@H](O)CN1C(=O)[C@H](C(C)C)n1cc(C2(C)CC2)nn1] | (2S,4R)-4-hydroxy-N-methyl-1-((S)-3-methyl-2-(4-(1-methylcyclopropyl)-1H-1,2,3-triazol-1-yl)butanoyl)pyrrolidine-2-carboxamide |

TABLE 1-continued

| Compound Number | Compound Structure | Compound Name |
|---|---|---|
| 22 | 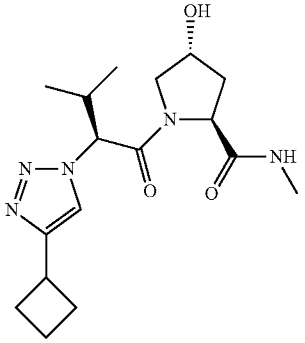 [SMILES: CNC(=O)[C@@H]1C[C@@H](O)CN1C(=O)[C@H](C(C)C)n1cc(C2CCC2)nn1] | (2S,4R)-1-((S)-2-(4-cyclobutyl-1H-1,2,3-triazol-1-yl)-3-methylbutanoyl)-4-hydroxy-N-methylpyrrolidine-2-carboxamide |
| 23 | 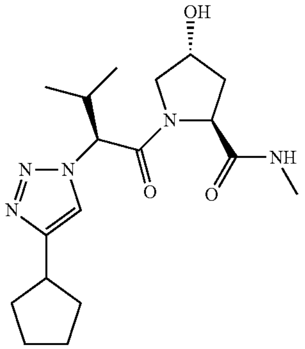 [SMILES: CNC(=O)[C@@H]1C[C@@H](O)CN1C(=O)[C@H](C(C)C)n1cc(C2CCCC2)nn1] | (2S,4R)-1-[(2S)-2-(4-cyclopentyltriazol-1-yl)-3-methyl-butanoyl]-4-hydroxy-N-methyl-pyrrolidine-2-carboxamide |
| 24 | 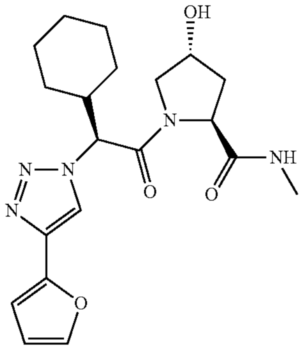 [SMILES: CNC(=O)[C@@H]1C[C@@H](O)CN1C(=O)[C@H](C1CCCCC1)n1cc(-c2ccco2)nn1] | (2S,4R)-1-((S)-2-cyclohexyl-2-(4-(furan-2-yl)-1H-1,2,3-triazol-1-yl)acetyl)-4-hydroxy-N-methylpyrrolidine-2-carboxamide |
| 26 | 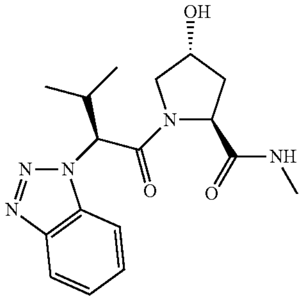 [SMILES: CNC(=O)[C@@H]1C[C@@H](O)CN1C(=O)[C@H](C(C)C)n1nnc2ccccc21] | (2S,4R)-1-((S)-2-(1H-benzo[d][1,2,3]triazol-1-yl)-3-methylbutanoyl)-4-hydroxy-N-methylpyrrolidine-2-carboxamide |

TABLE 1-continued

| Compound Number | Compound Structure | Compound Name |
|---|---|---|
| 28 | 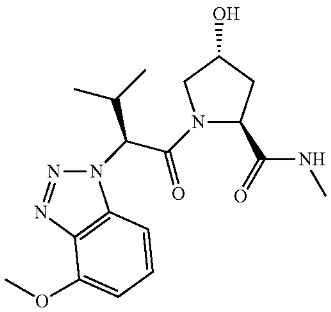 | (2S,4R)-4-hydroxy-1-((S)-2-(4-methoxy-1H-benzo[d][1,2,3]triazol-1-yl)-3-methylbutanoyl)-N-methylpyrrolidine-2-carboxamide |
| 30 | 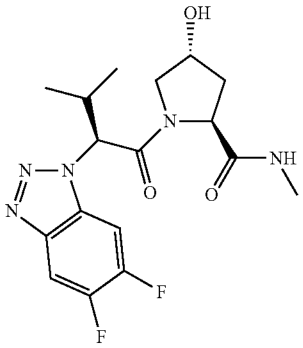 [SMILES: CNC(=O)[C@@H]1C[C@@H](O)CN1C(=O)[C@H](C(C)C)n1nnc2cc(F)c(F)cc21] | (2S,4R)-1-((S)-2-(5,6-difluoro-1H-benzo[d][1,2,3]triazol-1-yl)-3-methylbutanoyl)-4-hydroxy-N-methylpyrrolidine-2-carboxamide |
| 33 | 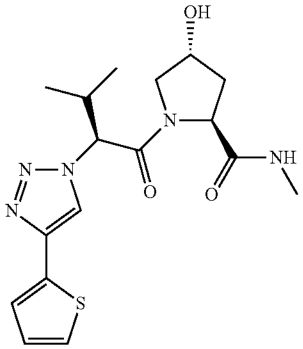 [SMILES: CNC(=O)[C@@H]1C[C@@H](O)CN1C(=O)[C@H](C(C)C)n1cc(-c2cccs2)nn1] | (2S,4R)-4-hydroxy-N-methyl-1-((S)-3-methyl-2-(4-(thiophen-2-yl)-1H-1,2,3-triazol-1-yl)butanoyl)pyrrolidine-2-carboxamide |
| 34 | 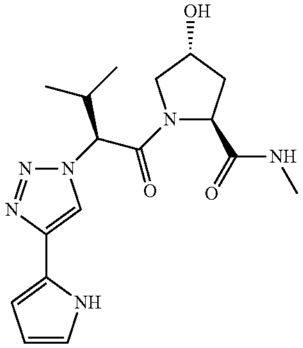 [SMILES: CNC(=O)[C@@H]1C[C@@H](O)CN1C(=O)[C@H](C(C)C)n1cc(-c2ccc[nH]2)nn1] | (2S,4R)-4-hydroxy-N-methyl-1-[rac-(2S)-3-methyl-2-[4-(1H-pyrrol-2-yl)triazol-1-yl]butanoyl]pyrrolidine-2-carboxamide |

TABLE 1-continued

| Compound Number | Compound Structure | Compound Name |
|---|---|---|
| 36 | 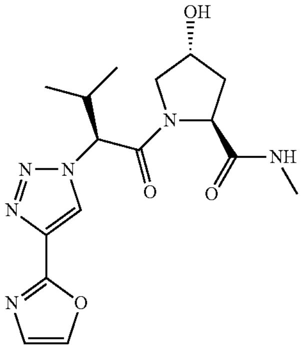 [SMILES: CNC(=O)[C@@H]1C[C@@H](O)CN1C(=O)[C@H](C(C)C)n1cc(-c2ncco2)nn1] | (2S,4R)-4-hydroxy-N-methyl-1-((S)-3-methyl-2-(4-(oxazol-2-yl)-1H-1,2,3-triazol-1-yl)butanoyl)pyrrolidine-2-carboxamide |
| 38 | 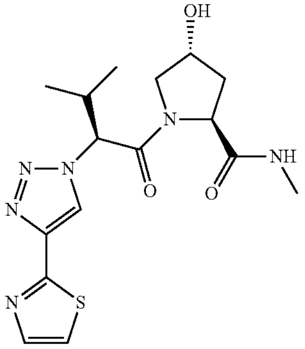 [SMILES: CNC(=O)[C@@H]1C[C@@H](O)CN1C(=O)[C@H](C(C)C)n1cc(-c2nccs2)nn1] | (2S,4R)-4-hydroxy-N-methyl-1-[rac-(2S)-3-methyl-2-(4-thiazol-2-yltriazol-1-yl)butanoyl]pyrrolidine-2-carboxamide |
| 40 | 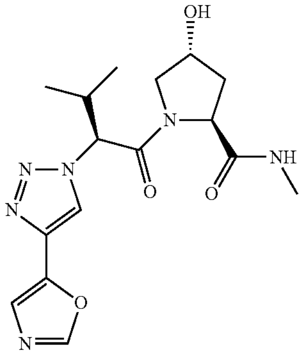 [SMILES: CNC(=O)[C@@H]1C[C@@H](O)CN1C(=O)[C@H](C(C)C)n1cc(-c2cnco2)nn1] | (2S,4R)-4-hydroxy-N-methyl-1-[(2S)-3-methyl-2-(4-oxazol-5-yltriazol-1-yl)butanoyl]pyrrolidine-2-carboxamide |
| 41 | 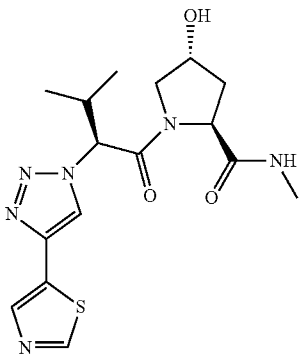 [SMILES: CNC(=O)[C@@H]1C[C@@H](O)CN1C(=O)[C@H](C(C)C)n1cc(-c2cncs2)nn1] | (2S,4R)-4-hydroxy-N-methyl-1-((S)-3-methyl-2-(4-(thiazol-5-yl)-1H-1,2,3-triazol-1-yl)butanoyl)pyrrolidine-2-carboxamide |

TABLE 1-continued

| Compound Number | Compound Structure | Compound Name |
|---|---|---|
| 43 | 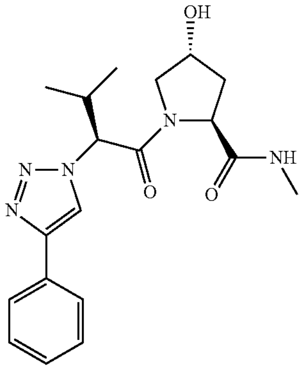 [SMILES: CNC(=O)[C@@H]1C[C@@H](O)CN1C(=O)[C@H](C(C)C)n1cc(-c2ccccc2)nn1] | (2S,4R)-4-hydroxy-N-methyl-1-((S)-3-methyl-2-(4-phenyl-1H-1,2,3-triazol-1-yl)butanoyl)pyrrolidine-2-carboxamide |
| 44 | 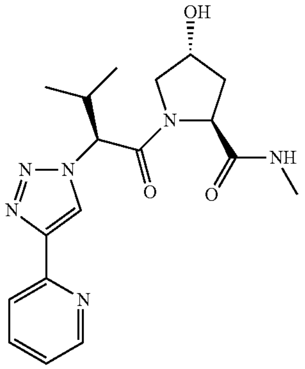 [SMILES: CNC(=O)[C@@H]1C[C@@H](O)CN1C(=O)[C@H](C(C)C)n1cc(-c2ccccn2)nn1] | (2S,4R)-4-hydroxy-N-methyl-1-((S)-3-methyl-2-(4-(pyridin-2-yl)-1H-1,2,3-triazol-1-yl)butanoyl)pyrrolidine-2-carboxamide |
| 45 | 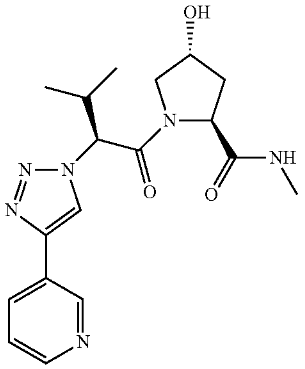 [SMILES: CNC(=O)[C@@H]1C[C@@H](O)CN1C(=O)[C@H](C(C)C)n1cc(-c2cccnc2)nn1] | (2S,4R)-4-hydroxy-N-methyl-1-((S)-3-methyl-2-(4-(pyridin-3-yl)-1H-1,2,3-triazol-1-yl)butanoyl)pyrrolidine-2-carboxamide |
| 46 | 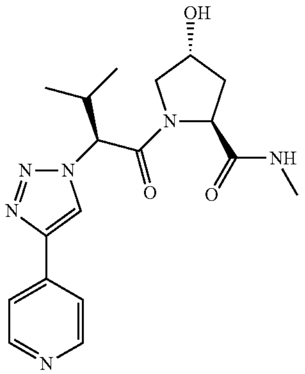 [SMILES: CNC(=O)[C@@H]1C[C@@H](O)CN1C(=O)[C@H](C(C)C)n1cc(-c2ccncc2)nn1] | (2S,4R)-4-hydroxy-N-methyl-1-((S)-3-methyl-2-(4-(pyridin-4-yl)-1H-1,2,3-triazol-1-yl)butanoyl)pyrrolidine-2-carboxamide |

TABLE 1-continued
| Compound Number | Compound Structure | Compound Name |
|---|---|---|
| 47 | 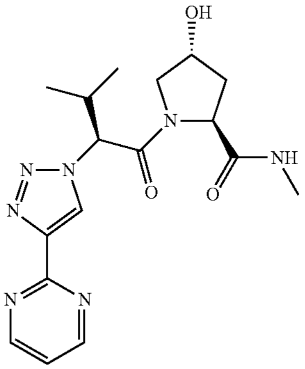 [SMILES: CNC(=O)[C@@H]1C[C@@H](O)CN1C(=O)[C@H](C(C)C)n1cc(-c2ncccn2)nn1] | (2S,4R)-4-hydroxy-N-methyl-1-((S)-3-methyl-2-(4-(pyrimidin-2-yl)-1H-1,2,3-triazol-1-yl)butanoyl)pyrrolidine-2-carboxamide |
| 48 | 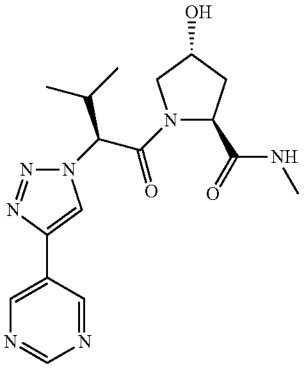 [SMILES: CNC(=O)[C@@H]1C[C@@H](O)CN1C(=O)[C@H](C(C)C)n1cc(-c2cncnc2)nn1] | (2S,4R)-4-hydroxy-N-methyl-1-((S)-3-methyl-2-(4-(pyrimidin-5-yl)-1H-1,2,3-triazol-1-yl)butanoyl)pyrrolidine-2-carboxamide |
| 49 | 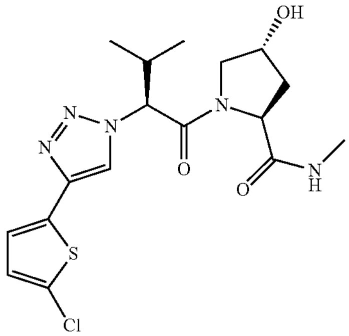 [SMILES: CNC(=O)[C@@H]1C[C@@H](O)CN1C(=O)[C@H](C(C)C)n1cc(-c2ccc(Cl)s2)nn1] | (2S,4R)-1-((S)-2-(4-(5-chlorothiophen-2-yl)-1H-1,2,3-triazol-1-yl)-3-methylbutanoyl)-4-hydroxy-N-methylpyrrolidine-2-carboxamide |

In one embodiment, provided herein is a compound of formula (I), or a stereoisomer or tautomer thereof, or a pharmaceutically acceptable salt of any of the foregoing, wherein the compound is selected from the group consisting of
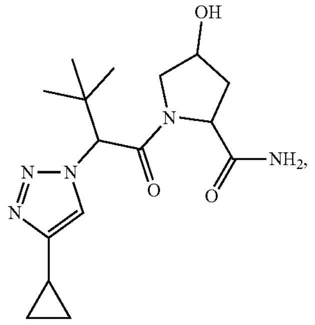
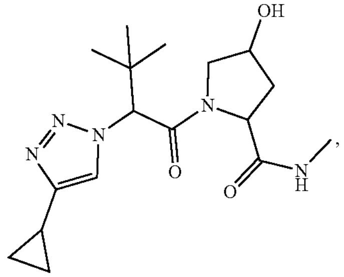
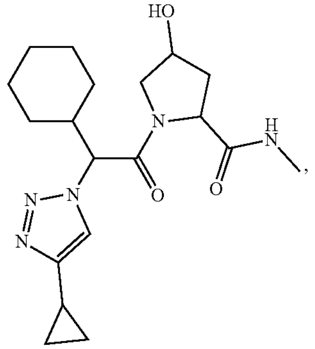
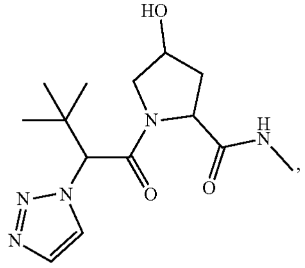
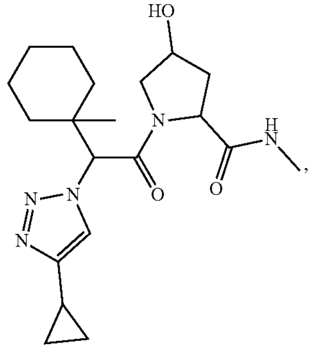
-continued
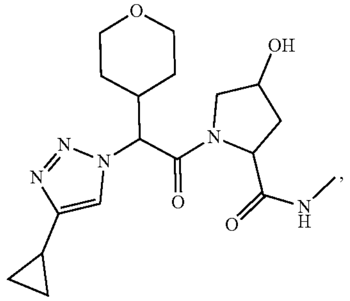
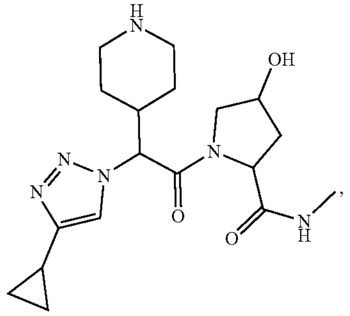
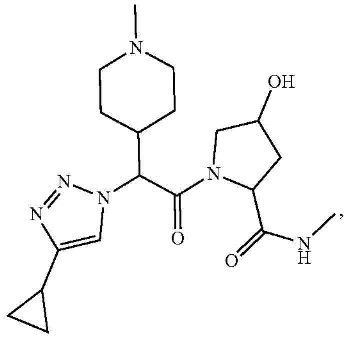
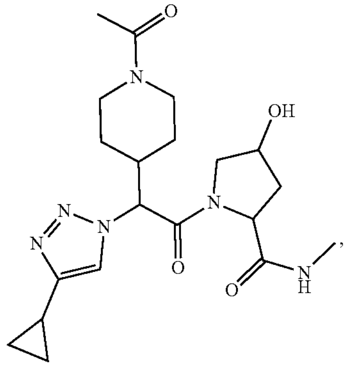
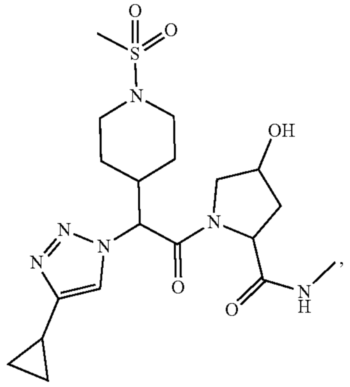

-continued
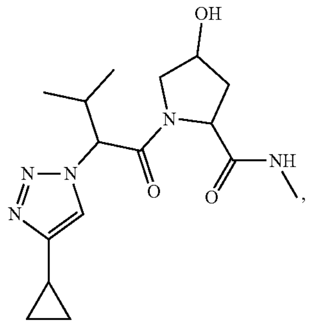
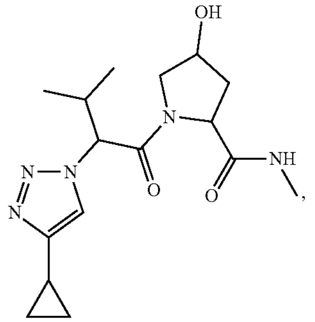
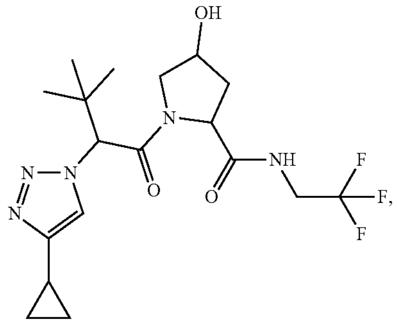
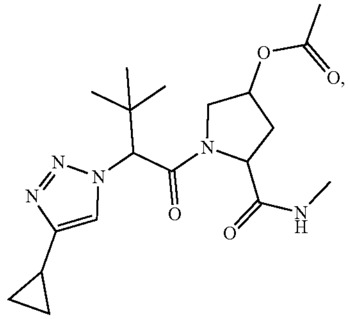
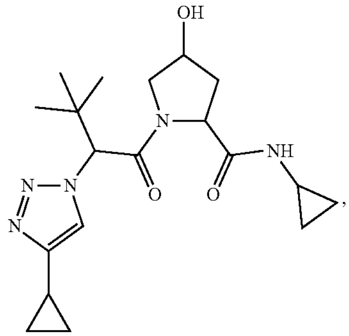
-continued
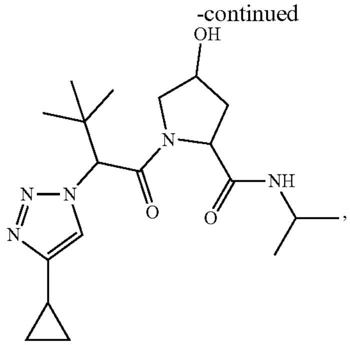
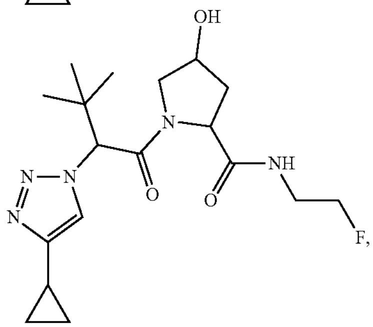
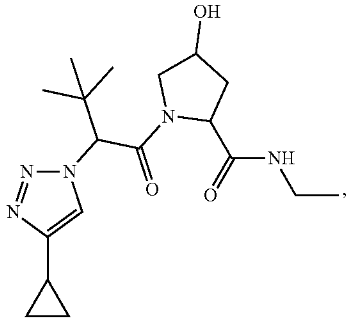
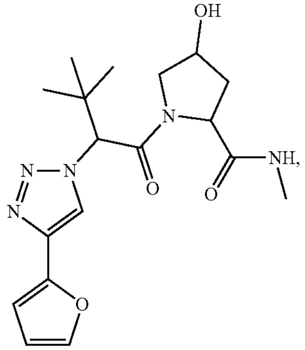
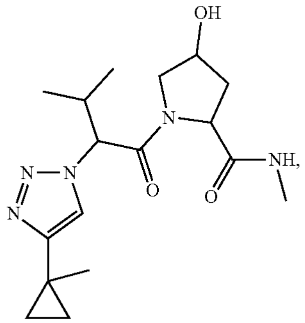

-continued
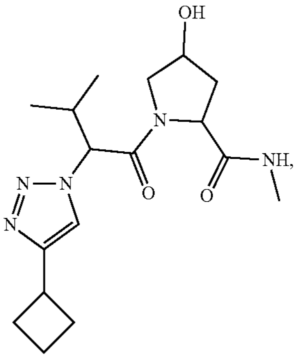
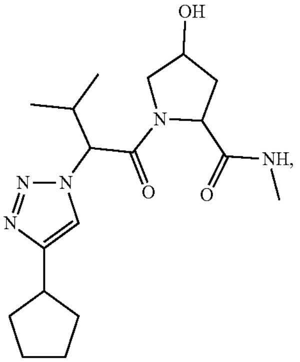
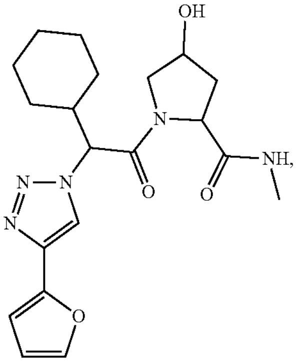
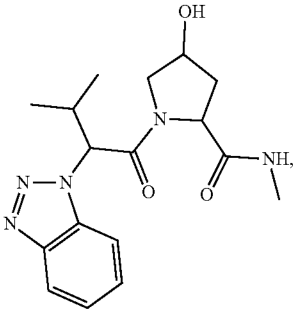
-continued
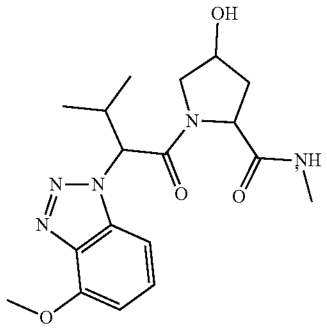
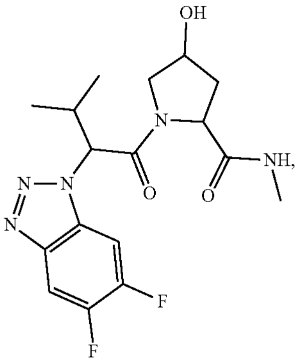
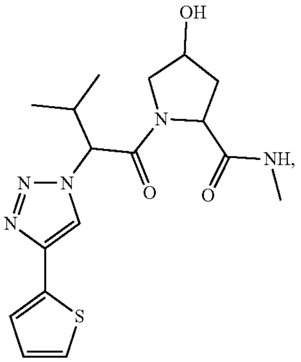
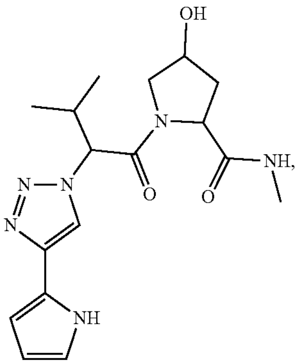

-continued
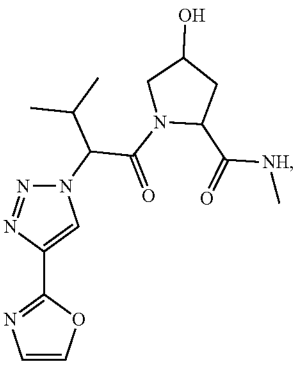
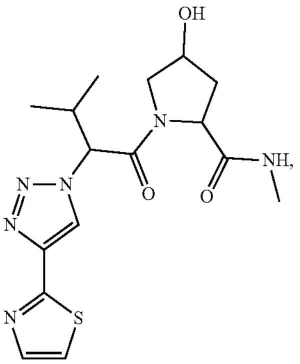
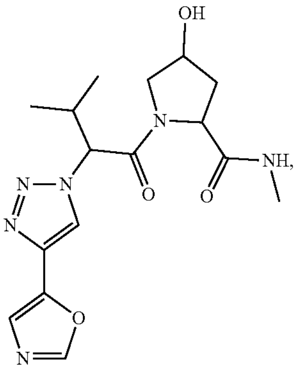
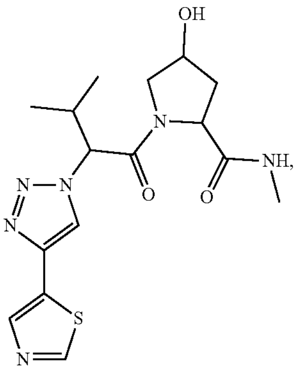
-continued
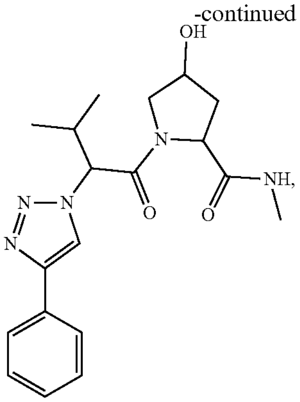
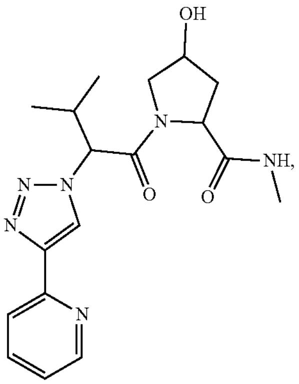
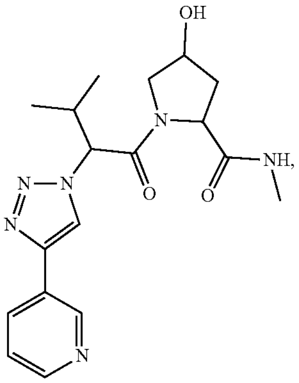
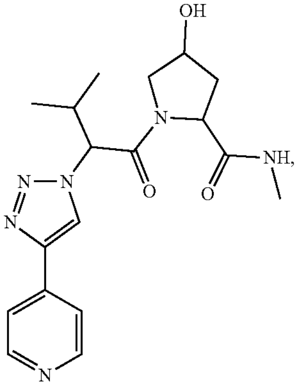

-continued

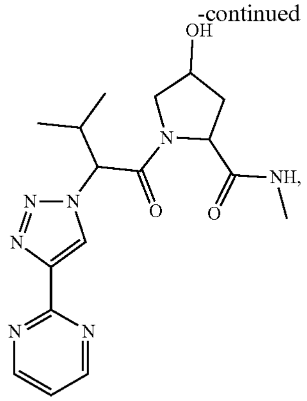

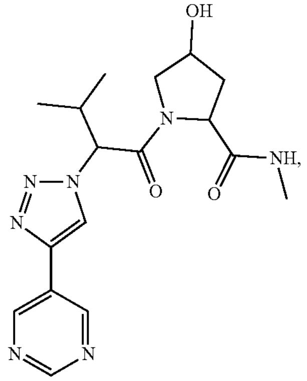

and

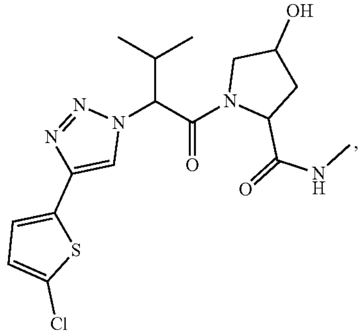 [SMILES: CNC(=O)C1CC(O)CN1C(=O)C(C(C)C)n1cc(-c2ccc(Cl)s2)nn1]

, or a stereoisomer or tautomer thereof, or a pharmaceutically acceptable salt of any of the foregoing.

In one embodiment, provided herein is a compound of formula (I), or a stereoisomer or tautomer thereof, or a pharmaceutically acceptable salt of any of the foregoing, wherein the compound is selected from the group consisting of:

1-(2-(4-cyclopropyl-1H-1,2,3-triazol-1-yl)-3,3-dimethylbutanoyl)-4-hydroxypyrrolidine-2-carboxamide;
1-(2-(4-cyclopropyl-1H-1,2,3-triazol-1-yl)-3,3-dimethylbutanoyl)-4-hydroxy-N-methylpyrrolidine-2-carboxamide;
1-(2-cyclohexyl-2-(4-cyclopropyl-1H-1,2,3-triazol-1-yl) acetyl)-4-hydroxy-N-methylpyrrolidine-2-carboxamide;
1-(3,3-dimethyl-2-(1H-1,2,3-triazol-1-yl)butanoyl)-4-hydroxy-N-methylpyrrolidine-2-carboxamide;
1-(2-(4-cyclopropyl-1H-1,2,3-triazol-1-yl)-2-(1-methylcyclohexyl)acetyl)-4-hydroxy-N-methylpyrrolidine-2-carboxamide;
1-(2-(4-cyclopropyl-1H-1,2,3-triazol-1-yl)-2-(tetrahydro-2H-pyran-4-yl)acetyl)-4-hydroxy-N-methylpyrrolidine-2-carboxamide;
1-(2-(4-cyclopropyl-1H-1,2,3-triazol-1-yl)-2-(piperidin-4-yl)acetyl)-4-hydroxy-N-methylpyrrolidine-2-carboxamide;
1-(2-(4-cyclopropyl-1H-1,2,3-triazol-1-yl)-2-(1-methylpiperidin-4-yl)acetyl)-4-hydroxy-N-methylpyrrolidine-2-carboxamide;
1-(2-(1-acetylpiperidin-4-yl)-2-(4-cyclopropyl-1H-1,2,3-triazol-1-yl)acetyl)-4-hydroxy-N-methylpyrrolidine-2-carboxamide;
1-(2-(4-cyclopropyl-1H-1,2,3-triazol-1-yl)-2-(1-(methylsulfonyl)piperidin-4-yl)acetyl)-4-hydroxy-N-methylpyrrolidine-2-carboxamide;
1-(2-(4-cyclopropyl-1H-1,2,3-triazol-1-yl)-3-methylbutanoyl)-4-hydroxy-N-methylpyrrolidine-2-carboxamide;
1-(2-(4-cyclopropyl-1H-1,2,3-triazol-1-yl)-3,3-dimethylbutanoyl)-4-hydroxy-N-(2,2,2-trifluoroethyl)pyrrolidine-2-carboxamide;
1-(2-(4-cyclopropyl-1H-1,2,3-triazol-1-yl)-3,3-dimethylbutanoyl)-5-(methylcarbamoyl)pyrrolidin-3-yl acetate;
N-cyclopropyl-1-(2-(4-cyclopropyl-1H-1,2,3-triazol-1-yl)-3,3-dimethylbutanoyl)-4-hydroxypyrrolidine-2-carboxamide;
1-(2-(4-cyclopropyl-1H-1,2,3-triazol-1-yl)-3,3-dimethylbutanoyl)-4-hydroxy-N-isopropylpyrrolidine-2-carboxamide;
1-(2-(4-cyclopropyl-1H-1,2,3-triazol-1-yl)-3,3-dimethylbutanoyl)-N-(2-fluoroethyl)-4-hydroxypyrrolidine-2-carboxamide;
1-(2-(4-cyclopropyl-1H-1,2,3-triazol-1-yl)-3,3-dimethylbutanoyl)-N-ethyl-4-hydroxypyrrolidine-2-carboxamide;
1-(2-(4-(furan-2-yl)-1H-1,2,3-triazol-1-yl)-3-methylbutanoyl)-4-hydroxy-N-methylpyrrolidine-2-carboxamide;
4-hydroxy-N-methyl-1-(3-methyl-2-(4-(1-methylcyclopropyl)-1H-1,2,3-triazol-1-yl)butanoyl)pyrrolidine-2-carboxamide;
1-(2-(4-cyclobutyl-1H-1,2,3-triazol-1-yl)-3-methylbutanoyl)-4-hydroxy-N-methylpyrrolidine-2-carboxamide;
1-[2-(4-cyclopentyltriazol-1-yl)-3-methyl-butanoyl]-4-hydroxy-N-methyl-pyrrolidine-2-carboxamide;
1-(2-cyclohexyl-2-(4-(furan-2-yl)-1H-1,2,3-triazol-1-yl) acetyl)-4-hydroxy-N-methylpyrrolidine-2-carboxamide;
1-(2-(1H-benzo[d] [1,2,3]triazol-1-yl)-3-methylbutanoyl)-4-hydroxy-N-methylpyrrolidine-2-carboxamide;
4-hydroxy-1-(2-(4-methoxy-1H-benzol[d][1,2,3]triazol-1-yl)-3-methylbutanoyl)-N-methylpyrrolidine-2-carboxamide;
1-((5,6-difluoro-1H-benzo[d] [1,2,3]triazol-1-yl)-3-methylbutanoyl)-4-hydroxy-N-methylpyrrolidine-2-carboxamide;
4-hydroxy-N-methyl-1-(3-methyl-2-(4-(thiophen-2-yl)-1H-1,2,3-triazol-1-yl)butanoyl)pyrrolidine-2-carboxamide;
4-hydroxy-N-methyl-1-[3-methyl-2-[4-(1H-pyrrol-2-yl)triazol-1-yl]butanoyl]pyrrolidine-2-carboxamide;
4-hydroxy-N-methyl-1-(3-methyl-2-(4-(oxazol-2-yl)-1H-1,2,3-triazol-1-yl)butanoyl)pyrrolidine-2-carboxamide;
4-hydroxy-N-methyl-1-[3-methyl-2-(4-thiazol-2-yltriazol-1-yl)butanoyl]pyrrolidine-2-carboxamide;
4-hydroxy-N-methyl-1-[3-methyl-2-(4-oxazol-5-yltriazol-1-yl)butanoyl]pyrrolidine-2-carboxamide;
4-hydroxy-N-methyl-1-(3-methyl-2-(4-(thiazol-5-yl)-1H-1,2,3-triazol-1-yl)butanoyl)pyrrolidine-2-carboxamide;
4-hydroxy-N-methyl-1-(3-methyl-2-(4-phenyl-1H-1,2,3-triazol-1-yl)butanoyl)pyrrolidine-2-carboxamide;
4-hydroxy-N-methyl-1-(3-methyl-2-(4-(pyridin-2-yl)-1H-1,2,3-triazol-1-yl)butanoyl)pyrrolidine-2-carboxamide;
4-hydroxy-N-methyl-1-(3-methyl-2-(4-(pyridin-3-yl)-1H-1,2,3-triazol-1-yl)butanoyl)pyrrolidine-2-carboxamide;
4-hydroxy-N-methyl-1-(3-methyl-2-(4-(pyridin-4-yl)-1H-1,2,3-triazol-1-yl)butanoyl)pyrrolidine-2-carboxamide;

4-hydroxy-N-methyl-1-(3-methyl-2-(4-(pyrimidin-2-yl)-1H-1,2,3-triazol-1-yl)butanoyl)pyrrolidine-2-carboxamide;

4-hydroxy-N-methyl-1-(3-methyl-2-(4-(pyrimidin-5-yl)-1H-1,2,3-triazol-1-yl)butanoyl)pyrrolidine-2-carboxamide; and 1-(2-(4-(5-chlorothiophen-2-yl)-1H-1,2,3-triazol-1-yl)-3-methylbutanoyl)-4-hydroxy-N-methylpyrrolidine-2-carboxamide;

or a stereoisomer or tautomer thereof, or a pharmaceutically acceptable salt of any of the foregoing.

The Compound Names included in Table 1 and in the list in the paragraph above were generated using ChemDraw® software version 18.2.0.48.

A VHL ligand, as described herein, can exist in solid or liquid form. In the solid state, the ligand may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes such solvates.

The skilled artisan will further appreciate that certain VHL ligands described herein that exist in crystalline form, including the various solvates thereof, may exhibit polymorphism (i.e. the capacity to occur in different crystalline structures). These different crystalline forms are typically known as "polymorphs." The subject matter disclosed herein includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

VHL ligands described herein, or a pharmaceutically acceptable salt thereof, may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of formula (I) may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/diastereomerically enriched mixtures. It is to be understood that the subject matter disclosed herein includes combinations and subsets of the particular groups defined hereinabove.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

VHL ligands as disclosed herein, and pharmaceutically acceptable salts thereof, that contain the aforementioned isotopes and/or other isotopes of other atoms are within the scope of the subject matter disclosed herein. Isotopically-labelled compounds are disclosed herein, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are commonly used for their ease of preparation and detectability. $^{11}C$ and $^{18}F$ isotopes are useful in PET (positron emission tomography), and $^{125}I$ isotopes are useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I can generally be prepared by carrying out the procedures disclosed in the Schemes and/or in the Examples below, by substituting a readily available isotopically labelled reagent for a non-isotopically labelled reagent.

In some embodiments, a VHL ligand provided herein is integrated into a heterobifunctional molecule. In some embodiments, the heterobifunctional molecule is a chemical inducer of degradation (CIDE) having (i) a VHL ligand, as provided herein, and (ii) a moiety that is capable of binding to a protein of interest that is targeted for degradation, wherein (i) and (ii) are covalently linked. In some embodiments, (i) and (ii) are covalently linked through a linker moiety, such as a polyethylene glycol (PEG) chain or an alkyl chain. In some embodiments, the CIDE is capable of selectively degrading a target protein by forming a ternary complex between the target protein, the heterobifunctional molecule described herein, and a ubiquitin ligase. In some embodiments, the ubiquitin ligase is a VHL E3 ubiquitin ligase. By way of illustration, and not limitation, the target protein may be, for example, a structural protein, an enzyme, a receptor, or a cell surface protein.

In some embodiments, the heterobifunctional molecule is a compound of formula (II):

[A]-[B]—[C] (II), wherein [A] is a moiety of a VHL ligand provided herein, [B] is a linker moiety, and [C] is a protein-binding moiety.

III. FORMULATIONS

In an additional aspect, the description provides therapeutic or pharmaceutical compositions comprising an effective amount of at least one of the compounds as described herein, including, e.g., at least one VHL ligand. Pharmaceutical compositions comprising an effective amount of at least one VHL ligand of the present disclosure, and optionally one or more of the compounds otherwise described herein, in effective amounts, in combination with a pharmaceutically effective amount of a carrier, additive, or excipient, and optionally an additional bioactive agent, represents a further aspect of the disclosure.

In certain embodiments, the compositions comprise pharmaceutically acceptable salts, in particular, acid or base addition salts of compounds as described herein. The acids that are used to prepare the pharmaceutically acceptable acid addition salts of the aforementioned base compounds include those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compositions as described herein may in certain embodiments be administered in single or divided unit doses by the oral, parenteral or topical routes. Administration of the compounds may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, by inhalation spray, rectally, vaginally, or via an implanted reservoir, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound according to the present disclosure, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but may also be administered in suppository and transdermal or other topical forms. Intramuscular injections in liposomal form may also be used to control or sustain the release of compound at an injection site.

Thus in one aspect, pharmaceutical formulations of VHL ligands, as described herein, can be prepared for parenteral administration with a pharmaceutically acceptable parenteral vehicle and in a unit dosage injectable form. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. A VHL ligand having the desired degree of purity is optionally mixed with one or more pharmaceutically acceptable excipients (Remington's Pharmaceutical Sciences (1980) 16th edition, Osol, A. Ed.), in the form of a lyophilized formulation for reconstitution or an aqueous solution.

The compositions of the present disclosure may be formulated in a conventional manner using one or more pharmaceutically acceptable carriers and may also be administered in controlled-release formulations. The compounds of the disclosure can be formulated in accordance with standard pharmaceutical practice as a pharmaceutical composition. According to this aspect, there is provided a pharmaceutical composition comprising a VHL ligand, as described herein, in association with one or more pharmaceutically acceptable excipients.

A typical formulation is prepared by mixing the compounds of the disclosure with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the compound is being applied. Other pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine;

monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations may also include one or more buffers, stabilizing agents, surfactants, wetting agents, lubricating agents, emulsifiers, suspending agents, preservatives, anti-oxidants, opaquing agents, glidants, processing aids, colorants, sweeteners, perfuming agents, flavoring agents and other known additives to provide an elegant presentation of the VHL ligand or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The pharmaceutical compositions may be in the form of a sterile injectable preparation, such as a sterile injectable aqueous or oleaginous suspension. In particular, formulations to be used for in vivo administration must be sterile. Such sterilization is readily accomplished by filtration through sterile filtration membranes. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables, as well as natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The VHL ligand compositions ordinarily can be stored as a solid composition, a lyophilized formulation or as an aqueous solution.

The pharmaceutical compositions comprising a VHL ligand of the present disclosure can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host or renders the host significantly more susceptible to unwanted side effects.

The VHL ligand can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present disclosure can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythropoiesis stimulating agents as otherwise identified herein.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for the herein-mentioned conditions is in the range from about 10 ng/kg to 300 mg/kg, preferably 0.1 to 100 mg/kg per day, more generally 0.5 to about 25 mg per kilogram body weight of the recipient/patient per day. One typical daily dosage might range from about 1 μg/kg to 100 mg/kg or more, depending on the factors mentioned above. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 mM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

IV. INDICATIONS AND METHODS OF TREATMENT

It is contemplated that the VHL ligands disclosed herein may be used to treat various diseases, disorders, or conditions. Thus, it is understood that any one of the compounds provided herein may find use in the treatment of a disease or condition modulated by VHL such as any of the diseases and conditions listed herein. It is also understood that any of the compounds provided herein may find use in the preparation of a medicament for treatment of a condition modulated by VHL such as any of the diseases and conditions listed herein.

It is contemplated that the compounds disclosed herein may be used in therapy. It is further contemplated that the compounds disclosed herein may be used to treat a disease or indication associated with VHL activity, such as the diseases and indications in Zhang et al., *J. Med. Chem.* 219, 62, 5725-5749, which is incorporated herein by reference in its entirety and specifically with respect to the indications and diseases disclosed therein (including conditions associated with anemia, ischemia and tumors). Thus, it is understood that any one of the compounds provided herein may find use in the treatment of a condition modulated by VHL. In some embodiments, the VHL ligands disclosed herein may be used to treat a cancer implicated by VHL modulation. In some embodiments, the VHL ligands disclosed herein may be used to treat a solid tumor. In some embodiments, the solid tumor is breast cancer (such as triple-negative breast cancer), lung cancer, multiple myeloma or renal cell carcinoma (RCC).

In alternative aspects, the present invention relates to a method for enhancing erythropoiesis in a patient or subject in need, the method comprising administering to said patient or subject an effective amount of at least one compound as described hereinabove, optionally in combination with an additional erythropoiesis stimulating compound. The method according to the present invention may be used to increase the number of red blood cells (erythrocytes) and/or the hematocrit of the patient by virtue of the administration of effective amounts of at least one compound described herein. Additional method aspects of the present invention relate to treating anemia, including chronic anemia or ischemia in a patient or subject in need, the method comprising administering to a patient in need an effective amount of at least one compound according to the present invention. The methods according to the present invention may be used to treat anemia, including chronic anemia such as anemia associate with chronic kidney disease, dialysis and chemotherapy and ischemia, including local ischemia, stroke and cardiovascular ischemia and limit the damage which occurs as a consequence of those disease states and/or conditions.

Additional method aspects of the present invention relate to enhancing wound healing and reducing scar tissue formation during wound healing by administering one or more compounds according to the present invention to a patient in need. Further methods include inducing local angiogenesis in a patient or subject in need by administering an effective amount of at least one compound of the present invention, optionally in combination with an additional erythropoiesis stimulating compound. Methods of stimulating erythropoiesis in a subject or patient, including increasing the number of red blood cells and/or hematocrit of the patient, treating anemia, including chronic anemia and anemia associated with chronic kidney disease, dialysis, and cancer chemotherapy, ischemia, stroke and damage to cardiovascular tissue during cardiovascular ischemia as well as enhancing wound healing processes and preventing/reducing scarring associated with or secondary to the healing process represent additional aspects of the present invention.

Other methods of the present invention relate to the local enhancement of angiogenesis through the induction of VEGF in a patient or subject using at least one compound according to the present invention, optionally in combination with an erythropoiesis stimulating compound as otherwise described herein. An additional method of the present invention relates to the reduction and/or inhibition of occlusion in a surgically implanted stent in a patient or subject.

The compounds described herein may be administered to a patient to treat a number of diseases, disorders, or conditions. In some embodiments, administration of a compound, as described herein, provides stimulation of erythropoiesis in a patient or subject, including inducement of EPO production in the patient or subject. In other embodiments, administration of a compound, as described herein, is provided for the treatment of chronic anemia and ischemia (which limits brain injury during episodes of localized anemia, ischemia and/or stroke and damage to cardiovascular tissue during cardiovascular ischemia), as well as enhancing wound healing processes. Methods of stimulating erythropoiesis in a subject or patient, including increasing the number of red blood cells and/or hematocrit of the patient, treating anemia, including chronic anemia and anemia associated with chronic kidney disease, dialysis, and cancer chemotherapy, ischemia, stroke and damage to cardiovascular tissue during cardiovascular ischemia as well as enhancing wound healing processes and preventing/reducing scarring secondary to healing represent additional treatment aspects of the present invention. Local enhancement of angiogenesis through induction of VEGF including wound healing and reduction of stent occlusion remain additional aspects of the present invention.

Also provided herein is the use of a compound as described herein in the manufacture of a medicament for use in the treatment of a number of diseases, disorders, and conditions. In one embodiments, provided herein is the use of a compound as described herein in the manufacture of a medicament for use in the treatment of anemia. In some embodiments, the anemia is chronic anemia or anemia associated with chronic kidney disease, dialysis, or cancer chemotherapy, or any combination thereof. In other embodiments, provided herein is the use of a compound as described herein in the manufacture of a medicament for use in the treatment of ischemia, stroke, or damage to the cardiovascular system during ischemia, or any combination thereof. In some embodiments, provided herein is the use of a compound as described herein in the manufacture of a medicament for use in the enhancement of wound healing in a human in need thereof. In other embodiments, provided herein is the use of a compound as described herein in the manufacture of a medicament for use in the reduction of scarring secondary to wound healing in a human in need thereof. In some embodiments, provided herein is the use of a compound as described herein in the manufacture of a medicament for use in the enhancement of angiogenesis or arteriogenesis, or both, in a human in need thereof. In certain embodiments, the enhancement of angiogenesis or arteriogenesis, or both, occurs locally in the human. In some embodiments, provided herein is the use of a compound as described herein in the manufacture of a medicament for use in reducing the likelihood of stent occlusion in a human in need thereof.

Also provided herein is a compound, as described elsewhere herein, for use in the treatment of anemia. In some embodiments, the anemia is chronic anemia or anemia associated with chronic kidney disease, dialysis, or cancer chemotherapy, or any combination thereof. In other embodiments, provided herein is a compound, as described elsewhere herein, for use in the treatment of ischemia, stroke, or damage to the cardiovascular system during ischemia, or any combination thereof. In some embodiments, provided herein is a compound, as described elsewhere herein, for use in the enhancement of wound healing in a human in need thereof. In other embodiments, provided herein is a compound, as described elsewhere herein, for use in the reduction of scarring secondary to wound healing in a human in need thereof. In some embodiments, provided herein is a compound, as described elsewhere herein, for use in the enhancement of angiogenesis or arteriogenesis, or both, in a human in need thereof. In some embodiments, the enhancement of the angiogenesis or arteriogenesis, or both, occurs locally in the human. In some embodiments, provided herein is a compound, as described elsewhere herein, for use in reducing the likelihood of stent occlusion in a human in need thereof.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the present compounds described above, are coadministered in combination with at least one additional bioactive agent having erythropoiesis stimulating activity as otherwise described herein in order to enhance erythropoiesis, treat chronic anemia and ischemia (limit brain injury during episodes of localized anemia, ischemia and/or stroke and damage to cardiovascular tissue during cardiovascular ischemia), as well as enhancing wound healing processes and stimulating angiogenesis and inhibiting or preventing occlusion in a surgically implanted stent. In particularly preferred aspects of the invention, the co-administration of compounds results in synergistic erythropoietic activity and/or therapy.

The term "additional erythropoiesis stimulating agent" shall mean a traditional polypeptide such as EPO (procrit or epogen) or darbapoietin alfa (a synthetic form of erythropoietin).

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylenepolyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1, 3-butanediol.

Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present invention or erythropoiesis stimulating agent (EPO, darbapoietin alfa) in order to inter alia enhance erythropoiesis, treat chronic anemia and ischemia (limits brain injury during episodes of localized anemia, ischemia and/or stroke and damage to cardiovascular tissue during cardiovascular ischemia), as well as enhancing wound healing processes. and stimulating angiogenesis and inhibiting or preventing occlusion in a surgically implanted stent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present invention can be treated by administering to the patient (subject) an effective amount of the compound according to the present invention including pharmaceutically acceptable salts, solvates or polymorphs, thereof optionally in a pharmaceutically acceptable carrier or diluent, either alone, or in combination with other known erythropoiesis stimulating agents as otherwise identified herein. These compounds can be administered by any appropriate route, for example, orally, parenterally, intravenously, intradermally, subcutaneously, or topically, including transdermally, in liquid, cream, gel, or solid form, or by aerosol form. The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier. The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

The active ingredient may be administered at once, or may be divided into a number of smaller doses to be administered at varying intervals of time. Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors. The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the invention, one or more compounds according to the present invention are coadministered with another bioactive agent, such as an erythropoietin stimulating agent or a wound healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers are physiological saline or phosphate buffered saline (PBS). In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

V. ARTICLES OF MANUFACTURE

In another aspect, described herein are articles of manufacture, for example, a "kit", containing materials useful for the treatment of the diseases and disorders described above is provided. The kit comprises a container comprising a VHL ligand. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

Suitable containers include, for example, bottles, vials, syringes, blister pack, etc. A "vial" is a container suitable for holding a liquid or lyophilized preparation. In one embodiment, the vial is a single-use vial, e.g. a 20-cc single-use vial with a stopper. The container may be formed from a variety of materials such as glass or plastic. The container may hold a VHL ligand or a formulation thereof which is effective for treating the condition and may have a sterile access port (for example, the container may be an intravenous solution bag or a vial having a stopper pierceable by a hypodermic injection needle).

At least one active agent in the composition is a VHL ligand of the present disclosure. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a VHL ligand can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the VHL ligand and, if present, the second pharmaceutical formulation. For example, if the kit comprises a first composition comprising a VHL ligand, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a VHL ligand, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a VHL ligand contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments, wherein the kit comprises a VHL ligand and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

VI. EXAMPLES

The following synthetic reaction schemes detailed in the General Schemes and Examples are merely illustrative of some of the methods by which the compounds of the present disclosure (or an embodiment or aspect thereof) can be synthesized. Various modifications to these synthetic reaction schemes can be made and will be suggested to one skilled in the art having referred to the disclosure contained in this Application.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15*; Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C.

Although certain exemplary embodiments are depicted and described herein, the compounds of the present disclosure (or an embodiment or aspect thereof) can be prepared using appropriate starting materials according to the methods described generally herein and/or by methods available to one of ordinary skill in the art.

All reactions involving air-sensitive reagents were performed under an inert atmosphere. Reagents were used as received from commercial suppliers unless otherwise noted.

Abbreviations

The following abbreviations are used in the examples:

ABPR—automated back pressure regulator
$Ac_2O$—acetic anhydride
ACN—acetonitrile
Boc—tert-butyloxycarbonyl
Cbz—carboxybenzyl
$CD_3OD$—Deuterated methanol
$CDCl_3$—Deuterochloroform
CV—Column volume
$Cy_3PHBF_4$— Tricyclohexylphosphine tetrafluoroborate
DBU—1,8-Diazabicyclo[5.4.0]undec-7-ene
DCM—dichloromethane
DEA—diethanolamine
DIPEA or DIEA—N,N-diisopropylethylamine
DME—dimethoxyethane
DMF—dimethylformamide
DMEM—Dulbecco's Modified Eagle's medium
DMSO—dimethyl sulfoxide
DMSO-d6—Deuterated dimethyl sulfoxide
DTT—dithiothreitol
EDCI—N-(3-Dimethylaminopropyl)-N'-ethylcarbodiimide hydrochloride
EDTA—ethylenediaminetetraacetic acid
ESI—electrospray ionization
ESI-MS—Electrospray ionization mass spectrometry
EtOAc—ethyl acetate
EtOH—ethanol
FA—formic acid
Fmoc—Fluorenylmethyloxycarbonyl
HATU—1-[Bis(dimethylamino)methylene]-1H-1,2,3-triazolo[4,5-b]pyridinium 3-oxide hexafluorophosphate
HEPES—4-(2-Hydroxyethyl)piperazine-1-ethanesulfonic acid
Hex—hexane
HOAc—acetic acid
HOBt or HOBT—hydroxybenzotriazole
HPLC—high performance liquid chromatography
hr—hour
KOH—Potassium hydroxide
LC/MS or LCMS—liquid chromatography-mass spectrometry
LG—leaving group
MeOH—methanol or methyl alcohol
MSD—mass selective detector
MTBE—methyl tert-butyl ether
NIS—N-iodosuccinimide
NMR—nuclear magnetic resonance
PBS—phosphate buffered saline
Pd/C—palladium on carbon
PEG—polyethylene glycol
PG—protecting group
r.t./RT—room temperature
$R_T$—retention time
RP-HPLC—Reversed-phase high-performance liquid chromatography
SFC—supercritical fluid chromatography
TAMRA—carboxytetramethylrhodamine
TCEP—Tris(2-carboxyethyl)phosphine
TEA—triethylamine
TFA—trifluoroacetic acid
THF—tetrahydrofuran
TMSI—trimethylsilyl iodide
UV—ultraviolet LC/MS Methods Method A: Experiments performed on an SHIMADZU 2020 HPLC with SHIMADZU MSD mass spectrometer using ESI as ionization source using an Shim-Pack XR-ODS C18 50×3.0 mm 2.2 μm column and a 1.2 ml/minute flow rate. The solvent A is water with 0.05% TFA and solvent B is acetonitrile with 0.05% TFA, The gradient consisted with 20-80% solvent B over 3.6 minutes, 80-100% solvent B over 0.4 minutes and hold 100% B for 0.5 minutes. LC column temperature is 40° C. UV absorbance was collected from 190 nm to 400 nm.

Method B: Experiments performed on an SHIMADZU 2020 HPLC with SHIMADZU MSD mass spectrometer using ESI as ionization source using a Shim-pack XR-ODS C18 50×3.0 mm column and a 1.2 ml/minute flow rate. The solvent system was a gradient starting with 95% water with 0.05% TFA (solvent A) and 5% acetonitrile with 0.05% TFA (solvent B), ramping up to 100% solvent B over 1.1 minutes. The final solvent system was held constant for a further 0.6 minutes. LC column temperature is 40° C. UV absorbance was collected from 190 nm to 400 nm.

Method C: Experiments performed on an SHIMADZU 2020 HPLC with SHIMADZU MSD mass spectrometer using ESI as ionization source using an Ascentis Express C18 50×2.1 mm column and a 1.0 ml/minute flow rate. The solvent system was a gradient starting with 95% water with 0.05% TFA (solvent A) and 5% acetonitrile with 0.05% TFA (solvent B), ramping up to 100% solvent B over 1.1 minutes. The final solvent system was held constant for a further 0.5 minutes. LC column temperature is 40° C. UV absorbance was collected from 190 nm to 400 nm.

Method D: Experiments performed on an SHIMADZU 2020 HPLC with SHIMADZU MSD mass spectrometer using ESI as ionization source using a Shim-pack XR-ODS 50×3.0 mm column and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes. LC column temperature is 40° C. UV absorbance was collected from 190 nm to 400 nm.

Method E: Experiments performed on an SHIMADZU 2020 HPLC with SHIMADZU MSD mass spectrometer using ESI as ionization source using a CORTECS C18 50×3.1 mm column and a 1.0 ml/minute flow rate. The solvent system was a gradient starting with 95% water with 0.05% TFA (solvent A) and 5% acetonitrile with 0.05% TFA (solvent B), ramping up to 100% solvent B over 1.1 minutes. The final solvent system was held constant for a further 0.5 minutes. LC column temperature is 45° C. UV absorbance was collected from 190 nm to 400 nm.

Method F: Experiments performed on a Shimadzu 2020 HPLC with Shimadzu MSD mass spectrometer using ESI as ionization source using a Poroshell HPH-C18 50×3.0 mm column and a 1.2 mL/minute flow rate. The solvent A is water with 0.05% $NH_4HCO_3$ and solvent B is acetonitrile. The gradient consisted with 10-50% solvent B over 3.5 minutes then 50-95% solvent B over 0.5 minutes and hold 95% B for 0.7 minutes. LC column temperature is 40° C. UV absorbance was collected from 190 nm to 400 nm.

Method G: Experiments performed on an SHIMADZU 2020 HPLC with SHIMADZU MSD mass spectrometer using ESI as ionization source using an XSELECT CSH C18 50×3.0 mm column and a 1.5 ml/minute flow rate. The solvent system was a gradient starting with 90% water with 0.1% FA (solvent A) and 10% acetonitrile with 0.1% FA (solvent B), ramping up to 100% solvent B over 1.1 minutes. The final solvent system was held constant for a further 0.6 minutes. LC column temperature is 40° C. UV absorbance was collected from 190 nm to 400 nm.

Method H: Experiments performed on an SHIMADZU 2020 HPLC with SHIMADZU MSD mass spectrometer using ESI as ionization source using an Accucore C18 50×2.1 mm column and a 1.0 ml/minute flow rate. The solvent system was a gradient starting with 90% water with 0.1% FA (solvent A) and 10% acetonitrile with 0.1% FA (solvent B), ramping up to 95% solvent B over 2 minutes. The final solvent system was held constant for a further 0.7 minutes. LC column temperature is 40° C. UV absorbance was collected from 190 nm to 400 nm.

Method I: Experiments performed on a Shimadzu LCMS-2020 coupled with SHIMADZU MSD mass spectrometer using ESI as ionization source. The LC separation was using a CAPCELL CORE C18, 50×2.1 mm column with a 1 ml/minute flow rate. Solvent A is water with 0.05% TFA and solvent B is acetonitrile with 0.05% TFA. The gradient consisted with 5-95% solvent B over 2.0 minutes and hold 95% B for 0.7 minutes. LC column temperature is 40° C. UV absorbance was collected from 190 nm to 400 nm.

Method J: Experiments performed on a Shimadzu LCMS-2020 coupled with SHIMADZU MSD mass spectrometer using ESI as ionization source. The LC separation was using a Shim-pack XR-ODS, 50×3.0 mm column with a 1.2 ml/minute flow rate. Solvent A is water with 0.05% TFA and solvent B is acetonitrile with 0.05% TFA. The gradient consisted with 5-70% solvent B over 3.7 minutes, 70-95% solvent B over 0.2 minutes and hold 95% B for 0.7 minutes. LC column temperature is 40° C. UV absorbance was collected from 190 nm to 400 nm.

Method K: Experiments performed on a Shimadzu LCMS-2020. The LC separation was using a Ascentis Express C18, 100×4.6 mm column with a 1.2 ml/minute flow rate. Solvent A is water with 0.05% TFA and solvent B is methanol. The gradient consisted with 30-95% solvent B over 10 minutes and hold 95% B for 2 minutes. LC column temperature is 40° C. UV absorbance was collected from 190 nm to 400 nm.

Method L: Experiments performed on a Shimadzu LCMS-2020 coupled with SHIMADZU MSD mass spectrometer using ESI as ionization source. The LC separation was using a Kinetex EVO C18, 50×2.1 mm column with a 1.0 ml/minute flow rate. Solvent A is water with 0.05% $NH_4HCO_3$ and solvent B is acetonitrile. The gradient consisted with 10-95% solvent B over 1.1 minutes, and hold 95% B for 0.5 minutes. LC column temperature is 35° C. UV absorbance was collected from 190 nm to 400 nm.

Method M: Experiments were performed on a HPLC column coupled with a mass spectrometer using ESI as an ionization source. The LC separation was using MK RP18e, 25×2 mm column with a 1.5 mL/minute flow rate. Solvent A was 1.5 mL TFA in 4 L water, and solvent B was 0.75 mL TFA in 4 L acetonitrile. The gradient consisted of 5-95% solvent B over 0.7 minutes, and holding at 95% for 0.4 minutes. LC column temperature was 50° C. UV absorbance was collected from 220 nm to 254 nm.

Method N: Experiments were performed on a HPLC column coupled with a mass spectrometer using ESI as an ionization source. The LC separation was using MK RP18e, 25×2 mm column with a 1.5 mL/minute flow rate. Solvent A was 1.5 mL TFA in 4 L water, and solvent B was 0.75 mL TFA in 4 L acetonitrile. The gradient consisted of 10-80% solvent B over 7 minutes, and holding at 95% for 0.4 minutes. LC column temperature was 50° C. UV absorbance was collected from 220 nm to 254 nm.

Method O: Experiments were performed on a HPLC column coupled with a mass spectrometer using ESI as an ionization source. The LC separation was using MK RP18e, 25×2 mm column with a 1.5 mL/minute flow rate. Solvent A was 1.5 mL TFA in 4 L water, and solvent B was 0.75 mL TFA in 4 L acetonitrile. The gradient consisted of 0-60% solvent B over 7 minutes, and holding at 95% for 0.4 minutes. LC column temperature was 50° C. UV absorbance was collected from 220 nm to 254 nm.

Method P: Experiments performed on SHIMADZU 2020 HPLC with SHIMADZU MSD mass spectrometer using ESI as ionization source using Shim-Pack XR-ODS C18 50×3.0 mm 2.2 μm column and a 1.2 ml/minute flow rate.

The solvent A is water with 0.05% TFA and solvent B is acetonitrile with 0.05% TFA. The gradient consisted with 5-95% solvent B over 2.0 minutes, hold 95% B for 0.7 minutes. LC column temperature is 40° C. UV absorbance was collected from 190 nm to 400 nm.

Method Q: Experiments performed on SHIMADZU 2020 HPLC with SHIMADZU MSD mass spectrometer using ESI as ionization source using Shim-Pack XR-ODS C18 50×3.0 mm 2.2 μm column and a 1.2 ml/minute flow rate. The solvent A is water with 0.05% TFA and solvent B is acetonitrile with 0.05% TFA. The gradient consisted with 5-60% solvent B over 3.2 minutes, 60-100% solvent B over 0.5 minutes, hold 100% B for 0.8 minutes. LC column temperature is 40° C. UV absorbance was collected from 190 nm to 400 nm.

Method R: Experiments performed on SHIMADZU 2020 HPLC with SHIMADZU MSD mass spectrometer using ESI as ionization source using Shim-Pack XR-ODS C18 50×3.0 mm 2.2 μm column and a 1.2 ml/minute flow rate. The solvent A is water with 0.05% TFA and solvent B is acetonitrile with 0.05% TFA. The gradient consisted with 20-60% solvent B over 3.6 minutes, 60-100% solvent B over 0.4 minutes, hold 100% B for 0.5 minutes. LC column temperature is 40° C. UV absorbance was collected from 190 nm to 400 nm.

Method S: Experiments performed on Shimadzu LCMS-2020. The LC separation was using Ascentis Express C18, 100×4.6 mm column with a 1.5 ml/minute flow rate. Solvent A is water with 0.05% TFA and solvent B is ACN/0.05% TFA. The gradient consisted with 5% B hold 0.8 min, 5-40% solvent B over 7.2 minutes, 40-95% solvent B over 2.0 minutes and hold 95% B for 2.0 minutes. LC column temperature is 60° C. UV absorbance was collected from 190 nm to 400 nm.

Method T: Experiments performed on Shimadzu LCMS-2020. The LC separation was using Ascentis Express C18, 100×4.6 mm column with a 1.5 ml/minute flow rate. Solvent A is water with 0.05% TFA and solvent B is ACN/0.05% TFA. The gradient consisted with 10-60% solvent B over 10 minutes, 60-95% solvent B over 1.0 minutes and hold 95% B for 2.0 minutes. LC column temperature is 60° C. UV absorbance was collected from 190 nm to 400 nm.

Method U: Experiments performed on Shimadzu LCMS-2020. The LC separation was using Ascentis Express C18, 100×4.6 mm column with a 1.0 ml/minute flow rate. Solvent A is water with 0.05% TFA and solvent B is ACN/0.05% TFA. The gradient consisted with 10-60% solvent B over 10 minutes, 60-95% solvent B over 2.0 minutes and hold 95% B for 2.0 minutes. LC column temperature is 60° C. UV absorbance was collected from 190 nm to 400 nm.

Method V: Experiments performed on Shimadzu LCMS-2020. The LC separation was using Ascentis Express C18, 100×4.6 mm column with a 1.0 ml/minute flow rate. Solvent A is water with 0.05% TFA and solvent B is ACN/0.05% TFA. The gradient consisted with 5-95% solvent B over 8 minutes, hold 95% B for 2.0 minutes. LC column temperature is 60° C. UV absorbance was collected from 190 nm to 400 nm.

Method W: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 10-95% solvent B over 2.0 minutes and hold 95% B for 0.7 minutes. LC column temperature is 40° C. UV absorbance was collected from 190 nm to 400 nm.

Method X: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 10-70% solvent B over 3.5 minutes, 70-95% solvent B over 0.5 minutes and hold 95% B for 0.7 minutes. LC column temperature is 40° C. UV absorbance was collected from 190 nm to 400 nm.

Method Y: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 30-70% solvent B over 4.0 minutes, 70-95% solvent B over 0.5 minutes and hold 95% B for 0.3 minutes. LC column temperature is 40° C. UV absorbance was collected from 190 nm to 400 nm.

Method Z: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 30-95% solvent B over 4.0 minutes and hold 95% B for 0.7 minutes. LC column temperature is 40° C. UV absorbance was collected from 190 nm to 400 nm.

Method AA: Experiments performed on SHIMADZU 2020 HPLC with SHIMADZU MSD mass spectrometer using ESI as ionization source using Accucore C18 50×2.1 mm column and a 1.0 ml/minute flow rate. The solvent A is water with 0.1% FA and solvent B is acetonitrile with 0.1% FA. The gradient consisted with 10-95% solvent B over 3.0 minutes and hold 95% B for 0.7 minutes. LC column temperature is 40° C. UV absorbance was collected from 190 nm to 400 nm.

Method BB: Experiments performed on SHIMADZU 2020 HPLC with SHIMADZU MSD mass spectrometer using ESI as ionization source using Accucore C18 50×2.1 mm column and a 1.0 ml/minute flow rate. The solvent A is water with 0.1% FA and solvent B is acetonitrile with 0.1% FA. The gradient consisted with 10-50% solvent B over 3.5, 50-95% solvent B over 0.5 minutes and hold 95% B for 0.7 minutes. LC column temperature is 40° C. UV absorbance was collected from 190 nm to 400 nm.

Method CC: Experiments performed on Shimadzu LCMS-2020 coupled with SHIMADZU MSD mass spectrometer using ESI as ionization source. The LC separation was using Shim-pack XR-ODS, 50×3.0 mm column with a 1.2 ml/minute flow rate. Solvent A is water with 0.05% TFA and solvent B is acetonitrile with 0.05% TFA. The gradient consisted with 5-50% solvent B over 3.5 minutes, 50-100% solvent B over 0.2 minutes and hold 100% B for 1.0 minutes. LC column temperature is 40° C. UV absorbance was collected from 190 nm to 400 nm.

Method DD: Experiments performed on Shimadzu LCMS-2020 coupled with SHIMADZU MSD mass spectrometer using ESI as ionization source. The LC separation was using Shim-pack XR-ODS, 50×3.0 mm column with a 1.2 ml/minute flow rate. Solvent A is water with 0.05% TFA and solvent B is acetonitrile with 0.05% TFA. The gradient consisted with 5-95% solvent B over 2.0 minutes and hold 95% B for 0.7 minutes. LC column temperature is 40° C. UV absorbance was collected from 190 nm to 400 nm.

Method EE: Experiments performed on SHIMADZU 2020 HPLC with SHIMADZU MSD mass spectrometer using ESI as ionization source using Ascentis Express C18

50×2.1 mm column and a 1.2 ml/minute flow rate. Solvent A is water with 0.05% TFA and solvent B is MeOH. The gradient consisted with 30-85% solvent B over 10 minutes and hold 80% B for 3.2 minutes. LC column temperature is 40° C. UV absorbance was collected from 190 nm to 400 nm.

Method FF: Experiments performed on MK RP18e 25-2 mm column with mass spectrometer using ESI as ionization source. Solvent A was 1.5 mL/4 L of TFA in water and solvent B was 0.75 mL/4 L of TFA in acetonitrile. The gradient consisted of 5-95% solvent B over 0.7 minutes, and holding at 95% for 0.4 minutes at a flow rate of 1.5 mL/min. LC column temperature was 50° C. UV absorbance was collected at 220 nm and 254 nm.

Method GG: Experiments performed on Xtimate C18 2.1*30 mm, 3 μm column, with mass spectrometer using ESI as ionization source. Solvent A was 1.5 mL/4 L of TFA in water, and solvent B was 0.75 mL/4 L of TFA in acetonitrile. The gradient consisted of 10-80% solvent B over 6 minutes, holding at 80% for 0.5 minutes at a flow rate of 0.8 m/min. LC column temperature was 50° C. UV absorbance was collected at 220 nm and 254 nm.

SFC Methods

Method 1: Column: Chiralpak AD-3 150×4.6 mm I.D., 3 um; Mobile phase: A: $CO_2$; B: ethanol (0.05% DEA); Gradient: from 5% to 40% of B in 5 minutes and from 40% to 5% of B in 0.5 minutes hold 5% of B for 1.5 minutes; Flow rate: 2.5 mL/minute; Column temperature: 35° C.; ABPR: 1500 psi.

Method 2: Column: Chiralcel OD-3 100×4.6 mm I.D., 3 um; Mobile phase: A: $CO_2$; B: ethanol (0.05% DEA); Gradient: from 5% to 40% of B in 4.5 minutes and hold 40% for 2.5 minutes, then 5% of B for 1 minute; Flow rate: 2.8 mL/minute; Column temperature: 40° C.

Method 3: Column: Chiralcel OJ-3 100×4.6 mm I.D., 3 um; Mobile phase: A: $CO_2$; B: methanol (0.05% DEA); Gradient: from 5% to 40% of B in 4.5 minutes and hold 40% for 0.5 minutes, then 5% of B for 1 minute; Flow rate: 2.8 mL/minute; Column temperature: 40° C.

Method 4: Column: ChiralCel OJ-H 150×4.6 mm I.D., Sum; Mobile phase: A: $CO_2$; B: ethanol (0.05% DEA); Gradient: from 5% to 40% of B in 5.5 minutes, then 5% of B for 1.5 minutes; Flow rate: 2.5 mL/minute; Column temperature: 40° C.

Method 5: Column: Chiralcel OJ-H 150*4.6 mm I.D., 5 um; Mobile phase: A: $CO_2$; B: ethanol (0.05% DEA); Gradient: hold 5% for 0.5 minutes, then from 5% to 40% of B in 3.5 minutes and hold 40% for 2.5 minutes, then 5% of B for 1.5 minutes; Flow rate: 3 mL/minute; Column temperature: 40° C.

Method 6: Column: Chiralpak AD-3 150×4.6 mm I.D., 3 um; Mobile phase: A: $CO_2$; B: iso-propanol (0.05% DEA); Gradient: from 5% to 40% of B in 5 minutes and hold 40% for 2.5 minutes, then 5% of B for 2.5 minutes; Flow rate: 2.5 mL/minute; Column temperature: 35° C.; ABPR: 1500 psi.

Method 7: Column: Chiralcel OJ-3 100×4.6 mm I.D., 3 um; Mobile phase: A: $CO_2$; B: ethanol (0.05% DEA); Gradient: from 5% to 40% of B in 4.5 minutes and hold 40% for 2.5 minutes, then 5% of B for 1 minute; Flow rate: 2.8 mL/minute; Column temperature: 40° C.

$^1$H-NMR spectra were recorded at 400 MHz, 500 MHz or 600 MHz, with a Bruker Bruker Avance 400, 500 or 600 spectrometers. $^1$H-NMR data are reported in the following format: chemical shift (multiplicity, coupling constants, and integration). Chemical shifts are reported in ppm with the residual solvent resonance as internal standard ($CDCl_3$: 7.26 ppm, DMSO-d6: 2.50 ppm, $CD_3OD$: 3.31 ppm). Multiplicity is abbreviated as follows: s=singlet, d=doublet, t=triplet, q=quartet, m=multiplet, br=broad, dt=doublet of triplets, dd=doublet of doublet, ddd=doublet of doublet of doublets, dddd=doublet of doublet of doublets of doublets, tt=triplet of triplets.

The following generalized schemes are used to prepare the disclosed compounds, intermediates, and pharmaceutically acceptable salts thereof. Disclosed compounds and intermediates may be prepared using standard organic synthetic techniques and from commerically available starting materials and reagents. It will be appreciated that synthetic procedures employed in the preparation of disclosed compounds and intermediates will depend on the particular substituents present in the compound or intermediate and that various protection, deprotection, and conversion steps that are standard in organic synthesis may be required, but may not be illustrated in the following general schemes. It is also to be understood that any of the steps shown in any of the following general schemes may be used in any combination and in any order that is chemically feasible to achieve a desired intermediate or disclosed compound. Note that, in the following generalized schemes, the various moieties are as defined elsewhere herein. In the following generalized schemes and examples, 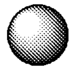 indicates a solid support—for example, a rink amide resin.

Scheme 1

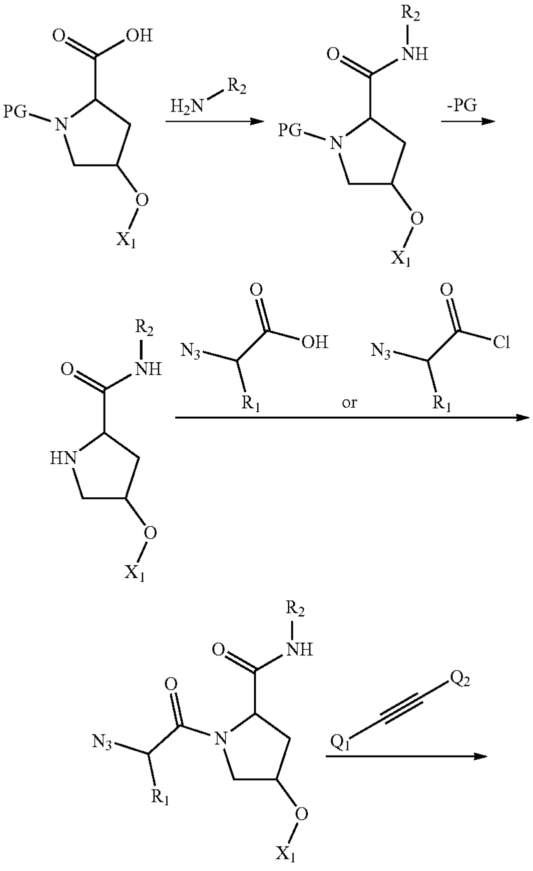

-continued
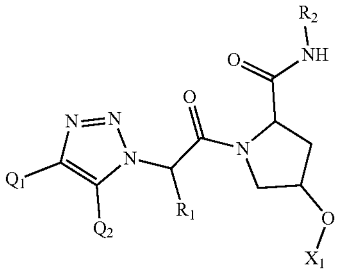
Scheme 2
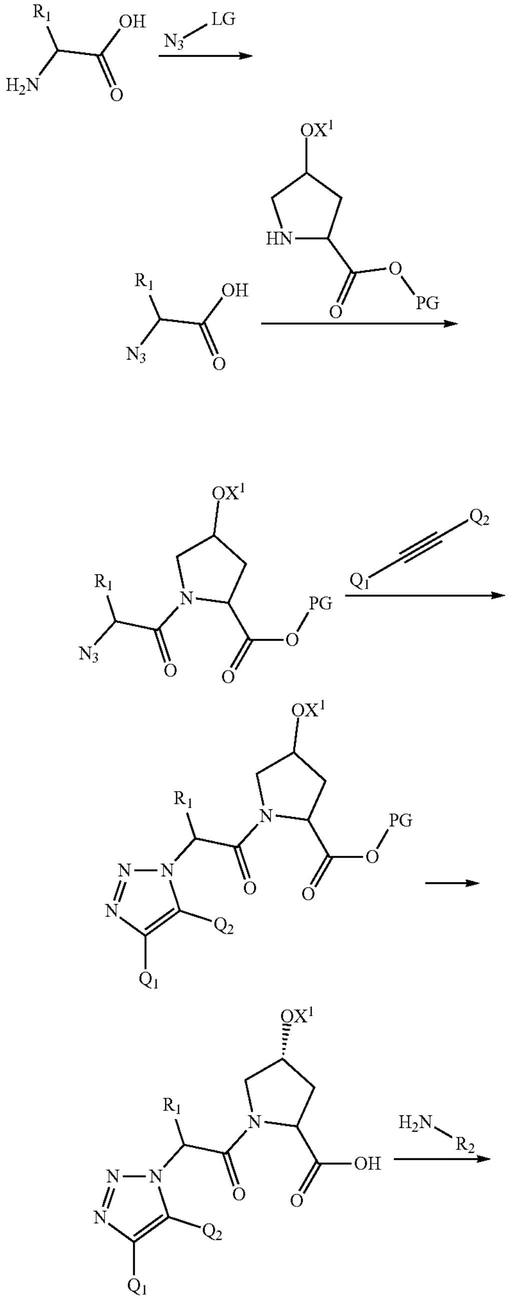
-continued
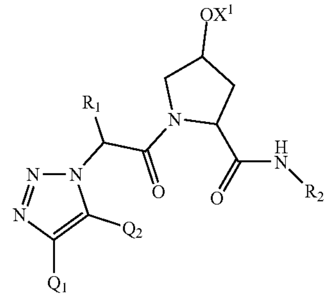
Scheme 3
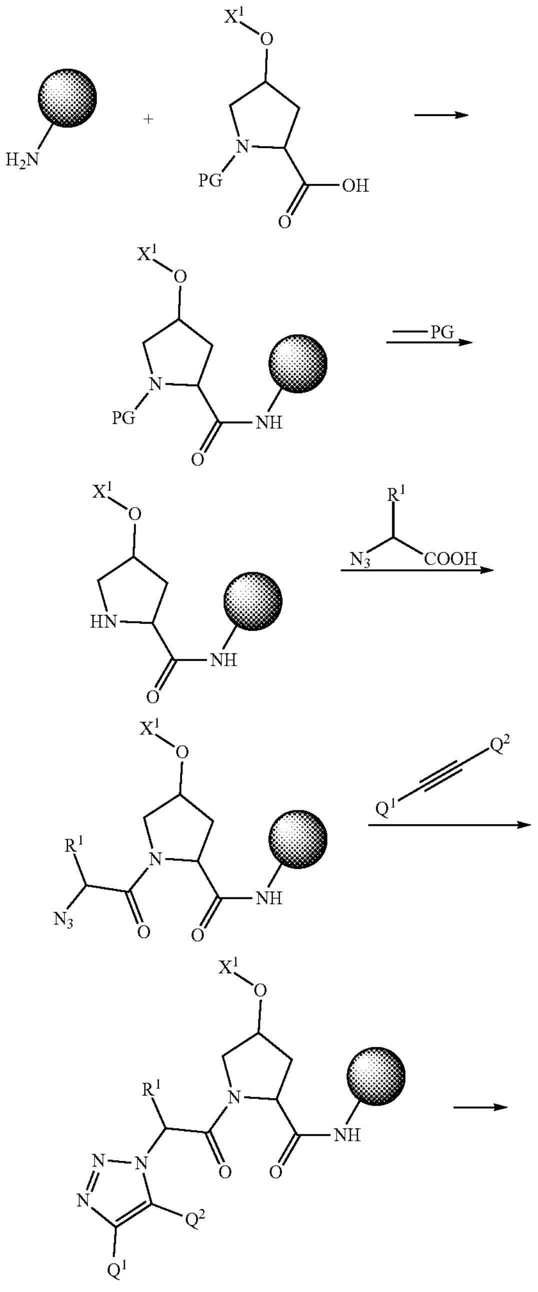

-continued
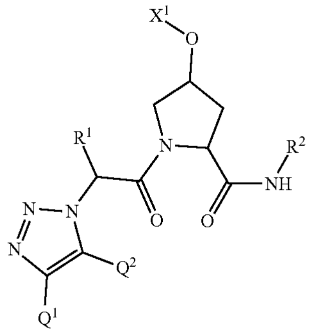
Scheme 4
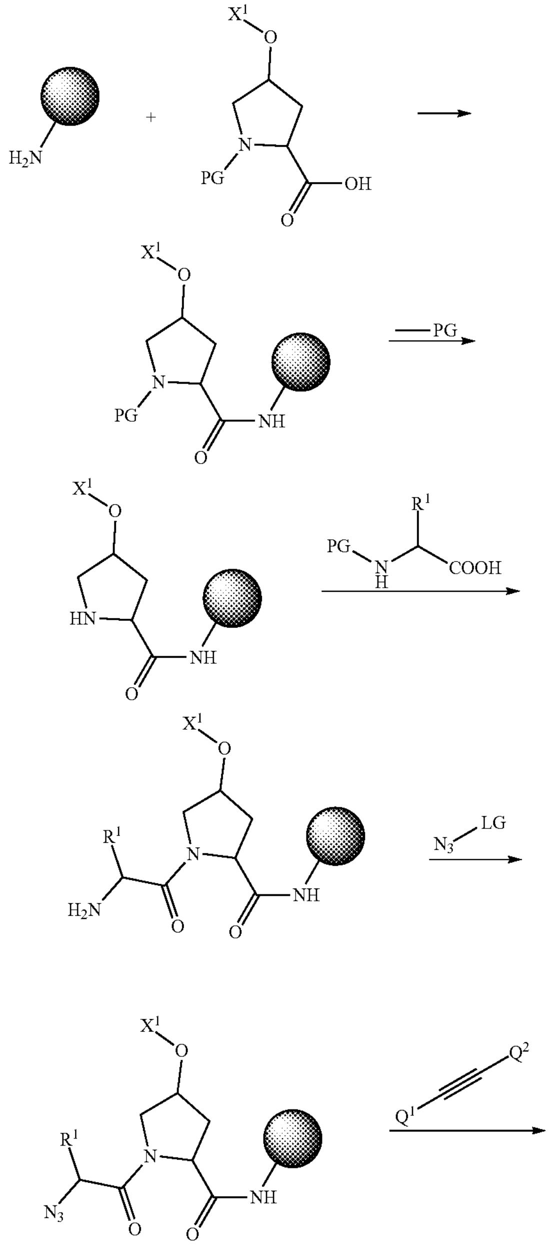
-continued
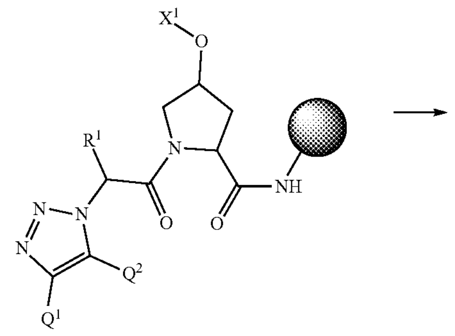
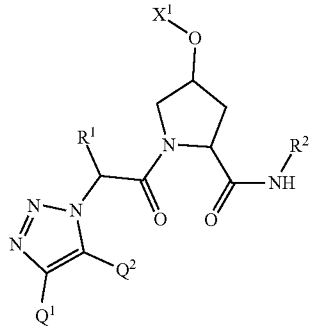
Scheme 5
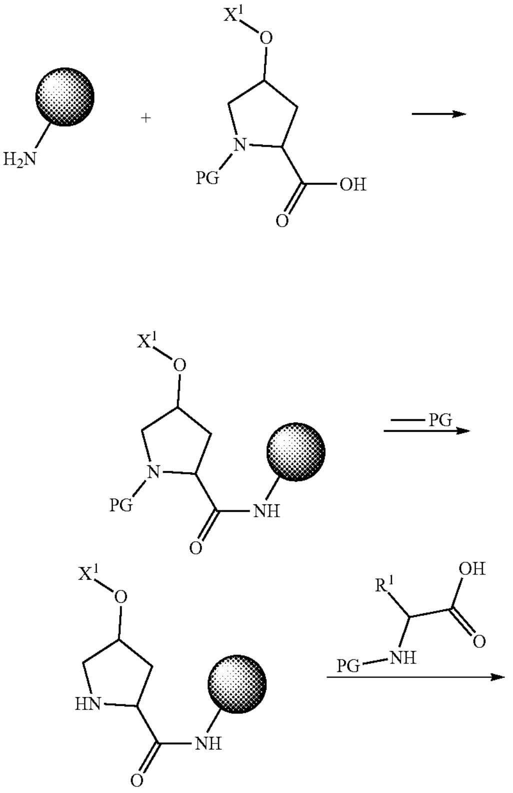

-continued
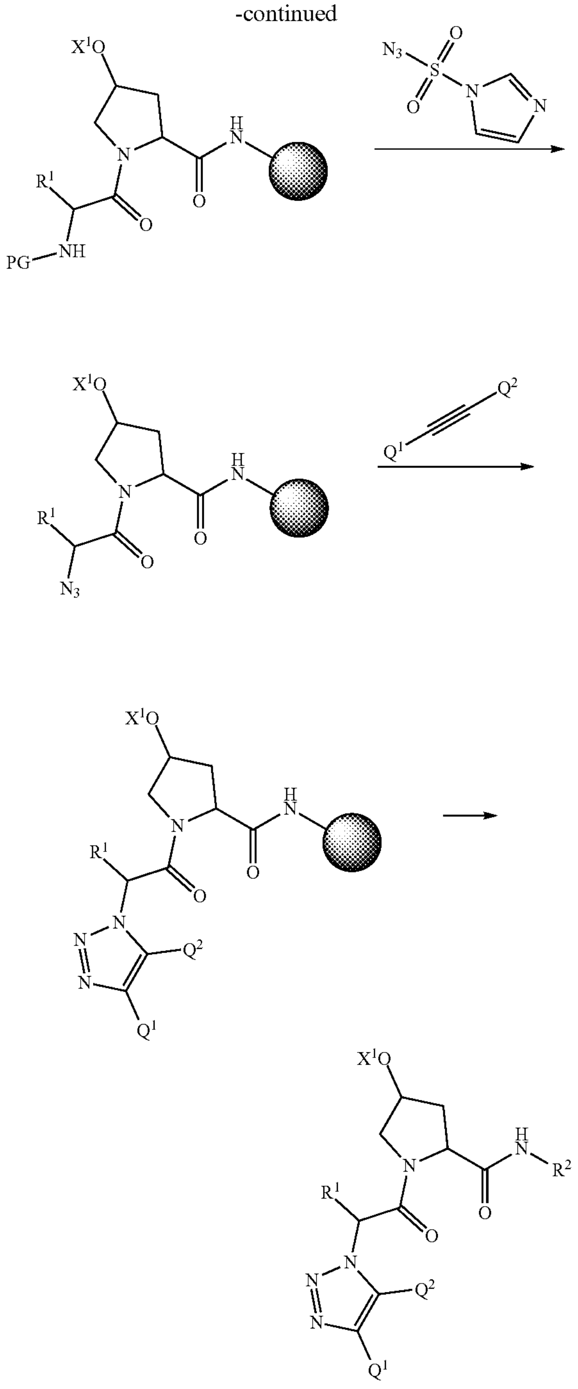
Scheme 6
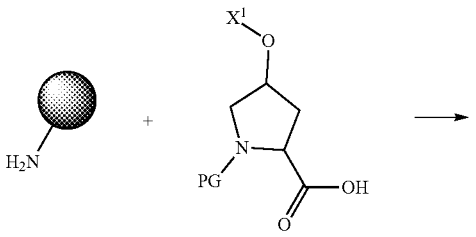
-continued
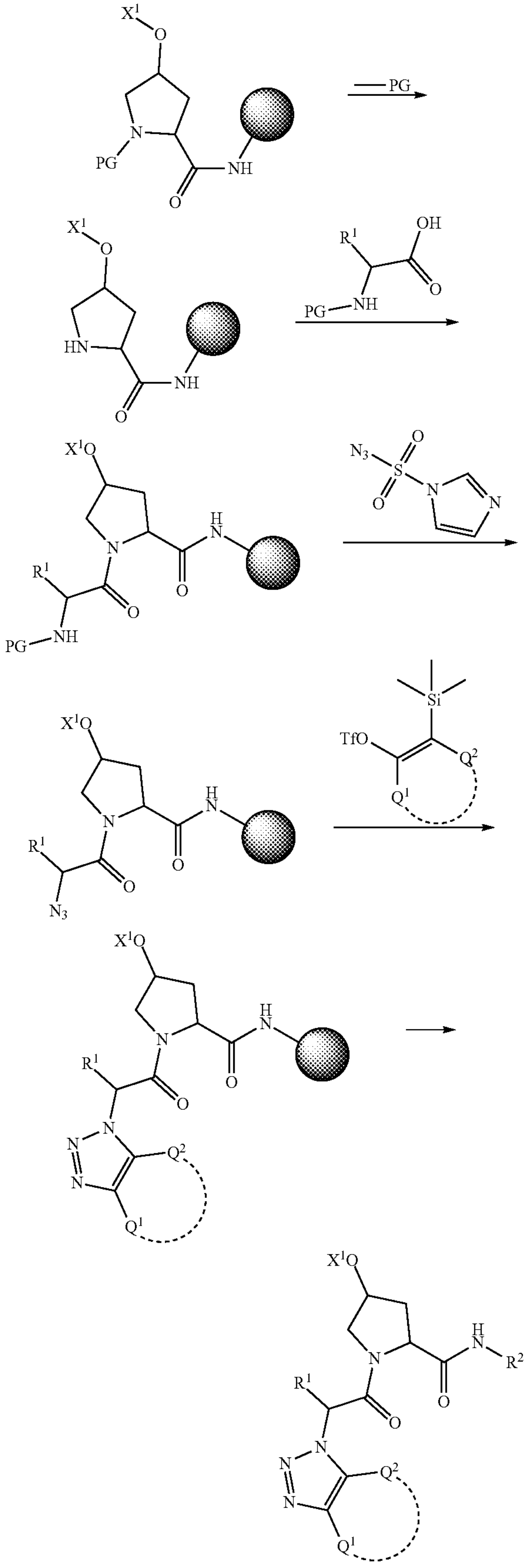

The following examples are offered by way of illustration and not by way of limitation. Some of the compounds used in the following examples may exists as tautomers. Although the illustrations of these compounds provided below depict only a single tautomer, these illustrations should not be viewed in a limiting sense; rather, the corresponding tautomers are also intended and embraced by the following examples, as if each and every one of the tautomers of the compound were individually depicted.

Example S1: Synthesis of (2S,4R)-1-((S)-2-(4-cyclopropyl-1H-1,2,3-triazol-1-yl)-3,3-dimethylbutanoyl)-4-hydroxypyrrolidine-2-carboxamide (Compound 1)

The synthesis was carried out following the solid phase synthetic scheme given below:

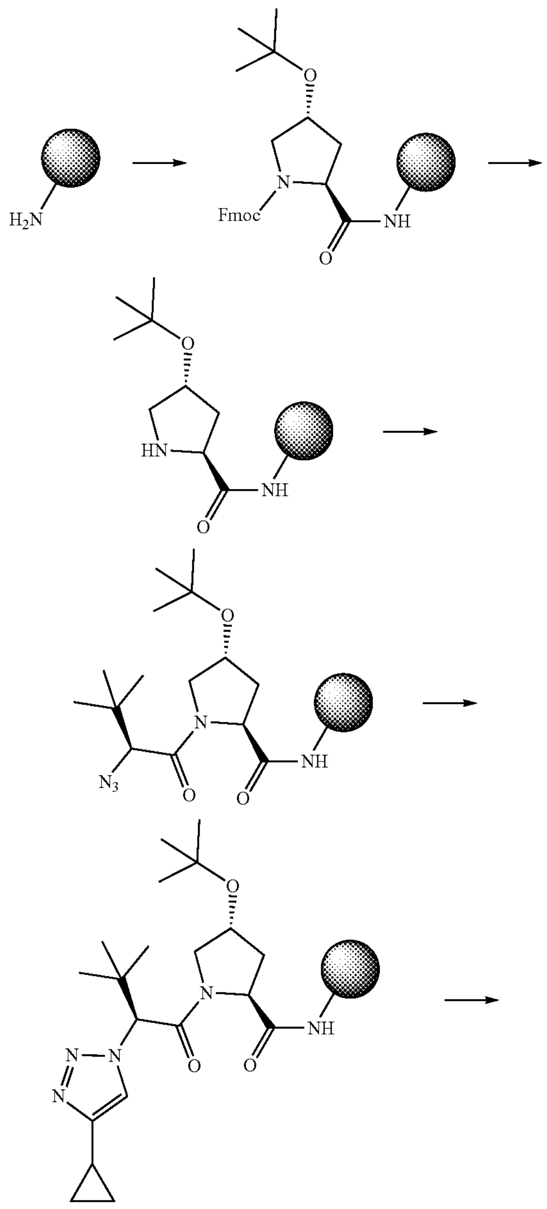

-continued

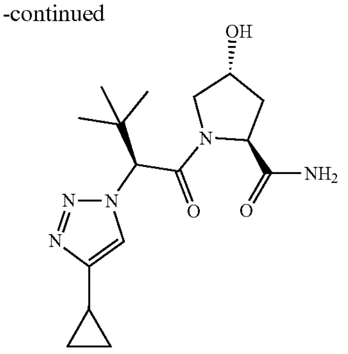

Compound 1

Rink Amide Resin (0.100 mmol) was added to a plastic peptide synthesis vessel. 10 mL N,N-Dimethylformamide was added to the vessel and the resin was allowed to swell for 30 min under nitrogen. The resin was then drained under vacuum. 10 mL of 20% 4-methylpiperidine in N,N-Dimethylformamide were drawn into the reaction vessel, and reacted under nitrogen for 15 min to deprotect the Fmoc group. The solvent was drained under vacuum, and the deprotection step was repeated. The resin was washed with 10 mL N,N-Dimethylformamide, then 10 mL dichloromethane, and drained under vacuum. The washing procedure was repeated 3 times. A mixture of (2S,4R)-1-(((9H-fluoren-9-yl)methoxy)carbonyl)-4-(tert-butoxy)pyrrolidine-2-carboxylic acid (3.0 equiv.), Ethyl cyano(hydroxyimino)acetate (3.0 equiv.) and N,N'-Diisopropylcarbodiimide (3.0 equiv.) in 10 mL N,N-Dimethylformamide was added, and then the mixture was drawn into a synthesis vessel and reacted for 2 hr under nitrogen. The resin was washed with 10 mL N,N-Dimethylformamide, then 10 mL dichloromethane, and drained under vacuum. The washing procedure was repeated 3 times. 10 mL of 20% 4-methylpiperidine in N,N-Dimethylformamide were drawn into a reaction vessel, and reacted under nitrogen for 15 min to deprotect the Fmoc group. The solvent was drained under vacuum, and the deprotection was repeated. The resin was washed with 10 mL N,N-Dimethylformamide, then 10 mL dichloromethane, and drained under vacuum. The washing procedure was repeated 3 times. A mixture of (S)-2-azido-3,3-dimethylbutanoic acid (3.0 equiv.), Ethyl cyano(hydroxyimino)acetate (3.0 equiv.) and N,N'-Diisopropylcarbodiimide (3.0 equiv.) in 10 mL N,N-Dimethylformamide was added, and then the combined mixture was drawn into a synthesis vessel and reacted for 2 hr under nitrogen. The resin was washed with 10 mL N,N-Dimethylformamide, then 10 mL dichloromethane, and drained under vacuum. The washing procedure was repeated 3 times. Tetrakis(acetonitrile)copper(I) hexafluorophosphate (0.2 equiv.) was added directly into the peptide synthesis vessel to perform on-resin "click" reaction. A mixture of ethynylcyclopropane (5.0 equiv.) and N,N-Diisopropylethylamine (10.0 equiv.) in 10 mL N,N-Dimethylformamide (nitrogen purged) was drawn into the reaction vessel, and reacted overnight under nitrogen. The resin was washed with 10 mL N,N-Dimethylformamide, then 10 mL dichloromethane, and drained under vacuum. A cleavage solution was prepared by mixing 5% Triisopropylsilane in 95% Trifluoroacetic acid. The cleavage solution was drawn into the reaction vessel and reacted for 1 hr. The trifluoroacetic acid was removed under vacuum. The remaining residue was mixed with 50 mL cold ether (−20° C.) to precipitate the compound.

The collected precipitate was purified by RP-HPLC (acetonitrile 30-60%/0.225% FA in water) to afford (2S,4R)-1-((S)-2-(4-cyclopropyl-1H-1,2,3-triazol-1-yl)-3,3-dimethylbutanoyl)-4-hydroxypyrrolidine-2-carboxamide (Compound 1) (15 mg, 44.7% yield) as a white solid. ESI-MS: m/z $[M+H]^+$ calculated: 336.2. found: 336.2.

$^1$H NMR (400 MHz, DMSO-$d_6$) δ 7.96 (d, J=4.8 Hz, 1H), 7.45 (s, 1H), 6.89 (s, 1H), 5.36 (d, J=16.9 Hz, 1H), 4.37-4.22 (m, 2H), 3.72 (dd, J=10.8, 4.0 Hz, 1H), 3.55 (dt, J=11.1, 1.8 Hz, 1H), 2.08-1.90 (m, 2H), 1.82 (dddd, J=17.2, 12.7, 8.1, 4.7 Hz, 1H), 1.01-0.91 (m, 9H), 0.91-0.84 (m, 2H), 0.80-0.66 (m, 2H).

Example S2: Synthesis of (2S,4R)-1-((S)-2-(4-cyclopropyl-1H-1,2,3-triazol-1-yl)-3,3-dimethylbutanoyl)-4-hydroxy-N-methylpyrrolidine-2-carboxamide (Compound 2)

Synthesis was carried out following the scheme given below:

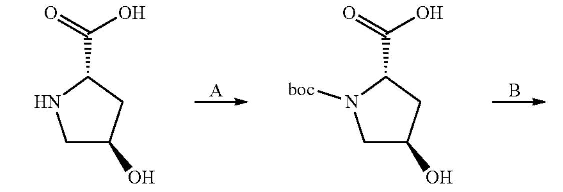

2a 2b

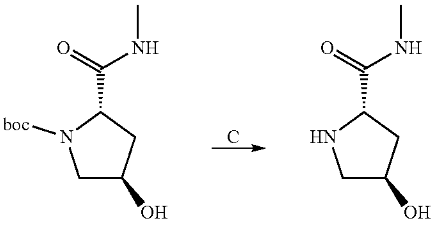

2c 2d

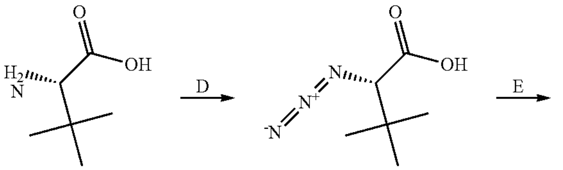

2e 2f

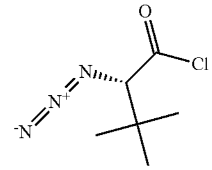

2g

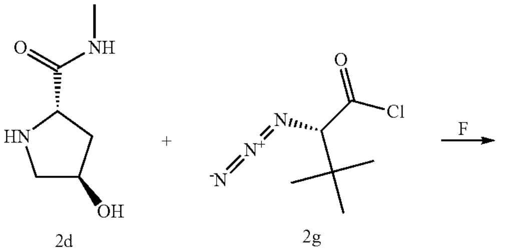

2d 2g

-continued

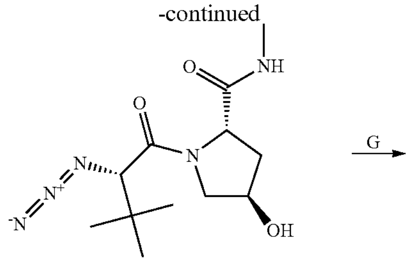

2h

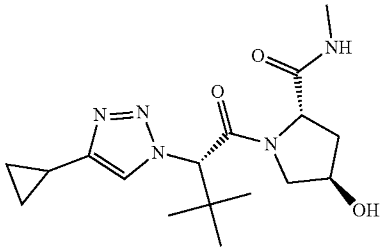

2

Preparation of Intermediate 2b

KOH (85.5 g, 1.526 mol) was dissolved in 1 L of distilled water and then treated with THF (1 L) followed by the addition of intermediate 2a (100 g, 0.763 mol) using an ice-cooled bath. Then $Boc_2O$ (250 g, 1.467 mol) was added dropwise. The reaction mixture was stirred at room temperature overnight and then THF was removed using a rotary evaporator. The aqueous layer was washed with MTBE (2×700 mL). The aqueous residue was adjusted to pH 3 by the addition of 1M aqueous $KHSO_4$. The acidic solution was extracted by ethyl acetate (3×700 mL). The combined organic extracts were washed with $H_2O$ and brine, and dried over anhydrous $Na_2SO_4$. The solvent was removed under reduced pressure to afford intermediate 2b as a yellow syrup (150 g, 0.649 mol, 85% yield), which was used without purification for the next step.

$^1$H NMR: (400 MHz, DMSO-d6) δ 12.44 (br s, 1H), 5.01 (br s, 1H), 4.28-4.11 (m, 1H), 4.11-3.95 (m, 1H), 3.50-3.25 (m, 1H), 3.25-3.04 (m, 1H), 2.19-1.95 (m, 1H), 1.95-1.68 (m, 1H), 1.31 (d, 9H).

Preparation of Intermediate 2c 126 mL (0.905 mol) of triethylamine were added at −40° C. to a solution of 150 g (0.649 mol) of intermediate 2b in 2700 mL of dry THF, and then a solution of 70 mL (0.563 mol) of ethyl chloroformate in 300 mL of dry THF was added at −30° C. The resulting mixture was stirred at the same temperature for 1 hour. Then 170 mL of a 40% by volume aqueous methylamine solution were added at −30° C., and the temperature of the reaction mixture was allowed to rise to room temperature. The reaction was then allowed to continue for 12 hours. At the end of this time, the THF was removed by rotary evaporation and mixed with a small amount of an aqueous solution of sodium chloride and extracted thrice with ethyl acetate. The combined extracts were washed with an aqueous solution of sodium chloride and dried over anhydrous $Na_2SO_4$. The solvent was removed under reduced pressure, yielding 100 g (0.410 mol, 63.3%) of intermediate 2c as a colorless oil.

$^1$H NMR: (400 MHz, DMSO-d6) δ 7.94-7.62 (m, 1H), 5.04-4.75 (m, 1H), 4.25-4.09 (m, 1H), 4.09-3.80 (m, 2H), 3.41-3.30 (m, 1H), 3.25-3.11 (m, 1H), 2.53 (d, J=8.3, 4.5 Hz, 3H), 2.00-1.92 (m, 1H), 1.82-1.65 (m, 1H), 1.31 (d, J=28.0 Hz, 9H).

Preparation of Intermediate 2d

To a solution of intermediate 2c (100 g, 0.410 mol) in MTBE (1 L) was added a solution of 10%-HCl in dioxane (500 mL) dropwise. At the end of addition, the mixture was stirred at r.t. for 8 hrs. Then the reaction was completed, the precipitate formed was filtered, treated with diethyl ether, filtered and the residue was dried in vacuum to give the title intermediate 2d (60 g, 0.335 mol, 82% yield) as white powder.

$^1$H NMR: (500 MHz, DMSO-d6) δ 10.28 (br s, 1H), 8.90-8.69 (m, 1H), 8.58 (br s, 1H), 5.60 (br s, 1H), 4.46-4.31 (m, 1H), 4.31-4.16 (m, 1H), 3.35-3.19 (m, 1H), 3.12-2.91 (m, 1H), 2.64 (d, J=4.7, 1.3 Hz, 3H), 2.36-2.13 (m, 1H), 1.91-1.63 (m, 1H).

Preparation of Intermediate 2f

Trifyl azide preparation: A solution of sodium azide (125 g, 1.92 mol) was dissolved in distilled water (620 mL) with DCM (1000 mL) and cooled using an ice bath. Triflyl anhydride (120 ml, 0.71 mol) was added slowly over 30 min with continuous stirring for 2 h. The organic phase was removed and the aqueous portion was extracted with DCM (2×200 mL). The organic fractions, containing the triflyl azide, were pooled and washed once with saturated disodium carbonate and used without further purification. Intermediate 2e (50 g, 0.38 mol) was combined with potassium carbonate (80 g, 0.58 mol), copper (II) sulfate pentahydrate (3 g, 0.012 mol), distilled water (630 ml), and methanol (1250 ml). The triflyl azide in DCM (1000 ml) was added and the mixture was stirred at ambient temperature and pressure overnight. Subsequently, the organic solvents were removed under reduced pressure and the aqueous slurry was diluted with water (1000 mL). The solution was acidified to pH=6 with sodium hydrosulfate and extracted with EtOAc three times to remove sulfonamide by-product. The aqueous phase was them acidified to pH=2 with conc. HCl. The product was obtained from another round of EtOAc extractions (3×600 mL). These organic phases were combined, dried by sodium sulfate and evaporated to dryness giving 30 g of intermediate 2f as white solid in 51% yield with no need for further purification.

$^1$H NMR: (400 MHz, DMSO-d6) δ 13.14 (br s, 1H), 3.83 (s, 1H), 0.93 (s, 9H). LCMS: (Method 5-95 AB, ESI, 2 min): $R_T$=1.159 min, $[M-H]^-$=156.2.

Preparation of Intermediate 2 g

To a solution of intermediate 2f (30 g, 0.19 mol) in dichloromethane (DCM) (250 ml) oxalyl chloride (25 ml, 0.29 mol) was added, followed by 2 drops of DMF. The mixture was stirred at room temperature for 2 h, and then an excess of oxalyl chloride and dichloromethane were removed in vacuo to provide crude intermediate 2 g (33 g, 99% yield).

$^1$H NMR: (400 MHz, Chloroform-d) δ 4.01 (s, 1H), 1.07 (s, 9H).

Preparation of Intermediate 2h

To a solution of intermediate 2d (80 g, 0.449 mol) in THF (1200 mL) triethylamine (120 mL, 0.862 mol) was added slowly under stirring at −20° C., followed by substance intermediate 2 g (60 g, 0.342 mol). The reaction mixture was further stirred at −20° C. for 2 hours and left stirred overnight at r.t. The mixture was evaporated to give slurry solution, diluted with ethyl acetate (1000 mL) and washed with 1N HCl (500 mL), followed by 10% aqueous sodium hydrocarbonate (500 mL) and brine (500 mL). The ethyl acetate layer was dried with sodium sulfate and concentrated under vacuum to give 55 g (56%) of pure product intermediate 2h (mixture of rotamers by NMR).

$^1$H NMR: (500 MHz, DMSO-d6) δ 8.27-7.82 (m, 1H), 5.16-4.89 (m, 1H), 4.51-4.34 (m, 1H), 4.34-4.19 (m, 1H), 3.87 (s, 1H), 3.73-3.57 (m, 1H), 3.56-3.38 (m, 2H), 2.62 (d, J=4.6 Hz, 3H), 2.27-1.97 (m, 1H), 1.97-1.69 (m, 1H), 0.97 (d, J=25.7 Hz, 9H).

LCMS: (Method 5-95 AB, ESI, 6 min): $R_T$=2.094 min, $[M+H]^+$=284.4

Preparation of (2S,4R)-1-((S)-2-(4-cyclopropyl-1H-1,2,3-triazol-1-yl)-3,3-dimethylbutanoyl)-4-hydroxy-N-methylpyrrolidine-2-carboxamide (Compound 2)

To a solution of intermediate 2h (0.5 g, 1.76 mmol) and cyclopropylacetylene (0.14 g, 2.12 mmol) in THF (5 mL) was added sodium ascorbate (0.34 g, 1.71 mmol) in distilled water (2 mL) and copper (II) sulfate pentahydrate (0.15 g, 0.6 mmol) in distilled water (3 mL). The mixture was stirred at 25° C. overnight. Then 25%-aqueous solution of ammonia was added and purified using preparative HPLC. Chromatography runs conditions are given below: Device (Mobile Phase, Column): SYSTEM 0-50% 0.5-6.5 min water-acetonitrile; flow 30 ml/min (loading pump 4 ml/min acetonitrile); target mass 349; column SunFireC18 100×19 mm 5 um (R)

As result, a target compound ((2S,4R)-1-((S)-2-(4-cyclopropyl-1H-1,2,3-triazol-1-yl)-3,3-dimethylbutanoyl)-4-hydroxy-N-methylpyrrolidine-2-carboxamide; Compound 2) was obtained (104 mg, 0.298 mmol) with total yield 16.8%.

ESI-MS: m/z $[M+H]^+$ calculated: 350.2. found: 350.2.

$^1$H NMR (400 MHz, DMSO-d6) δ 7.99-7.88 (m, 2H), 5.39 (s, 1H), 5.11 (d, J=3.6 Hz, 1H), 4.35-4.23 (m, 2H), 3.71 (dd, J=10.9, 3.9 Hz, 1H), 3.61-3.50 (m, 1H), 2.62-2.51 (m, 3H), 2.05-1.88 (m, 2H), 1.82 (ddd, J=13.1, 9.0, 4.4 Hz, 1H), 0.97 (s, 8H), 0.93 (s, 2H), 0.87 (ddd, J=8.3, 4.0, 2.2 Hz, 2H), 0.72 (tt, J=4.7, 2.0 Hz, 2H).

Example S3: Synthesis of (2S,4R)-1-((S)-2-cyclohexyl-2-(4-cyclopropyl-1H-1,2,3-triazol-1-yl)acetyl)-4-hydroxy-N-methylpyrrolidine-2-carboxamide (Compound 3)

Synthesis was carried out following the solid phase synthesis scheme given below:

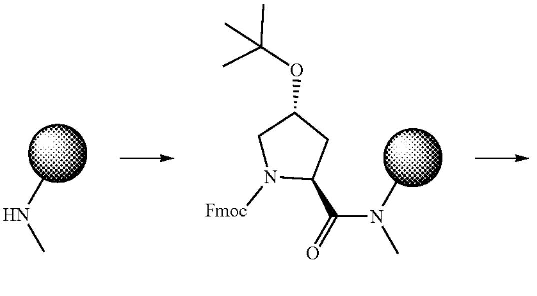

-continued

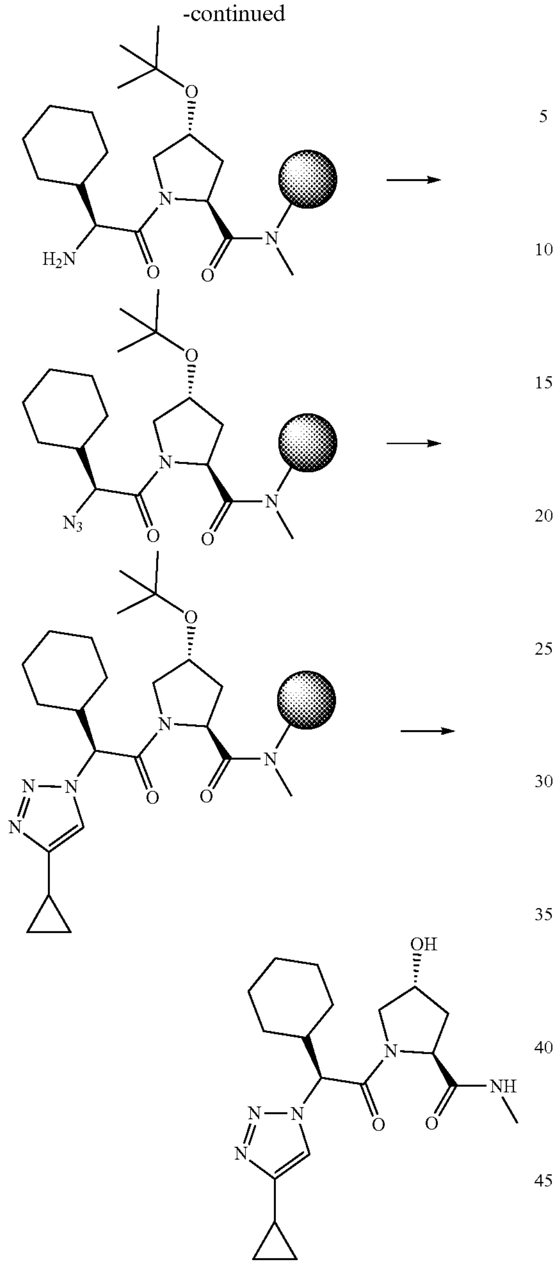

3

4-Formyl-3-methoxy-phenyloxymethyl polystyrene resin (0.100 mmol) was added to a plastic peptide synthesis vessel. 10 mL 1,2-Dichloroethane was added to the vessel and the resin was allowed to swell for 30 min under nitrogen. The resin was then drained under vacuum. Methylamine (DEA controlled substance, 2.0 M solution in tetrahydrofuran, 1 mL) was added to the plastic reactor and the mixture was reacted for 2 hr at room temperature. The reactor was opened, and sodium cyanoborohydride (10.0 equiv.) and acetic acid (2 equiv.) were added to the reactor. The reactor was left opened on manifold, and the contents were mixed by pipetting and reacted overnight at RT. The resin was washed with 10 mL methanol, 10 mL N,N-Dimethylformamide, then 10 mL dichloromethane, and drained under vacuum. The washing procedure was repeated 3 times. A mixture of (2S,4R)-1-(((9H-fluoren-9-yl)methoxy)carbonyl)-4-(tert-butoxy)pyrrolidine-2-carboxylic acid (3.0 equiv.), 1-[Bis(dimethylamino)methylene]-1H-1,2,3-triazolo[4,5-b]pyridinium 3-oxide hexafluorophosphate (3.0 equiv.), 1-hydroxy-7-azabenzotriazole (3.0 equiv.), and N,N-Diisopropylethylamine (6.0 equiv.) in 10 mL N,N-Dimethylformamide was added and the resulting mixture was drawn into the synthesis vessel and reacted for 2 hr under nitrogen. The resin was washed with 10 mL N,N-Dimethylformamide, then 10 mL dichloromethane, and drained under vacuum. The washing procedure was repeated 3 times. 10 mL of 20% 4-methylpiperidine in N,N-Dimethylformamide was drawn into the reaction vessel and reacted under nitrogen for 15 min to deprotect Fmoc group. The solvent was drained under vacuum, and the deprotection was repeated. The resin was washed with 10 mL N,N-Dimethylformamide, then 10 mL dichloromethane, and drained under vacuum. The washing procedure was repeated 3 times. A mixture of (S)-2-((((9H-fluoren-9-yl)methoxy)carbonyl)amino)-2-cyclohexylacetic acid (3.0 equiv.) and N,N'-Diisopropylcarbodiimide (3.0 equiv.) in 10 mL N,N-Dimethylformamide was added and the resulting mixture was drawn into the synthesis vessel and reacted for 2 hr under nitrogen. The resin was washed with 10 mL N,N-Dimethylformamide, then 10 mL dichloromethane, and drained under vacuum. The washing procedure was repeated 3 times. 10 mL of 20% 4-methylpiperidine in N,N-Dimethylformamide was drawn into the reaction vessel, and reacted under nitrogen for 15 min to deprotect Fmoc group. The solvent was drained under vacuum, and the deprotection was repeated. The resin was washed with 10 mL N,N-Dimethylformamide, then 10 mL dichloromethane, and drained under vacuum. The washing procedure was repeated 3 times. 1H-imidazole-1-sulfonyl azide hydrochloride (3.0 equiv.) and N,N-Diisopropylethylamine (6.0 equiv.) were mixed in dichloromethane, and the mixture was drawn into the reaction vessel, and reacted under nitrogen for 1 hr to convert amine to azide. The solvent was drained under vacuum, and the deprotection was repeated. The resin was washed with 10 mL N,N-Dimethylformamide, then 10 mL dichloromethane, and drained under vacuum. The washing procedure was repeated 3 times. Tetrakis(acetonitrile)copper (I) hexafluorophosphate (0.2 equiv.) was added directly into the peptide synthesis vessel to perform on-resin "click" reaction. The mixture of ethynylcyclopropane (5.0 equiv.), N,N-Diisopropylethylamine (10.0 equiv.) in 10 mL N,N-Dimethylformamide (nitrogen purged) was drawn into the reaction vessel and the mixture was reacted overnight under nitrogen. The resin was washed with 10 mL N,N-Dimethylformamide, then 10 mL dichloromethane, and drained under vacuum. A cleavage solution was prepared by mixing 5% Triisopropylsilane in 95% Trifluoroacetic acid. The solution was drawn into the reaction vessel and reacted for 1 hr. The trifluoroacetic acid was removed under vacuum. The remaining residue was mixed with 50 mL cold ether (−20° C.) to precipitate the compound of interest.

The collected precipitate was purified by RP-HPLC (acetonitrile 30-60%/0.225% FA in water) to afford (2S,4R)-1-((S)-2-cyclohexyl-2-(4-cyclopropyl-1H-1,2,3-triazol-1-yl)acetyl)-4-hydroxy-N-methylpyrrolidine-2-carboxamide (Compound 3) (13.4 mg, 35.6% yield) as a white solid. ESI-MS: m/z $[M+H]^+$ calculated: 376.2. found: 376.2.

$^1$H NMR (400 MHz, DMSO-$d_6$) 1H NMR (400 MHz, DMSO-d6) δ 7.91 (q, J=4.6 Hz, 0H), 5.21 (d, J=10.4 Hz, 0H), 4.37-4.17 (m, 1H), 3.91 (s, 16H), 3.76 (dd, J=10.7, 4.2 Hz, 0H), 3.59 (dt, J=10.7, 1.7 Hz, 0H), 2.57 (d, J=4.6 Hz, 2H), 2.08 (s, 1H), 2.03-1.77 (m, 2H), 1.68 (d, J=11.7 Hz,

1H), 1.63-1.56 (m, 1H), 1.08 (ddt, J=34.5, 12.1, 6.7 Hz, 2H), 0.96-0.80 (m, 2H), 0.78-0.66 (m, 1H).

Example S4: Synthesis of (2S,4R)-1-((S)-3,3-dimethyl-2-(1H-1,2,3-triazol-1-yl)butanoyl)-4-hydroxy-N-methylpyrrolidine-2-carboxamide (Compound 4)

Synthesis was carried out following the solid phase synthesis scheme given below:

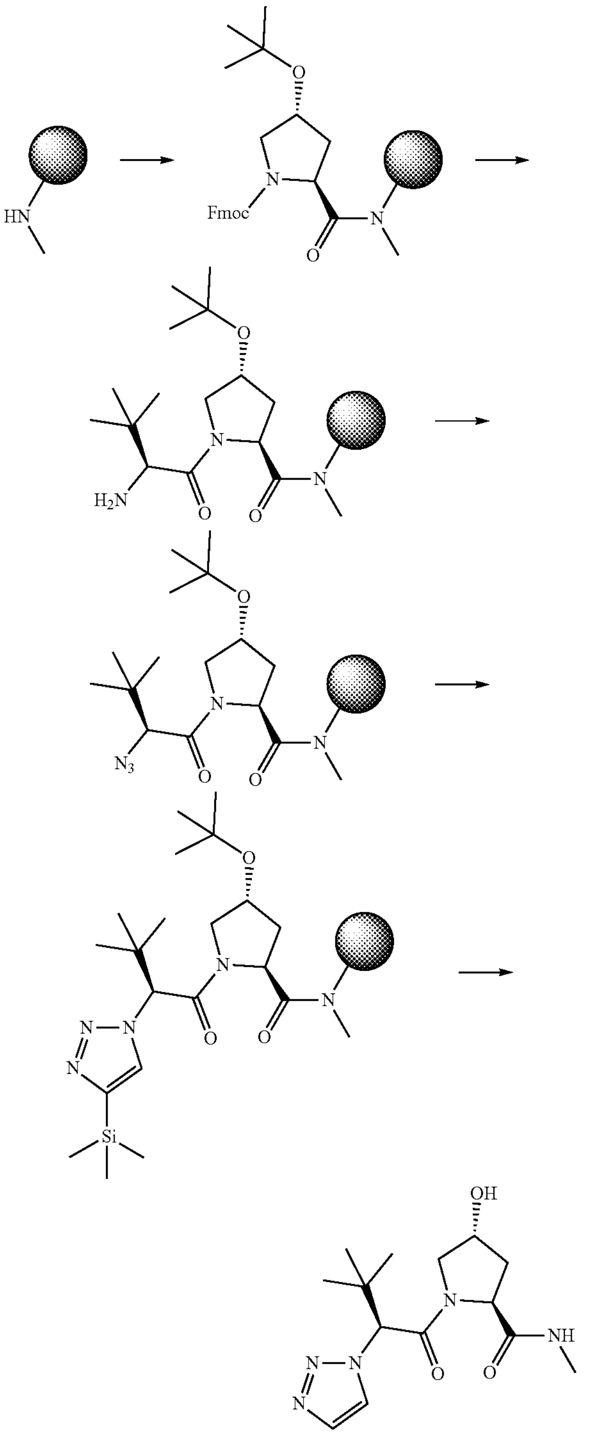

4

4-Formyl-3-methoxy-phenyloxymethyl polystyrene resin (0.100 mmol) was added to a plastic peptide synthesis vessel. 10 mL 1,2-Dichloroethane was added and the resin was allowed to swell for 30 min under nitrogen. The resin was drained under vacuum. Methylamine (DEA controlled substance, 2.0 M solution in tetrahydrofuran, 1 mL) was added to the plastic reactor and reacted for 2 hr at room temperature. The reactor was opened, and sodium cyanoborohydride (10.0 equiv.) and acetic acid (2 equiv.) were added to the reactor. The reactor was left opened on manifold, mixed by pipetting, and reacted overnight at RT. The resin was washed by 10 mL methanol, 10 mL N,N-Dimethylformamide, then 10 mL dichloromethane, and drained under vacuum. The washing procedure was repeated 3 times. A mixture of (2S,4R)-1-(((9H-fluoren-9-yl)methoxy)carbonyl)-4-(tert-butoxy)pyrrolidine-2-carboxylic acid (3.0 equiv.), Ethyl cyano(hydroxyimino)acetate (3.0 equiv.) and N,N'-Diisopropylcarbodiimide (3.0 equiv.) in 10 mL N,N-Dimethylformamide was added, and then the mixture was drawn into the synthesis vessel and reacted for 2 hr under nitrogen. The resin was washed with 10 mL N,N-Dimethylformamide, then 10 mL dichloromethane, and drained under vacuum. The washing procedure was repeated 3 times. 10 mL of 20% 4-methylpiperidine in N,N-Dimethylformamide were drawn into the reaction vessel, and reacted under nitrogen for 15 min to deprotect Fmoc group. The solvent was drained under vacuum, and the deprotection was repeated. The resin was washed with 10 mL N,N-Dimethylformamide, then 10 mL dichloromethane, and drained under vacuum. The washing procedure was repeated 3 times. A mixture of (S)-2-azido-3,3-dimethylbutanoic acid (3.0 equiv.), Ethyl cyano(hydroxyimino)acetate (3.0 equiv.) and N,N'-Diisopropylcarbodiimide (3.0 equiv.) in 10 mL N,N-Dimethylformamide was added, and the mixture was drawn into the synthesis vessel and reacted for 2 hr under nitrogen. The resin was washed with 10 mL N,N-Dimethylformamide, then 10 mL dichloromethane, and drained under vacuum. The washing procedure was repeated 3 times. Tetrakis(acetonitrile)copper(I) hexafluorophosphate (0.2 equiv.) was added directly into the peptide synthesis vessel to perform on-resin "click" reaction. The mixture of ethynyltrimethylsilane (5.0 equiv.) and N,N-Diisopropylethylamine (10.0 equiv.) in 10 mL N,N-Dimethylformamide (nitrogen purged) was drawn into the reaction vessel and reacted overnight under nitrogen. The resin was washed with 10 mL N,N-Dimethylformamide, then 10 mL dichloromethane, and drained under vacuum. A cleavage solution was prepared by mixing 5% Triisopropylsilane in 95% Trifluoroacetic acid. The solution was drawn into the reaction vessel and reacted for 1 hr. The trifluoroacetic acid was removed under vacuum. The remaining residue was mixed with 50 mL cold ether (−20° C.) to precipitate the compound.

The collected precipitate was purified by RP-HPLC (acetonitrile 30-60%/0.225% FA in water) to afford (2S,4R)-1-((S)-3,3-dimethyl-2-(1H-1,2,3-triazol-1-yl)butanoyl)-4-hydroxy-N-methylpyrrolidine-2-carboxamide (Compound 4) (14.1 mg, 45.4% yield) as a white solid. ESI-MS: m/z $[M+H]^+$ calculated: 310.2. found: 310.2.

$^1H$ NMR (400 MHz, DMSO-$d_6$) δ 8.27 (d, J=1.1 Hz, 1H), 7.94 (q, J=4.6 Hz, 1H), 7.73 (d, J=1.1 Hz, 1H), 5.53 (s, 1H), 4.34-4.26 (m, 3H), 2.59 (d, J=4.6 Hz, 3H), 2.10-1.89 (m, 2H), 1.82 (dtd, J=12.9, 8.7, 4.4 Hz, 2H), 0.98 (s, 9H).

Example S5: Synthesis of (2S,4R)-1-[2-(4-cyclopropyltriazol-1-yl)-2-(1-methylcyclohexyl)acetyl]-4-hydroxy-N-methyl-pyrrolidine-2-carboxamide (Compound 5)

Synthesis was carried out following the solid phase synthesis scheme given below:

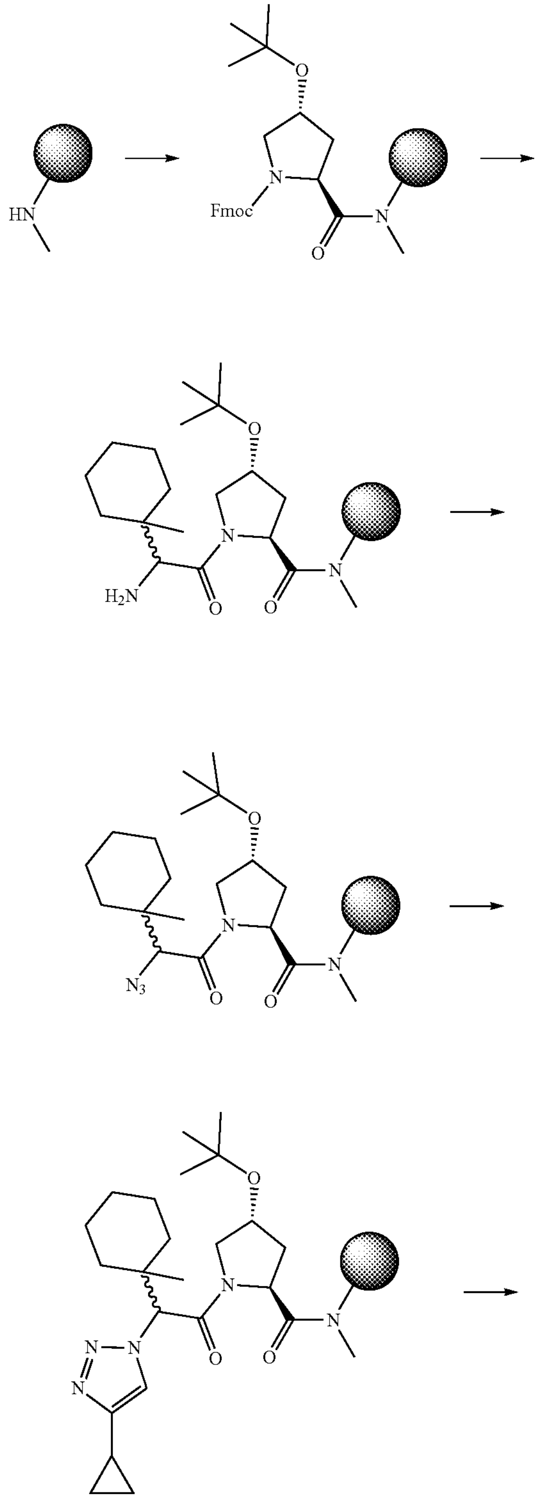

-continued

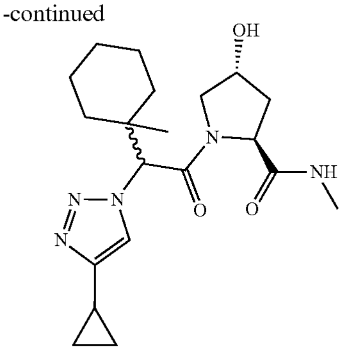

5

4-Formyl-3-methoxy-phenyloxymethyl polystyrene resin (0.100 mmol) was added to a plastic peptide synthesis vessel. 10 mL of 1,2-Dichloroethane were added and the resin was allowed to swell for 30 min under nitrogen. The resin was drained under vacuum. Methylamine (DEA controlled substance, 2.0 M solution in tetrahydrofuran, 1 mL) was added to the plastic reactor and the mixture was reacted for 2 hr at room temperature. The reactor was opened, and sodium cyanoborohydride (10.0 equiv.) and acetic acid (2 equiv.) were added to the reactor. The reactor was left opened on manifold, mixed by pipetting, and reacted overnight at RT. The resin was washed with 10 mL methanol, 10 mL N,N-Dimethylformamide, then 10 mL dichloromethane, and drained under vacuum. The washing procedure was repeated 3 times. A mixture of (2S,4R)-1-(((9H-fluoren-9-yl)methoxy)carbonyl)-4-(tert-butoxy)pyrrolidine-2-carboxylic acid (3.0 equiv.), 1-[Bis(dimethylamino)methylene]-1H-1,2,3-triazolo[4,5-b]pyridinium 3-oxide hexafluorophosphate (3.0 equiv.), 1-hydroxy-7-azabenzotriazole (3.0 equiv.), and N,N-Diisopropylethylamine (6.0 equiv.) in 10 mL N,N-Dimethylformamide was added, drawn into the synthesis vessel, and reacted for 2 hr under nitrogen. The resin was washed with 10 mL N,N-Dimethylformamide, then 10 mL dichloromethane, and drained under vacuum. The washing procedure was repeated 3 times. 10 mL 20% 4-methylpiperidine in N,N-Dimethylformamide were drawn into the reaction vessel and reacted under nitrogen for 15 min to deprotect Fmoc group. The solvent was drained under vacuum and the deprotection was repeated. The resin was washed with 10 mL N,N-Dimethylformamide, then 10 mL dichloromethane, and drained under vacuum. The washing procedure was repeated 3 times. A mixture of 2-((((9H-fluoren-9-yl)methoxy)carbonyl)amino)-2-(1-methylcyclohexyl)acetic acid (3.0 equiv.) and N,N'-Diisopropylcarbodiimide (3.0 equiv.) in 10 mL N,N-Dimethylformamide was added, and the mixture was drawn into the synthesis vessel and reacted for 2 hr under nitrogen. The resin was washed with 10 mL N,N-Dimethylformamide, then 10 mL dichloromethane, and drained under vacuum. The washing procedure was repeated 3 times. 10 mL of 20% 4-methylpiperidine in N,N-Dimethylformamide were drawn into the reaction vessel, and reacted under nitrogen for 15 min to deprotect Fmoc group. The solvent was drained under vacuum, and the deprotection was repeated. The resin was washed with 10 mL N,N-Dimethylformamide, then 10 mL dichloromethane, and drained under vacuum. The washing procedure was repeated 3 times. 1H-imidazole-1-sulfonyl azide hydrochloride (3.0 equiv.) and N,N-Diisopropylethylamine (6.0 equiv.) were mixed in dichloromethane. The mixture was drawn into the reaction vessel, and reacted under nitrogen for 1 hr to convert amine to azide. The solvent was drained under vacuum, and the deprotection was repeated. The resin was washed with 10 mL N,N-Dimethylformamide, then 10 mL dichloromethane, and drained under vacuum. The washing procedure was repeated 3 times. Tetrakis(acetonitrile)copper (I) hexafluorophosphate (0.2 equiv.) was added directly into the peptide synthesis vessel to perform on-resin "click" reaction. The mixture of ethynylcyclopropane (5.0 equiv.), N,N-Diisopropylethylamine (10.0 equiv.) in 10 mL N,N-Dimethylformamide (nitrogen purged) was drawn into the reaction vessel and reacted overnight under nitrogen. The resin was washed with 10 mL N,N-Dimethylformamide, then 10 mL dichloromethane, and drained under vacuum. A cleavage solution was prepared by mixing 5% Triisopropylsilane in 95% Trifluoroacetic acid. The solution was drawn into the reaction vessel and reacted for 1 hr. The trifluoroacetic acid was removed under vacuum. The remaining residue was mixed with 50 mL cold ether (−20° C.) to precipitate the compound. The collected precipitate was purified by RP-HPLC (acetonitrile 30-60%/0.05% TFA in water) to afford (2S,4R)-1-(2-(4-cyclopropyl-1H-1,2,3-triazol-1-yl)-2-(1-methylcyclohexyl)acetyl)-4-hydroxy-N-methylpyrrolidine-2-carboxamide (Compound 5) (2.0 mg, 2.0% yield) as a white solid. ESI-MS: m/z $[M+H]^+$ calculated: 390.2. found: 390.2. $^1H$ NMR (400 MHz, MeOD) δ 7.88 (d, J=33.3 Hz, 1H), 5.42 (d, J=21.9 Hz, 1H), 4.49-4.37 (m, 2H), 3.92-3.45 (m, 2H), 2.86-2.62 (m, 3H), 2.16 (dddd, J=15.4, 7.6, 3.7, 1.7 Hz, 1H), 2.08-1.90 (m, 2H), 1.64-1.17 (m, 10H), 1.14-1.04 (m, 3H), 1.02-0.89 (m, 2H), 0.86-0.70 (m, 2H).

Example S6: Synthesis of (2S,4R)-1-((S)-2-(4-cyclopropyl-1H-1,2,3-triazol-1-yl)-2-(tetrahydro-2H-pyran-4-yl)acetyl)-4-hydroxy-N-methylpyrrolidine-2-carboxamide (Compound 6)

Synthesis was carried out following the scheme given below:

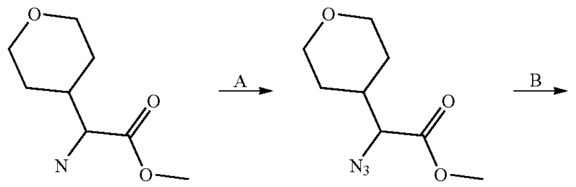

6a 6b

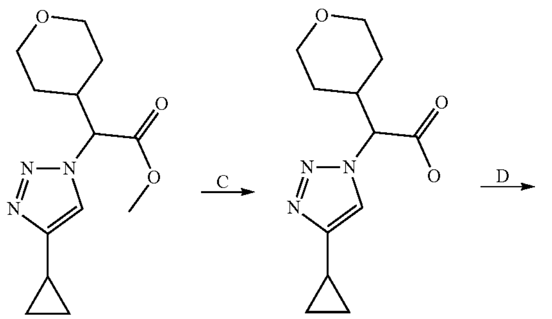

6c 6d

-continued

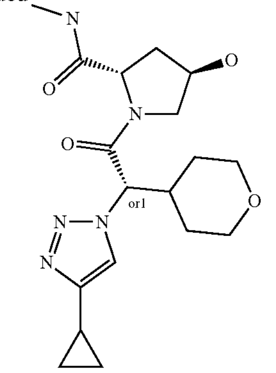

6

Preparation of Intermediate 6b

Preparation of $TfN_3$ $NaN_3$ (105 g, 1615 mmol, 20 eq) was added to a mixture of DCM (700 mL) and distilled water (434 mL) and cooled to 0-5° C. $Tf_2O$ (54.6 mL, 91.56 g, 324 mmol, 4 eq) was added dropwise slowly, keeping temperature below 5° C. Then the mixture was stirred for additional 2 hours at 5-10° C. and the layers were separated. Organic layer was washed with $NaHCO_3$ saturated solution (3×500 mL). Obtained $TfN_3$ was used as DCM solution immediately for the next step (Caution! Do not concentrate solution of $TfN_3$, it can spontaneously explode!).

Intermediate 6a (14 g, 80.8 mmol, 1 eq) was dissolved in MeOH (200 mL). $CuSO_4$ solution (20.16 mL, 0.8 mmol, 1 mol %, 0.04 M in distilled water) was added to the obtained solution, followed by the addition of TEA (16.8 mL, 12.2 g, 120.7 mmol, 1.5 eq). Freshly prepared solution of $TfN_3$ (app. 4 eq) was added dropwise at room temperature and then reaction mass left while stirring for 18 hours. Then the mixture was concentrated in vacuum and diluted with MTBE (500 mL), washed with ammonia aq solution (2×500 mL), washed with $NaHSO_4$ 1M aq solution (2×500 mL), dried over anhydrous sodium sulfate and concentrated under reduced pressure to obtain crude intermediate 6b (26 g) as yellow oil, which was used in the next step without additional purification.

$^1H$ NMR (500 MHz, DMSO-$d_6$) δ4.20 (d, J=5.7 Hz, 1H), 3.82 (dd, 2H), 3.72 (s, 3H), 3.33-3.21 (m, 2H), 2.05-1.96 (m, 1H), 1.48-1.29 (m, 4H). LCMS is not informative.

Preparation of Intermediate 6c

Crude intermediate 6b (26 g) was dissolved in mixture of THF (866 mL) and distilled water (216 mL). The resulting solution was cooled to 0-5° C. Cyclopropylacetylene (22.1 mL, 17.26 g, 261.1 mmol), sodium ascorbate (26 g, 131.2 mmol) and $CuSO_4$ pentahydrate (9.5 g, 38 mmol) was added consequently and the reaction mixture was left while stirring for 18 hour at room temperature. After that period mixture was concentrated in vacuum and diluted with MTBE (700 mL), washed with ammonia aq solution (2×500 mL), washed with brine (2×500 mL), dried over anhydrous sodium sulfate and concentrated under reduced pressure to obtain crude intermediate 6c (6.2 g, 23.4 mmol, 29% yield over 2 steps) as yellow oil, which was used in the next step without additional purification.

$^1$H NMR (600 MHz, DMSO-$d_6$) δ 7.95 (s, 1H), 5.24 (d, J=9.1 Hz, 1H), 3.82 (dd, J=11.2, 3.3 Hz, 1H), 3.76 (dd, J=11.0, 2.6 Hz, 1H), 3.67 (s, 3H), 3.27 (td, J=11.9, 2.0 Hz, 1H), 3.25-3.17 (m, 1H), 2.46-2.40 (m, 1H), 1.98-1.88 (m, 1H), 1.56 (dd, 1H), 1.28-1.20 (m, 2H), 0.97 (dd, J=12.9 Hz, 1H), 0.90-0.84 (m, 2H), 0.73-0.68 (m, 2H).

LCMS (Method 5-95 AB, ESI, 2 min): $R_T$=0.835 min, $[M+H]^+$=266.2.

Preparation of Intermediate 6d

Intermediate 6c (6.2 g, 23.4 mmol, 1 eq) was dissolved in THF (150 mL) and water (30 mL), then LiOH*$H_2O$ (1.47 g, 35 mmol, 1.49 eq) was added and the resulting solution was stirred at room temperature overnight. Then the mixture was concentrated under reduced pressure, the residue was diluted with water (300 mL) and washed with MTBE (300 mL), then the water layer was acidified to pH 2 with $NaHSO_4$ 1M solution, extracted with EtOAc (2×300 mL), and the organic layers were combined, dried over anhydrous sodium sulfate and concentrated in vacuum to obtain intermediate 6d (5.52 g, 22 mmol, 94% yield) as pale yellow solid.

1H NMR (400 MHz, DMSO-$d_6$) δ 13.53 (s, 1H), 7.90 (s, 1H), 5.06 (d, J=8.8 Hz, 1H), 3.78 (dd, J=26.3, 11.3 Hz, 2H), 3.32-3.13 (m, 2H), 2.42-2.31 (m, 1H), 1.96-1.85 (m, 1H), 1.61 (dd, J=13.5 Hz, 1H), 1.30-1.13 (m, 2H), 0.99 (dd, J=12.7 Hz, 1H), 0.90-0.81 (m, 2H), 0.74-0.63 (m, 2H).

LCMS (Method 5-95 AB, ESI, 2 min): $R_T$=0.943 min, $[M+H]^+$=252.2.

Preparation of Compound 6

Intermediate 6d (3.8 g, 15.1 mmol, 1 eq) was dissolved in dry DMF (50 mL), then (2S,4R)-4-hydroxy-N-methylpyrrolidine-2-carboxamide hydrochloride (3 g, 16.6 mmol, 1.1 eq), HATU (6.3 g, 16.6 mmol, 1.1 eq), DIPEA (6.59 mL, 4.9 g, 37.8 mmol, 2.5 eq) were added consequently and the reaction mixture was left under stirring for 18 hour at room temperature. The resulting mixture was concentrated in vacuum and diluted with water (100 mL), washed with EtOAc (2×200 mL) and the water layer was concentrated under reduced pressure.

Obtained crude residue (9.9 g) was purified by flash chromatography (1-Column: 330-330.0 g (5 bar). Eluent: MTBE/MeOH gradient 100/0% at 0 CV to 0/100% at 19.13 CV; elution steps: 1-0 CV 100/0%, 2-1 CV 100/0%, 3-3.52 CV 77/23%, 4-4.92 CV 77/23%, flow rate: 100.0 mL/min; 5-8.27 CV 77/23%, 6-13.10 CV 33/67%, 7-15.53 CV 33/67%, 8-15.53 CV 0/100%, 9-19.13 CV 0/100%, flow rate: 150.0 m/min. Detection: Channel 1: UV400: SIG1→205 nm; Channel 2: UV400:SIG2→235 nm. Temperature: ambient. 2—Column: 80 g-80.0 g (5 bar). Eluent: MeCN/MeOH gradient 100/0% at 0 CV to 0/100% at 19.84 CV; elution steps: 1-0 CV 100/0%, 2-1.25 CV 100/0%, 3-1.89 CV 94/6%, 4-2.50 CV 90/10%, 5-7.38 CV 90/10%, 6-7.38 CV 0/100%, flow rate: 100.0 mL/min; 7-7.42 CV 0/100%, 8-19.84 CV 0/100%, flow rate: 200.0 m/min. Detection: Channel 1: UV400:SIG1→205 nm; Channel 2: UV400:SIG2→235 nm. Temperature: ambient.) to afford crude (2 g), which contained approximately 50% (by HNMR and LC-MS) of the desired diastereoisomer. This mixture was purified by prep HPLC (Device (Mobile Phase, Column): SYSTEM. 15-15% 2-9 min water-acn; flow 30 mL/min (loading pump 4 ml/min acn); target mass 378; column sunfire 150*50 mm 5 um (R)) to obtain 538.5 mg of mixture, which contained approximately 80% (by HNMR and LC-MS) of desired diastereoisomer. 100 mg of this crude was sent for chiral separation (System: Chiralpak AD-H-I (250*20.5 mkm), Mobile phase: $CO_2$-MeOH, 70-30. Flow rate: 40 ml/min, makeup=15 ml/min, 40° C., Wavelength: 215 nm. Retention time(isomer 1(S))=2.42. Retention time (isomer 2(R))=4.54) to afford Compound 6 (49.86 mg, 0.132 mmol, 0.9% yield) as yellow oil.

$^1$H NMR (500 MHz, Chloroform-d) δ 7.68 (s, 1H), 6.37 (d, J=4.4 Hz, 1H), 5.24 (d, J=10.4 Hz, 1H), 4.59-4.55 (m, 1H), 4.43 (dd, J=7.9 Hz, 1H), 4.01 (dd, J=11.5, 3.3 Hz, 1H), 3.91 (dd, J=9.7 Hz, 2H), 3.81 (dd, J=10.9, 4.0 Hz, 1H), 3.40 (t, J=11.3 Hz, 1H), 3.30 (t, J=11.8 Hz, 1H), 2.83 (d, J=4.7 Hz, 3H), 2.45-2.40 (m, 1H), 2.32-2.25 (m, 2H), 2.14-2.09 (m, 1H), 1.98-1.90 (m, 1H), 1.87 (dd, J=12.9 Hz, 1H), 1.43-1.32 (m, 2H), 0.99-0.96 (m, 2H), 0.87-0.83 (m, 2H).

LCMS (Method 5-95 AB, ESI, 2 min): $R_T$=0.628 min, $[M+H]^+$=378.2.

Example S7: Synthesis of (2S,4R)-1-((S)-2-(4-cyclopropyl-1H-1,2,3-triazol-1-yl)-2-(piperidin-4-yl) acetyl)-4-hydroxy-N-methylpyrrolidine-2-carboxamide (Compound 7)

Synthesis was carried out by the scheme below:

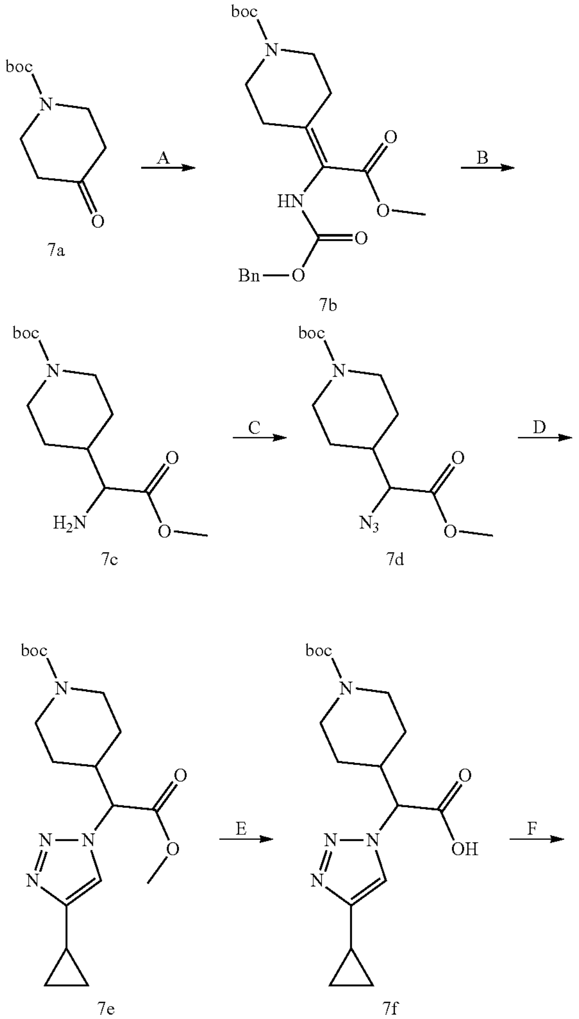

7a 7b 7c 7d 7e 7f

-continued

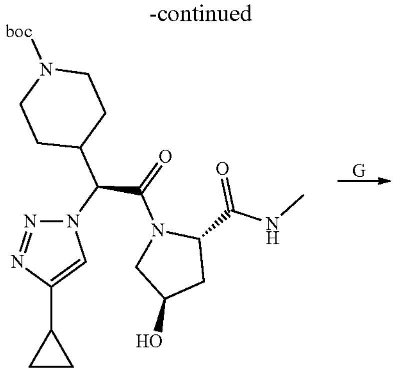

7g

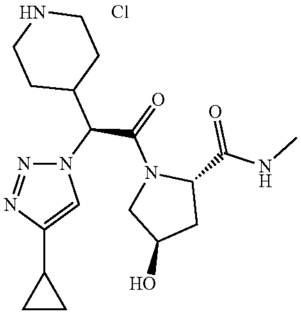

7

Preparation of Intermediate 7b

DBU (81 mL, 82.46 g, 541.8 mmol, 1.35 eq) was added dropwise to a solution of N-Cbz-2-phosphonoglycine Trimethyl Ester (164 g, 495 mmol, 1.23 eq) in dry THF (700 mL) at −20° C. under inert atmosphere of argon. Mixture was stirred for additional hour at −20° C. and intermediate 7a (80 g, 401.4 mmol, 1 eq) solution in dry THF (300 mL) was added dropwise thereto at the same temperature. After that, the resulting mixture was allowed to warm up to room temperature and left under stirring for 18 hours. When the solvent was removed under reduced pressure, the residue was dissolved in EtOAc (1000 mL) and the organic phase was washed with water (1000 mL), washed with 1M $NaHSO_4$ solution (2×1000 mL), and then dried over anhydrous sodium sulfate. The crude product obtained after evaporation of solvents was purified by crystallization from MTBE, and then triturated with hexane to give intermediate 7b (90.1 g, 222.7 mmol, 55.5% yield) as a slightly yellow solid.

$^1$H NMR (600 MHz, Chloroform-d) δ 7.39-7.28 (m, 5H), 6.04 (s, 1H), 5.12 (s, 2H), 3.74 (s, 3H), 3.52-3.43 (m, 4H), 2.91-2.80 (m, 2H), 2.42-2.35 (m, 2H), 1.45 (s, 9H).

LCMS (Method 5-95 AB, ESI, 2 min): $R_T$=1.148 min, $[M+H-(t-BuCO_2)]^+$=305.2.

Preparation of Intermediate 7c

Intermediate 7b (90.1 g, 222.7 mmol, 1 eq) was dissolved in dry THF (900 mL), then Pd on activated charcoal (15 g, 5% w/w, 7 mmol, 3.1 mol %) was added and the reaction mixture was hydrogenated under 1 atm. for 18 hours. Then the catalyst was removed by filtration and the filtrate was concentrated in vacuum. The obtained crude residue (60 g) was purified by silica gel chromatography (Column: 800 g-800.0 g (5 bar). Eluent: MTBE/MeOH gradient 100/0% at 0 CV to 0/100% at 16 CV; elution steps: 1-0 CV 100/0%, 2-2.15 CV 95/5%, 3-3.47 CV 95/5%, 4-3.63 CV 89/11%, 5-3.64 CV 89/11%, 6-5.48 CV 74/26%, 7-7.29 CV 74/26%, 8-16 CV 0/100. Flow rate: 150.0 mL/min. Detection: Channel 1: UV400:SIG1→205 nm; Channel 2: UV400: SIG2→235 nm. Temperature: ambient.) to afford Intermediate 7c (37.2 g, 136.6 mmol, 61.3% yield) as pale yellow oil.

$^1$H NMR (400 MHz, Chloroform-d) δ 4.20-4.04 (m, 2H), 3.71 (s, 3H), 3.31 (d, J=5.7 Hz, 1H), 2.72-2.55 (m, 2H), 1.81-1.71 (m, 1H), 1.66-1.57 (m, 1H), 1.56-1.48 (m, 1H), 1.42 (s, 10H), 1.39-1.21 (m, 3H).

LCMS (Method 5-95 AB, ESI, 2 min): $R_T$=0.921 min, $[M+H-(t-Bu)]^+$=217.2.

Preparation of Intermediate 7d

Preparation of $TfN_3$. $NaN_3$ (56.15 g, 863.8 mmol, 7.5 eq) was added to the mixture of DCM (739 mL) and distilled water (471 mL) and cooled to 0-5° C. $Tf_2O$ (58.2 mL, 97.6 g, 346 mmol, 3 eq) was added dropwise slowly, keeping temperature below 5° C. The resulting mixture was stirred for additional 2 hours at 5-10° C., then layers were separated. Organic layer was washed with $NaHCO_3$ saturated solution (3×500 mL). Obtained $TfN_3$ was used as DCM solution immediately for the next step (Caution! Do not concentrate solution of TfN3, it can spontaneously explode!).

Intermediate 7c (31.4 g, 115.3 mmol, 1 eq) was dissolved in MeOH (300 mL), $CuSO_4$ solution (28.75 mL, 1.15 mmol, 1 mol %, 0.04 M in distilled water) was added to the obtained solution, followed by the addition of TEA (24 mL, 17.4 g, 172.4 mmol, 1.5 eq). Freshly prepared $TfN_3$ solution (app. 3 eq) was added dropwise at room temperature and then the reaction mixture was left under stirring for 18 hours. The resulting mixture was concentrated in vacuum and diluted with MTBE (700 mL), washed with ammonia aq solution (2×500 mL), washed with $NaHSO_4$ 1M aq solution (2×500 mL), dried over anhydrous sodium sulfate and evaporated under reduced pressure to obtain crude intermediate 7d (32 g, 107.27 mmol, 93% yield) as yellow oil, which was used in the next step without additional purification.

$^1$H NMR (400 MHz, DMSO-$d_6$) δ 4.23 (d, J=5.6 Hz, 1H), 3.97-3.84 (m, 2H), 3.70 (s, 3H), 2.79-2.54 (m, 2H), 1.98-1.86 (m, 1H), 1.47 (dd, J=23.8, 13.4 Hz, 2H), 1.34 (s, 9H), 1.21-1.07 (m, 2H).

LCMS (Method 5-95 AB, ESI, 2 min): $R_T$=1.327 min, $[M+H-(t-Bu)]^+$=243.2.

Preparation of Intermediate 7e

Intermediate 7d (32 g, 107.27 mmol, 1 eq) was dissolved in mixture of THF (800 mL) and distilled water (200 mL) and the obtained solution was cooled to 0-5° C. Cyclopropylacetylene (18 mL, 14 g, 212.7 mmol, 2 eq), sodium ascorbate (21.2 g, 107.27 mmol, 1 eq) and $CuSO_4$ pentahydrate (2.7 g, 10.8 mmol, 0.1 eq) were added consequently and reaction mixture was left while stirring for 18 hour at room temperature. The resulting mixture was concentrated in vacuum and diluted with MTBE (700 mL), washed with ammonia aq solution (2×500 mL), brine (2×500 mL), dried over anhydrous sodium sulfate and evaporate under reduced pressure to obtain crude intermediate 7e (39 g, 107 mmol, 99% yield) as yellow oil, which was used in the next step without additional purification.

$^1H$ NMR (500 MHz, DMSO-$d_6$) δ 7.95 (s, 1H), 5.31 (d, J=8.8 Hz, 1H), 3.92 (dd, J=30.8, 11.0 Hz, 2H), 3.70 (s, 3H), 2.79-2.60 (m, 1H), 2.46-2.33 (m, 1H), 1.99-1.90 (m, 1H), 1.69-1.62 (m, 1H), 1.36 (s, 10H), 1.09-1.00 (m, 2H), 0.94-0.86 (m, 2H), 0.78-0.68 (m, 2H).

LCMS (Method 5-95 AB, ESI, 2 min): $R_T$=1.342 min, $[M+H]^+$=365.2, $[M+H-(t-Bu)]^+$=309.2.

Preparation of Intermediate 7f

Intermediate 7e (39 g, 107 mmol, 1 eq) was dissolved in THF (350 mL) and water (70 mL), then LiOH*$H_2O$ (6.7 g, 159.5 mmol, 1.49 eq) was added and the resulting solution was stirred at room temperature overnight. The resulting mixture was concentrated under reduced pressure, the residue was diluted with water (300 mL) and washed with MTBE (300 mL), then the water layer was acidified to pH 2 with $NaHSO_4$ 1M solution, extracted with EtOAc (2×300 mL), the organic layers were combined, dried over anhydrous sodium sulfate and evaporated in vacuum to obtain intermediate 7f (33 g, 94.2 mmol, 88% yield) as pale yellow solid.

$^1H$ NMR (500 MHz, DMSO-$d_6$) δ 13.55 (s, 1H), 7.89 (s, 1H), 5.12 (d, J=8.5 Hz, 1H), 3.90 (dd, J=29.8, 13.2 Hz, 2H), 2.75-2.57 (m, 2H), 2.40-2.29 (m, 1H), 1.96-1.88 (m, 1H), 1.73-1.67 (m, 1H), 1.35 (s, 9H), 1.17-0.96 (m, 3H), 0.92-0.82 (m, 2H), 0.77-0.65 (m, 2H).

LCMS (Method 5-95 AB, ESI, 2 min): $R_T$=1.186 min, $[M+H]^+$=351.2, $[M+H-(t-Bu)]^+$=295.0.

Preparation of Intermediate 7 g

Intermediate 7f (16 g, 45.7 mmol, 1 eq) was dissolved in dry DMF (200 mL), then (2S,4R)-4-hydroxy-N-methylpyrrolidine-2-carboxamide hydrochloride (9.1 g, 50.4 mmol, 1.1 eq), HATU (19.2 g, 50.5 mmol, 1.1 eq), DIPEA (20 mL, 14.8 g, 114.9 mmol, 2.5 eq) were added in that order and reaction mixture was left while stirring for 18 hour at room temperature. After that period mixture was concentrated in vacuum and diluted with EtOAc (1000 mL), washed with $NaHCO_3$ saturated aq solution (1000 mL), $NaHSO_4$ 1M aq solution (2×1000 mL), dried over anhydrous sodium sulfate and concentrated under reduced pressure.

Obtained crude residue (32.2 g) was purified by silica gel chromatography (Column: 330 g-330.0 g (5 bar). Eluent: Hexane/IPA+MeOH (2:1) gradient 100/0% at 0 CV to 0/100% at 23.47 CV; elution steps: 1-0 CV 100/0%, 2-1.33 CV 99/1%, 3-1.34 CV 84/16%, 4-4.20 CV 84/16%, 5-4.21 CV 80/20%, 6-4.22 CV 77/23%, 7-11.62 CV 50/50%, 8-14.34 CV 50/50%, 9-14.34 CV 0/100%, 10-23.47 CV 0/100%. Flow rate: 150.0 m/min. Detection: Channel 1: UV400:SIG1→205 nm; Channel 2: UV400:SIG2→215 nm; Channel 3: UV400:SIG3→235 nm. Temperature: ambient.) to afford crude (3 g), which contained approximately 70% (by HNMR) of desired diastereoisomer. 2 g of this crude was sent for chiral separation (System: Column OD-H (250*20, 5 mkm), Mobile phase: Hexane-IPA-MeOH, 90-5-5. Flow rate: 22 mL/min. 20° C. Wavelength: 205 nm, 225 nm. Retention time (desired isomer)=12.6. Retention time (side isomer)=15.7.) to obtain intermediate 7 g (1.32 g, 2.77 mmol, 6% yield) as pale beige solid.

$^1H$ NMR (400 MHz, Chloroform-d) δ 7.64 (s, 1H), 6.52 (d, J=3.3 Hz, 1H), 5.18 (d, J=10.5 Hz, 1H), 4.55-4.50 (m, 1H), 4.38 (dd, J=7.8 Hz, 1H), 4.21-4.11 (m, 1H), 4.10-4.01 (m, 1H), 3.89-3.71 (m, 2H), 2.81 (d, J=4.8 Hz, 3H), 2.74-2.67 (m, 1H), 2.61-2.53 (m, 1H), 2.31 (dd, J=19.4, 8.2 Hz, 1H), 2.24-2.16 (m, 1H), 2.14-2.03 (m, 1H), 1.97-1.86 (m, 2H), 1.41 (s, 9H), 1.26-1.20 (m, 1H), 1.16-1.10 (m, 1H), 1.05-0.90 (m, 3H), 0.90-0.76 (m, 3H).

LCMS (Method 5-95 AB, ESI, 2 min): $R_T$=0.952 min, $[M+H]^+$=477.4, $[M+H-(t-Bu)]^+$=421.2.

Preparation of Compound 7

Intermediate 7 g (1.32 g, 2.77 mmol, 1 eq) was dissolved in MeOH (20 mL), HCl (4.95 mL, 8.71 mmol, 3 eq, 1.76M in $Et_2O$) was added thereto and the obtained solution was stirred for 12 hours at room temperature. The resulting mixture was evaporated in vacuum at 40° C. to obtain Compound 7 (1.11 g, 2.69 mmol, 97% yield) as white solid.

$^1H$ NMR (500 MHz, Chloroform-d) δ 8.39 (s, 1H), 5.73 (d, J=9.6 Hz, 1H), 4.47-4.42 (m, 1H), 4.42-4.33 (m, 1H), 3.83 (dd, J=11.1, 3.7 Hz, 1H), 3.77 (dd, J=10.8 Hz, 1H), 3.43-3.37 (m, 1H), 3.37-3.30 (m, 1H), 3.01-2.88 (m, 2H), 2.68 (d, J=4.0 Hz, 3H), 2.65-2.60 (m, 1H), 2.25-2.12 (m, 2H), 2.10-2.01 (m, 1H), 1.99-1.89 (m, 1H), 1.62 (p, J=12.8 Hz, 2H), 1.45-1.39 (m, 1H), 1.15-1.10 (m, 2H), 0.95-0.86 (m, 2H).

LCMS (Method 5-95 AB, ESI, 2 min): $R_T$=0.637 min, $[M+H]^+$=377.4.

Example S8: Synthesis of (2S,4R)-1-((S)-2-(4-cyclopropyl-1H-1,2,3-triazol-1-yl)-2-(1-methylpiperidin-4-yl)acetyl)-4-hydroxy-N-methylpyrrolidine-2-carboxamide (Compound 8)

Synthesis was carried out by the scheme below:

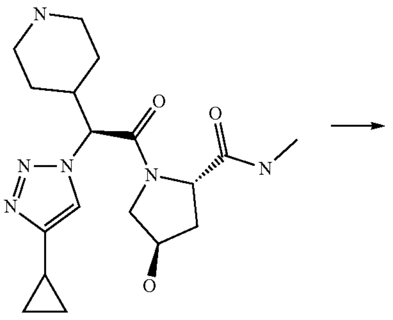

7

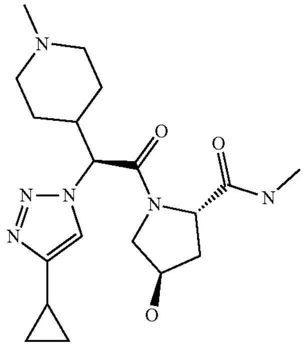

8

Compound 7 (0.2 g, 0.48 mmol, 1 eq) was dissolved in MeOH (4 mL), then paraform (0.108 g, 3.6 mmol, 7.5 eq), TEA (0.334 mL, 0.242 g, 2.4 mmol, 5 eq), HOAc (0.274 mL, 0.288 g, 4.8 mmol, 10 eq), $NaBH_3CN$ (0.150 g, 2.4 mmol, 5 eq) were added consequently and the obtained mixture was stirred for 16 hours at room temperature. The resulting mixture was carefully quenched with TFA (2 mL), stirred for additional 1 hour and sent for prep HPLC purification (Device (Mobile Phase, Column): SYSTEM 0-25% 0.5-6.5 min water-acetonitrile; flow 30 ml/min (loading pump 4 ml/min $H_2O$+TFA); target mass 391; column SunFireC18 100×19 mm 5 um (R)) to obtain Compound 8 (0.1283 g, 0.25 mmol, 53% yield) as yellow oil.

$^1$H NMR (400 MHz, Methanol-$d_4$) δ 7.82 (s, 1H), 5.41 (d, J=9.8 Hz, 1H), 4.48-4.43 (m, 1H), 4.40 (dd, J=8.3 Hz, 1H), 3.86 (dd, J=10.9, 4.0 Hz, 1H), 3.66 (dd, J=10.9 Hz, 1H), 3.54 (dd, J=12.8 Hz, 1H), 3.45 (dd, J=12.3 Hz, 1H), 3.03-2.87 (m, 2H), 2.83 (s, 3H), 2.73 (s, 3H), 2.59-2.47 (m, 1H), 2.27-2.12 (m, 2H), 2.02-1.88 (m, 3H), 1.58 (pd, J=13.3, 4.1 Hz, 2H), 1.33 (dd, J=15.1 Hz, 1H), 1.00-0.90 (m, 2H), 0.78-0.72 (m, 2H).

LCMS (Method 5-95 AB, ESI): $R_T$=0.756 min, $[M+H]^+$=391.2.

Example S9: Synthesis of (2S,4R)-1-((S)-2-(1-acetylpiperidin-4-yl)-2-(4-cyclopropyl-1H-1,2,3-triazol-1-yl)acetyl)-4-hydroxy-N-methylpyrrolidine-2-carboxamide (Compound 9)

Synthesis was carried out by the scheme below:

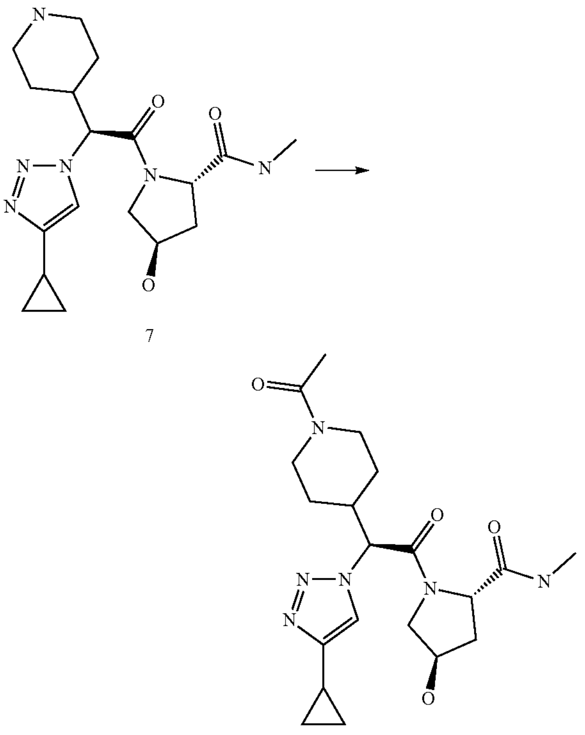

7

9

Compound 7 (0.31 g, 0.75 mmol, 1 eq) was dissolved in DMF (3 mL), then pyridine (0.182 mL, 0.178 g, 2.25 mmol, 3 eq) and $Ac_2O$ (0.091 mL, 0.098 g, 0.96 mmol, 1.3 eq) were consequently and the obtained mixture was stirred for 16 hours at room temperature. Then the reaction mixture was purified by prep HPLC purification (Device (Mobile Phase, Column): SYSTEM 15-15% 0.5-6 min water-acn; flow 30 ml/min (loading pump 4 ml/min $H_2O$); target mass 419; column SunFireC18 100×19 mm 5 um (R)) to obtain Compound 9 (0.0778 g, 0.19 mmol, 25% yield) as white solid.

$^1$H NMR (400 MHz, Chloroform-d) δ 7.67 (s, 1H), 6.70 (s, 1H), 5.25-5.14 (m, 1H), 4.67-4.47 (m, 2H), 4.38 (dd, J=8.0 Hz, 1H), 3.87 (dd, J=11.7 Hz, 1H), 3.81-3.68 (m, 2H), 3.68-3.35 (m, 2H), 2.99 (dt, J=45.5, 12.8 Hz, 1H), 2.81 (s, 3H), 2.58-2.32 (m, 2H), 2.17-2.08 (m, 2H), 2.03 (d, J=11.1 Hz, 3H), 1.99-1.85 (m, 2H), 1.29-1.04 (m, 3H), 0.99-0.90 (m, 2H), 0.84-0.75 (m, 2H).

LCMS (Method 5-95 AB, ESI, 6 min): $R_T$=1.268 min, $[M+H]^+$=419.0.

Example S10: Synthesis of (2S,4R)-1-((S)-2-(4-cyclopropyl-1H-1,2,3-triazol-1-yl)-2-(1-(methylsulfonyl)piperidin-4-yl)acetyl)-4-hydroxy-N-methylpyrrolidine-2-carboxamide (Compound 10)

Synthesis was carried out by the scheme below:

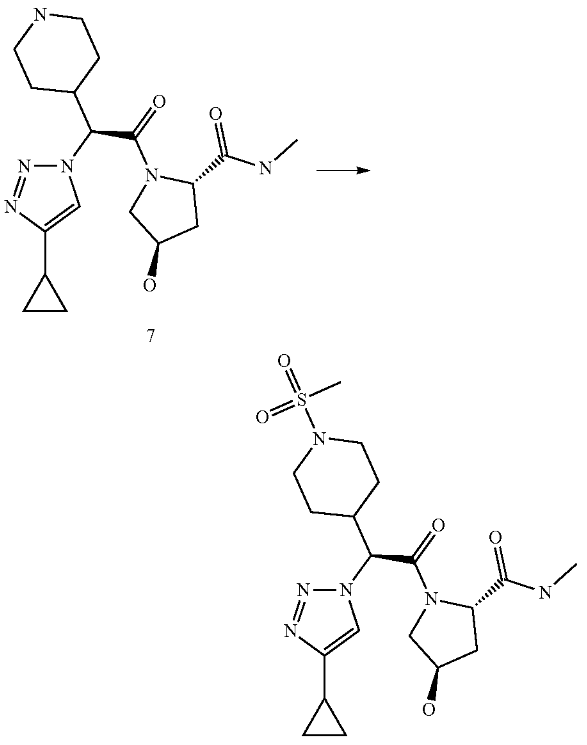

7

10

Compound 7 (0.3 g, 0.73 mmol, 1 eq) was dissolved in DMF (5 mL), then DIPEA (0.393 mL, 0.291 g, 2.26 mmol, 3.1 eq) and MsCl (0.062 mL, 0.092 g, 0.8 mmol, 1.1 eq) were added consequently and the resulting mixture was stirred for 16 hours at room temperature. Then the mixture was purified by prep HPLC purification (Device (Mobile Phase, Column): SYSTEM 0-25% 0.5-6.5 min water-acetonitrile; flow 30 ml/min (loading pump 4 ml/min $H_2O$); target mass 377; 455; column SunFireC18 100×19 mm 5 um (R)) to obtain Compound 10 (0.0778 g, 0.19 mmol, 25% yield) as yellow solid.

$^1$H NMR (500 MHz, Methanol-$d_4$) δ 7.83 (s, 1H), 5.40 (d, J=10.5 Hz, 1H), 4.51-4.46 (m, 1H), 4.40 (dd, J=8.5 Hz, 1H), 3.92 (dd, J=11.0, 4.0 Hz, 1H), 3.77 (dd, J=9.2 Hz, 2H), 3.68 (dd, J=12.1 Hz, 1H), 2.82 (s, 3H), 2.75 (s, 3H), 2.72 (d, J=11.6 Hz, 1H), 2.67 (td, J=12.1, 2.5 Hz, 1H), 2.44-2.31 (m, 1H), 2.21-2.13 (m, 1H), 2.11 (dd, J=13.0 Hz, 1H), 2.05-1.93 (m, 2H), 1.47 (qd, J=12.9, 4.3 Hz, 1H), 1.37 (qd, J=12.4, 3.9 Hz, 1H), 1.15 (dd, J=13.4 Hz, 1H), 0.99-0.93 (m, 2H), 0.80-0.74 (m, 2H).

LCMS (Method 5-95 AB, ESI): $R_T$=2.202 min, $[M+H]^+$=455.4.

Example S11: Synthesis of (2S,4R)-1-((S)-2-(4-cyclopropyl-1H-1,2,3-triazol-1-yl)-3-methylbutanoyl)-4-hydroxy-N-methylpyrrolidine-2-carboxamide (Compound 11) and (2S,4R)-1-((R)-2-(4-cyclopropyl-1H-1,2,3-triazol-1-yl)-3-methylbutanoyl)-4-hydroxy-N-methylpyrrolidine-2-carboxamide (Compound 12)
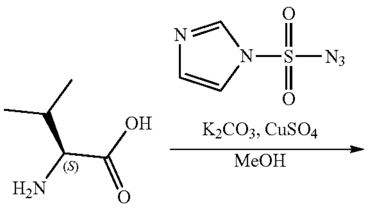
11a
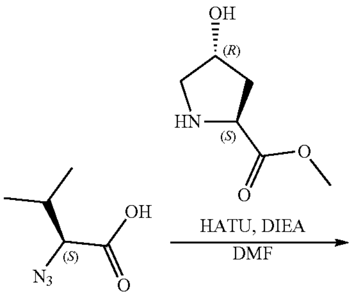
11b
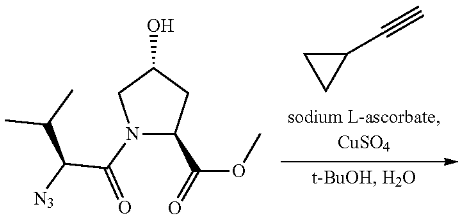
11c
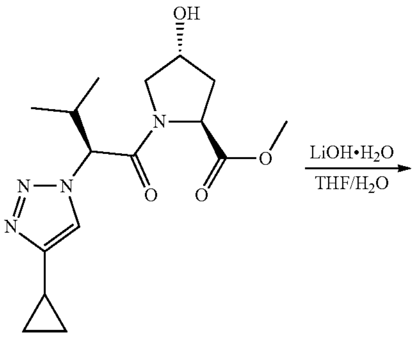
11d
-continued
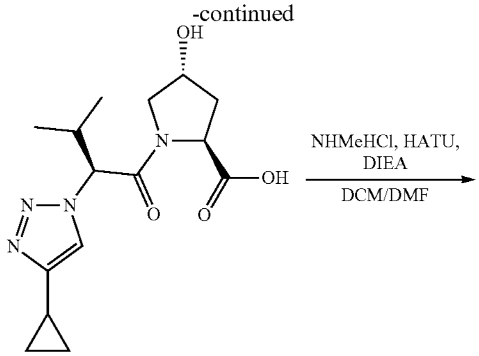
11e
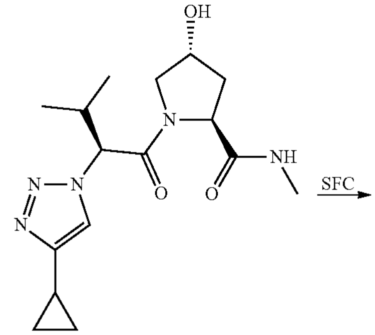
11f
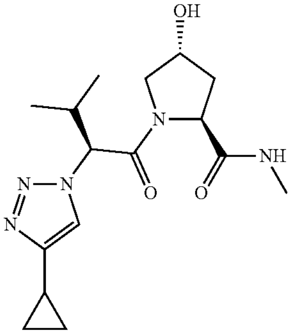
11
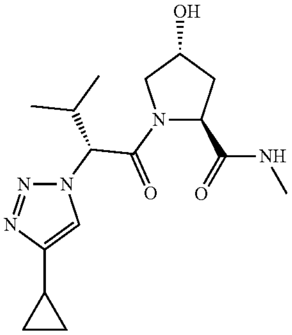
12

Preparation of Intermediate 11b

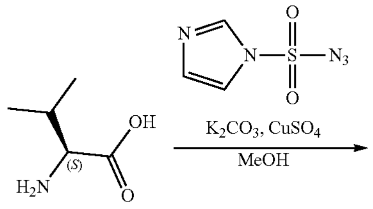

11a 11b

To a mixture of (S)-2-amino-3-methylbutanoic acid (1.00 g, 8.54 mmol), potassium carbonate (2.97 g, 21.3 mmol) and copper sulfate (136.6 mg, 0.85 mmol) in methanol (20 mL) was added 1H-imidazole-1-sulfonyl azide (1.79 g, 8.54 mmol) at 25° C. The reaction was stirred for 16 h and diluted with water (60 mL). The methanol was removed under reduced pressure and the aqueous residue was washed with ethyl acetate (100 mL). The aqueous was then adjusted to pH=5 by addition of potassium bisulfate and extracted with ethyl acetate (2×150 mL). The combined organic layers were dried and concentrated in vacuum to give crude (S)-2-azido-3-methylbutanoic acid (1.20 g, 98.2% yield) as a yellow oil.

Preparation of intermediate 11c

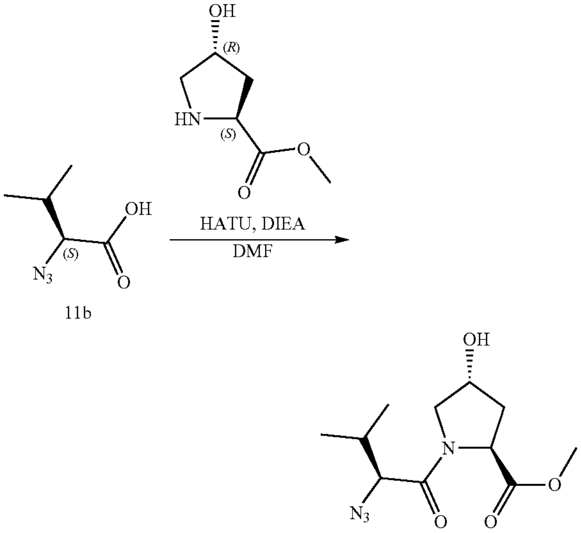

11b

11c

A mixture of (S)-2-azido-3-methylbutanoic acid (1.00 g, 6.99 mmol), (2S, 4R)-methyl 4-hydroxypyrrolidine-2-carboxylate (1.01 g, 6.99 mmol), N,N-diisopropylethylamine (5.77 mL, 34.9 mmol) and (1-[Bis(dimethylamino)methylene]-1H-1,2,3-triazolo[4,5-b]pyridinium 3-oxid hexafluorophosphate (2.66 g, 6.99 mmol) in N,N-dimethylformamide (10 mL) was stirred at 25° C. for 3 h and diluted with water (50 mL). The mixture was extracted with ethyl acetate (3×50 mL). The combined organic layers were washed with brine (50 mL), dried and concentrated to afford crude (2S, 4R)-methyl 1-((S)-2-azido-3-methylbutanoyl)-4-hydroxypyrrolidine-2-carboxylate (1.00 g, 53% yield) as a blue oil.

Preparation of Intermediate 11d

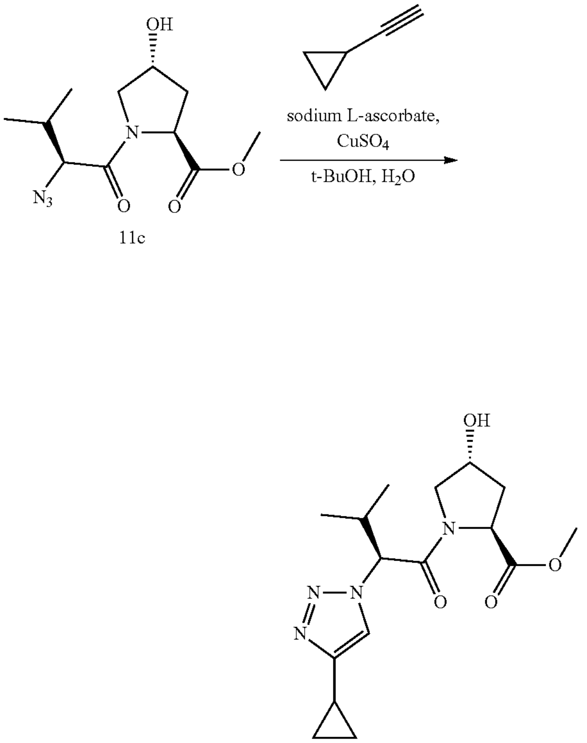

11c

11d

To a solution of sodium L-ascorbate (2.93 g, 14.8 mmol) in water (20 mL) and tert-butyl alcohol (20 mL) was added ethynylcyclopropane (0.31 mL, 3.7 mmol), copper sulfate pentahydrate (1.51 g, 4.81 mmol) and (2S,4R)-methyl 1-((S)-2-azido-3-methylbutanoyl)-4-hydroxypyrrolidine-2-carboxylate (1.00 g, 3.70 mmol). The reaction was stirred at 25° C. for 16 h and concentrated under reduced pressure. The residue was purified by column chromatography (silica gel, 100-200 mesh, 0-4% ethyl acetate in petroleum ether) to afford (2S,4R)-methyl 1-((S)-2-(4-cyclopropyl-1H-1,2,3-triazol-1-yl)-3-methylbutanoyl)-4-hydroxypyrrolidine-2-carboxylate (1.10 g, 88.4% yield) as a yellow solid.

Preparation of Intermediate 11e

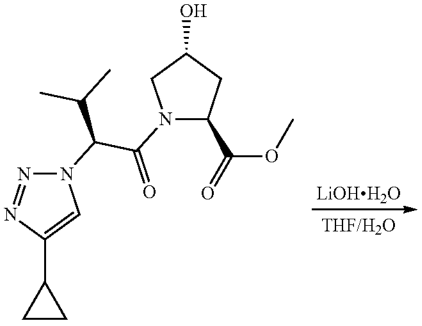

11d

-continued

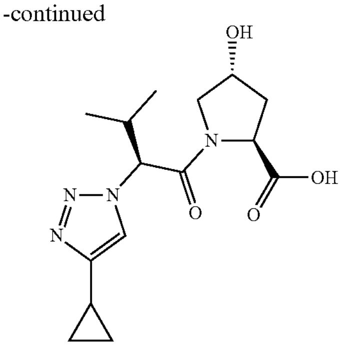

11e

To a solution of (2S,4R)-methyl 1-((S)-2-(4-cyclopropyl-1H-1,2,3-triazol-1-yl)-3-methylbutanoyl)-4-hydroxypyrrolidine-2-carboxylate (300 mg, 0.89 mmol) in water (5 mL) and tetrahydrofuran (10 mL) were added lithium hydroxide monohydrate (37.42 mg, 0.89 mmol). The reaction was stirred at 25° C. for 16 h. The reaction mixture was partitioned between ethyl acetate (20 mL) and water (15 mL). The aqueous layer was adjusted to pH=4 by addition of hydrochloric acid (2 M) and extracted with ethyl acetate (3×50 mL). The combined organic layers were dried and concentrated under reduced pressure to give crude (2S,4R)-1-((S)-2-(4-cyclopropyl-1H-1,2,3-triazol-1-yl)-3-methylbutanoyl)-4-hydroxypyrrolidine-2-carboxylic acid (200 mg, 69.6% yield) as a light yellow oil.

Preparation of Intermediate 11f

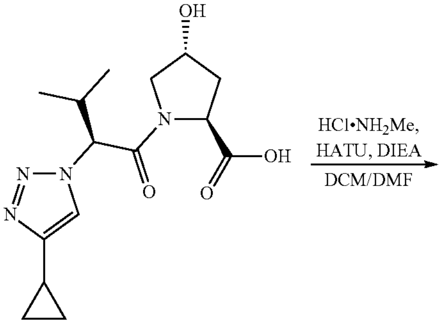

11e

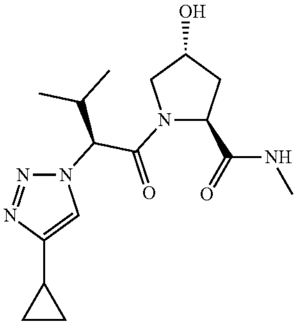

11f

A mixture of (2S, 4R)-1-((S)-2-(4-cyclopropyl-1H-1,2,3-triazol-1-yl)-3-methylbutanoyl)-4-hydroxypyrrolidine-2-carboxylic acid (100 mg, 0.31 mmol), N,N-diisopropylethylamine (0.22 mL, 1.24 mmol), methanamine hydrochloride (20.8 mg, 0.31 mmol) and (1-[Bis(dimethylamino)methylene]-1H-1,2,3-triazolo[4,5-b] pyridinium 3-oxid hexafluorophosphate (0.15 g, 0.40 mmol) in N,N-dimethylformamide (5 mL) was stirred at 25° C. for 16 h and concentrated under reduced pressure. The residue was purified by RP-HPLC (acetonitrile 10-40/0.075% TFA in water) to afford (2S, 4R)-1-((S)-2-(4-cyclopropyl-1H-1,2,3-triazol-1-yl)-3-methylbutanoyl)-4-hydroxy-N-methylpyrrolidine-2-carboxamide (50.0 mg, 48.1% yield) as a white solid.

Preparation of Compound 11 and Compound 12

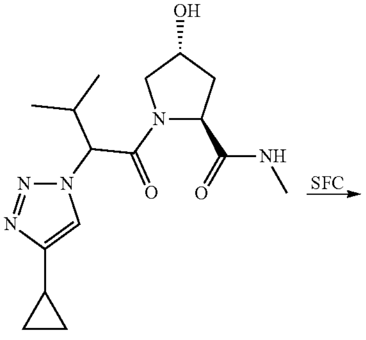

11f

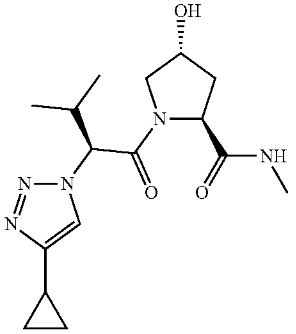

11

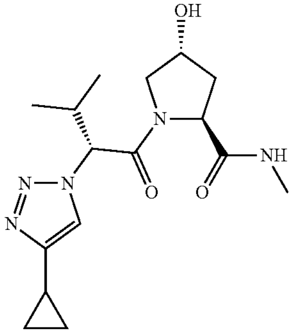

12

The above diastereomeric mixture was further separated by chiral SFC to give a first-eluting Isomer A and a second-eluting Isomer B:

Isomer A: (Peak 1, retention time=3.089 min) (28.1 mg, 54.6% yield) as a white solid. $^1H$ NMR (400 MHz, $CDCl_3$) δ 7.63 (s, 1H), 6.61 (br d, J=4.4 Hz, 1H), 5.17 (d, J=10.0 Hz, 1H), 4.54 (br s, 1H), 4.44 (t, J=7.6 Hz, 1H), 3.94 (br d, J=10.4 Hz, 2H), 3.79-3.76 (m, 1H), 2.82 (d, J=4.8 Hz, 3H), 2.71 (d, J=4.8 Hz, 1H), 2.48-2.46 (m, 1H), 2.31-2.30 (m, 1H), 2.01-2.10 (m, 1H), 1.89-1.96 (m, 1H), 1.08 (d, J=6.8

Hz, 3H), 0.91-0.98 (m, 2H), 0.75-0.84 (m, 5H). LCMS (Method 5-95 AB, ESI): $R_T$=0.796 min, $[M+H]^+$=336.1.

Isomer B: (Peak 2, retention time=3.461 min) (16.7 mg, 33% yield) as a white solid. $^1$H NMR (400 MHz, $CDCl_3$) δ 7.55 (s, 1H), 6.60 (br s, 1H), 5.15 (d, J=9.2 Hz, 1H), 4.62-4.77 (m, 1H), 4.45-4.59 (m, 1H), 3.60-3.76 (m, 1H), 3.55-3.52 (m, 1H), 2.91 (d, J=4.8 Hz, 1H), 2.74 (d, J=4.8 Hz, 3H), 2.46-2.57 (m, 1H), 2.31-2.41 (m, 1H), 2.11-2.25 (m, 1H), 1.89-2.04 (m, 1H), 1.05 (d, J=6.4 Hz, 2H), 0.91-1.03 (m, 3H), 0.79-0.87 (m, 2H), 0.72-0.75 (m, 1H), 0.75 (d, J=6.8 Hz, 1H), 0.68 (d, J=6.8 Hz, 1H). LCMS (Method 5-95 AB, ESI): $R_T$=0.616 min, $[M+H]^+$=336.1.

Example S12: Synthesis of (3R,5S)-1-((S)-2-(4-cyclopropyl-1H-1,2,3-triazol-1-yl)-3,3-dimethylbutanoyl)-5-(methylcarbamoyl)pyrrolidin-3-yl Acetate (Compound 13)

Synthesis was carried out following the scheme given below:

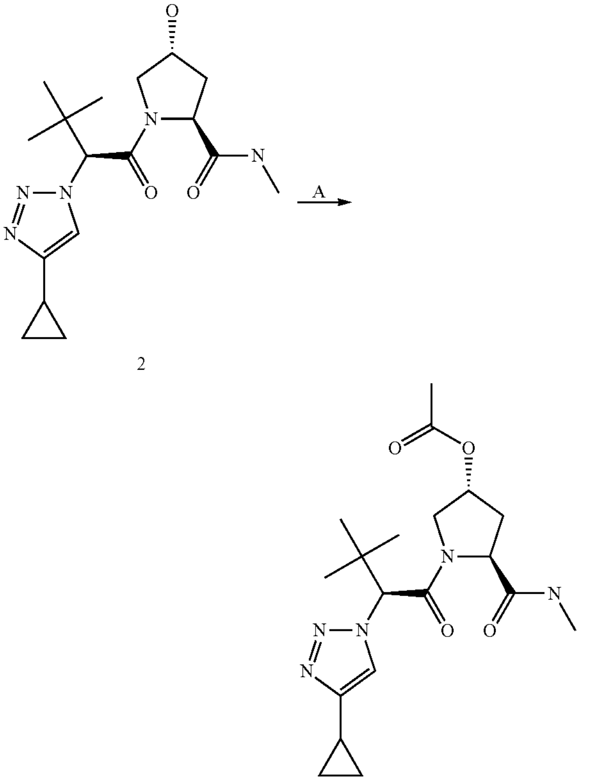

2

13

To a solution of Compound 2 (50 mg, 0.143 mmol), 4-dimethylaminopyridine (1.74 mg, 0.0143 mmol) and N,N-diisopropylethylamine (29 μL, 0.172 mmol) in dichloromethane (5 ml) cooled at 0° C., acetyl chloride (12.35 μL, 0.172 mmol) was added. The resulting mixture was stirred for 1.5 hours at 0° C. and left stirred overnight under r.t. The reaction outcome was monitored by LCMS analysis. After the full conversion of starting material (1), the reaction mixture was quenched with 1 mL of saturated aqueous $NH_4Cl$ and purified by prep. HPLC.

Sample Info: 20-35% 2-7 min water-acetonitrile; flow 30 ml/min; (loading pump 4 ml/min acetonitrile); target mass 392; column SunFireC18 100×19 mm 5 um (L). As result, a target compound was obtained (Compound 13) (21 mg, 0.053 mmol) in total yield 37.6%.

ESI-MS: m/z $[M+H]^+$ calculated: 392.2. found: 392.2.

$^1$H NMR (400 MHz, DMSO-d6) δ 7.96 (d, J=6.9 Hz, 2H), 5.41 (s, 1H), 5.29-5.16 (m, 1H), 4.30 (t, J=8.3 Hz, 1H), 3.90 (dd, J=12.0, 4.2 Hz, 1H), 3.80-3.67 (m, 1H), 2.63-2.51 (m, 3H), 2.19 (ddt, J=13.8, 8.0, 1.9 Hz, 1H), 2.12-1.91 (m, 2H), 1.92 (s, 2H), 1.00-0.82 (m, 12H), 0.78-0.66 (m, 2H)

Example S13: Synthesis of (2S,4R)—N-cyclopropyl-1-((S)-2-(4-cyclopropyl-1H-1,2,3-triazol-1-yl)-3,3-dimethylbutanoyl)-4-hydroxypyrrolidine-2-carboxamide (Compound 14)

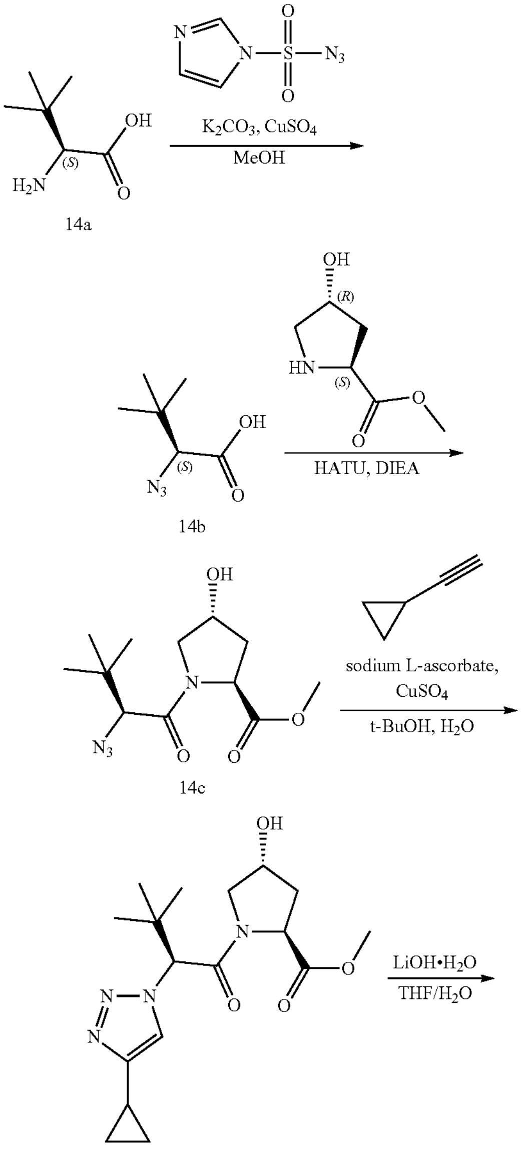

14a

14b

14c

14d

-continued

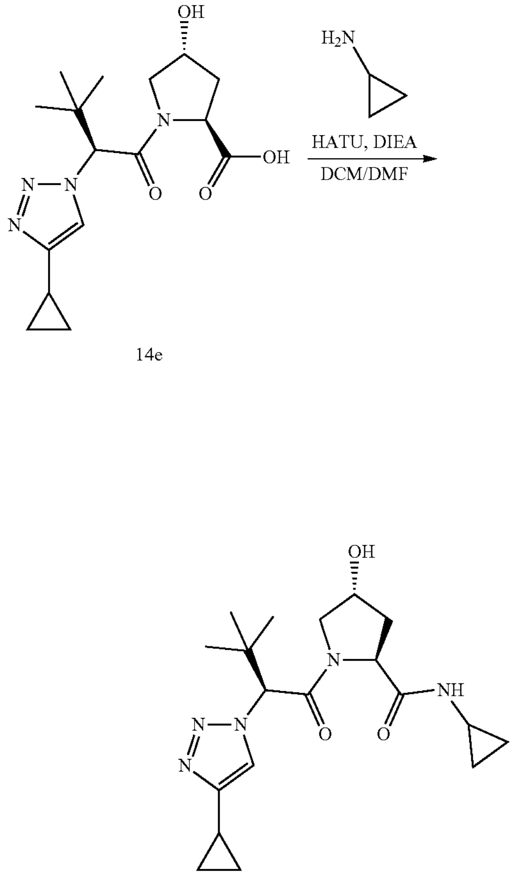

14e

14

Preparation of Intermediate 14b

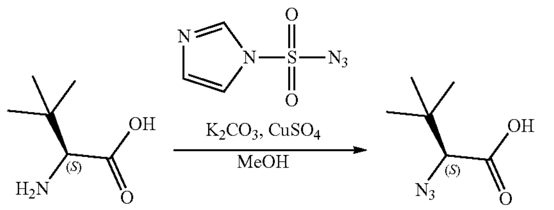

14a

14b

To a mixture of (S)-2-amino-3,3-dimethylbutanoic acid (8.0 g, 61.0 mmol), potassium carbonate (21.2 g, 152 mmol) and copper (II) sulfate (976 mg, 6.10 mmol) in methanol (100 mL) was added 1H-imidazole-1-sulfonyl azide (12.8 g, 61.0 mmol) at 25° C. The reaction was stirred for 16 h and diluted with water (60 mL). The methanol was removed under reduced pressure and the aqueous residue was washed with ethyl acetate (100 mL). The separated water phase was adjusted to pH=3 by addition of potassium bisulfate and extracted with ethyl acetate (2×150 mL). The combined organic layers were dried and concentrated to dryness to give crude (S)-2-azido-3,3-dimethylbutanoic acid (8.00 g, 83.5% yield) as yellow oil.

Preparation of Intermediate 14c

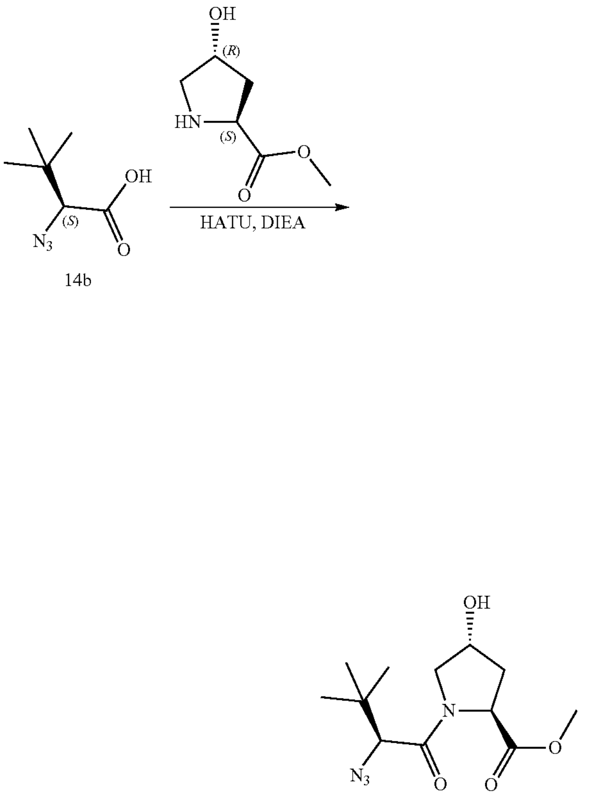

14b

14c

A solution of (S)-2-azido-3,3-dimethylbutanoic acid (7.00 g, 44.5 mmol), (1-[bis(dimethylamino)methylene]-1H-1,2,3-triazolo[4,5-b] pyridinium 3-oxid hexafluorophosphate (16.9 g, 44.5 mmol) and N,N-diisopropylethylamine (36.8 mL, 223 mmol) in N,N-dimethylformamide (10 mL) was stirred at 20° C. for 5 min and then (2S,4R)-methyl 4-hydroxypyrrolidine-2-carboxylate (6.47 g, 44.5 mmol) was added. The reaction mixture was stirred at 25° C. for 8 h and partitioned between water (50 mL) and ethyl acetate (50 mL). The separated organic layer was washed with brine (50 mL), dried and concentrated to afford crude (2S,4R)-methyl 1-((S)-2-azido-3,3-dimethylbutanoyl)-4-hydroxypyrrolidine-2-carboxylate (12.0 g, 94.8% yield) as a blue oil.

Preparation of Intermediate 14d

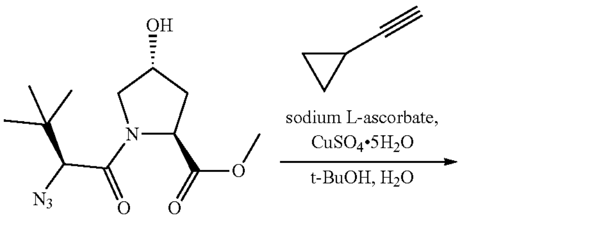

14c

-continued

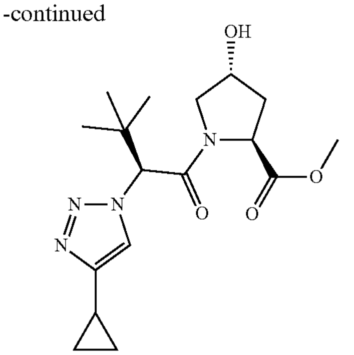

14d

To a solution of sodium L-ascorbate (25.1 g, 127 mmol) in water (100 mL) and tert-Butyl alcohol (100 mL) were added ethynylcyclopropane (3.58 mL, 42.21 mmol), copper (II) sulfate (14.5 g, 46.4 mmol) and (2S,4R)-methyl 1-((S)-2-azido-3,3-dimethylbutanoyl)-4-hydroxypyrrolidine-2-carboxylate (12.0 g, 42.2 mmol). The reaction was stirred at 25° C. for 16 h and concentrated under reduced pressure. The residue was purified by column chromatography (silica gel, 100-200 mesh, 0-4% methyl alcohol in dichloromethane) to afford (2S,4R)-methyl 1-((S)-2-(4-cyclopropyl-1H-1,2,3-triazol-1-yl)-3,3-dimethylbutanoyl)-4-hydroxypyrrolidine-2-carboxylate (6.00 g, 40.6% yield) as yellow oil.

Preparation of Intermediate 14e

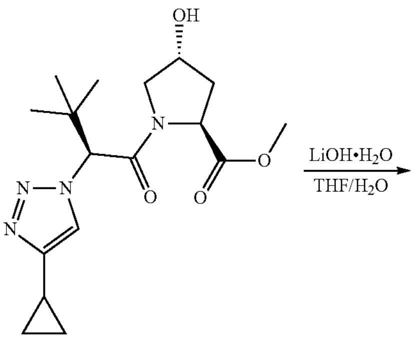

14d

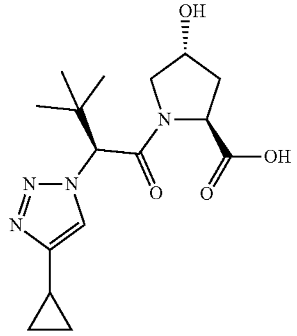

14e

To a solution of (2S,4R)-methyl 1-((S)-2-(4-cyclopropyl-1H-1,2,3-triazol-1-yl)-3,3-dimethylbutanoyl)-4-hydroxypyrrolidine-2-carboxylate (6.00 g, 17.1 mmol) in water (10 mL) and tetrahydrofuran (50 mL) was added lithium hydroxide monohydrate (2.05 g, 85.6 mmol). The reaction was stirred at 25° C. for 16 h and partitioned between ethyl acetate (50 mL) and water (15 mL). The aqueous layer was adjusted to pH=4 by addition of hydrochloric acid (2 M) and extracted with ethyl acetate (3×100 mL). The combined organic layers were dried and concentrated under reduced pressure to give crude (2S,4R)-1-((S)-2-(4-cyclopropyl-1H-1,2,3-triazol-1-yl)-3,3-dimethylbutanoyl)-4-hydroxypyrrolidine-2-carboxylic acid (3.00 g, 52.1% yield) as a light yellow solid.

Synthesis of (2S,4R)—N-cyclopropyl-1-((S)-2-(4-cyclopropyl-1H-1,2,3-triazol-1-yl)-3,3-dimethylbutanoyl)-4-hydroxypyrrolidine-2-carboxamide (Compound 14)

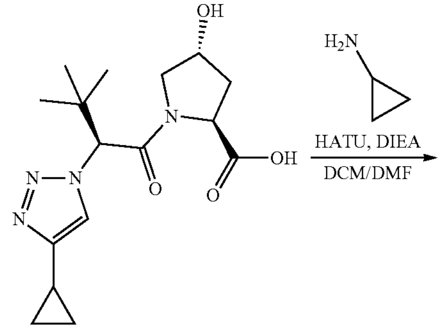

14e

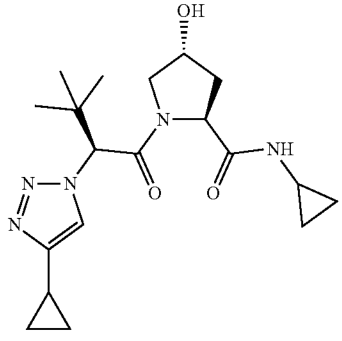

14

A mixture of (2S,4R)-1-((S)-2-(4-cyclopropyl-1H-1,2,3-triazol-1-yl)-3,3-dimethyl butanoyl)-4-hydroxypyrrolidine-2-carboxylic acid (70.0 mg, 0.21 mmol), cyclopropylamine (0.02 mL, 0.25 mmol), N,N-diisopropylethylamine (0.09 mL, 0.52 mmol) and (1-[Bis(dimethylamino)methylene]-1H-1,2,3-triazolo[4,5-b] pyridinium 3-oxid hexafluorophosphate (95.0 mg, 0.25 mmol) in N,N-dimethylformamide (3 mL) was stirred at 20° C. for 16 h and concentrated under reduced pressure. The residue was purified by RP-HPLC (acetonitrile 22-52/0.2% FA in water) to afford Compound 14, (2S, 4R)—N-cyclopropyl-1-((S)-2-(4-cyclopropyl-1H-1,2,3-triazol-1-yl)-3,3-dimethylbutanoyl)-4-hydroxypyrrolidine-2-carboxamide (29.1 mg, 35% yield) as a white solid. $^1H$ NMR (400 MHz, MeOH-$d_4$) δ 8.09-8.04 (m, 1H), 5.48 (s, 1H), 4.50-4.34 (m, 2H), 3.89-3.85 (m, 1H), 3.78-3.69 (m, 1H), 2.71-2.56 (m, 1H), 2.19-2.11 (m, 1H), 2.05-1.95 (m, 2H), 1.14-1.02 (m, 9H), 1.02-0.95 (m, 2H), 0.86-0.68 (m, 4H), 0.67-0.44 (m, 2H). LCMS (Method 5-95 AB, ESI): $R_T$=0.873 min, $[M+H]^+$=376.2.

Example S14: Synthesis of (2S,4R)-1-((S)-2-(4-cyclopropyl-1H-1,2,3-triazol-1-yl)-3,3-dimethylbutanoyl)-4-hydroxy-N-(2,2,2-trifluoroethyl)pyrrolidine-2-carboxamide (Compound 15)

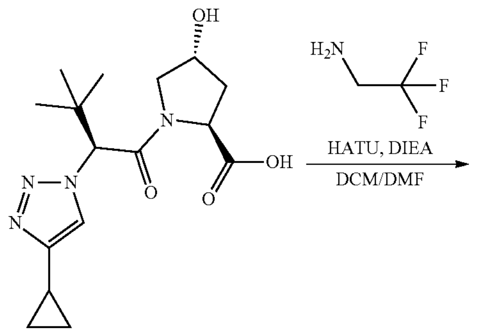

14e

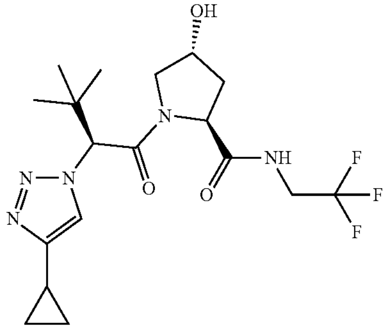

15

To a mixture of (2S,4R)-1-((S)-2-(4-cyclopropyl-1H-1,2,3-triazol-1-yl)-3,3-dimethylbutanoyl)-4-hydroxypyrrolidine-2-carboxylic acid (80.0 mg, 0.24 mmol) in N,N-dimethylformamide (5 mL) was added 2,2,2-trifluoroethan-1-amine (35.4 mg, 0.36 mmol), N,N-Diisopropylethylamine (0.09 mL, 0.52 mmol) and 1-[Bis(dimethylamino)methylene]-1H-1,2,3-triazolo[4,5-b]pyridinium 3-Oxide Hexafluorophosphate (135.6 mg, 0.36 mmol) at 0° C. The reaction was stirred at 25° C. for 16 h and concentrated in vacuum to remove the solvent. The residue was purified by pre-HPLC (water (0.225% FA)-CAN 32%-62%) to afford compound 15, (2S,4R)-1-((S)-2-(4-cyclopropyl-1H-1,2,3-triazol-1-yl)-3,3-dimethylbutanoyl)-4-hydroxy-N-(2,2,2-trifluoroethyl)pyrrolidine-2-carboxamide (55 mg, 54.8% yield) as a white solid. $^1$H NMR (400 MHz, DMSO-d6) δ 8.74 (d, J=6.4 Hz, 1H), 7.97 (s, 1H), 5.40 (s, 1H), 5.19 (d, J=3.6 Hz, 1H), 4.39 (t, J=8.4 Hz, 1H), 4.33 (s, 1H), 4.05-3.96 (m, 1H), 3.86-3.80 (m, 1H), 3.73 (dd, J=3.6, 10.8 Hz, 1H), 3.60 (d, J=10.8 Hz, 1H), 2.07-2.02 (m, 1H), 1.98-1.92 (m, 1H), 1.84-1.77 (m, 1H), 0.95-0.83 (m, 11H), 0.77-0.69 (m, 2H). LCMS (Method 5-95 AB, ESI): $R_T$=0.754 min, $[M+H]^+$=418.1.

Example S15 Synthesis of (2S,4R)-1-((S)-2-(4-cyclopropyl-1H-1,2,3-triazol-1-yl)-3,3-dimethylbutanoyl)-4-hydroxy-N-isopropylpyrrolidine-2-carboxamide (Compound 16)

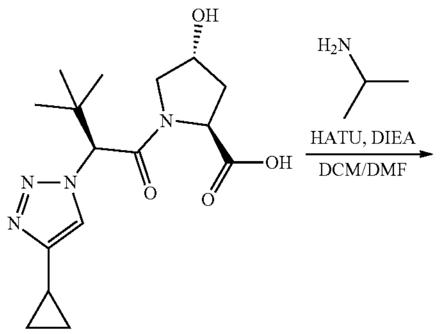

14e

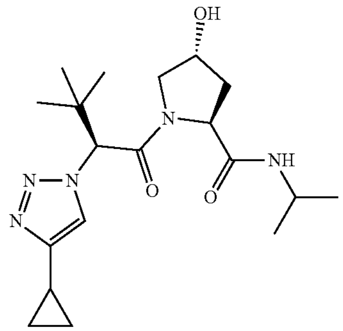

16

A mixture of (2S,4R)-1-((S)-2-(4-cyclopropyl-1H-1,2,3-triazol-1-yl)-3,3-dimethylbutanoyl)-4-hydroxypyrrolidine-2-carboxylic acid (70.0 mg, 0.21 mmol), propan-2-amine (0.02 mL, 0.25 mmol), N,N-diisopropylethylamine (0.09 mL, 0.52 mmol) and (1-[Bis(dimethylamino)methylene]-1H-1,2,3-triazolo[4,5-b] pyridinium 3-oxid hexafluorophosphate (95.0 mg, 0.25 mmol) in N,N-dimethylformamide (3 mL) was stirred at 20° C. for 16 h and concentrated under reduced pressure. The residue was purified by RP-HPLC (acetonitrile 25-55/0.2% FA in water) to afford Compound 16, (2S,4R)-1-((S)-2-(4-cyclopropyl-1H-1,2,3-triazol-1-yl)-3,3-dimethylbutanoyl)-4-hydroxy-N-isopropylpyrrolidine-2-carboxamide (23.4 mg, 29.5% yield) as a white solid. $^1$H NMR (400 MHz, MeOH-$d_4$) δ 8.06-8.02 (m, 1H), 5.47 (s, 1H), 4.47-4.39 (m, 2H), 4.00-3.85 (m, 2H), 3.74-3.70 (m, 1H), 2.19-2.14 (m, 1H), 2.08-1.93 (m, 2H), 1.25 (d, J=8.8 Hz, 3H), 1.14 (d, J=8.8 Hz, 3H), 1.07-1.03 (m, 9H), 1.01-0.96 (m, 2H), 0.81-0.75 (m, 2H). LCMS (Method 5-95 AB, ESI): $R_T$=0.912 min, $[M+H]^+$=378.5.

Example S16: Synthesis of (2S,4R)-1-((S)-2-(4-cyclopropyl-1H-1,2,3-triazol-1-yl)-3,3-dimethylbutanoyl)-N-(2-fluoroethyl)-4-hydroxypyrrolidine-2-carboxamide (Compound 17)

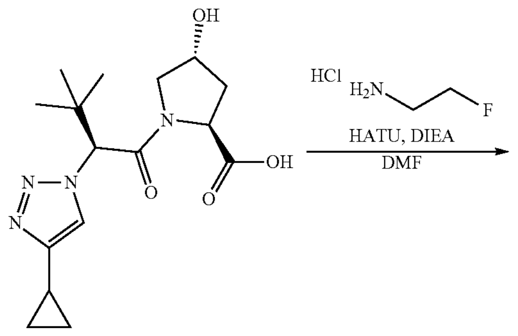

14e

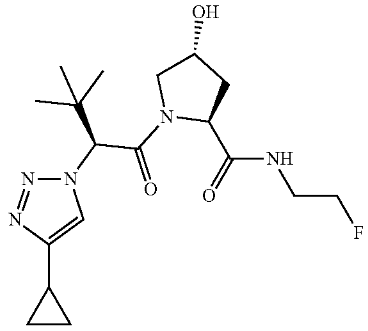

17

A mixture of (2S,4R)-1-((S)-2-(4-cyclopropyl-1H-1,2,3-triazol-1-yl)-3,3-dimethylbutanoyl)-4-hydroxypyrrolidine-2-carboxylic acid (70.0 mg, 0.21 mmol), 2-fluoroethanamine hydrochloride (0.04 mL, 0.25 mmol), N,N-diisopropylethylamine (0.09 mL, 0.52 mmol) and (1-[Bis(dimethylamino)methylene]-1H-1,2,3-triazolo[4,5-b]pyridinium 3-oxid hexafluorophosphate (95.0 mg, 0.25 mmol) in N,N-dimethylformamide (3 mL) was stirred at 20° C. for 16 h and concentrated under reduced pressure. The residue was purified by RP-HPLC (acetonitrile 25-55/0.225% FA in water) to afford Compound 17, (2S,4R)-1-((S)-2-(4-cyclopropyl-1H-1,2,3-triazol-1-yl)-3,3-dimethylbutanoyl)-N-(2-fluoroethyl)-4-hydroxypyrrolidine-2-carboxamide (26.6 mg, 33.2% yield) as a white solid. $^1$H NMR (400 MHz, MeOH-$d_4$) δ 7.97 (s, 1H), 5.46 (s, 1H), 4.55-4.41 (m, 4H), 3.90-3.86 (m, 1H), 3.73 (br d, J=11.2 Hz, 1H), 3.62-3.40 (m, 2H), 2.23-2.17 (m, 1H), 2.09-1.93 (m, 2H), 1.06-1.03 (m, 9H), 1.00-0.96 (m, 2H), 0.81-0.74 (m, 2H). LCMS (Method 5-95 AB, ESI): $R_T$=0.831 min, $[M+H]^+$=382.3.

Example S17: Synthesis of (2S,4R)-1-((S)-2-(4-cyclopropyl-1H-1,2,3-triazol-1-yl)-3,3-dimethylbutanoyl)-N-ethyl-4-hydroxypyrrolidine-2-carboxamide (Compound 18)

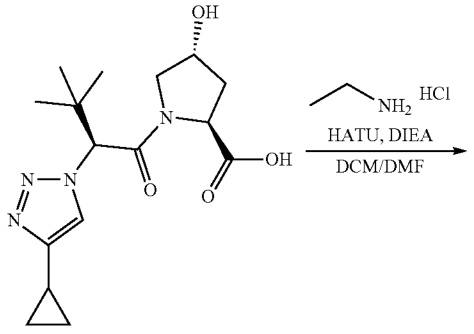

14e

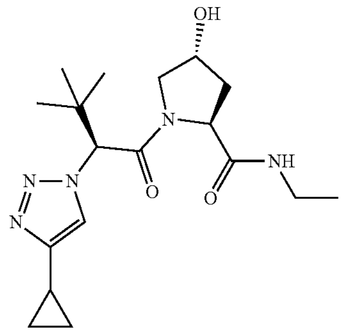

18

A mixture of (2S,4R)-1-((S)-2-(4-cyclopropyl-1H-1,2,3-triazol-1-yl)-3,3-dimethylbutanoyl)-4-hydroxypyrrolidine-2-carboxylic acid (70.0 mg, 0.21 mmol), ethanamine hydrochloride (0.03 mL, 0.25 mmol), N,N-diisopropylethylamine (0.09 mL, 0.52 mmol) and (1-[Bis(dimethylamino)methylene]-1H-1,2,3-triazolo[4,5-b] pyridinium 3-oxid hexafluorophosphate (95.0 mg, 0.25 mmol) in N,N-dimethylformamide (3 mL) was stirred at 20° C. for 16 h and concentrated under reduced pressure. The residue was purified by RP-HPLC (acetonitrile 25-55%/0.225% FA in water) to afford Compound 18, (2S,4R)-1-((S)-2-(4-cyclopropyl-1H-1,2,3-triazol-1-yl)-3,3-dimethylbutanoyl)-N-ethyl-4-hydroxypyrrolidine-2-carboxamide (19.9 mg, 26.0% yield) as a white solid. $^1$H NMR (400 MHz, MeOH-$d_4$) δ 7.98-7.97 (m, 1H), 5.46 (s, 1H), 4.74-4.40 (m, 2H), 3.90-3.56 (m, 2H), 3.26-3.07 (m, 2H), 2.40-2.17 (m, 1H), 2.06-1.93 (m, 2H), 1.17-1.11 (m, 3H), 1.07-1.03 (m, 9H), 0.99-0.96 (m, 2H), 0.79-0.76 (m, 2H). LCMS (Method 5-95 AB, ESI): $R_T$=0.847 min, $[M+H]^+$=364.2.

Example S18: Synthesis of (2S, 4R)-1-((S)-2-(4-cyclopropyl-1H-1,2,3-triazol-1-yl)-3,3-dimethylbutanoyl)-4-hydroxy-N-(1-(trifluoromethyl)cyclopropyl)pyrrolidine-2-carboxamide (Compound 19)

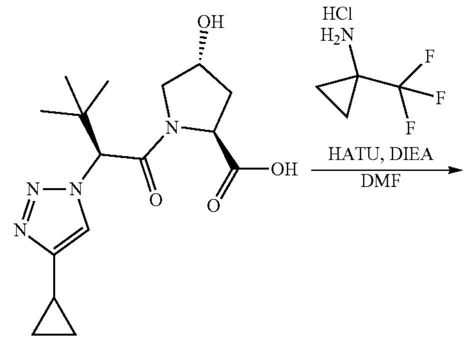

14e

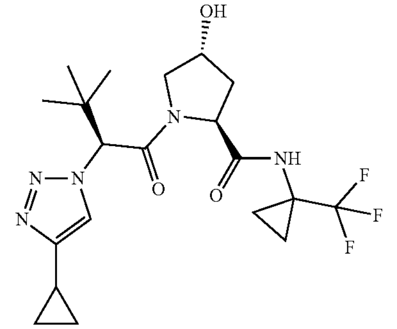

19

To a solution of (2S, 4R)-1-((S)-2-(4-cyclopropyl-1H-1,2,3-triazol-1-yl)-3,3-dimethylbutanoyl)-4-hydroxypyrrolidine-2-carboxylic acid (50.0 mg, 0.15 mmol), 1-(trifluoromethyl)cyclopropanamine; hydrochloride (28.8 mg, 0.18 mmol) and N,N-diisopropylethylamine (0.08 mL, 0.4500 mmol) in N,N-dimethylformamide (2 mL) was added 2-(7-azabenzotriazol-1-yl)-N,N,N',N'-tetramethyluronium hexafluorophosphate (67.8 mg, 0.18 mmol). The mixture was stirred at 25° C. for 2 h. The reaction mixture was partitioned between water (10 mL) and ethyl acetate (20 mL). The organic layer was separated and concentrated to dryness. The residue was purified by reverse phase chromatography (water (0.2% FA)-ACN 31%~61%) to afford compound 19, (2S, 4R)-1-((S)-2-(4-cyclopropyl-1H-1,2,3-triazol-1-yl)-3,3-dimethylbutanoyl)-4-hydroxy-N-(1-(trifluoromethyl)cyclopropyl)pyrrolidine-2-carboxamide (21.0 mg, 30.3% yield) as a white solid. $^1$H NMR (400 MHz, MeOH-$d_4$) (ppm) δ=7.96 (s, 1H), 5.45 (s, 1H), 4.49-4.37 (m, 2H), 3.88-3.85 (m, 1H), 3.75-3.72 (m, 1H), 2.18-2.01 (m, 1H), 1.98-1.94 (m, 2H), 1.26-1.06 (m, 3H), 1.05 (s, 9H), 1.00-0.95 (m, 3H), 0.78-0.77 (m, 2H). LCMS (5-95AB, ESI): RT=0.765 min, $[M+H]^+$=444.1.

Example S19: Synthesis of (2S, 4R)-1-((S)-2-(4-(furan-2-yl)-1H-1,2,3-triazol-1-yl)-3-methylbutanoyl)-4-hydroxy-N-methylpyrrolidine-2-carboxamide (Compound 20)

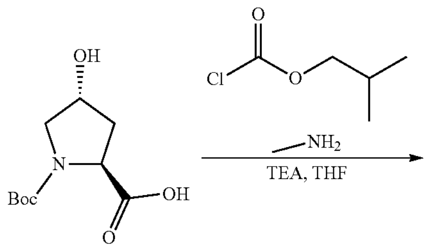

20a

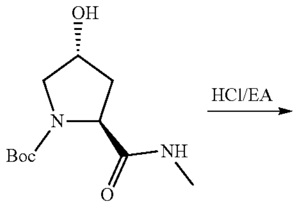

20b

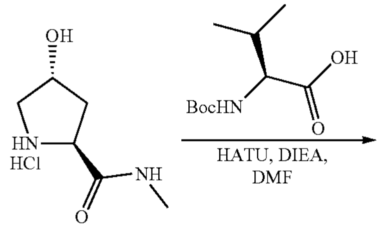

20c

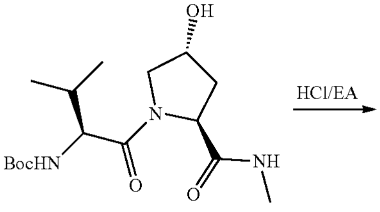

20d

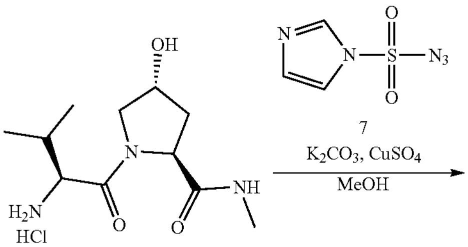

20e

-continued

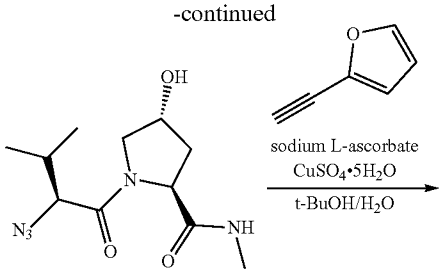

20f

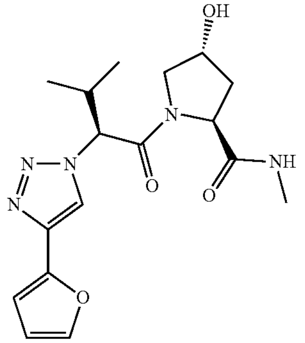

20

Preparation of Intermediate 20b

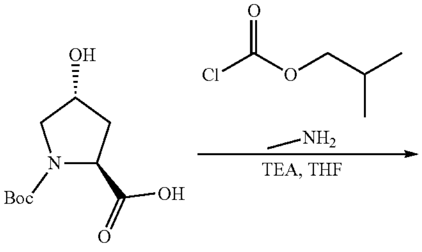

20a

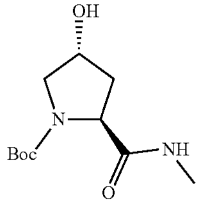

20b

To a solution of (2S, 4R)-1-(tert-butoxycarbonyl)-4-hydroxypyrrolidine-2-carboxylic acid (10.0 g, 43.2 mmol) and triethylamine (6.03 mL, 43.2 mmol) in tetrahydrofuran (120 mL), a solution of isobutyl chloroformate (5.61 mL, 43.2 mmol) in tetrahydrofuran (15 mL) was added at −40° C. The resulting mixture was stirred for 1 h at −40° C. Methanamine (11.2 mL, 100 mmol) (40% aqueous) was added to the reaction mixture and the reaction mixture was warmed to 25° C. and stirred for another 1 h.

The reaction mixture was partitioned between water (200 mL) and ethyl acetate (300 mL). The organic layers were combined, dried over anhydrous sodium sulfate and concentrated under reduced pressure. The residue was purified by flash chromatography (silica gel, 100-200 mesh, 0-50% ethyl acetate in petroleum ether) to afford tert-butyl rac-(2S, 4R)-4-hydroxy-2-(methylcarbamoyl)pyrrolidine-1-carboxylate (7.6 g, 71.9% yield) as a colorless oil.

Preparation of Intermediate 20c

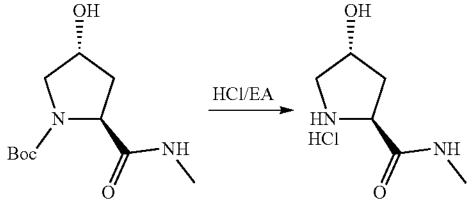

20b 20c

To a solution of tert-butyl rac-(2S, 4R)-4-hydroxy-2-(methylcarbamoyl)pyrrolidine-1-carboxylate (3.0 g, 12.3 mmol) in methanol (10.0 mL) was added hydrochloric acid (15.4 mL, 6.14 mmol) (4 M in methanol). The reaction mixture was stirred for 1 h at 25° C. The reaction mixture was concentrated under reduced pressure to afford (2S, 4R)-4-hydroxy-N-methyl-pyrrolidine-2-carboxamide hydrochloride (2.10 g, 94.7% yield) as a white solid.

Preparation of Intermediate-20d

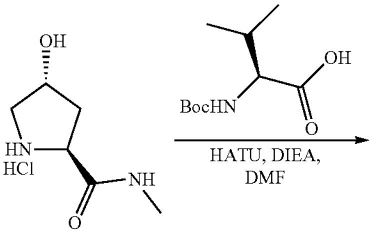

20c

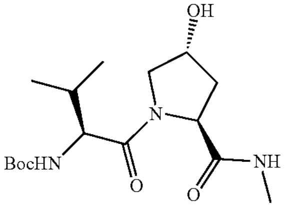

20d

To a solution of (2S, 4R)-4-hydroxy-N-methyl-pyrrolidine-2-carboxamide hydrochloride (5.0 g, 27.7 mmol), (2S)-2-(tert-butoxycarbonylamino)-3-methyl-butanoic acid (6.01 g, 27.68 mmol) and N,N-diisopropylethylamine (18.3 mL, 110.72 mmol) in N,N-dimethylformamide (60 mL) was added 1-[Bis(dimethylamino)methylene]-1H-1,2,3-triazolo [4,5-b]pyridinium 3-Oxide hexafluorophosphate (13.7 g, 36.0 mmol) at 0° C. The reaction mixture was stirred at 25° C. for 2 h. The reaction was quenched by water (50 mL) and extracted with ethyl acetate (3x30 mL). The organic layers were combined, dried over anhydrous sodium sulfate and concentrated under reduced pressure. The residue was purified by flash chromatography (silica gel, 100-200 mesh, 0-6% methanol/dichloromethane) to afford tert-butyl N-[rac-(1S)-2-methyl-1-[rac-(2S, 4R)-4-hydroxy-2-(methylcarbamoyl) pyrrolidine-1-carbonyl]propyl]carbamate (9.50 g, 99.9% yield) as a white solid.

Preparation of Intermediate 20e

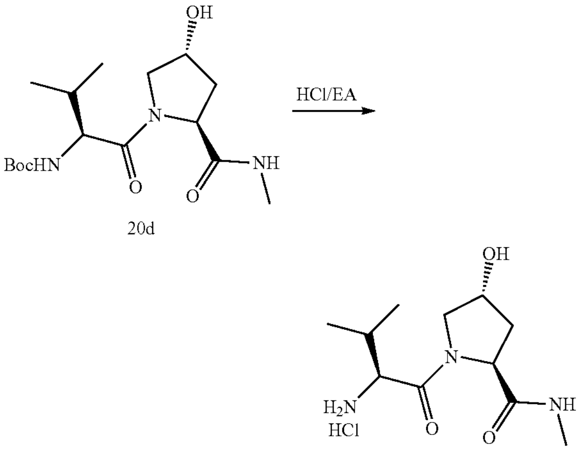

20d

20e

To a solution of tert-butyl N-[rac-(1S)-2-methyl-1-[rac-(2S, 4R)-4-hydroxy-2-(methylcarbamoyl)pyrrolidine-1-carbonyl]propyl]carbamate (1.50 g, 4.38 mmol) in ethyl acetate (5.0 mL) was added hydrochloric acid (10.4 mL, 41.8 mmol) (4 M in ethyl acetate). The mixture was stirred at 20° C. for 2 h. The reaction mixture was partitioned between water (100 mL) and ethyl acetate (200 mL). The reaction solvent was concentrated under reduced pressure to afford (2S, 4R)-1-[(2S)-2-amino-3-methyl-butanoyl]-4-hydroxy-N-methyl-pyrrolidine-2-carboxamide hydrochloride (1.20 g, 97.9% yield) as a white solid.

Preparation of Intermediate 20f

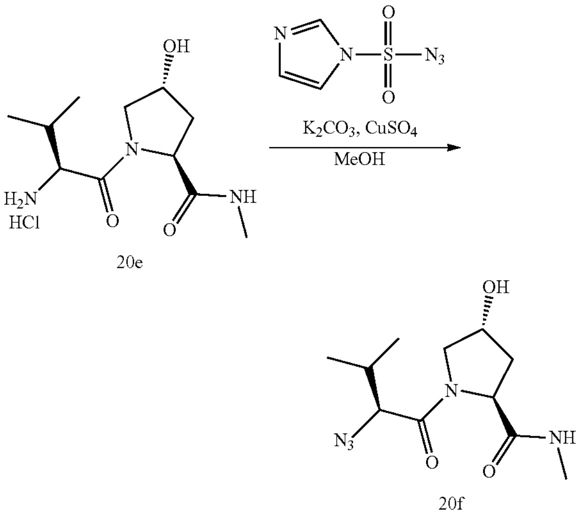

20e

20f

To a mixture of (2S, 4R)-1-((S)-2-amino-3-methylbutanoyl)-4-hydroxy-N-methylpyrrolidine-2-carboxamide hydrochloride (7.70 g, 27.5 mmol), potassium carbonate (11.5 g, 82.6 mmol) and copper (II) sulfate (440 mg, 2.75 mmol) in methanol (80 mL) was added 1H-imidazole-1-sulfonyl azide hydrochloride (5.77 g, 27.5 mmol). The reaction was stirred for 2 h at 25° C. The reaction was quenched by water (100 mL) and extracted with ethyl acetate (150 mL). The organic layer was separated, dried over anhydrous sodium sulfate and concentrated under reduced pressure. The residue was purified by flash chromatography (silica gel, 100-200 mesh, 0-10% methanol/dichloromethane) to afford (2S, 4R)-1-[(2S)-2-azido-3-methyl-butanoyl]-4-hydroxy-N-methyl-pyrrolidine-2-carboxamide (5.00 g, 67.5% yield) as a white solid.

Synthesis of Compound 20

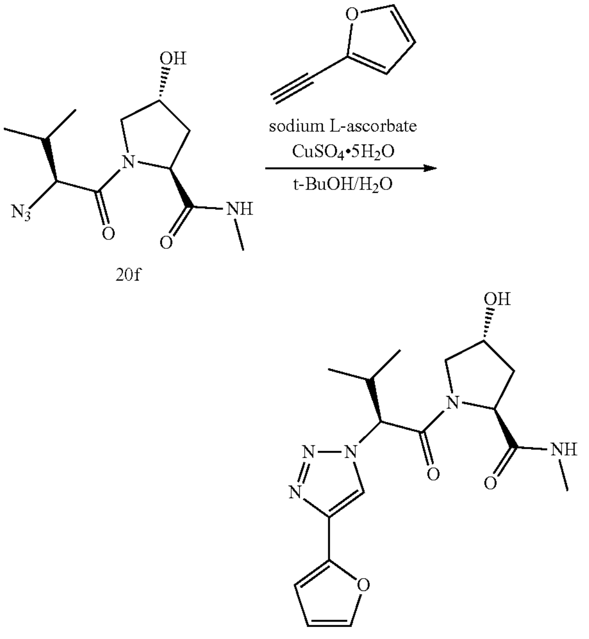

20f

20

A mixture of copper (II) sulfate pentahydrate (233 mg, 0.74 mmol) and sodium ascorbate (29.4 mg, 0.15 mmol) in tert-butanol (5.00 mL) and water (10.0 mL) was stirred at 25° C. for 10 min. Then (2S, 4R)-1-[(2S)-2-azido-3-methyl-butanoyl]-4-hydroxy-N-methyl-pyrrolidine-2-carboxamide (400 mg, 1.49 mmol) and 2-ethenylfuran (205 mg, 2.23 mmol) was added. The reaction mixture was stirred vigorously at 25° C. for 8 h. The reaction mixture was diluted with water (50 mL) and extracted with ethyl acetate (2×30 mL). The combined organic layers were dried over anhydrous sodium sulfate and concentrate under reduced pressure. The residue was purified by reverse phase chromatography (water (0.225% FA)-ACN, 10%~40%) to afford compound 20, (2S, 4R)-1-((S)-2-(4-(furan-2-yl)-1H-1,2,3-triazol-1-yl)-3-methylbutanoyl)-4-hydroxy-N-methylpyrrolidine-2-carboxamide (160 mg, 29.8% yield) as a white solid. $^1$H NMR (400 MHz, MeOH-$d_4$) δ=8.29 (s, 1H), 7.58 (s, 1H), 6.81-6.79 (m, 1H), 6.54 (s, 1H), 5.38-5.35 (m, 1H), 4.57-4.40 (m, 2H), 3.97-3.83 (m, 2H), 2.76 (s, 3H), 2.75-2.58 (m, 1H), 2.17-2.05 (m, 2H), 1.17-1.12 (m, 3H), 0.82-0.75 (m, 3H). LCMS (5-95AB, ESI): RT=0.697 min. $[M+H]^+$=362.0.

Example S20: Synthesis of (2S,4R)-4-hydroxy-N-methyl-1-((S)-3-methyl-2-(4-(1-methylcyclopropyl)-1H-1,2,3-triazol-1-yl)butanoyl)pyrrolidine-2-carboxamide (Compound 21)

Synthesis was carried out following the scheme given below:

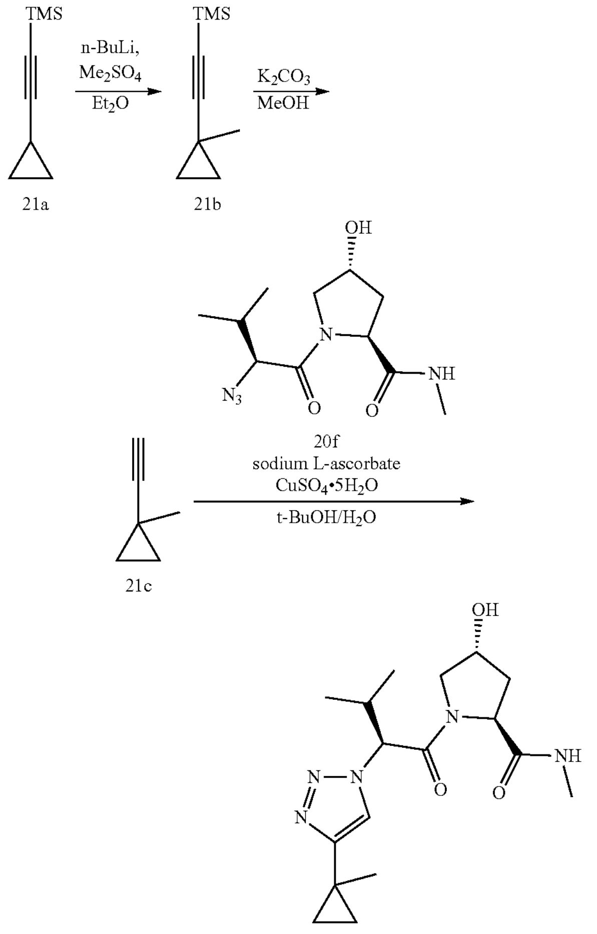

21a 21b 20f 21c 21

Preparation of Intermediate 21b

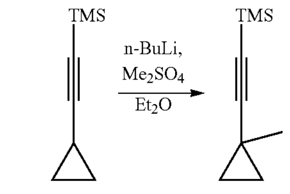

21a 21b

To a solution of cyclopropyl (trimethylsilyl) acetylene (1.60 g, 11.57 mmol) in diethyl ether (40.0 mL) was added n-butyllithium (5.55 mL, 13.9 mmol, 2.5 M/L) at −78° C. The mixture was slowly warmed to 25° C. and stirred for 4 h, then dimethyl sulfate (3.02 mL, 31.92 mmol) was added. The reaction was warmed to 25° C. and stirred for another 5 h. The reaction mixture was quenched with saturated ammonium chloride (40 mL, aqueous), and extracted with tert-butyl methyl ether (2×20 mL). The combined organic layers were dried over anhydrous sodium sulfate and concentrate under reduced pressure. The residue was purified by flash chromatography (silica gel, 100-200 mesh, petroleum ether, 100%) to afford trimethyl-[2-(1-methylcyclopropyl)ethynyl]silane (650 mg, 36.9% yield) as colorless oil. $^1H$ NMR (400 MHz, $CDCl_3$-d) (ppm) δ=1.18-1.11 (m, 3H), 0.80-0.78 (m, 2H), 0.46-0.41 (m, 2H), 0.02--0.00 (m, 9H).

Preparation of Intermediate 21c

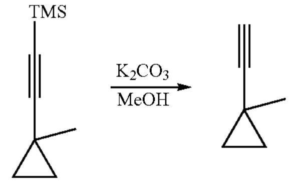

21b 21c

To a solution of trimethyl-[2-(1-methylcyclopropyl)ethynyl]silane (300 mg, 1.97 mmol) was dissolved in methanol (10.0 mL), then potassium carbonate (817 mg, 5.91 mmol) was added. The reaction mixture was stirred at 25° C. for 8 h. The reaction mixture was filtered and used for next step directly.

Synthesis of Compound 21

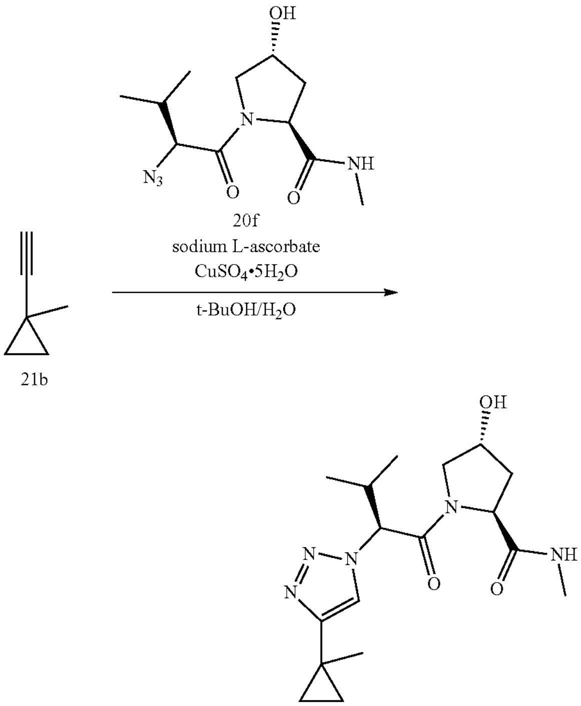

20f 21b 21

To a solution of copper (II) sulfate pentahydrate (174 mg, 0.56 mmol) and sodium ascorbate (22.1 mg, 0.11 mmol) in tert-butanol (5.0 mL) and water (10.0 mL) was stirred at 25° C. for 10 min. Then (2S, 4R)-1-[(2S)-2-azido-3-methyl-butanoyl]-4-hydroxy-N-methyl-pyrrolidine-2-carboxamide (300 mg, 1.11 mmol) and 1-ethynyl-1-methyl-cyclopropane (134 mg, 1.67 mmol) was added. The reaction mixture was stirred vigorously at 25° C. for 8 h. The reaction mixture was diluted with water (50 mL) and extracted with ethyl acetate (2×30 mL). The combined organic layers were dried over anhydrous sodium sulfate and concentrate under reduced pressure. The residue was purified by reverse phase chromatography (water (0.225% FA)-ACN, 10%~40%) to afford compound 21, (2S,4R)-4-hydroxy-N-methyl-1-((S)-3-methyl-2-(4-(1-methylcyclopropyl)-1H-1,2,3-triazol-1-yl)butanoyl)pyrrolidine-2-carboxamide (6.7 mg, 1.6% yield) as a yellow solid. $^1$H NMR (400 MHz, MeOH-$d_4$) δ 7.89-7.77 (m, 1H), 5.25-5.20 (m, 1H), 4.49-4.37 (m, 2H), 3.94-3.90 (m, 1H), 3.81-3.79 (m, 1H), 2.76-2.73 (m, 3H), 2.53-2.50 (m, 1H), 2.16-2.14 (m, 1H), 2.05-2.03 (m, 1H), 1.43 (s, 3H), 1.13-1.00 (m, 5H), 0.79-0.74 (m, 5H). LCMS (5-95AB, ESI): RT=0.729 min $[M+H]^+$=350.1.

Example S21: Synthesis of (2S,4R)-1-((S)-2-(4-cyclobutyl-1H-1,2,3-triazol-1-yl)-3-methylbutanoyl)-4-hydroxy-N-methylpyrrolidine-2-carboxamide (Compound 22)

Synthesis was carried out following the scheme given below:

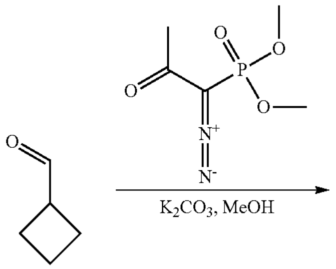

22a

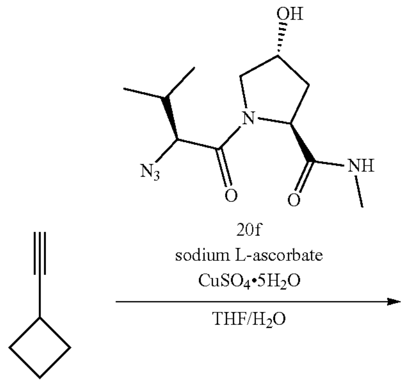

22b

-continued

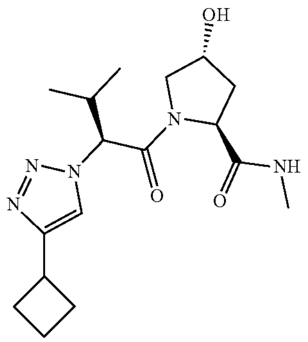

22

Preparation of Intermediate 22b

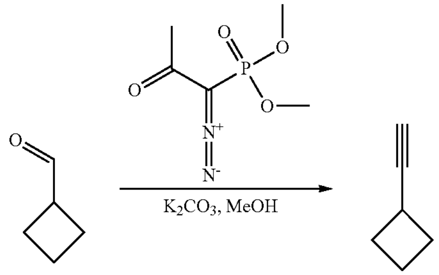

22a 22b

A mixture of cyclobutanecarbaldehyde (0.18 mL, 2.38 mmol), dimethyl (1-diazo-2-oxopropyl)phosphonate (594 mg, 3.09 mmol) and potassium carbonate (1.33 g, 9.51 mmol) in methanol (3 mL) was stirred at 25° C. for 2 h. The reaction mixture was filtered and used for next step directly.

Synthesis of Compound 22

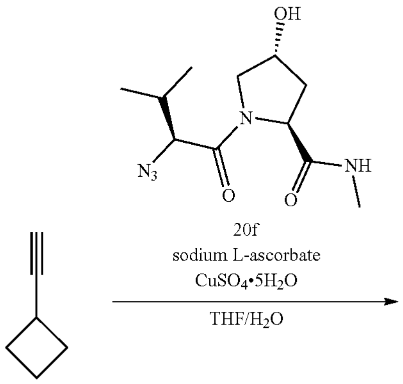

22b

-continued

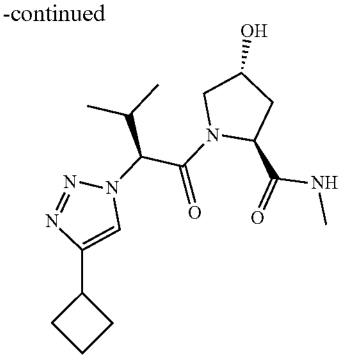

22

-continued

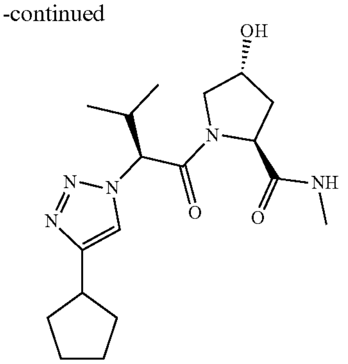

23

To a mixture of (2S, 4R)-1-((S)-2-azido-3-methylbutanoyl)-4-hydroxy-N-methylpyrrolidine-2-carboxamide (29.7 mg, 0.15 mmol) and copper (II) sulfate pentahydrate (23.9 mg, 0.15 mmol) in tetrahydrofuran (2.00 mL) and water (0.1 mL) was added ethynylcyclobutane (60.0 mg, 0.75 mmol). The reaction mixture was stirred at 25° C. for 16 h. The reaction mixture was partitioned between water (10.0 mL) and ethyl acetate (20.0 mL). The organic layer was separated and concentrated to dryness. The residue was purified by reverse phase chromatography (water (0.225% FA)-ACN 16%~46%) to afford compound 22, (2S, 4R)-4-hydroxy-N-methyl-1-[rac-(2S)-2-(4-cyclobutyltriazol-1-yl)-3-methyl-butanoyl]pyrrolidine-2-carboxamide (44.0 mg, 15.3% yield) as a white solid. $^1$H NMR (400 MHz, MeOH-$d_4$) (ppm) δ=8.04-7.97 (m, 1H), 5.28 (d, J=8.4 Hz, 1H), 4.50 (s, 1H), 4.42-4.38 (m, 1H), 3.92-3.64 (m, 3H), 2.76 (s, 3H), 2.42-1.95 (m, 9H), 1.14-1.08 (m, 3H), 0.77-0.70 (m, 3H). LCMS (5-95AB, ESI): RT=0.678 min, $[M+H]^+$=350.2.

Example S22: Synthesis of (2S, 4R)-1-[(2S)-2-(4-cyclopentyltriazol-1-yl)-3-methyl-butanoyl]-4-hydroxy-N-methyl-pyrrolidine-2-carboxamide (Compound 23)

Synthesis was carried out following the scheme given below:

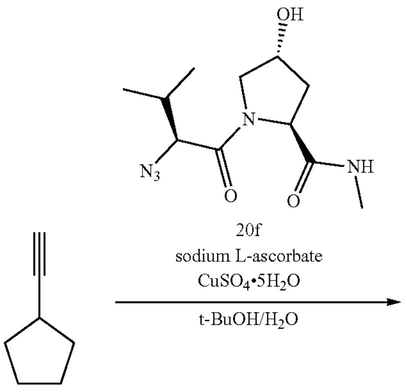

23a

Synthesis of Compound 23

To a mixture of (2S, 4R)-1-((S)-2-azido-3-methylbutanoyl)-4-hydroxy-N-methylpyrrolidine-2-carboxamide (450 mg, 1.59 mmol), sodium ascorbate (62.9 mg, 0.32 mmol), copper sulfate pentahydrate (II) (50.7 mg, 0.32 mmol) in tert-butanol (5.0 mL) and water (2.0 mL) was added ethynyl cyclopentane (0.22 mL, 1.91 mmol). The mixture was stirred at 25° C. for 16 h. The reaction mixture was filtered, the filtrate was concentrated under reduced pressure. The residue was partitioned between water (10 mL) and ethyl acetate (20 mL). The organic layer was separated and concentrated to dryness. The residue was purified by reverse phase chromatography (water (0.2% FA)-ACN 24%~54%) to afford compound 23, (2S, 4R)-1-[(2S)-2-(4-cyclopentyltriazol-1-yl)-3-methyl-butanoyl]-4-hydroxy-N-methyl-pyrrolidine-2-carboxamide (16.5 mg, 2.8% yield) as a white solid. $^1$H NMR (MeOH-$d_4$, 400 MHz): (ppm) δ=7.98-7.92 (m, 1H), 5.29-5.26 (m, 1H), 4.50 (s, 1H), 4.42-4.38 (m, 1H), 3.94-3.80 (m, 2H), 3.27-3.17 (m, 1H), 2.75 (s, 3H), 2.74-2.55 (m, 1H), 2.15-2.03 (m, 4H), 1.79-1.66 (m, 6H), 1.14-1.08 (m, 3H), 0.76-0.72 (m, 3H). LCMS (5-95AB, ESI): RT=0.699 min, $[M+H]^+$ 364.1.

Example S23: Synthesis of (2S,4R)-1-((S)-2-cyclohexyl-2-(4-(furan-2-yl)-1H-1,2,3-triazol-1-yl) acetyl)-4-hydroxy-N-methylpyrrolidine-2-carboxamide (Compound 24) and (2S, 4R)-1-((R)-2-cyclohexyl-2-(4-(furan-2-yl)-1H-1,2,3-triazol-1-yl) acetyl)-4-hydroxy-N-methylpyrrolidine-2-carboxamide (Compound 25)

Synthesis was carried out following the scheme given below:

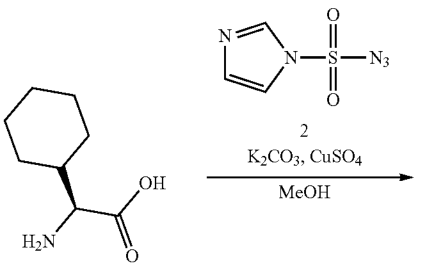

24a

-continued

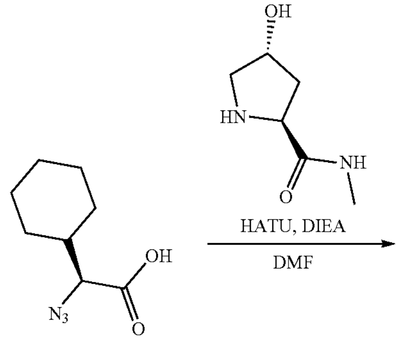

24b

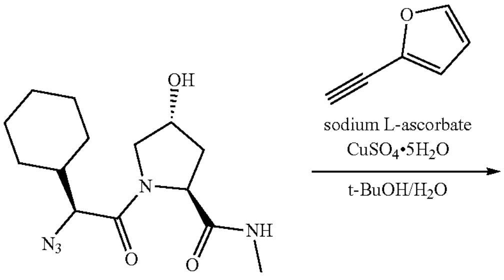

24c

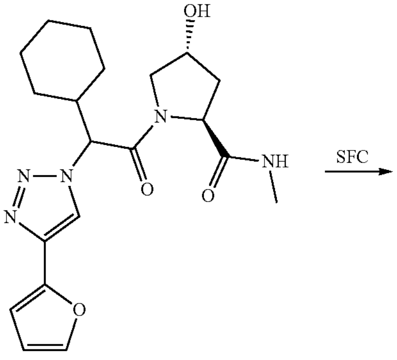

24d

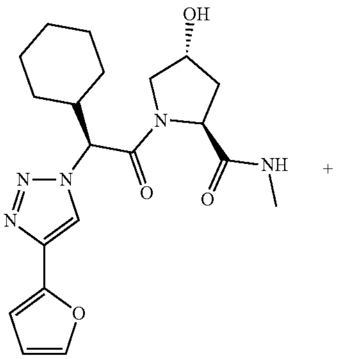

24

-continued

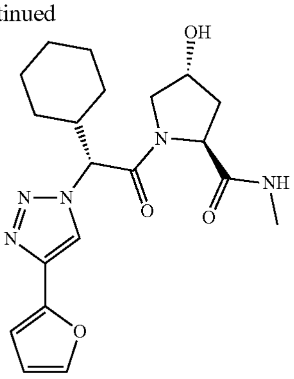

25

Preparation of Intermediate 24b

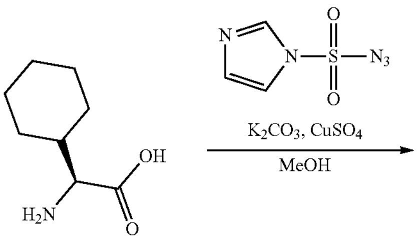

24a

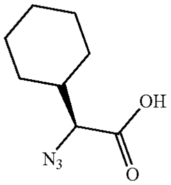

24b

To a mixture of (S)-2-amino-2-cyclohexylacetic acid (300 mg, 1.91 mmol), potassium carbonate (664 mg, 4.77 mmol) and copper (II) sulfate (30.5 mg, 0.19 mmol) in methyl alcohol (10.0 mL) was added 1H-imidazole-1-sulfonyl azide hydrochloride (400 mg, 1.91 mmol) at 25° C. The reaction mixture was stirred for 16 h. The reaction was quenched by water (30 mL) and concentrated to dryness under reduced pressure. The pH of water phase was adjust to 3 with potassium hydrogen sulfate aqueous and extracted with ethyl acetate (50 mL). The organic layer was dried over anhydrous sodium sulfate and concentrated to dryness under reduced pressure to afford a solution of (S)-2-azido-2-cyclohexylacetic acid (~349 mg, 99.8% yield) dissolved in ethyl acetate (15 mL).

Preparation of Intermediate 24c

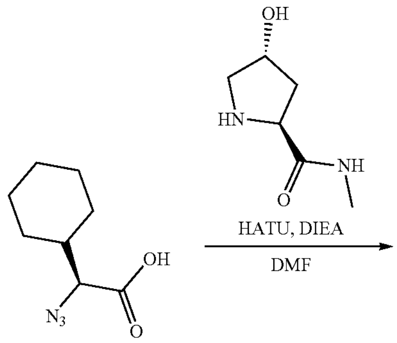

24b

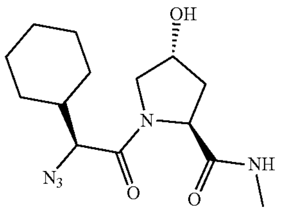

24c

To a solution of (S)-2-azido-2-cyclohexylacetic acid (349 mg, 1.90 mmol) and (2S, 4R)-4-hydroxy-N-methylpyrrolidine-2-carboxamide (413 mg, 2.29 mmol) in anhydrous N,N-dimethylformamide (5.0 mL) were added N,N-diisopropylethylamine (0.94 mL, 5.71 mmol) and 1-[Bis(dimethylamino)methylene]-1H-1,2,3-triazolo[4,5-b]pyridinium 3-Oxide hexafluorophosphate (869 mg, 2.29 mmol). The reaction mixture was stirred at 25° C. for 1 h. The reaction mixture was quenched with water (30 mL) and extracted with ethyl acetate (30 mL). The organic layer was separated, dried over anhydrous sodium sulfate and concentrated to dryness. The residue was purified by flash chromatography (silica gel, 100-200 mesh, 5-10% methanol in dichloromethane) to afford (2S, 4R)-1-((S)-2-azido-2-cyclohexylacetyl)-4-hydroxy-N-methylpyrrolidine-2-carboxamide (167 mg, 28.3% yield) as colorless oil.

Preparation of Intermediate 24d

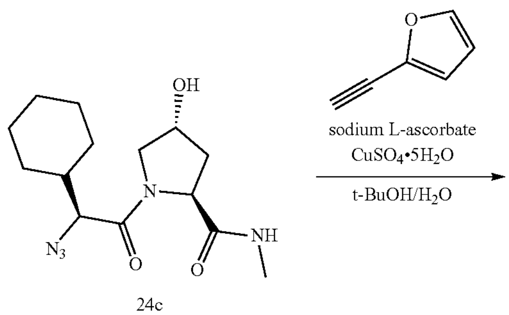

24c

-continued

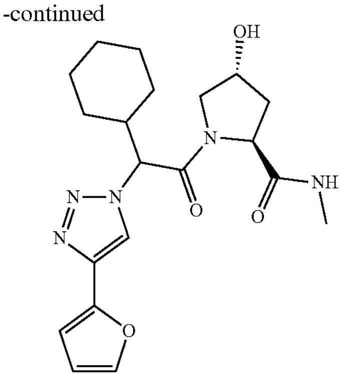

24d

A mixture of copper sulfate pentahydrate (84.5 mg, 0.27 mmol) and sodium ascorbate (10.7 mg, 0.05 mmol) in tert-butanol (5.0 mL) and water (10.0 mL) was stirred at 25° C. for 10 min. Then (2S, 4R)-1-((S)-2-azido-2-cyclohexylacetyl)-4-hydroxy-N-methylpyrrolidine-2-carboxamide (167 mg, 0.54 mmol) and 2-ethynylfuran (103 mg, 1.12 mmol) was added. The reaction mixture was stirred vigorously at 25° C. for 8 h. The reaction mixture was diluted with water (50 mL) and extracted with ethyl acetate (2×30 mL). The combined organic layers were dried over anhydrous sodium sulfate and concentrated to dryness. The residue was purified by reverse phase chromatography (water (0.2% FA)-ACN 26%~56%) to afford the racemic product (56 mg, 25.8% yield) as a white solid.

Preparation of Compound 24 and Compound 25

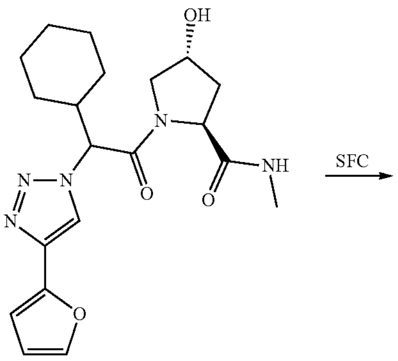

24d

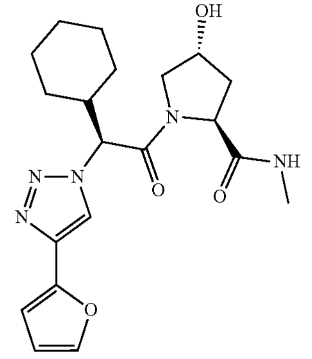

24

-continued

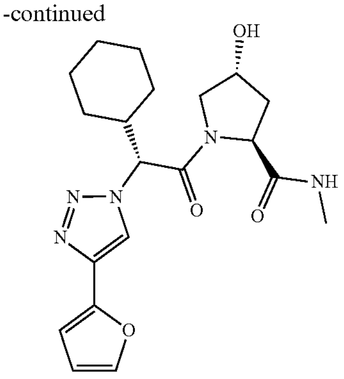

25

-continued

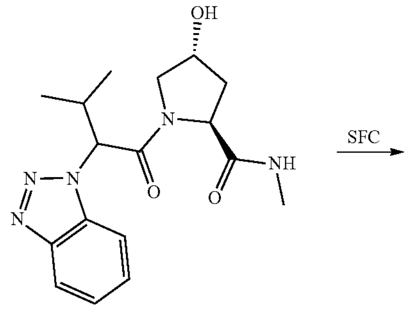

26a

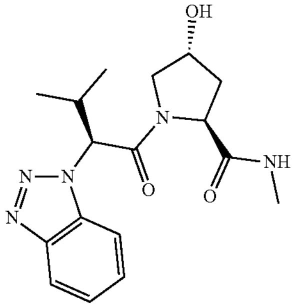

26

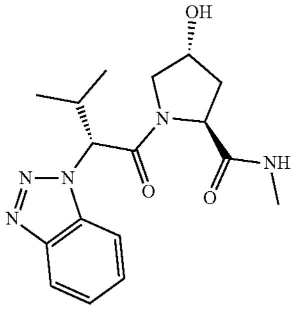

27

The above diastereomeric mixture was further separated by chiral SFC to give a first-eluting Isomer A and a second-eluting Isomer B:

Isomer A: (peak1, retention time=2.462 min, 98% ee). Compound 24, (2S,4R)-1-((S)-2-cyclohexyl-2-(4-(furan-2-yl)-1H-1,2,3-triazol-1-yl)acetyl)-4-hydroxy-N-methylpyrrolidine-2-carboxamide (19 mg 8.3% yield). $^{1}$H NMR (400 MHz, $CDCl_3$-d) δ=8.11 (s, 1H), 7.45 (s, 1H), 6.84-6.79 (m, 1H), 6.49-6.45 (m, 2H), 5.30 (d, J=12 Hz, 1H), 4.63 (s, 1H), 4.48 (t, J=8.0 Hz, 1H), 3.94-3.81 (m, 2H), 2.85 (d, J=4.0 Hz, 3H), 2.45-2.38 (m, 1H), 2.30-2.22 (m, 1H), 2.09-2.04 (m, 1H), 1.92-1.89 (m, 1H), 1.68 (s, 1H), 1.34-1.25 (m, 2H), 1.18 (s, 4H), 1.10-0.98 (m, 2H). LCMS (5-95 AB, ESI): RT=0.774 min, [M+H]+ 402.1.

Isomer B: (peak 2, retention time=2.884 min, 98% ee). Compound 25, (2S, 4R)-1-((R)-2-cyclohexyl-2-(4-(furan-2-yl)-1H-1,2,3-triazol-1-yl)acetyl)-4-hydroxy-N-methylpyrrolidine-2-carboxamide (13.0 mg 5.8% yield). $^{1}$H NMR (400 MHz, $CDCl_3$-d) δ=7.27 (s, 1H), 7.95 (s, 1H), 6.36 (s, 1H), 5.69 (s, 1H), 4.60 (s, 1H), 4.10 (s, 1H), 3.78-3.68 (m, 2H), 2.74 (s, 3H), 2.38-2.35 (m, 4H), 1.78-1.52 (m, 6H), 1.12-0.89 (m, 5H). LCMS (5-95 AB, ESI): RT=0.772 min, [M+H]+ 402.1.

Example S24: Synthesis of (2S,4R)-1-((S)-2-(1H-benzo[d][1,2,3]triazol-1-yl)-3-methylbutanoyl)-4-hydroxy-N-methylpyrrolidine-2-carboxamide (Compound 26) and (2S, 4R)-1-((R)-2-(1H-benzo[d][1,2,3]triazol-1-yl)-3-methylbutanoyl)-4-hydroxy-N-methylpyrrolidine-2-carboxamide (Compound 27)

Synthesis was carried out following the scheme given below:

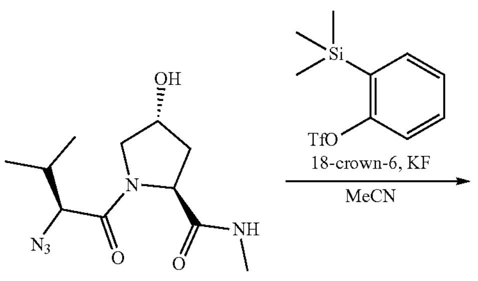

20f

Preparation of Intermediate 26a

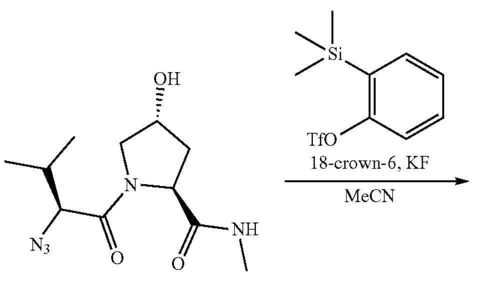

20f

-continued

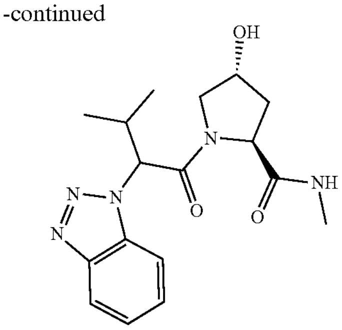

26a

A mixture of (2S, 4R)-1-((S)-2-azido-3-methylbutanoyl)-4-hydroxy-N-methylpyrrolidine-2-carboxamide (100 mg, 0.37 mmol), 18-crown-6 (196 mg, 0.74 mmol), 2-(trimethylsilyl)phenyl trifluoromethanesulfonate (0.14 mL, 0.56 mmol) and cesium fluoride (226 mg, 1.49 mmol) in acetonitrile (2.00 mL) was stirred for 30 min at 125° C. under microwave atmosphere. After cooled to room temperature, the reaction mixture was filtered, the filtrate was concentrated under reduced pressure. The residue was purified by reverse phase chromatography (water (0.2% FA)-ACN 22%~52%) to afford (2S, 4R)-1-(2-(1H-benzo[d][1,2,3]triazol-1-yl)-3-methylbutanoyl)-4-hydroxy-N-methylpyrrolidine-2-carboxamide (107 mg, 83.4% yield) as a white solid.

Preparation of Compound 26 and Compound 27

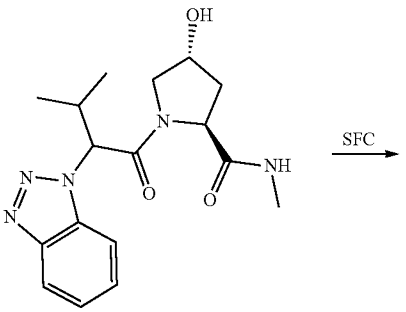

26a

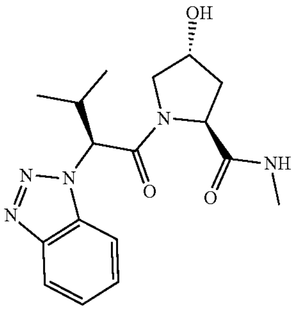

26

-continued

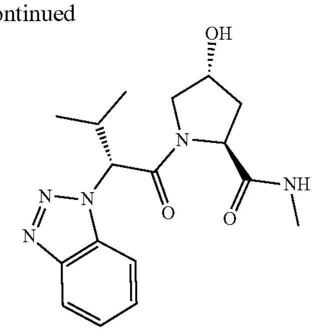

27

The above diastereomeric mixture was further separated by chiral SFC to give a first-eluting Isomer A and a second-eluting Isomer B:

Isomer A: (peak1, retention time=1.558 min, 100% ee). Compound 26, (2S,4R)-1-((S)-2-(1H-benzo[d] [1,2,3]triazol-1-yl)-3-methylbutanoyl)-4-hydroxy-N-methylpyrrolidine-2-carboxamide (21.0 mg, 37.7% yield). $^1$H NMR (400 MHz, $CDCl_3$-d) (ppm) δ=8.08-7.94 (m, 1H), 7.77-7.62 (m, 1H), 7.53-7.39 (m, 2H), 6.60 (s, 1H), 5.44-5.18 (m, 1H), 4.78-4.75 (m, 1H), 4.39 (s, 1H), 3.80-3.68 (m, 2H), 3.05-2.89 (m, 2H), 2.57 (d, J=4 Hz, 3H), 2.26-2.15 (m, 2H), 1.14-1.06 (m, 3H), 0.61-0.48 (m, 3H). LCMS (5-95AB, ESI): RT=0.714 min, [M+H]+ 346.1.

Isomer B: (peak2, retention time=1.810 min 99.5% ee). Compound 27, (2S, 4R)-1-((R)-2-(1H-benzo[d][1,2,3]triazol-1-yl)-3-methylbutanoyl)-4-hydroxy-N-methylpyrrolidine-2-carboxamide (27 mg, 48% yield). $^1$H NMR (400 MHz, $CDCl_3$-d) δ=8.00-7.95 (m, 2H), 7.47-7.32 (m, 2H), 6.80 (s, 1H), 5.38 (d, J=12 Hz, 1H), 4.42-4.32 (m, 2H), 3.79-3.67 (m, 2H), 3.06-3.03 (m, 2H), 2.80 (s, 3H), 2.16 (s, 1H), 1.77 (s, 1H), 1.25-1.15 (m, 3H), 0.62-0.45 (m, 3H). LCMS (5-95AB, ESI): RT=0.697 min, [M+H]+ 346.1.

Example S25: Synthesis of (2S,4R)-4-hydroxy-1-((S)-2-(4-methoxy-1H-benzo[d][1,2,3]triazol-1-yl)-3-methylbutanoyl)-N-methylpyrrolidine-2-carboxamide (Compound 28) and (2S,4R)-4-hydroxy-1-((R)-2-(4-methoxy-1H-benzo[d][1,2,3]triazol-1-yl)-3-methylbutanoyl)-N-methylpyrrolidine-2-carboxamide (Compound 29)

Synthesis was carried out following the scheme given below:

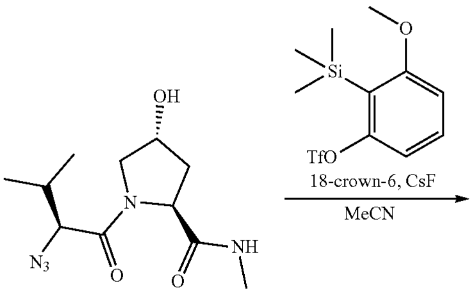

20f

-continued

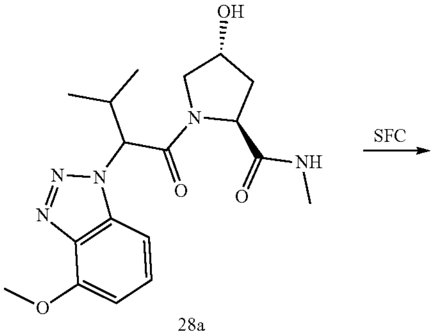

28a

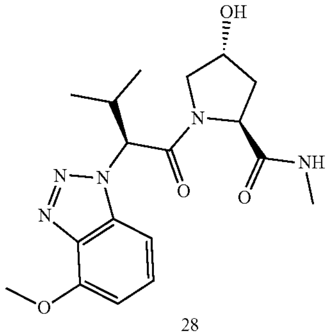

28

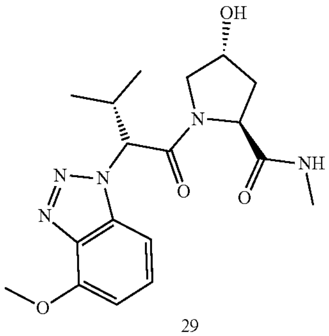

29

Preparation of Intermediate 28a

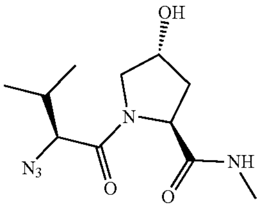

20f

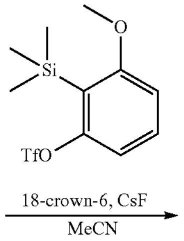

-continued

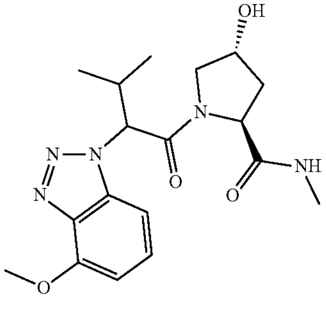

28a

A mixture of (2S, 4R)-1-((S)-2-azido-3-methylbutanoyl)-4-hydroxy-N-methylpyrrolidine-2-carboxamide (100 mg, 0.37 mmol), 18-crown-6 (196 mg, 0.74 mmol), 3-methoxy-2-(trimethylsilyl)phenyl trifluoromethanesulfonate (183 mg, 0.56 mmol) and cesium fluoride (226 mg, 1.49 mmol) in acetonitrile (2.0 mL) was stirred for 30 min at 125° C. under microwave atmosphere. After cooled to room temperature, the reaction mixture was filtered, the filtrate was concentrated under reduced pressure. The residue was purified by reverse phase chromatography (water (0.2% FA)-ACN 22%~52%) to afford (2S, 4R)-4-hydroxy-1-(2-(4-methoxy-1H-benzo[d][1,2,3]triazol-1-yl)-3-methylbutanoyl)-N-methylpyrrolidine-2-carboxamide (60 mg, 38.3% yield) as a white solid.

Preparation of Compound 28 and Compound 29

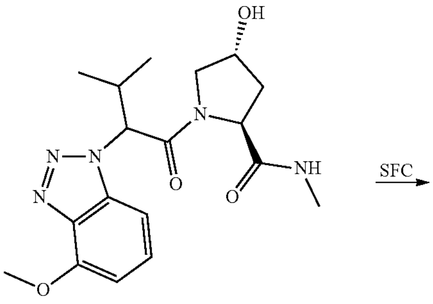

28a

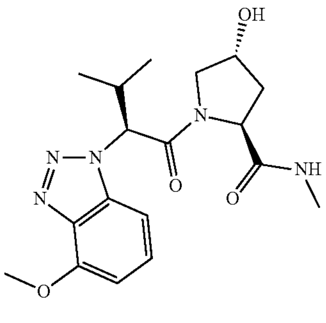

28

-continued

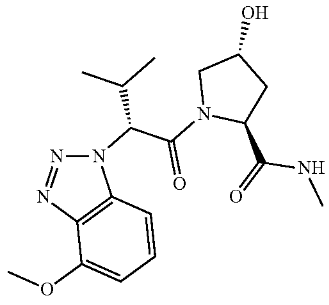

29

-continued

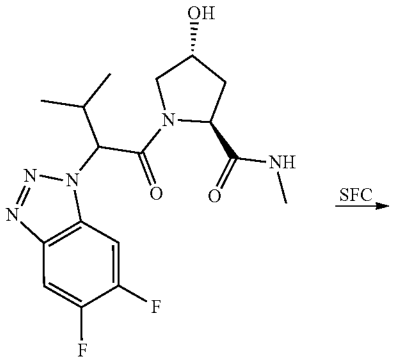

30a

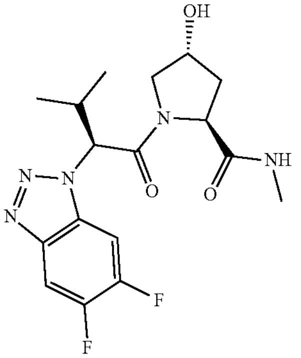

30

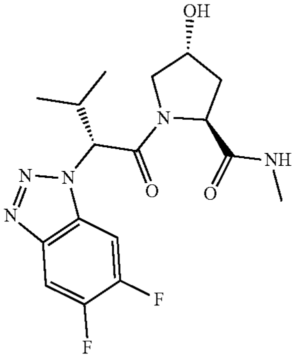

31

The above diastereomeric mixture was further separated by chiral SFC to give a first-eluting Isomer A and a second-eluting Isomer B:

Isomer A: (peak1, retention time=1.558 min, 100% ee). Compound 28, (2S,4R)-4-hydroxy-1-((S)-2-(4-methoxy-1H-benzo[d][1,2,3]triazol-1-yl)-3-methylbutanoyl)-N-methylpyrrolidine-2-carboxamide (60.0 mg, 0.16 mmol). $^1H$ NMR (400 MHz, MeOH-$d_4$) δ=7.48-7.39 (m, 2H), 6.86-6.84 (m, 1H), 5.58-5.56 (m, 1H), 4.53-4.49 (m, 1H), 4.37 (s, 1H), 4.07 (s, 3H), 3.84-3.81 (m, 1H), 3.64-3.59 (m, 2H), 3.00-2.92 (m, 1H), 2.61 (s, 3H), 1.93-1.88 (m, 2H), 1.18-1.09 (m, 3H), 0.60-0.49 (m, 3H). LCMS (5-95AB, ESI): RT=0.717 min, [M+H]+ 376.0.

Isomer B: (peak2, retention time=2.027 min 100% ee). Compound 29, (2S,4R)-4-hydroxy-1-((R)-2-(4-methoxy-1H-benzo[d][1,2,3]triazol-1-yl)-3-methylbutanoyl)-N-methylpyrrolidine-2-carboxamide (60.0 mg, 0.16 mmol). $^1H$ NMR (400 MHz, MeOH-$d_4$) δ=7.51-7.42 (m, 2H), 6.85-6.81 (m, 1H), 5.53-5.50 (m, 1H), 4.45 (s, 1H), 4.37-4.35 (m, 3H), 4.06-4.05 (m, 3H), 4.00-3.96 (m, 1H), 3.77-3.76 (m, 1H), 2.78-2.77 (m, 1H), 2.60 (s, 3H), 2.08-1.97 (m, 2H), 1.20-1.15 (m, 3H), 0.63-0.56 (m, 3H). LCMS (5-95AB, ESI): RT=0.702 min, [M+H]+ 376.0.

Example S26: Synthesis of (2S, 4R)-1-((S)-2-(5,6-difluoro-1H-benzo[d][1,2,3]triazol-1-yl)-3-methylbutanoyl)-4-hydroxy-N-methylpyrrolidine-2-carboxamide (Compound 30) and (2S, 4R)-1-((S)-2-(5,6-difluoro-1H-benzo[d][1,2,3]triazol-1-yl)-3-methylbutanoyl)-4-hydroxy-N-methylpyrrolidine-2-carboxamide (Compound 31)

Synthesis was carried out following the scheme given below:

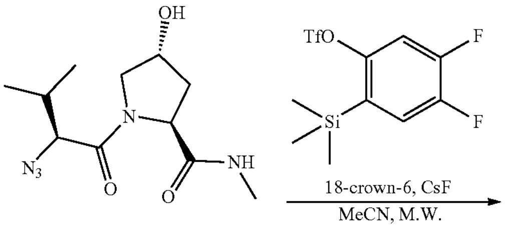

20f

Preparation of Intermediate 30a

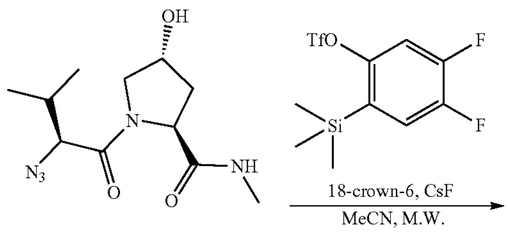

20f

-continued

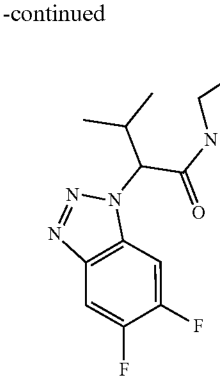

30a

A mixture of (2S, 4R)-1-((S)-2-azido-3-methylbutanoyl)-4-hydroxy-N-methylpyrrolidine-2-carboxamide (100 mg, 0.37 mmol), potassium fluoride (86.3 mg, 1.49 mmol), (4,5-difluoro-2-trimethylsilyl-phenyl) trifluoromethanesulfonate (186 mg, 0.56 mmol) and 18-crown-6 (196 mg, 0.74 mmol) in acetonitrile (3.0 mL) was stirred for 30 min at 125° C. under microwave atmosphere. After cooled to room temperature, the reaction mixture was filtered, the filtrate was concentrated under reduced pressure. The residue was purified by reverse phase chromatography (water (0.2% FA)-ACN 22%~52%) to afford rac-(2S, 4R)-1-[2-(5,6-difluorobenzotriazol-1-yl)-3-methyl-butanoyl]-4-hydroxy-N-methyl-pyrrolidine-2-carboxamide (30 mg, 21.2% yield) as a white solid.

Preparation of Compound 30 and Compound 31

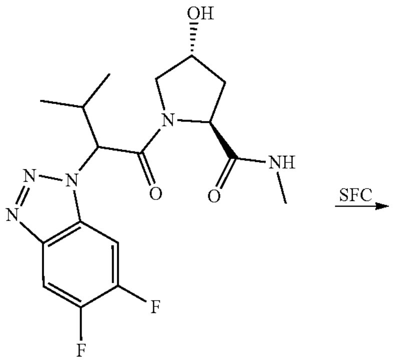

30a

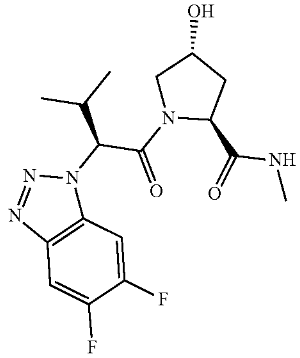

30

-continued

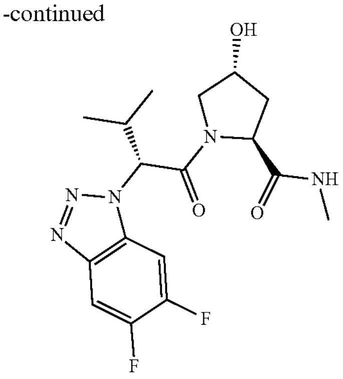

31

The above diastereomeric mixture was further separated by chiral SFC to give a first-eluting Isomer A and a second-eluting Isomer B:

Isomer A: (peak1, retention time=3.442 min, 100% ee). Compound 30, (2S, 4R)-1-((S)-2-(5,6-difluoro-1H-benzo[d][1,2,3]triazol-1-yl)-3-methylbutanoyl)-4-hydroxy-N-methylpyrrolidine-2-carboxamide. $^{1}H$ NMR (400 MHz, MeOH-$d_4$) δ=7.92-7.87 (m, 1H), 7.84-7.80 (m, 1H), 5.62-5.60 (m, 1H), 3.44-3.41 (m, 1H), 2.96-2.78 (m, 2H), 2.81 (s, 3H), 1.91-1.84 (m, 1H), 1.31-1.21 (m, 2H), 1.16-1.07 (m, 3H), 0.58-0.48 (m, 3H). LCMS (5-95AB, ESI): RT=0.779 min, $[M+H]^+$ 382.0.

Isomer B: (peak2, retention time=4.794 min, 98% ee). Compound 31, (2S, 4R)-1-((S)-2-(5,6-difluoro-1H-benzo[d][1,2,3]triazol-1-yl)-3-methylbutanoyl)-4-hydroxy-N-methylpyrrolidine-2-carboxamide. $^{1}H$ NMR (400 MHz, MeOH-$d_4$) δ=8.01-7.96 (m, 1H), 7.94-7.90 (m, 1H), 5.60-5.97 (m, 1H), 4.47 (s, 1H), 4.38-4.34 (m, 1H), 3.99-3.96 (m, 1H), 3.76-3.74 (m, 1H), 2.95-2.87 (m, 1H), 2.78 (s, 3H), 2.15-2.10 (m, 1H), 2.05-1.98 (m, 1H), 1.21-1.16 (m, 3H), 0.64-0.55 (m, 3H). LCMS (5-95AB, ESI): RT=0.773 min, [M+H]+ 382.0.

Example S27: Synthesis of (2S, 4R)-1-[2-(4-cyclopropyltriazol-1-yl)-3-methyl-but-2-enoyl]-4-hydroxy-N-methyl-pyrrolidine-2-carboxamide (Compound 32)

Synthesis was carried out following the scheme given below:

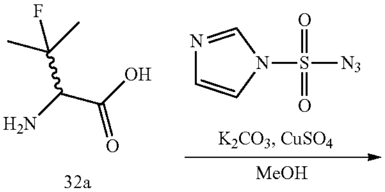

32a

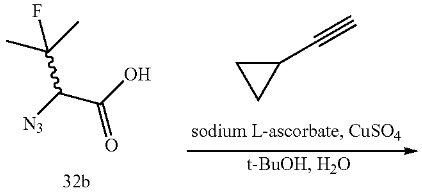

32b

-continued

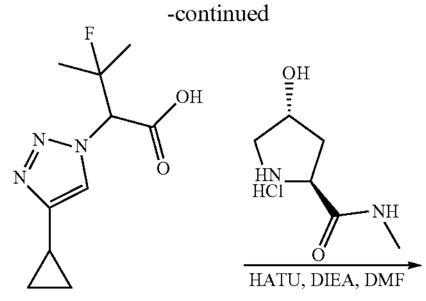

32c

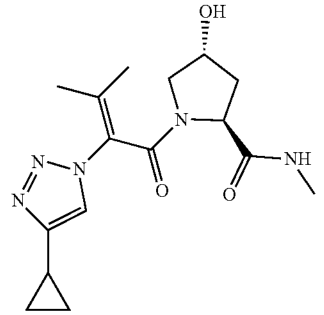

32

Preparation of Intermediate 32b

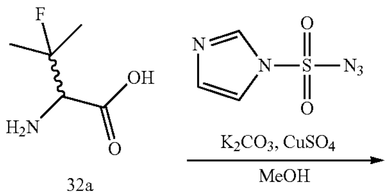

32a

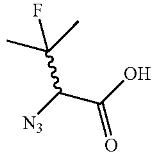

32b

To a mixture of 3-fluorovaline (50.0 mg, 0.37 mmol), potassium carbonate (128 mg, 0.92 mmol) and copper(II) sulfate (5.92 mg, 0.04 mmol) in methanol (3.00 mL) was added 1H-imidazole-1-sulfonyl azide hydrochloride (77.6 mg, 0.37 mmol) at 25° C. The reaction was stirred for 16 h. The reaction was quenched by water (5 mL) and concentrated under reduced pressure to remove methanol. The pH of water phase was adjust to 3 with potassium hydrogen sulfate aqueous and extracted with ethyl acetate (10 mL). The organic layer was dried over anhydrous sodium sulfate and concentrated under reduced pressure to afford 2-azido-3-fluoro-3-methylbutanoic acid (50 mg, 83.9% yield) as yellow oil.

Preparation of Intermediate 32c

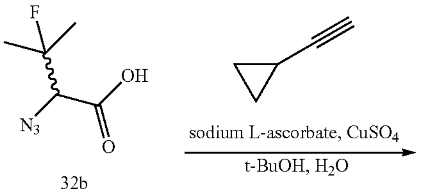

32b

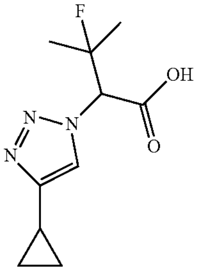

32c

To a solution of 2-azido-3-fluoro-3-methyl-butanoic acid (50.0 mg, 0.31 mmol), sodium ascorbate (12.4 mg, 0.06 mmol), copper (II) sulfate (9.96 mg, 0.06 mmol) in tert-butanol (5.0 mL) and water (2.00 mL) was added ethynylcyclopropane (20.6 mg, 0.31 mmol). The mixture was stirred at 25° C. for 3 h. The reaction mixture was partitioned between water (10 mL) and ethyl acetate (20 mL). The organic layer was separated and concentrated to dryness to afford 2-(4-cyclopropyltriazol-1-yl)-3-fluoro-3-methyl-butanoic acid (70 mg, 98.7% yield) as a colorless oil. The crude product was used directly for the next step.

Preparation of Compound 32d

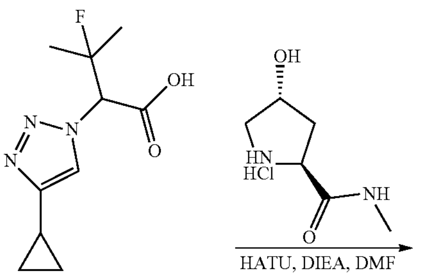

32c

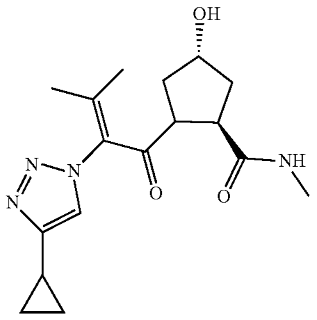

32

To a solution of 2-(4-cyclopropyltriazol-1-yl)-3-fluoro-3-methyl-butanoic acid (70.0 mg, 0.31 mmol) and (2S, 4R)-4-hydroxy-N-methyl-pyrrolidine-2-carboxamide; hydrochloride (61.2 mg, 0.34 mmol) in anhydrous tetrahydrofuran (3.00 mL) was added N,N-diisopropylethylamine (0.15 mL, 0.92 mmol). Then 2-(7-azabenzotriazol-1-yl)-N,N,N',N'-tetramethyluronium hexafluorophosphate (140.55 mg, 0.3700 mmol) was added. The reaction mixture was stirred at 25° C. for 3 h. The reaction mixture was concentrated to dryness. The residue was purified by reverse phase chromatography (water (0.2% FA)-ACN 12%-42%) afford compound 32, (2S, 4R)-1-[2-(4-cyclopropyltriazol-1-yl)-3-methyl-but-2-enoyl]-4-hydroxy-N-methyl-pyrrolidine-2-carboxamide (14.6 mg, 28.6% yield) as a white solid. β-H elimination product was formed during the amide coupling reaction. $^1$H NMR (400 MHz, $CDCl_3$-d) δ=7.44 (s, 1H), 6.82-6.67 (m, 1H), 4.68-4.60 (m, 1H), 4.47 (s, 1H), 3.88-3.85 (m, 1H), 3.47-3.44 (m, 1H), 2.82-2.77 (m, 3H), 2.40-2.10 (m, 2H), 2.02 (s, 3H), 1.96-1.92 (m, 1H), 1.74 (s, 3H), 1.64-1.51 (m, 1H), 1.00-0.97 (m, 3H), 0.87-0.86 (m, 3H). LCMS (5-95AB, ESI): RT=0.645 min, [M+H]+ 334.0.

Example S28: Synthesis of (2S, 4R)-4-hydroxy-N-methyl-1-((S)-3-methyl-2-(4-(thiophen-2-yl)-1H-1,2,3-triazol-1-yl)butanoyl)pyrrolidine-2-carboxamide (Compound 33)

Synthesis was carried out following the scheme given below:

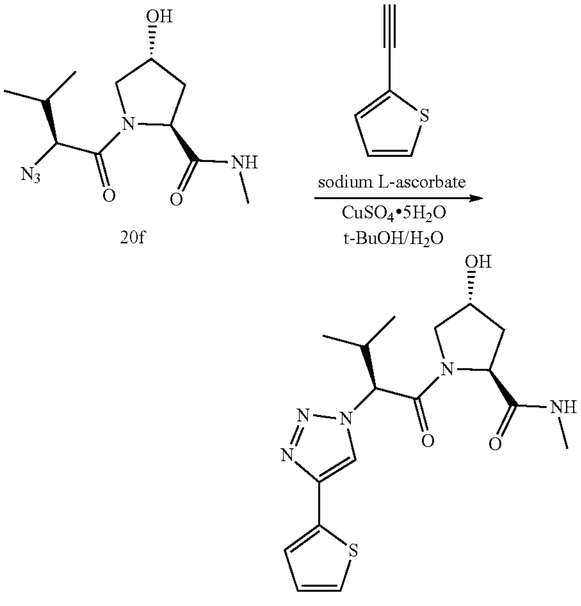

20f

33

To a solution of 2-ethynylthiophene (40.2 mg, 0.37 mmol) in water (1.00 mL) and tert-butanol (1.0 mL) were added copper (II) sulfate (23.2 mg, 0.09 mmol) and sodium ascorbate (3.68 mg, 0.02 mmol). Then added (2S, 4R)-1-((S)-2-azido-3-methylbutanoyl)-4-hydroxy-N-methylpyrrolidine-2-carboxamide (50.0 mg, 0.19 mmol). The mixture was stirred at 25° C. for 2 h.

The reaction mixture was filtered, the filtrate was concentrated under reduced pressure. The residue was purified by reverse phase chromatography (water (0.225% FA)-ACN 27%~57%) to afford compound 33, (2S, 4R)-4-hydroxy-N-methyl-1-((S)-3-methyl-2-(4-(thiophen-2-yl)-1H-1,2,3-triazol-1-yl)butanoyl)pyrrolidine-2-carboxamide (18.0 mg, 25.4% yield) as grey solid. $^1$H NMR (400 MHz, $CDCl_3$-d) δ=8.04 (s, 1H), 7.27-6.97 (m, 2H), 6.77-6.64 (m, 2H), 5.19-5.17 (m, 1H), 4.41 (s, 1H), 4.34-4.30 (m, 1H), 3.85-3.82 (m, 1H), 3.71-3.68 (m, 1H), 2.72 (s, 3H), 2.53-2.38 (m, 1H), 2.11-2.08 (m, 1H), 2.07-1.97 (m, 1H), 1.04-1.02 (m, 3H), 0.75-0.62 (m, 3H). LCMS (5-95AB, ESI): RT=0.739 min, $[M+H]^+$ 378.4.

Example S29: Synthesis of (2S, 4R)-4-hydroxy-N-methyl-1-[rac-(2S)-3-methyl-2-[4-(1H-pyrrol-2-yl)triazol-1-yl]butanoyl]pyrrolidine-2-carboxamide (Compound 34) and (2S, 4R)-4-hydroxy-N-methyl-1-[rac-(2R)-3-methyl-2-[4-(1H-pyrrol-2-yl)triazol-1-yl]butanoyl]pyrrolidine-2-carboxamide (Compound 35)

Synthesis was carried out following the scheme given below:

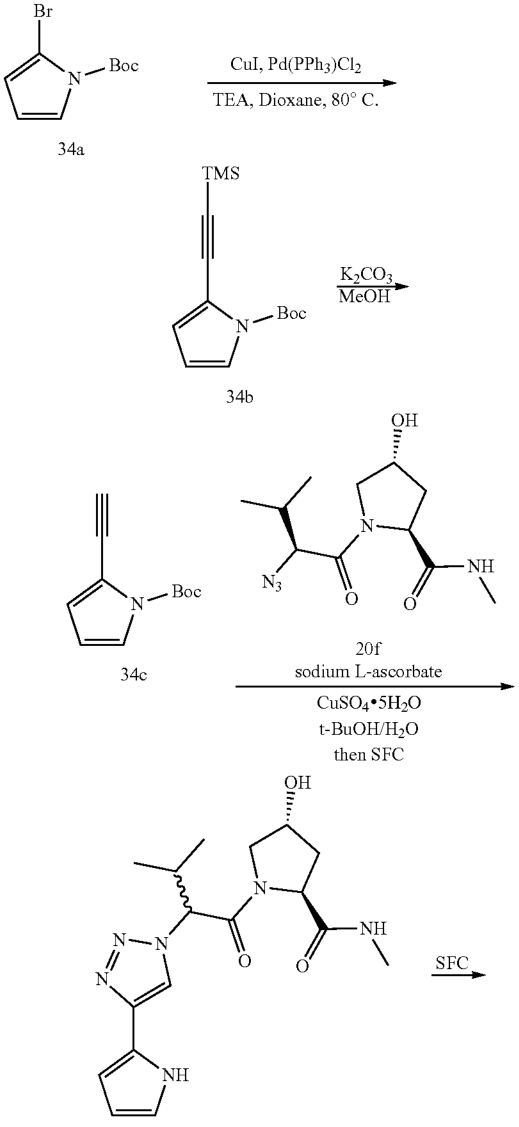

34a

34b

34c

20f

34d

-continued

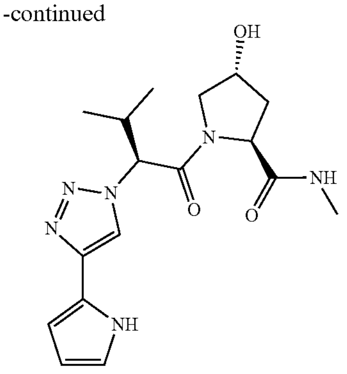

34

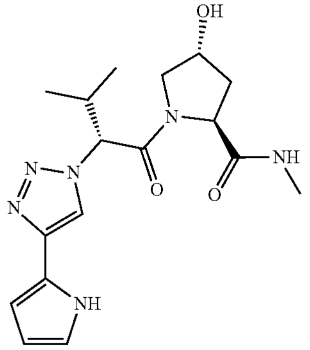

35

Preparation of Intermediate 34b

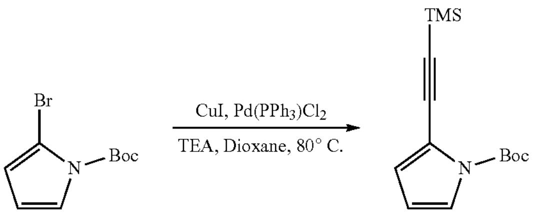

34a

34b

To a solution of tert-butyl 2-bromopyrrole-1-carboxylate (500 mg, 2.03 mmol) in 1,4-dioxane (20.0 mL) were added trimethylsilylacetylene (274 mg, 2.78 mmol), copper (I) iodide (24.0 mg, 0.13 mmol), bis(triphenylphosphine) palladium(II)dichloride (45.2 mg, 0.06 mmol) and N,N-Diisopropylethylamine (0.68 mL, 3.82 mmol). Then the reaction mixture was stirred at 80° C. for 8 h under N2 atmosphere. After cooled to room temperature, the reaction was quenched by water (20 mL). The resulting mixture was extracted with ethyl acetate (3×20 mL). The combined organic layers was dried over anhydrous sodium sulfate and concentrated under reduced pressure. The residue was purified by column chromatography (silica gel, 100-200 mesh, petroleum ether, 100%) to afford tert-butyl 2-(2-trimethylsilylethynyl)pyrrole-1-carboxylate (500 mg, 93.4% yield) as a brown oil.

Preparation of Intermediate 34c

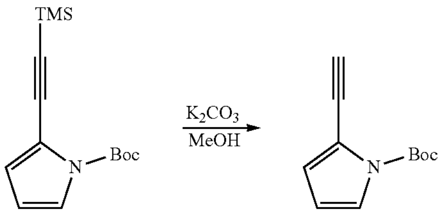

34b

34c

To a solution of tert-butyl 2-(2-trimethylsilylethynyl)pyrrole-1-carboxylate (500 mg, 1.90 mmol) was dissolved in methyl alcohol (10.0 mL), then potassium carbonate (787 mg, 5.69 mmol) was added. The reaction mixture was stirred at 25° C. for 8 h. The reaction mixture was filtered, the filtrate was concentrated to dryness. The residue was used for next step directly.

Preparation of Intermediate 34d

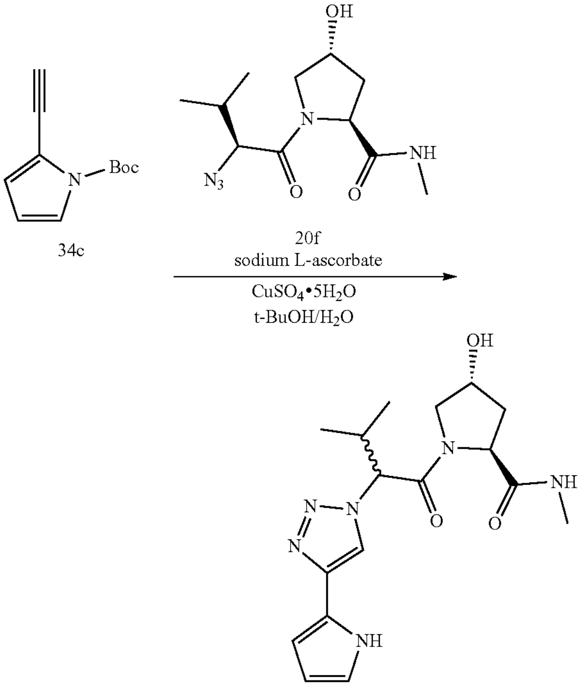

34d

To a mixture of (2S, 4R)-1-((S)-2-azido-3-methylbutanoyl)-4-hydroxy-N-methylpyrrolidine-2-carboxamide (300 mg, 1.11 mmol) and tert-butyl 2-ethynylpyrrole-1-carboxylate (320 mg, 1.67 mmol) in tert-butanol (5.0 mL) and water (10 mL) were added sodium ascorbate (22.1 mg, 0.11 mmol) and copper (II) sulfate (124 mg, 0.56 mmol). The reaction mixture was stirred vigorously at 80° C. for 8 h. After cooled to room temperature, the reaction was quenched by water (20 mL). The resulting mixture was extracted with ethyl acetate (3×50 mL). The combined organic layers was dried over anhydrous sodium sulfate and concentrated to dryness. The residue was purified by reverse phase chromatography (water (0.1% TFA)-ACN, 20%~40%)) and the mixture was purified by SFC to give (2S, 4R)-1-(2-(4-(1H-pyrrol-2-yl)-1H-1,2,3-triazol-1-yl)-3-methylbutanoyl)-4-hydroxy-N-methylpyrrolidine-2-carboxamide (65 mg, 16.3% yield) as a white solid.

Preparation of Compound 34 and Compound 35

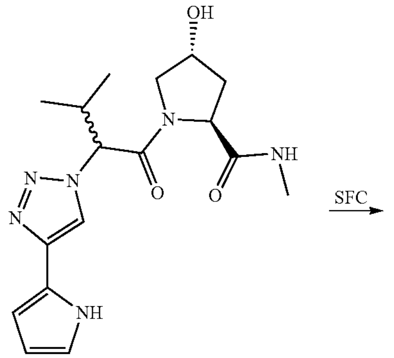

34d

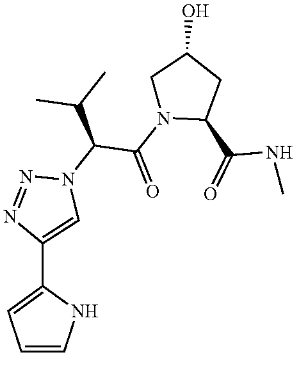

34

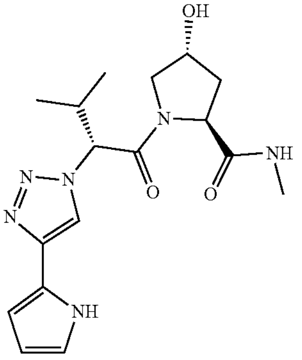

35

The above diastereomeric mixture was further separated by chiral SFC to give a first-eluting Isomer A and a second-eluting Isomer B:

Isomer A: (peak1, retention time=2.059, 100% ee). Compound 34, (2S, 4R)-4-hydroxy-N-methyl-1-[rac-(2S)-3-methyl-2-[4-(1H-pyrrol-2-yl)triazol-1-yl]butanoyl]pyrrolidine-2-carboxamide (22.9 mg, 35.5% yield). $^1$H NMR (400 MHz, MeOH-$d_4$) δ=8.25 (br s, 1H), 6.81-6.80 (m, 1H), 6.57 (br s, 1H), 6.15 (s, 1H), 5.31-5.28 (m, 1H), 4.50-4.38 (m, 2H), 3.95-3.76 (m, 2H), 2.75 (s, 3H), 2.68-2.57 (m, 1H), 2.19-1.99 (m, 2H), 1.15-1.09 (m, 3H), 0.80-0.74 (m, 3H). LCMS (5-95AB, ESI): RT=0.616 min, $[M+H]^+$ 361.0

Isomer B: (peak2, retention time=1.788, 100% ee). Compound 35, (2S, 4R)-4-hydroxy-N-methyl-1-[rac-(2R)-3-methyl-2-[4-(1H-pyrrol-2-yl)triazol-1-yl]butanoyl]pyrrolidine-2-carboxamide (9.9 mg, 15.3% yield). $^1$H NMR (400 MHz, MeOH-$d_4$) δ=8.10-8.06 (m, 1H), 6.81-6.80 (m, 1H), 6.52 (d, J=4.0 Hz, 1H), 6.16 (t, J=4.0 Hz, 1H), 5.34 (d, J=8.0 Hz, 1H), 4.52-4.42 (m, 2H), 3.82-3.79 (m, 1H), 3.66-3.57 (m, 1H), 2.69-2.57 (m, 3H), 2.29-2.13 (m, 1H), 2.00-1.93 (m, 1H), 1.11-1.01 (m, 3H), 0.80-0.71 (m, 3H). LCMS (5-95AB, ESI): RT=0.679 min, [M+H]+ 361.0

Example S30: Synthesis of (2S,4R)-4-hydroxy-N-methyl-1-((S)-3-methyl-2-(4-(oxazol-2-yl)-1H-1,2,3-triazol-1-yl)butanoyl)pyrrolidine-2-carboxamide (Compound 36) and (2S,4R)-4-hydroxy-N-methyl-1-((R)-3-methyl-2-(4-(oxazol-2-yl)-1H-1,2,3-triazol-1-yl)butanoyl)pyrrolidine-2-carboxamide (Compound 37)

Synthesis was carried out following the scheme given below:

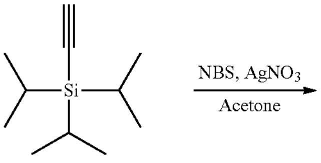

36a

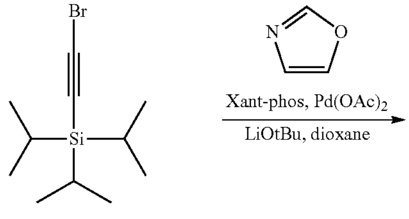

36b

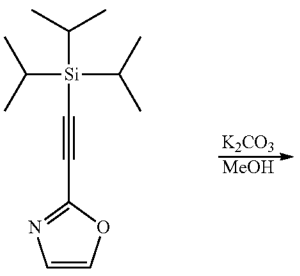

36c

-continued

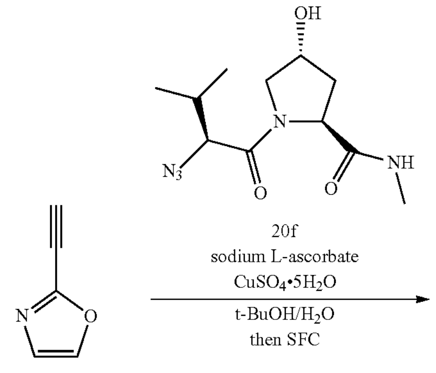

36d

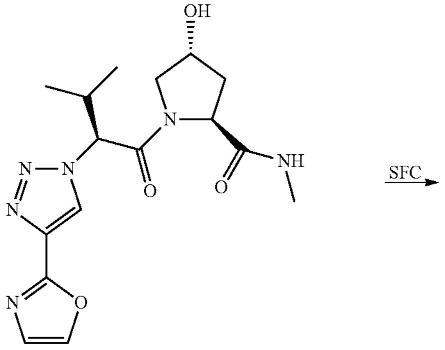

36e

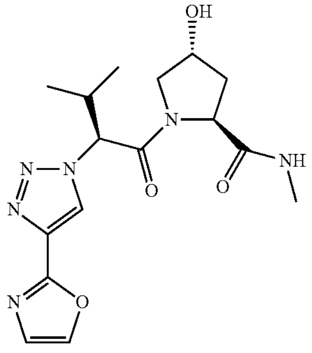

36

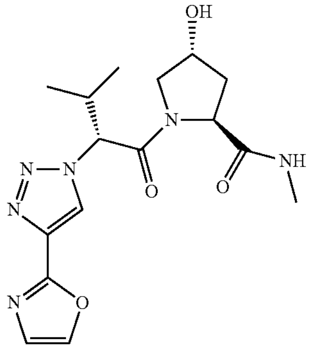

37

Preparation of Intermediate 36b

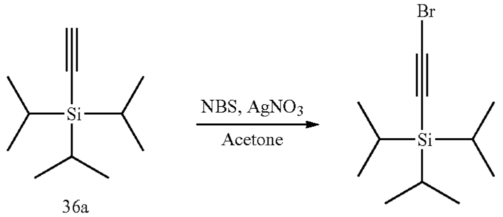

36a

36b

To a solution of ethynyltriisopropylsilane (6.15 mL, 27.4 mmol) in acetone (80 mL) were added N-Bromosuccinimide (5.66 g, 31.8 mmol), followed by silver nitrate (466 mg, 2.74 mmol). The reaction mixture was stirred at 80° C. for 8 h. The reaction was quenched by addition of water (20 mL) which was extracted with ethyl acetate (3×20 mL). The combined organic layers was dried over anhydrous sodium sulfate and concentrated under reduced pressure to afford (bromoethynyl)triisopropylsilane (7.0 g, 97.7% yield) as a colorless oil.

Preparation of Intermediate 36c

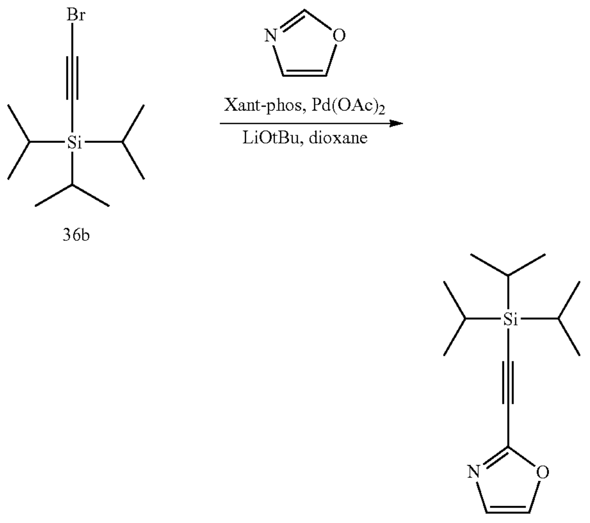

36b

36c

To a solution of oxazole (2.78 g, 40.2 mmol) and (bromoethynyl)triisopropylsilane (7.0 g, 26.8 mmol) in 1,4-dioxane (80 mL) were added lithiumtert-butoxide (4.29 g, 53.6 mmol), palladium(II) acetate (300 mg, 1.34 mmol) and 4,5-bis(diphenylphosphino)-9,9-dimethylxanthene (775 mg, 1.34 mmol) at 25° C. The reaction mixture was heated to 100° C. and stirred for 16 h.

After cooled to room temperature, the reaction was quenched by water (200 mL). The resulting mixture was extracted with ethyl acetate (3×100 mL). The combined organic layers were dried over anhydrous sodium sulfate and concentrated under reduced pressure. The residue was purified by column chromatography (silica gel, 100-200 mesh, 0-25% ethyl acetate in petroleum ether) to afford triisopropyl(2-oxazol-2-ylethynyl)silane (3.5 g, 52.4% yield) as a yellow oil.

Preparation of Intermediate 36d

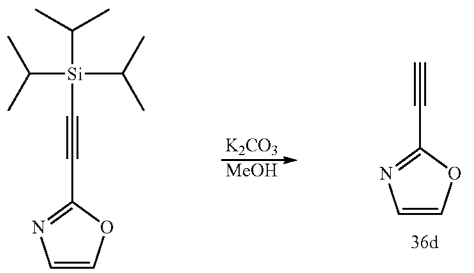

36c

36d

To a solution of 2-((triisopropylsilyl)ethynyl)oxazole (1.70 g, 6.82 mmol) was dissolved in methyl alcohol (10.0 mL), then potassium carbonate (2.83 g, 20.5 mmol) was added. The reaction mixture was stirred at 25° C. for 8 h. The reaction mixture filtered and concentrated to dryness. The residue was used to next step without purification.

Preparation of Intermediate 36e

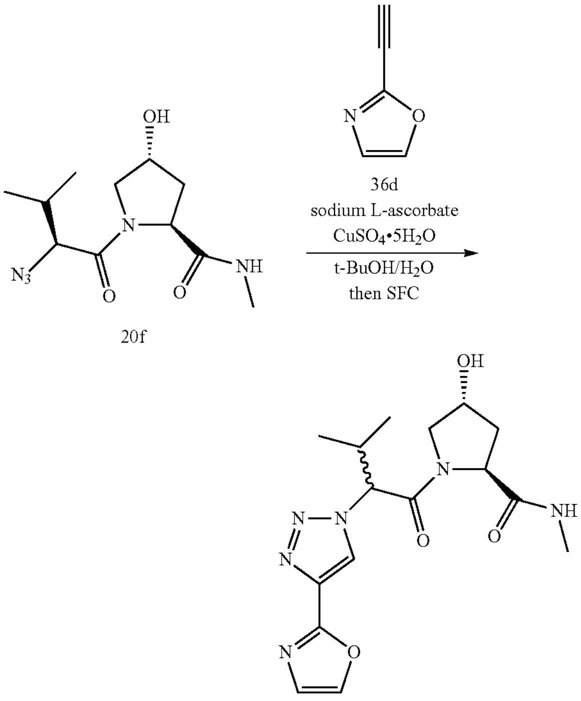

36d

20f

36e

To a mixture of (2S, 4R)-1-((S)-2-azido-3-methylbutanoyl)-4-hydroxy-N-methylpyrrolidine-2-carboxamide (350 mg, 1.30 mmol) and 2-ethynyloxazole (181 mg, 1.95 mmol) in tert-butanol (5 mL) and water (10 mL) were added sodium ascorbate (25.8 mg, 0.13 mmol) and copper(II) sulfate (203 mg, 0.65 mmol). The reaction mixture was stirred vigorously at 80° C. for 8 h. The resulting mixture was diluted with water (50 mL) and extracted with ethyl acetate (3×50 mL). The combined organic layers was dried over anhydrous sodium sulfate and concentrated under reduced pressure. The residue was purified by reverse phase chromatography (water (0.225% TFA)-ACN, 13%~43%) to give the racemic (2S, 4R)-4-hydroxy-N-methyl-1-(3-methyl-2-(4-(oxazol-2-yl)-1H-1, 2, 3-triazol-1-yl)butanoyl) pyrrolidine-2-carboxamide (160 mg, 32% yield) as white solid.

Preparation of Compound 36 and Compound 37

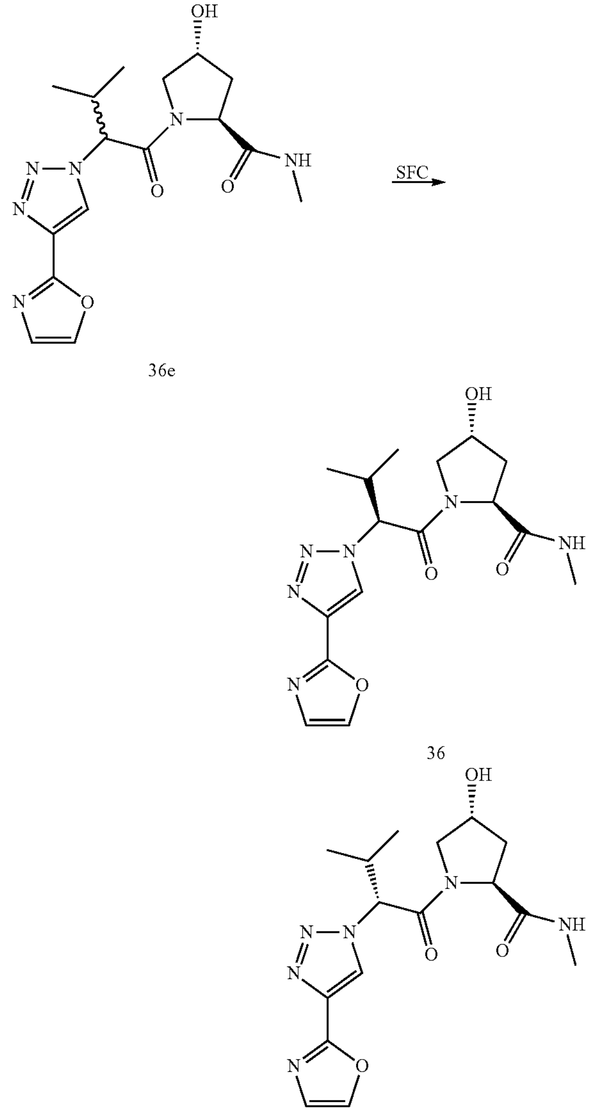

36e

36

37

The above diastereomeric mixture was further separated by chiral SFC to give a first-eluting Isomer A and a second-eluting Isomer B:

Isomer A: (peak1, retention time=1.868 min, 96.09% ee). Compound 36, (2S,4R)-4-hydroxy-N-methyl-1-((S)-3-methyl-2-(4-(oxazol-2-yl)-1H-1,2,3-triazol-1-yl)butanoyl) pyrrolidine-2-carboxamide (42.6 mg, 26.6% yield). $^1$H NMR (400 MHz, MeOH-$d_4$) δ=8.69-8.67 (m, 1H), 8.01 (s, 1H), 7.32 (s, 1H), 5.47 (d, J=12 Hz, 1H), 4.58-4.40 (m, 2H), 3.96-3.79 (m, 2H), 2.76-2.75 (m, 3H), 2.65-2.51 (m, 1H), 2.20-2.01 (m, 2H), 1.17-1.11 (m, 3H), 0.87-0.76 (m, 3H). LCMS (5-95AB, ESI): RT=0.628 min, [M+H]+ 363.0.

Isomer B: (peak2, retention time=2.322 min, 95.24% ee). Compound 37, (2S,4R)-4-hydroxy-N-methyl-1-((R)-3-methyl-2-(4-(oxazol-2-yl)-1H-1,2,3-triazol-1-yl)butanoyl) pyrrolidine-2-carboxamide (15.3 mg, 9.5% yield). $^1$H NMR (400 MHz, MeOH-$d_4$) δ=8.67-8.60 (m, 1H), 8.02 (s, 1H), 7.33 (s, 1H), 5.50 (d, J=20 Hz, 1H), 4.59-4.41 (m, 2H), 3.94-3.83 (m, 1H), 3.74-3.70 (m, 1H), 2.85-2.57 (m, 3H), 2.28-2.16 (m, 1H), 2.02-1.95 (m, 1H), 1.16-1.02 (m, 3H), 0.83-0.74 (m, 3H). LCMS (5-95AB, ESI): RT=0.570 min, [M+H]+ 363.0.

Example S31: Synthesis of (2S, 4R)-4-hydroxy-N-methyl-1-[rac-(2S)-3-methyl-2-(4-thiazol-2-yltriazol-1-yl)butanoyl]pyrrolidine-2-carboxamide (Compound 38) and (2S, 4R)-4-hydroxy-N-methyl-1-((R)-3-methyl-2-(4-(thiazol-2-yl)-1H-1, 2, 3-triazol-1-yl)butanoyl)pyrrolidine-2-carboxamide (Compound 39)

Synthesis was carried out following the scheme given below:

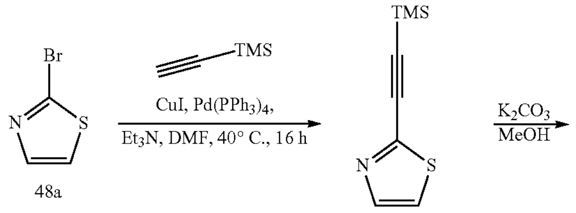

48a

38b

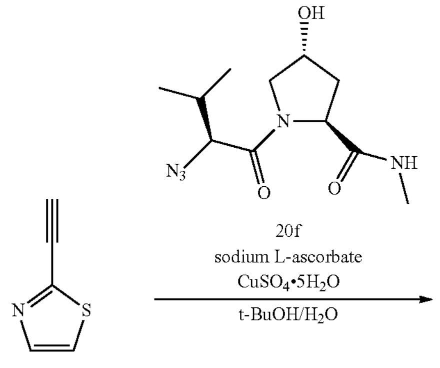

38c

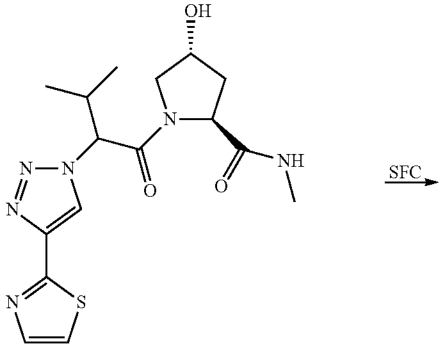

38d

-continued

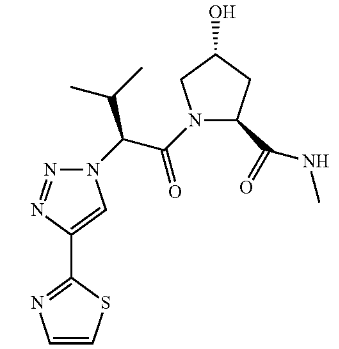

38

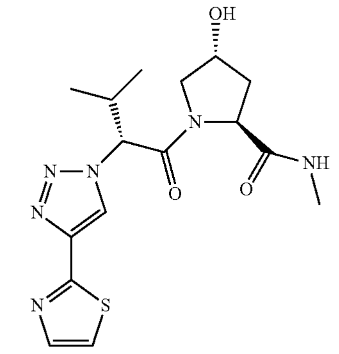

39

Preparation of Intermediate 38b

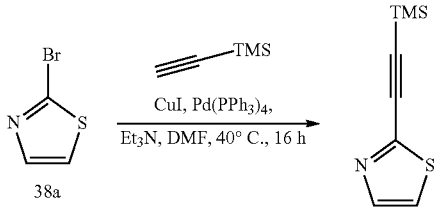

38a

38b

To a solution of 2-bromothiazole (0.27 mL, 3.05 mmol) and 1-(trimethylsilyl)-1-propyne (0.9 mL, 6.10 mmol) in 1,4-dioxane (10.0 mL) were added copper (I) iodide (58 mg, 0.30 mmol), 1,1'-bis(diphenylphosphino)ferrocene palladium dichloride (223 mg, 0.30 mmol) and triethylamine (1.27 mL, 9.15 mmol). The reaction mixture was stirred for 16 h at 100° C. under $N_2$ atmosphere. The reaction mixture was concentrated to dryness under reduced pressure. The residue was purified by column chromatography eluting with (0-30% ethyl acetate in petroleum ether) to afford trimethyl(2-thiazol-2-ylethynyl)silane (300 mg, 54.3% yield) as a yellow oil.

Preparation of Intermediate 38c

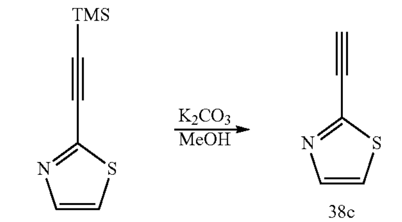

38b

38c

To a solution of trimethyl (2-thiazol-2-ylethynyl)silane (300 mg, 1.65 mmol) in methanol (5.0 mL) was added potassium carbonate (686 mg, 4.96 mmol). The reaction mixture was stirred at 25° C. for 2 h. The reaction mixture concentrated to dryness and used to next step without any purification.

Preparation of Intermediate 38d

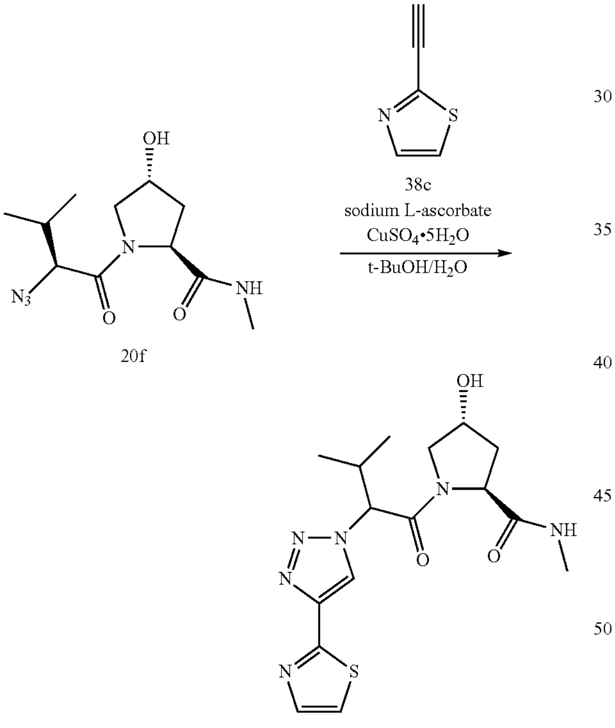

38c

20f

38d

To a mixture of (2S, 4R)-1-((S)-2-azido-3-methylbutanoyl)-4-hydroxy-N-methylpyrrolidine-2-carboxamide (247 mg, 0.92 mmol) in tert-butanol (5.0 mL) and water (5.0 mL) was added sodium ascorbate (18.2 mg, 0.09 mmol), copper(II) sulfate (143 mg, 0.46 mmol) and 2-ethynylthiazole (150 mg, 1.37 mmol). The reaction mixture was stirred at 50° C. for 16 h. After cooled to room temperature, the reaction was quenched by water (20 mL). The resulting mixture was extracted with ethyl acetate (3×50 mL). The combined organic layers were dried over anhydrous sodium sulfate and concentrated to dryness. The residue was purified by reverse phase chromatography (water (0.225% TFA)-ACN, 15%~45%) to afford (2S, 4R)-4-hydroxy-N-methyl-1-(3-methyl-2-(4-(thiazol-2-yl)-1H-1, 2, 3-triazol-1-yl)butanoyl)pyrrolidine-2-carboxamide (50 mg, 9.6% yield) as a white solid.

Preparation of Compound 38 and Compound 39

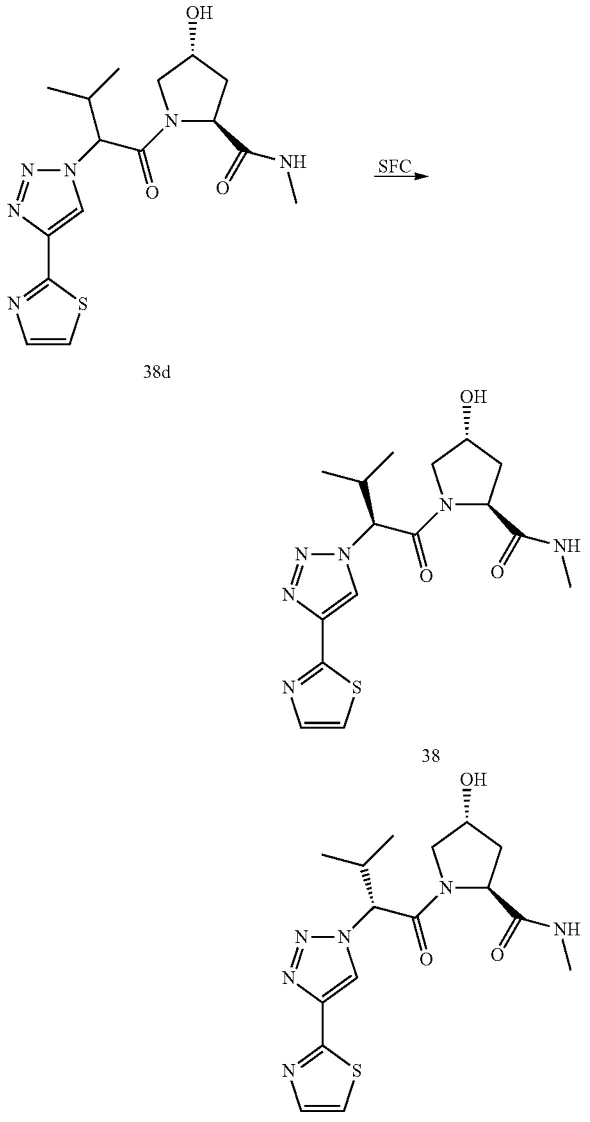

38d

38

39

The above diastereomeric mixture was further separated by chiral SFC to give a first-eluting Isomer A and a second-eluting Isomer B:

Isomer A: (peak1, retention time=1.494 min, 100% ee). Compound 38, (2S, 4R)-4-hydroxy-N-methyl-1-[rac-(2S)-3-methyl-2-(4-thiazol-2-yltriazol-1-yl)butanoyl]pyrrolidine-2-carboxamide (30.8 mg, 59.1% yield). $^1$H NMR (400 MHz, MeOH-$d_4$) δ 8.65-8.60 (m, 1H), 7.88 (s, 1H), 7.63 (s, 1H), 5.45-5.42 (m, 1H), 4.51 (s, 1H), 4.46-4.40 (m, 1H), 3.97-3.84 (m, 2H), 2.63 (s, 3H), 2.61-2.60 (m, 1H), 2.19-2.05 (m, 2H), 1.18-1.12 (m, 3H), 0.85-0.83 (m, 3H). LCMS (5-95AB, ESI): RT=0.723 min, [M+H]+ 379.0.

Isomer B: (peak2, retention time=2.131 min, 100% ee). Compound 39, (2S, 4R)-4-hydroxy-N-methyl-1-((R)-3-methyl-2-(4-(thiazol-2-yl)-1H-1, 2, 3-triazol-1-yl)butanoyl) pyrrolidine-2-carboxamide. $^{1}$H NMR (400 MHz, MeOH-$d_4$) δ 8.60-8.52 (m, 1H), 7.88 (s, 1H), 7.63 (s, 1H), 5.48-5.46 (m, 1H), 4.61-4.50 (m, 2H), 3.86-3.76 (m, 1H), 3.75-3.72 (m, 1H), 2.66 (s, 3H), 2.63-2.60 (m, 1H), 2.21-2.19 (m, 1H), 2.02-1.95 (m, 1H), 1.13-1.02 (m, 3H), 0.84-0.76 (m, 3H). LCMS (5-95AB, ESI): RT=0.726 min, [M+Na]+401.0.

Example S32: Synthesis of (2S, 4R)-4-hydroxy-N-methyl-1-[(2S)-3-methyl-2-(4-oxazol-5-yltriazol-1-yl)butanoyl]pyrrolidine-2-carboxamide (Compound 40)

Synthesis was carried out following the scheme given below:

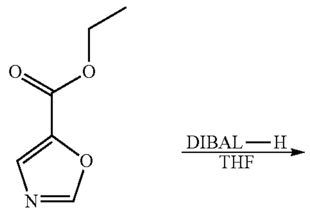

40a

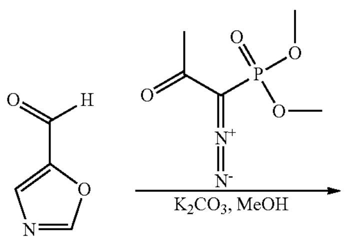

40b

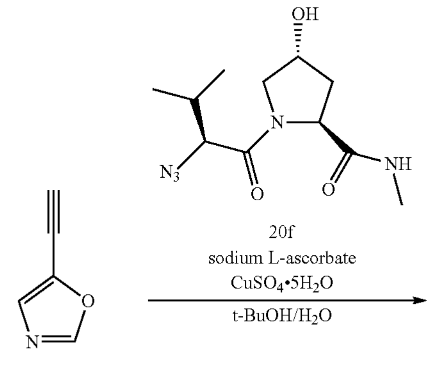

40c

-continued

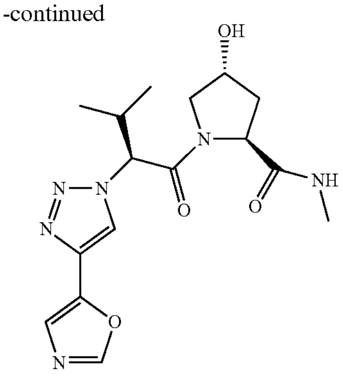

40

Preparation of Intermediate 40b

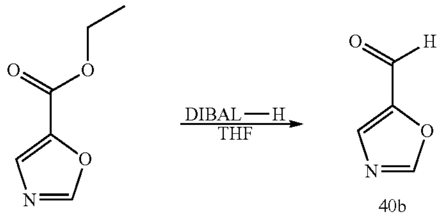

40a 40b

To a solution of ethyloxazole-5-carboxylate (1.20 g, 8.50 mmol) in dichloromethane (20.0 mL) was added diisobutylaluminumhydride (12.8 mL, 12.76 mmol, 1 M in toluene) at −78° C. The mixture was stirred for 2 h at −78° C. The reaction mixture was quenched with methanol (5.0 mL) and warmed to room temperature slowly and poured into HCl (2 M aqueous, 50 mL). The resulting solution was extracted with dichloromethane (40.0 mL) and the organic layer was separated and dried over anhydrous sodium sulfate and concentrated to dryness to afford oxazole-5-carbaldehyde (800 mg, 96.9% yield) as a colorless oil.

Preparation of Intermediate 40c

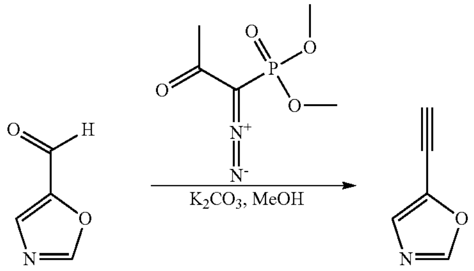

40b 40c

To a mixture of 1,3-oxazole-5-carbaldehyde (800 mg, 8.24 mmol) and potassium carbonate (1.14 g, 8.24 mmol) in methanol (8.0 mL) was added dimethyl(1-diazo-2-oxopropyl)phosphonate (1.58 g, 8.24 mmol). The reaction mixture was stirred for 2 h at 15° C. The reaction mixture was filtered, the filtrate was concentrated to dryness. The residue was used to next step without purification.

Preparation of Compound 40

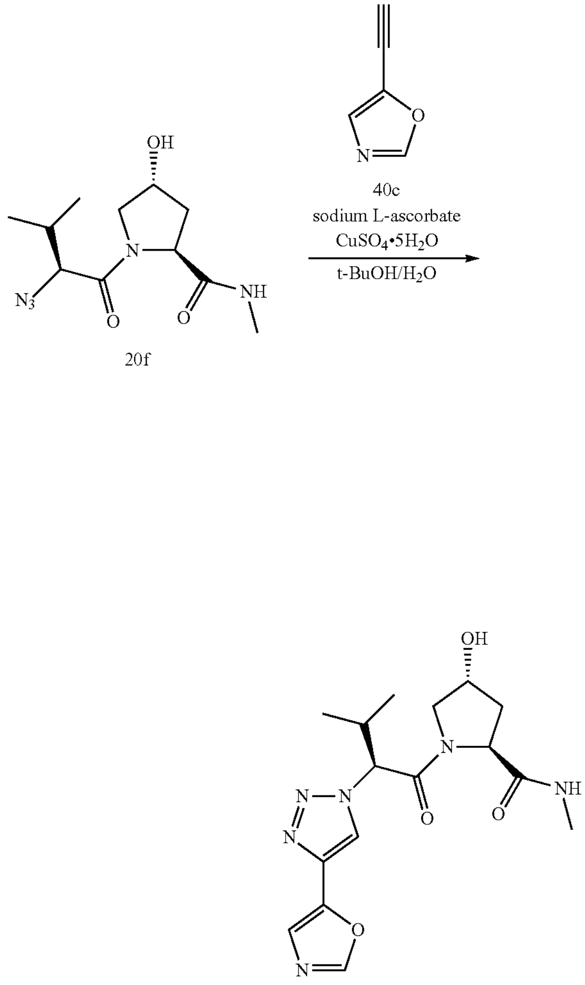

40

To a solution of (2S, 4R)-1-((S)-2-azido-3-methylbutanoyl)-4-hydroxy-N-methylpyrrolidine-2-carboxamide (250 mg, 0.93 mmol) and 5-ethynyloxazole (259 mg, 2.78 mmol) in tert-butanol (6.0 mL) and water (6.0 mL) was added sodium ascorbate (92.0 mg, 0.46 mmol), copper (II) sulfate (145 mg, 0.46 mmol) and potassium carbonate (192 mg, 1.39 mmol). The reaction mixture was warmed to 50° C. and stirred for 16 h. After cooled to room temperature, the reaction mixture was filtered and filtrate was concentrated to dryness. The residue was purified by reverse phase chromatography (water (0.225% FA)-ACN 12%~42%) to afford compound 40, (2S, 4R)-4-hydroxy-N-methyl-1-[(2S)-3-methyl-2-(4-oxazol-5-yltriazol-1-yl)butanoyl]pyrrolidine-2-carboxamide (7 mg, 2% yield) as a white solid. $^1H$ NMR (400 MHz, MeOH-$d_4$): δ 8.48 (s, 1H), 8.29 (s, 1H), 7.52 (s, 1H), 5.44-5.41 (m, 1H), 4.51-4.40 (m, 2H), 3.96-3.85 (m, 2H), 2.76 (s, 3H), 2.74-2.61 (m, 1H), 2.18-2.01 (m, 3H), 1.20-1.16 (m, 3H), 0.83-0.81 (m, 3H). LCMS (5-95AB, ESI): RT=0.607 min, [M+H]+ 363.0

Example S33: Synthesis of (2S,4R)-4-hydroxy-N-methyl-1-((S)-3-methyl-2-(4-(thiazol-5-yl)-1H-1,2,3-triazol-1-yl)butanoyl)pyrrolidine-2-carboxamide (Compound 41) and (2S,4R)-4-hydroxy-N-methyl-1-((R)-3-methyl-2-(4-(thiazol-5-yl)-1H-1,2,3-triazol-1-yl)butanoyl)pyrrolidine-2-carboxamide (Compound 42)

Synthesis was carried out following the scheme given below:

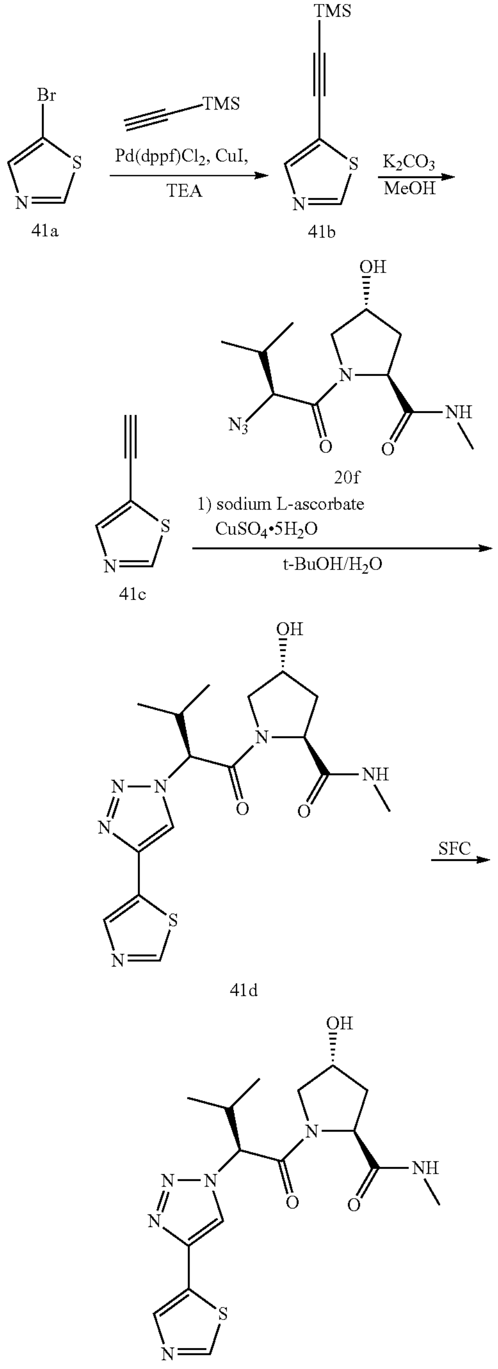

41

-continued

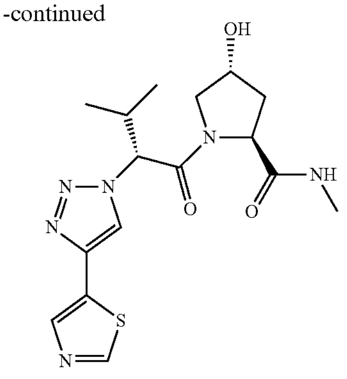

42

Preparation of Intermediate 41b

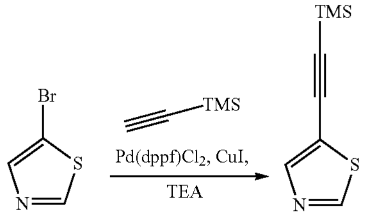

41a 41b

To a solution of 5-bromothiazole (500 mg, 3.05 mmol) in 1,4-dioxane (10.0 mL) were added 1-(trimethylsilyl)-1-propyne (0.90 mL, 6.10 mmol), copper (J) iodide (58.0 mg, 0.30 mmol), triethylamine (1.27 mL, 9.15 mmol) and 1,1'-bis (diphenylphosphino)ferrocene palladium dichloride (223 mg, 0.30 mmol). The mixture was stirred for 16 h at 100° C. under $N_2$ atmosphere. The reaction mixture was concentrated under reduced pressure. The residue was purified by column chromatography eluting with (silica gel, 100-200 mesh, 0-10% ethyl acetate in petroleum ether) to afford 5-((trimethylsilyl)ethynyl)thiazole (300 mg, 54.3% yield) as a brown oil.

Preparation of Intermediate 41c

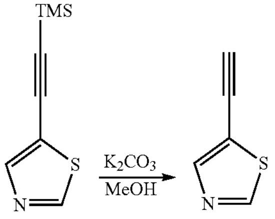

41b 41c

To a solution of trimethyl (2-thiazol-5-ylethynyl)silane (113 mg, 0.62 mmol) in methyl alcohol (3.00 mL) was added potassium carbonate (258 mg, 1.87 mmol). The reaction mixture was stirred at 25° C. for 2 h.

The reaction mixture was filtered, the filtrate was concentrated to dryness. The residue was used to next step without purification.

Preparation of Intermediate 41d

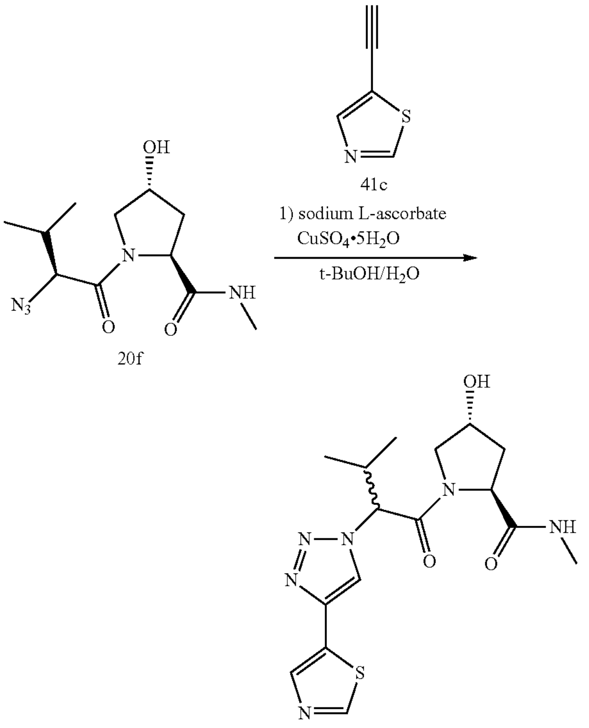

41d

To a mixture of (2S, 4R)-1-((S)-2-azido-3-methylbutanoyl)-4-hydroxy-N-methylpyrrolidine-2-carboxamide (80.0 mg, 0.30 mmol) in tert-butanol (2.00 mL) and water (2 mL) were added sodium ascorbate (5.89 mg, 0.03 mmol), copper (II) sulfate (46.5 mg, 0.15 mmol) and 5-ethynylthiazole (64.0 mg, 0.59 mmol). The reaction mixture was stirred at 20° C. for 2 h. The reaction was quenched by water (20 mL). The resulting mixture was extracted with ethyl acetate (3×50 mL). The combined organic layers was dried over anhydrous sodium sulfate and concentrated under reduced pressure.

The residue was purified by reverse phase chromatography (water (0.225% FA)-ACN 7-37%) to afford (2S, 4R)-4-hydroxy-N-methyl-1-((S)-3-methyl-2-(4-(thiazol-5-yl)-1H-1,2,3-triazol-1-yl)butanoyl)pyrrolidine-2-carboxamide (40 mg, 35.2% yield) as white solid.

Preparation of Compound 41 and Compound 42

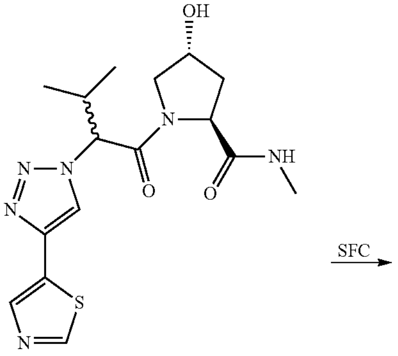

41d

-continued

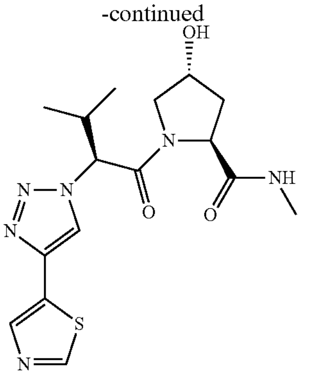

41

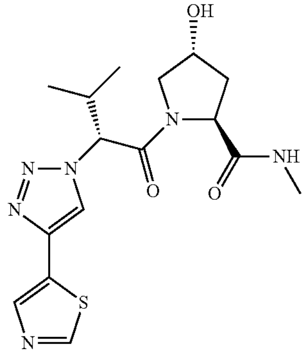

42

The above diastereomeric mixture was further separated by chiral SFC to give a first-eluting Isomer A and a second-eluting Isomer B:

Isomer A: (peak1, retention time=2.093 min, 99.5% ee). Compound 41, (2S,4R)-4-hydroxy-N-methyl-1-((S)-3-methyl-2-(4-(thiazol-5-yl)-1H-1,2,3-triazol-1-yl)butanoyl) pyrrolidine-2-carboxamide (16.0 mg, 25.6% yield). $^1$H NMR (400 MHz, MeOH-$d_4$) δ 9.00 (s, 1H), 8.53 (s, 1H), 8.24 (s, 1H), 5.40-5.38 (m, 1H), 4.51-4.50 (m, 1H), 4.44-4.40 (m, 1H), 3.97-3.93 (m, 1H), 3.88-3.85 (m, 1H), 2.76 (s, 3H), 2.63-2.60 (m, 1H), 2.18-2.16 (m, 1H), 2.08-2.04 (m, 1H), 1.18-1.06 (m, 3H), 0.84-0.77 (m, 3H). LCMS (5-95AB, ESI): RT=0.630 min, [M+H]+ 379.0 showed 99% purity.

Isomer B: (peak2, retention time=2.344 min, 99.7% ee). Compound 42, (2S,4R)-4-hydroxy-N-methyl-1-((R)-3-methyl-2-(4-(thiazol-5-yl)-1H-1,2,3-triazol-1-yl)butanoyl) pyrrolidine-2-carboxamide. $^1$H NMR (400 MHz, MeOH-$d_4$) δ 9.00 (s, 1H), 8.53 (s, 1H), 8.24 (s, 1H), 5.40-5.38 (m, 1H), 4.54-4.51 (m, 1H), 4.44-4.40 (m, 1H), 3.97-3.93 (m, 1H), 3.88-3.85 (m, 1H), 2.76 (s, 3H), 2.63-2.60 (m, 1H), 2.18-2.16 (m, 1H), 2.08-2.04 (m, 1H), 1.18-1.06 (m, 3H), 0.84-0.77 (m, 3H). LCMS (5-95AB, ESI): RT=0.630 min, [M+H]+ 379.0.

Example S34: Synthesis of (2S,4R)-4-hydroxy-N-methyl-1-((S)-3-methyl-2-(4-phenyl-1H-1,2,3-triazol-1-yl)butanoyl)pyrrolidine-2-carboxamide (Compound 43)

Synthesis was carried out following the scheme given below:

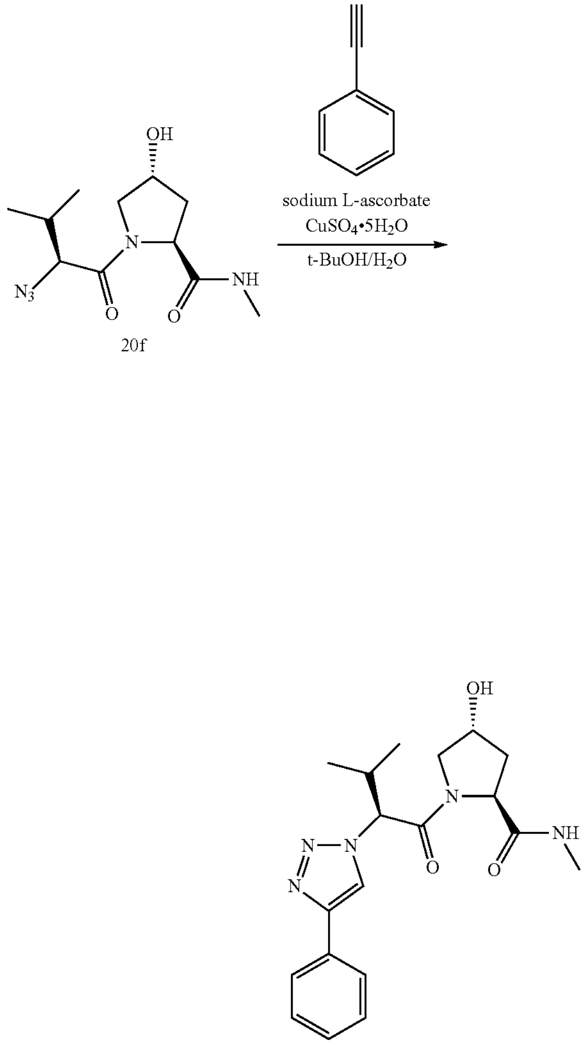

20f

43

To a mixture of (2S, 4R)-1-((S)-2-azido-3-methylbutanoyl)-4-hydroxy-N-methylpyrrolidine-2-carboxamide (157.0 mg, 0.58 mmol) in tert-butanol (2.0 mL) and water (2 mL) were added sodium ascorbate (11.6 mg, 0.06 mmol), copper(II) sulfate (91.3 mg, 0.29 mmol) and phenyl acetylene (0.14 mL, 1.23 mmol). The reaction mixture was stirred at 20° C. for 2 h. The reaction was quenched by water (20 mL). The resulting mixture was extracted with ethyl acetate (3×50 mL). The combined organic layers was dried over anhydrous sodium sulfate and concentrated under reduced pressure. The residue was purified by reverse phase chromatography (water (0.225% FA)-ACN 7-37%) to afford compound 43, (2S,4R)-4-hydroxy-N-methyl-1-((S)-3-methyl-2-(4-phenyl-1H-1,2,3-triazol-1-yl)butanoyl)pyrrolidine-2-carboxamide (50 mg, 23.1% yield) as white solid. LCMS (5-95AB, ESI): RT=0.74 min, [M+H]+ 371.2

Example S35: Synthesis of (2S,4R)-4-hydroxy-N-methyl-1-((S)-3-methyl-2-(4-(pyridin-2-yl)-1H-1,2,3-triazol-1-yl)butanoyl)pyrrolidine-2-carboxamide (Compound 44)

Synthesis was carried out following the scheme given below:

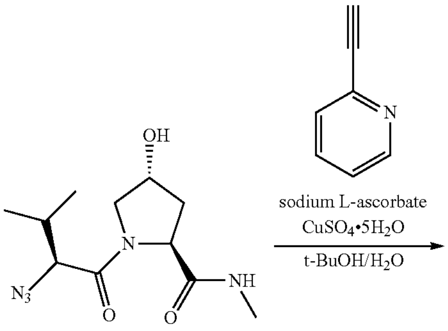

20f

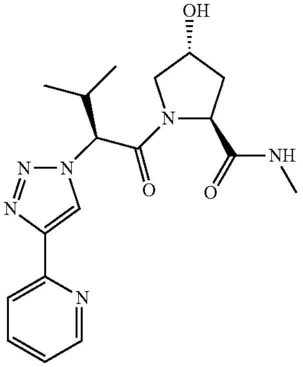

44

To a mixture of (2S, 4R)-1-((S)-2-azido-3-methylbutanoyl)-4-hydroxy-N-methylpyrrolidine-2-carboxamide (150 mg, 0.56 mmol) in tert-butanol (1.0 mL) and water (1.0 mL) were added sodium ascorbate (11.0 mg, 0.06 mmol), copper (II) sulfate (87.2 mg, 0.28 mmol) and 2-ethynylpyridine (0.12 mL, 1.17 mmol). The reaction mixture was stirred at 25° C. for 8 h. The reaction was quenched by water (20 mL). The resulting mixture was extracted with ethyl acetate (3x20 mL). The combined organic layers was dried over anhydrous sodium sulfate and concentrated under reduced pressure. The residue was purified by reverse phase chromatography (water (0.225% FA)-ACN 7-37%) to afford compound 44, (2S,4R)-4-hydroxy-N-methyl-1-((S)-3-methyl-2-(4-(pyridin-2-yl)-1H-1,2,3-triazol-1-yl)butanoyl) pyrrolidine-2-carboxamide (99.0 mg, 47.7% yield) as white solid. LCMS (5-95AB, ESI): RT=0.74 min, [M+H]+ 373.2

Example S36: Synthesis of (2S,4R)-4-hydroxy-N-methyl-1-((S)-3-methyl-2-(4-(pyridin-3-yl)-1H-1,2,3-triazol-1-yl)butanoyl)pyrrolidine-2-carboxamide (Compound 45)

Synthesis was carried out following the scheme given below:

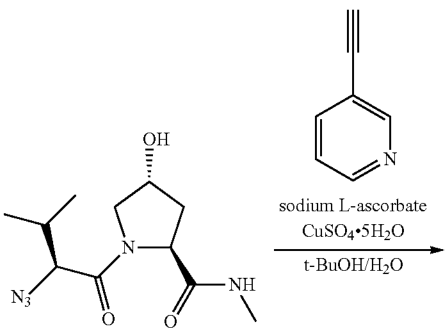

20f

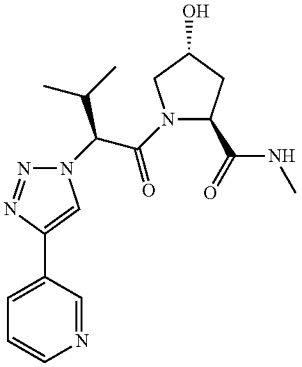

45

To a mixture of (2S, 4R)-1-((S)-2-azido-3-methylbutanoyl)-4-hydroxy-N-methylpyrrolidine-2-carboxamide (130 mg, 0.48 mmol) in tert-butanol (2.00 mL) and water (2.0 mL) were added sodium ascorbate (9.56 mg, 0.05 mmol), copper(II) sulfate (75.6 mg, 0.24 mmol) and 3-ethynylpyridine (99.6 mg, 0.97 mol). The reaction mixture was stirred at 25° C. for 2 h. The reaction was quenched by water (20 mL). The resulting mixture was extracted with ethyl acetate (3x20 mL). The combined organic layers was dried over anhydrous sodium sulfate and concentrated under reduced pressure. The residue was purified by reverse phase chromatography (water (0.225% FA)-ACN 3-33%) to afford compound 45, (2S,4R)-4-hydroxy-N-methyl-1-((S)-3-methyl-2-(4-(pyridin-3-yl)-1H-1,2,3-triazol-1-yl)butanoyl) pyrrolidine-2-carboxamide (50 mg, 27% yield) as yellow solid. $^1H$ NMR (400 MHz, MeOH-$d_4$) δ 8.67-8.64 (m, 1H), 8.32-8.16 (m, 2H), 7.61 (s, 1H), 5.42-5.40 (m, 1H), 4.52-4.45 (m, 1H), 4.43-4.41 (m, 1H), 3.98-3.95 (m, 1H), 3.90-3.79 (m, 1H), 2.77 (s, 3H), 2.67-2.58 (m, 1H), 2.21-2.02 (m, 2H), 1.19-1.13 (m, 3H), 0.84-0.77 (m, 3H). LCMS (5-95AB, ESI): RT=0.602 min, $[M+H]^+$ 373.1.

Example S37: Synthesis of (2S,4R)-4-hydroxy-N-methyl-1-((S)-3-methyl-2-(4-(pyridin-4-yl)-1H-1,2,3-triazol-1-yl)butanoyl)pyrrolidine-2-carboxamide (Compound 46)

Synthesis was carried out following the scheme given below:

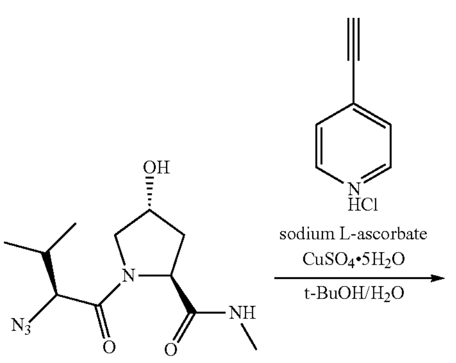

20f

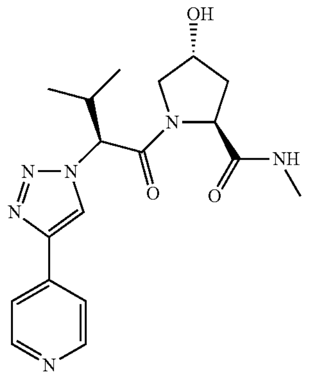

46

To a mixture of (2S,4R)-1-((S)-2-azido-3-methylbutanoyl)-4-hydroxy-N-methylpyrrolidine-2-carboxamide (100.0 mg, 0.37 mmol) in tert-butanol (1.00 mL) and water (1.00 mL) were added sodium ascorbate (7.36 mg, 0.04 mmol), copper(II) sulfate (58.2 mg, 0.19 mmol) and 4-ethynylpyridine hydrochloride (77.8 mg, 0.56 mmol). The reaction mixture was stirred at 25° C. for 8 h. The reaction was quenched by water (20 mL). The resulting mixture was extracted with ethyl acetate (3×20 mL). The combined organic layers was dried over anhydrous sodium sulfate and concentrated to dryness. The residue was purified by reverse phase chromatography (water (0.225% FA)-ACN 1%~30%) to afford compound 46, (2S,4R)-4-hydroxy-N-methyl-1-((S)-3-methyl-2-(4-(pyridin-4-yl)-1H-1,2,3-triazol-1-yl)butanoyl)pyrrolidine-2-carboxamide (40 mg, 28.6% yield) as a yellow solid. $^1$H NMR (400 MHz, MeOH-$d_4$) δ 8.78-8.75 (m, 2H), 8.34-8.01 (m, 3H), 5.44-5.42 (m, 1H), 4.52-4.40 (m, 2H), 3.98-3.81 (m, 2H), 2.77 (s, 3H), 2.58-2.40 (m, 2H), 2.21-2.01 (m, 2H), 1.19-1.12 (m, 3H), 0.84-0.77 (m, 3H). LCMS (0-60 CD, ESI): RT=1.481 min, $[M+H]^+$ 373.1.

Example S38: Synthesis of (2S,4R)-4-hydroxy-N-methyl-1-((S)-3-methyl-2-(4-(pyrimidin-2-yl)-1H-1,2,3-triazol-1-yl)butanoyl)pyrrolidine-2-carboxamide (Compound 47)

Synthesis was carried out following the scheme given below:

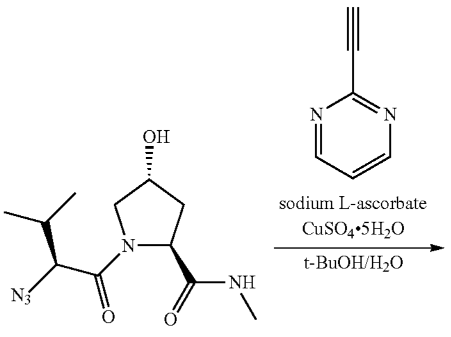

20f

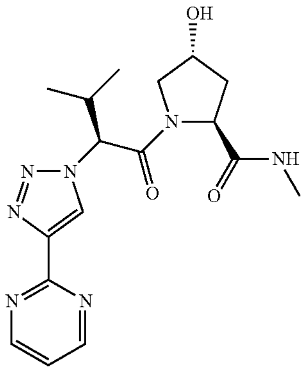

47

To a mixture of (2S,4R)-1-((S)-2-azido-3-methylbutanoyl)-4-hydroxy-N-methylpyrrolidine-2-carboxamide (52.0 mg, 0.1900 mmol) in tert-butanol (1.00 mL) and water (1.00 mL) were added sodium ascorbate (3.83 mg, 0.02 mmol), copper (II) sulfate (24.1 mg, 0.10 mmol) and 2-ethynylpyrimidine (40.2 mg, 0.39 mmol). The reaction mixture was stirred at 25° C. for 16 h. The reaction was quenched by water (20 mL). The resulting mixture was extracted with ethyl acetate (3×20 mL). The combined organic layers was dried over anhydrous sodium sulfate and concentrated to dryness. The residue was purified by reverse phase chromatography (water (0.225% FA)-ACN 6%~36%) to afford compound 47, (2S,4R)-4-hydroxy-N-methyl-1-((S)-3-methyl-2-(4-(pyrimidin-2-yl)-1H-1,2,3-triazol-1-yl)butanoyl)pyrrolidine-2-carboxamide (65 mg, 87.4% yield) as grey solid. $^1$H NMR (400 MHz, MeOH-$d_4$) δ=8.85-8.75 (m, 3H), 7.41 (s, 1H), 5.46-5.44 (m, 1H), 4.51-4.41 (m, 2H), 3.98-3.78 (m, 2H), 2.77 (s, 3H), 2.67-2.56 (m, 2H), 2.21-2.02 (m, 2H), 1.18-1.12 (m, 3H), 2.22-2.00 (m, 2H), 0.85-0.78 (m, 3H). LCMS (5-95AB, ESI): RT=0.648 min, [M+H]+ 374.0.

Example S39: Synthesis of (2S,4R)-4-hydroxy-N-methyl-1-((S)-3-methyl-2-(4-(pyrimidin-5-yl)-1H-1,2,3-triazol-1-yl)butanoyl)pyrrolidine-2-carboxamide (Compound 48)

Synthesis was carried out following the scheme given below:

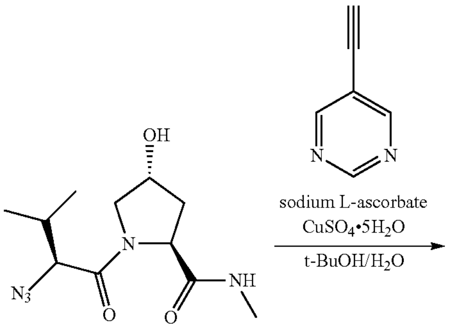

20f

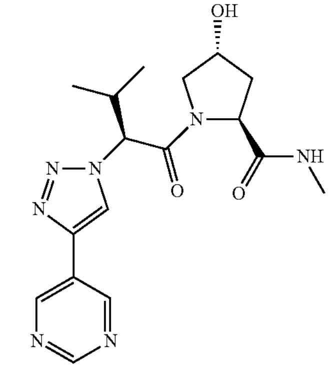

48

To a mixture of (2S, 4R)-4-hydroxy-N-methyl-1-[rac-(2S)-2-azido-3-methyl-butanoyl]pyrrolidine-2-carboxamide (150 mg, 0.56 mmol) in tert-butanol (1.0 mL) and water (1.0 mL) were added sodium ascorbate (11.0 mg, 0.06 mmol), copper (II) sulfate (24.11 mg, 0.10 mmol) and 5-ethynylpyrimidine (122 mg, 1.17 mmol). The reaction mixture was stirred at 25° C. for 8 h. The reaction was quenched by water (20 mL). The resulting mixture was extracted with ethyl acetate (3×20 mL). The combined organic layers was dried over anhydrous sodium sulfate and concentrated under reduced pressure. The residue was purified by reverse phase chromatography (water (0.225% FA)-ACN 6%~36%) to afford compound 48, (2S,4R)-4-hydroxy-N-methyl-1-((S)-3-methyl-2-(4-(pyrimidin-5-yl)-1H-1,2,3-triazol-1-yl)butanoyl)pyrrolidine-2-carboxamide (59 mg, 28.4% yield) as a white solid. LCMS (5-95AB, ESI): RT=0.624 min, [M+H]+ 373.2.

Example S40: Synthesis of (2S,4R)-1-((S)-2-(4-(5-chlorothiophen-2-yl)-1H-1,2,3-triazol-1-yl)-3-methylbutanoyl)-4-hydroxy-N-methylpyrrolidine-2-carboxamide (Compound 49)

Synthesis was carried out following the scheme given below:

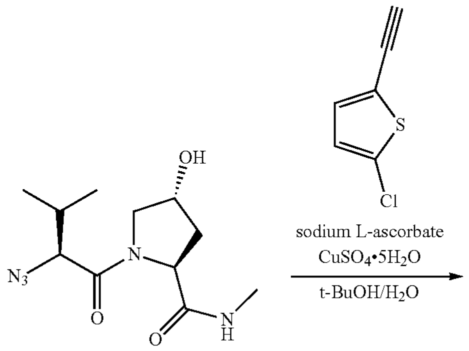

20f

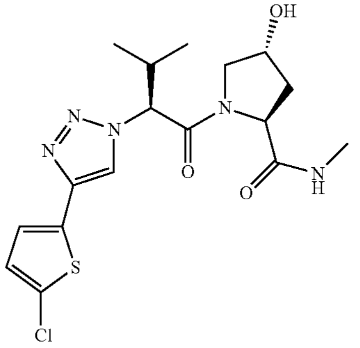

49

To a mixture of (2S, 4R)-1-((S)-2-azido-3-methylbutanoyl)-4-hydroxy-N-methylpyrrolidine-2-carboxamide (130.0 mg, 0.48 mmol) in tert-butanol (5.0 mL) and water (10 mL) were added sodium ascorbate (9.56 mg, 0.05 mmol), copper(II) sulfate (75.6 mg, 0.24 mmol) and 2-chloro-5-ethynyl-thiophene (103 mg, 0.72 mmol). The reaction mixture was stirred at 50° C. for 8 h.

After cooled to room temperature, the reaction was quenched by water (20 mL). The resulting mixture was extracted with ethyl acetate (3×20 mL). The combined organic layers was dried over anhydrous sodium sulfate and concentrated under reduced pressure. The residue was purified by reverse phase chromatography (water (0.225% FA)-ACN 30%-60%) to afford compound 49, (2S,4R)-1-((S)-2-(4-(5-chlorothiophen-2-yl)-1H-1,2,3-triazol-1-yl)-3-methylbutanoyl)-4-hydroxy-N-methylpyrrolidine-2-carboxamide (43 mg, 21.4% yield) as a white solid. $^1H$ NMR (400 MHz, MeOH-$d_4$) δ 8.40-8.38 (m, 1H), 7.25-7.24 (m, 1H), 6.99-6.98 (m, 1H), 5.36-5.34 (m, 1H), 4.60-4.51 (m, 1H), 4.43-4.39 (m, 1H), 3.96-3.83 (m, 2H), 2.76 (s, 3H), 2.71-2.58 (m, 1H), 2.17-2.04 (m, 2H), 1.16-1.12 (m, 3H), 0.82-0.75 (m, 3H). LCMS (5-95AB, ESI): RT=0.757 min, [M+H]+ 412.0.

Example S41: Synthesis of (2S,4R)-1-((S)-2-(4-cyclopropyl-1H-1,2,3-triazol-1-yl)-3-methylbutanoyl)-4-hydroxy-N,N-dimethylpyrrolidine-2-carboxamide (Compound 50)

Synthesis was carried out following the scheme given below:

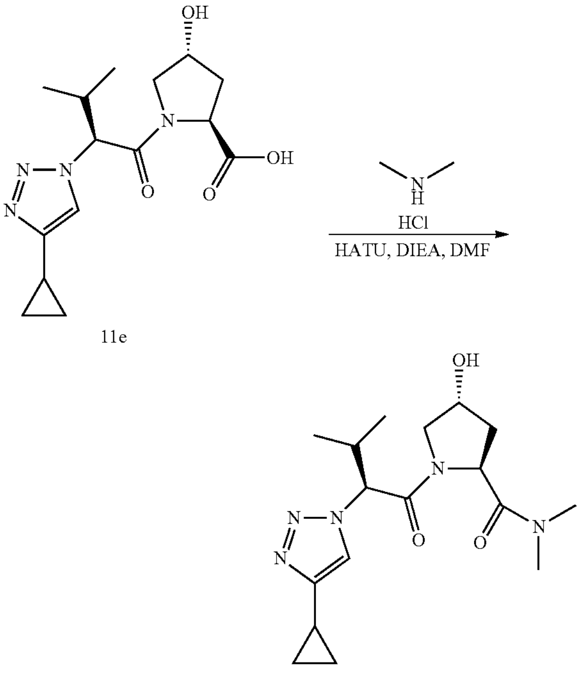

11e

50

To a solution of (2S, 4R)-1-((S)-2-(4-cyclopropyl-1H-1,2,3-triazol-1-yl)-3-methylbutanoyl)-4-hydroxypyrrolidine-2-carboxylic acid (766 mg, 2.38 mmol) and N,N-dimethylamine hydrochloride (194 mg, 2.38 mmol) in N,N-dimethylformamide (10.0 mL), N,N-diisopropylethylamine (1.24 mL, 7.13 mmol) and 2-(7-Azabenzotriazol-1-yl)-N,N,N',N'-tetramethyluronium hexafluorophosphate (994 mg, 2.61 mmol) were added at 0° C. The reaction mixture was stirred for 2 h at 25° C. The resulting residue was purified by reverse phase chromatography (water (0.225% FA)-ACN 15-45%) to afford compound 50, (2S, 4R)-1-((S)-2-(4-cyclopropyl-1H-1, 2, 3-triazol-1-yl)-3-methylbutanoyl)-4-hydroxy-N,N-dimethylpyrrolidine-2-carboxamide (217 mg, 88.6% yield) as a white solid. $^1$H NMR (400 MHz, MeOH-$d_4$) δ 7.81 (s, 1H), 5.34-5.22 (m, 1H), 4.95-4.91 (m, 1H), 4.51 (s, 1H), 3.94-3.82 (m, 2H), 3.15 (s, 3H), 2.96 (s, 3H), 2.50-2.49 (m, 1H), 2.04-2.03 (m, 1H), 1.98-1.94 (m, 2H), 1.14-0.74 (m, 10H). LCMS (5-95 AB, ESI): RT=0.665 min, [M+H]+ 350.1.

Biological Assays

Example A: Fluorescence Polarization (FP) VHL Binding Assay

The binding of test compounds to the VHL Elongin B/C complex is measured using a fluorescence polarization tracer competition assay. The VHL/Elongin B/C protein complex used in the assay is generated as follows. The coding region for amino acids E55-D213 of human VHL with N-terminal His6 tag with a TEV-protease cleavage site is co-expressed with Elongin B (residues M1-Q118) and Elongin C (Residues M17-C112) in *E. coli*. The VHL/Elongin B/C complex is purified using an affinity nickel column, anion exchange HiTrap QP HP column chromatography, and gel filtration using a Superdex 75 26/60 column. The purified VHL/Elongin B/C complex is dialyzed into formulation buffer: 20 mM Bis-Tris pH7.0, 150 mM NaCl, 1 mM DTT. A VHL fluorescence polarization probe consists of a VHL ligand coupled to carboxytetramethylrhodamine (TAMRA); (2S, 4R)—N-(2-(2-(3',6'-bis(dimethylamino)-3-oxo-3H-spiro[isobenzofuran-1,9'-xanthene]-5-carboxamido)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide. Compounds are prepared as a serial dilution in DMSO at a concentration 25-fold higher than the final desired concentration and acoustically dispensed (400 nl) into a ProxiPlate-384 Plus F, Black 384-shallow well Microplate (Part Number 6008260). DMSO is dispensed into wells designated for "VHL control" (without compound) wells. The "Assay Buffer" consists of 50 mM Tris pH 8.0, 120 mM NaCl, 0.005% Nonidet P-40, and 1% DMSO (v/v). Assay Buffer containing 5.28 μM VHL Elongin B/C complex is prepared and 5 μl dispensed using a BioRapTR (Beckman Coulter) into each well of the assay plate. Assay Buffer is also dispensed into "no VHL control" wells using the same method. A "pre-assay" fluorescence measurement is made using an Infinite® M1000 (Tecan) plate reader (Excitation 530 nm, Emission 574 nm, Bandwidth 10 nm). Assay Buffer containing 3.34 nM of the VHL FP probe is prepared in Assay Buffer and 5 μl dispensed into each well of the assay plate using a BioRapTR (Beckman Coulter). The final VHL/Elongin B/C protein concentration is 2.64 nM and the final probe concentration is 1.67 nM. Assay plates are briefly centrifuged and incubated for 1 hour at room temperature. "Post-assay" fluorescence polarization measurements are made as described for the "pre-assay" fluorescence measurement. Fluorescence polarization is calculated for each sample; taking into account the "pre-assay" fluorescence measurements and subtracting the fluorescence signal of the compound/VHL only ("pre-assay") measurements from the "post-assay" fluorescence polarization measurements, for each plane of polarization. The data are analyzed using Genedata Screener software and normalized to the "no VHL control" and "VHL control" (without compound). $IC_{50}$ values are calculated using a four parameter curve fit (Robust method).

Example B: Surface Plasmon Resonance Assay

Using a Biacore T200, Avidin tagged VHL co-expressed with Elongins B and C are immobilized to a Biacore SA chip in running buffer without DMSO. Compounds are tested individually at varying concentrations in running buffer (50 mM HEPES pH 7.2, 150 mM NaCl, 0.5 mM TCEP, 0.001% Tween 20, 0.2% PEG3350, 2% DMSO) at 20° C. Sensorgrams are run in order from low to high concentration using a flow rate of 80 μL/min. Association and disassociation times are varied depending on the estimated potency of the compound tested. Analysis of the binding curves and determination of the kinetic parameters is done using evaluation software (Version 2.0, Biacore).

Example C: VHL HEK-293 BRET Assay

The VHL NanoBRET™ Target Engagement Assay analyzes the apparent affinity of test compounds for VHL in cells by competitive displacement of a VHL NanoBRET™ tracer reversibly bound to a NanoLuc® VHL fusion protein stably expressed in the cells.

Test compounds were transferred to the assay plate (384 Well White Non-Binding Corning Assay Plates (Corning-3574)) using an Echo 555 Liquid Handler (Labcyte) in 2.5 nL increments and, as appropriate, intermediate stock concentrations of compounds, in order to prepare a titration series. 50 nL of control compound (10 mM; parental unlabeled VHL antagonist; see structure below) and 50 nL of DMSO (negative control) were dispensed into the appropriate control wells. DMSO was backfilled to a final volume of 50 nL as required. 50 nl per well of 1 mM VHL NanoBRET™ Tracer in DMSO (NanoBRET™ Tracer-PEG2-590 (see structure below)) was transferred into each well using an Echo 555 (ultimately yielding a final concentration of 1 uM). HEK 293 RT VHL-NanoLuc® stable cells were cultured in DMEM High Glucose with Pyruvate, 10% fetal bovine serum, 2 mg/mL of Geneticin Selective Antibiotic (50 mg/ml) and 2 mM HEPES (1 M). Cells were seeded in Opti-MEM (Life Technologies-11058-021), $1.7\times10^5$ cells/mL, 40 μl per well into the assay plate, centrifuged at 500 rpm for 30 seconds and incubated for 2 hours. Max Signal control wells consisted of DMSO only treated wells. Minimum Signal control wells contained of 10 uM parental unlabeled VHL antagonist (control compound—see structure below). 3× Complete Substrate plus Inhibitor Solution was prepared in Opti-MEM (consists of a 1:166 dilution of NanoBRET™ Nano-Glo® Substrate plus a 1:500 dilution of Extracellular NanoLuc® Inhibitor in Opti-MEM), and 20 ul was dispensed into each well of the 384-well plate and centrifuged at 1000 rpm for 1 minute, then incubated for 2 minutes at room temperature. Background Signal control wells were prepared without tracer for background correction steps.

Plates were read using a PerkinElmer Envision Reader (model 2104-0020) equipped with Luminescence option (Mirror: BRET2 Enh (PE Barcode 659), Emission Filter: Omega 610LP (Barcode 504), 2nd Emission Filter: Umbelliferone 460 (Barcode 207), Measurement height: 6.5 mm, Measurement time: 1 s). The raw BRET ratio values were calculated by dividing the acceptor emission value (610 nm) by the donor emission value (460 nm) for each sample. To correct for background, the BRET ratio in the absence of tracer (average of no-tracer control samples) was subtracted from the BRET ratio of each sample. Raw BRET units were converted to milliBRET units (mBU) by multiplying each raw BRET value by 1,000. The normalized NanoBRET™ signal was calculated relative to the Max Signal control wells (DMSO treated control wells) and the Minimum Signal control wells. Percentage inhibition was calculated relative to the Minimum Signal control and Maximum Signal control wells. $IC_{50}$ values were derived by four parameter curve fitting using the Robust method.

NanoBRET™ Tracer-PEG2-590:

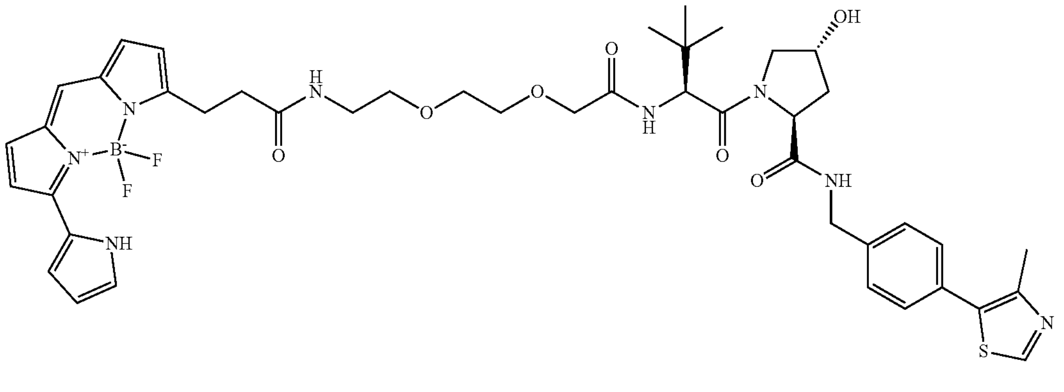 [SMILES: Cc1ncsc1-c1ccc(CNC(=O)[C@@H]2C[C@@H](O)CN2C(=O)[C@@H](NC(=O)COCCOCCNC(=O)CCc2ccc3n2[B-](F)(F)[N+]2=C(c4ccc[nH]4)C=CC2=C3)C(C)(C)C)cc1]

Parental Unlabeled VHL Antagonist (Control Compound):

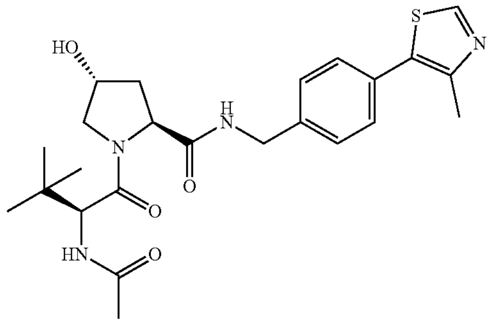 [SMILES: CC(=O)N[C@H](C(=O)N1C[C@H](O)C[C@H]1C(=O)NCc1ccc(-c2scnc2C)cc1)C(C)(C)C]

The results for VHL binding $IC_{50}$ values from the FP assay and the HEK-293 BRET assay are shown in Table 2. Where more than one measurement was performed for the same assay, the value reported is the geometric mean of all values.

TABLE 2

| Compound | VHL binding FP (μM) | VHL binding in cells (HEK293 nanoBRET, μM) | VHL nanoBRET (+Digitonin) EC50 (μM) | Ratio cell permeability shift |
|---|---|---|---|---|
| Final product from Example S1 | 1.17 | 2.00 | 2.14 | 1.71 |
| Final product from Example S2 | — | 2.99 | 2.55 | 1.17 |
| Final product from Example S3 | — | 1.61 | 1.67 | 0.96 |
| Final product from Example S4 | — | 15.20 | 12.10 | 1.26 |
| Final product from Example S5 | — | 10.50 | 8.45 | 1.24 |
| Final product from Example S6 | — | 8.04 | 2.68 | 3.00 |
| Final product from Example S7 | — | >100.00 | 8.96 | >10.00 |
| Final product from Example S8 | — | >100.00 | 10.80 | >10.00 |

TABLE 2-continued

| Compound | VHL binding FP (μM) | VHL binding in cells (HEK293 nanoBRET, μM) | VHL nanoBRET (+Digitonin) EC50 (μM) | Ratio cell permeability shift |
|---|---|---|---|---|
| Final product from Example S9 | — | 69.50 | 2.67 | 26.03 |
| Final product from Example S10 | — | 10.00 | 2.07 | 4.83 |
| Isomer A from Example S11 | — | 3.00 | 3.10 | 0.97 |
| Isomer B from Example S11 | — | >100.00 | >100.00 | — |
| Final product from Example S12 | — | 62.80 | 92.80 | 0.68 |
| Final product from Example S13 | — | 9.68 | 6.27 | 1.54 |
| Final product from Example S14 | — | 6.55 | 5.30 | 1.24 |
| Final product from Example S15 | — | 9.09 | 5.99 | 1.52 |
| Final product from Example S16 | — | 2.43 | 3.56 | 0.68 |
| Final product from Example S17 | — | 4.15 | 3.89 | 1.07 |
| Final product from Example S18 | | 4.99 | 4.99 | 1 |
| Final product from Example S19 | | 0.8 | 0.89 | 0.90 |
| Final product from Example S20 | | 2.12 | 1.24 | 1.71 |
| Final product from Example S21 | | 2.83 | 3.29 | 0.86 |
| Final product from Example S22 | | 3.21 | 2.78 | 1.15 |
| Final product from Example S23 | | 0.32 | 0.47 | 0.68 |
| Final product from Example S24 | | 2.15 | 2.84 | 0.76 |
| Final product from Example S25 | | 2.6 | 3.8 | 0.68 |
| Final product from Example S26 | | 1.02 | 1.98 | 0.51 |
| Final product from Example S27 | | 4.75 | 4.94 | 0.96 |
| Final product from Example S28 | | 0.59 | 0.79 | 0.75 |
| Final product from Example S29 | | 2.65 | 2.11 | 1.26 |
| Final product from Example S30 | | 0.92 | 0.97 | 0.95 |
| Final product from Example S31 | | 1.1 | 1.2 | 0.92 |
| Final product from Example S32 | | 3.2 | 2.12 | 1.51 |
| Final product from Example S33 | | 0.9 | 1.12 | 0.80 |
| Final product from Example S34 | | 1.38 | 1.27 | 1.09 |
| Final product from Example S35 | | 1.7 | 2.01 | 0.85 |
| Final product from Example S36 | | 1.22 | 1.01 | 1.21 |
| Final product from Example S37 | | 1.96 | 1.47 | 1.33 |
| Final product from Example S38 | | 13.8 | 4.06 | 3.40 |
| Final product from Example S39 | | 1.69 | 0.72 | 2.35 |
| Final product from Example S40 | | 0.57 | 0.46 | 1.24 |
| Final product from Example S41 | | 49.9 | 72.3 | 0.69 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

ENUMERATED EMBODIMENTS

The following enumerated embodiments are representative of some aspects of the invention.

Embodiment 1: A compound of formula (I):

(I)

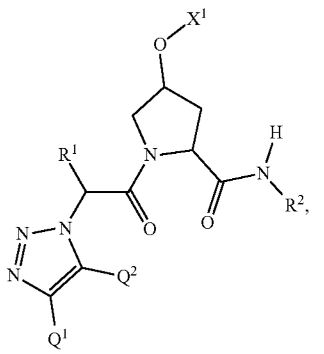

or a stereoisomer or tautomer thereof, or a pharmaceutically acceptable salt of any of the foregoing, wherein:

$X^1$ is H, $C_{1-12}$alkyl, or —C(O)—$C_{1-12}$alkyl;

$R^1$ is $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN;

$Q^1$ is H, halo, cyano, $C_{1-12}$alkyl, $C_{3-5}$cycloalkyl, $C_{6-20}$aryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$ alkoxy, or

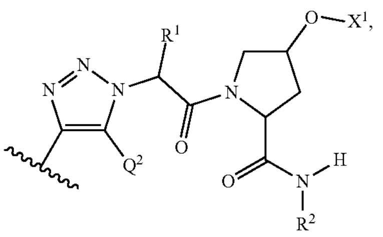

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-5}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

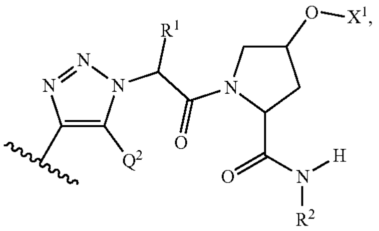

wherein the $C_{1-12}$alkyl of $R^q$ is independently further optionally substituted with one or more halo or —NHC(O)—$C_{1-12}$alkyl, and $Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

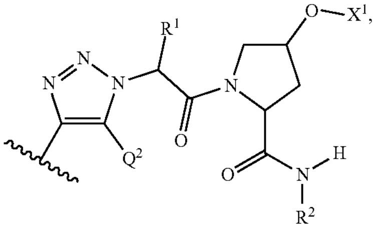

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, or $C_{1-12}$alkyl, wherein the $C_{1-12}$alkyl of $R^s$ is independently further optionally substituted with one or more halo, cyano, or OH.

Embodiment 2: The compound of embodiment 1, or a stereoisomer or tautomer thereof, or a pharmaceutically acceptable salt of any of the foregoing, wherein $R^2$ is, independently at each occurrence, $C_{1-6}$alkyl, wherein the $C_{1-6}$alkyl of $R^2$ is optionally substituted with one or more halo or —CN.

Embodiment 3: The compound of embodiment 1 or embodiment 2, or a stereoisomer or tautomer thereof, or a pharmaceutically acceptable salt of any of the foregoing, wherein $R^2$ is, independently at each occurrence, ethyl, wherein the ethyl of $R^2$ is optionally substituted with one or more halo.

Embodiment 4: The compound of embodiment 1 or embodiment 2, or a stereoisomer or tautomer thereof, or a pharmaceutically acceptable salt of any of the foregoing, wherein $R^2$ is, independently at each occurrence, methyl, wherein the methyl of $R^2$ is optionally substituted with one or more halo.

Embodiment 5: The compound of embodiment 1 or embodiment 2, or a stereoisomer or tautomer thereof, or a pharmaceutically acceptable salt of any of the foregoing, wherein $R^2$ is, independently at each occurrence, unsubstituted methyl.

Embodiment 6: The compound of any one of embodiments 1-5, or a stereoisomer or tautomer thereof, or a pharmaceutically acceptable salt of any of the foregoing, wherein:

$Q^1$ is H, halo, cyano, $C_{1-12}$alkyl, $C_{3-5}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

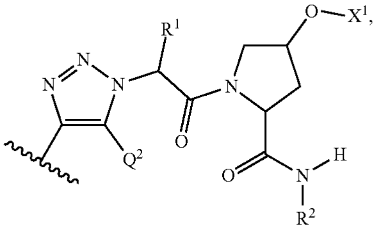

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-5}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

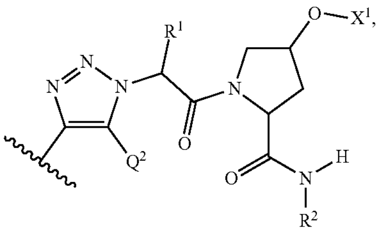

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

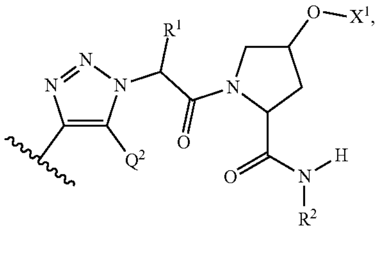

wherein the $C_{1-12}$alkyl or $C_{1-12}$alkoxy of $R^q$ is independently further optionally substituted with one or more halo or —NHC(O)—$C_{1-12}$alkyl.

Embodiment 7: The compound of any one of embodiments 1-6, or a stereoisomer or tautomer thereof, or a pharmaceutically acceptable salt of any of the foregoing, wherein $Q^1$ is $C_{3-5}$cycloalkyl, wherein the $C_{3-5}$cycloalkyl of $Q^1$ is independently optionally substituted with one or more $R^q$, wherein $R^q$ is $C_{1-12}$alkyl, $C_{2-12}$alkenyl, $C_{2-12}$alkynyl, or

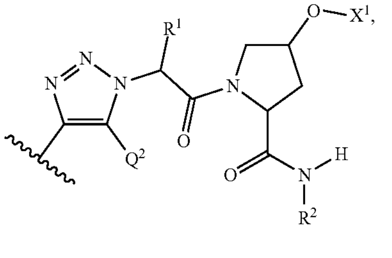

wherein the $C_{1-12}$alkyl of $R^q$ is independently further optionally substituted with one or more halo or —NHC(O)—$C_{1-12}$alkyl.

Embodiment 8: The compound of any one of embodiments 1-7, or a stereoisomer or tautomer thereof, or a pharmaceutically acceptable salt of any of the foregoing, wherein $Q^1$ is unsubstituted $C_{3-5}$cycloalkyl.

Embodiment 9: The compound of any one of embodiments 1-8, or a stereoisomer or tautomer thereof, or a pharmaceutically acceptable salt of any of the foregoing, wherein $Q^1$ is unsubstituted cyclopropyl.

Embodiment 10: The compound of any one of embodiments 1-9, or a stereoisomer or tautomer thereof, or a pharmaceutically acceptable salt of any of the foregoing, wherein $Q^2$ is, independently at each occurrence, H.

Embodiment 11: The compound of any one of embodiments 1-5, or a stereoisomer or tautomer thereof, or a pharmaceutically acceptable salt of any of the foregoing, wherein $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2$ $C_{1-12}$alkyl, —$SO_2NH_2$, or $C_{1-12}$alkyl, wherein the $C_{1-12}$alkyl of $R^s$ is independently further optionally substituted with one or more halo or OH.

Embodiment 12: The compound of embodiment 11, or a stereoisomer or tautomer thereof, or a pharmaceutically acceptable salt of any of the foregoing, wherein $Q^1$ and $Q^2$ are taken, together with the atoms to which they are attached, to form a $C_{6-20}$aryl.

Embodiment 13: The compound of any one of embodiments 1-12, or a stereoisomer or tautomer thereof, or a pharmaceutically acceptable salt of any of the foregoing, wherein $R^1$ is, independently at each occurrence, $C_{1-12}$alkyl, wherein the $C_{1-12}$alkyl of $R^1$ is independently optionally substituted with one or more $C_{6-20}$aryl, —$S(O)_2$—$C_{1-12}$alkyl, or —C(O)—$C_{1-12}$alkyl.

Embodiment 14: The compound of embodiment 13, or a stereoisomer or tautomer thereof, or a pharmaceutically acceptable salt of any of the foregoing, wherein $R^1$ is, independently at each occurrence, tert-butyl.

Embodiment 15: The compound of any one of embodiments 1-12, or a stereoisomer or tautomer thereof, or a pharmaceutically acceptable salt of any of the foregoing, wherein $R^1$ is, independently at each occurrence, $C_{3-15}$cycloalkyl, wherein the $C_{3-15}$cycloalkyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

Embodiment 16: The compound of embodiment 15, or a stereoisomer or tautomer thereof, or a pharmaceutically acceptable salt of any of the foregoing, wherein $R^1$ is, independently at each occurrence, cyclohexyl, wherein the cyclohexyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

Embodiment 17: The compound of any one of embodiments 1-12, or a stereoisomer or tautomer thereof, or a pharmaceutically acceptable salt of any of the foregoing, wherein $R^1$ is, independently at each occurrence, 3-15 membered heterocyclyl, wherein the 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

Embodiment 18: The compound of embodiment 17, or a stereoisomer or tautomer thereof, or a pharmaceutically acceptable salt of any of the foregoing, wherein $R^1$ is, independently at each occurrence, a 6-membered heterocyclyl, wherein the 6-membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

Embodiment 19: The compound of any one of embodiments 1-18, or a stereoisomer or tautomer thereof, or a pharmaceutically acceptable salt of any of the foregoing, wherein $X^1$ is, independently at each occurrence, H.

Embodiment 20: The compound of embodiment 1, or a stereoisomer or tautomer thereof, or a pharmaceutically acceptable salt of any of the foregoing, wherein the compound of formula (I) is a compound of formula (IA):

(IA)

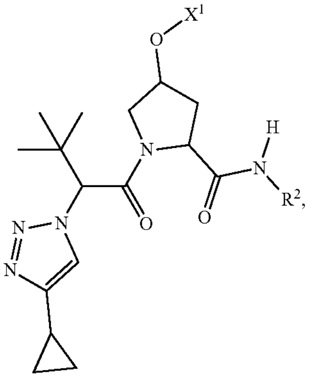

or a stereoisomer or tautomer thereof, or a pharmaceutically acceptable salt of any of the foregoing.

Embodiment 21: The compound of embodiment 20, or a stereoisomer or tautomer thereof, or a pharmaceutically acceptable salt of any of the foregoing, wherein the compound of formula (IA) is selected from the group consisting of

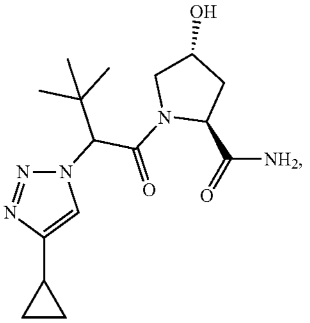

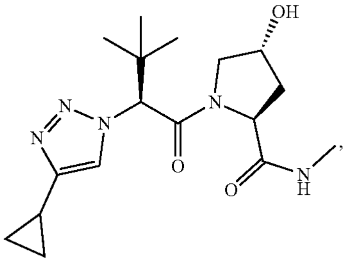

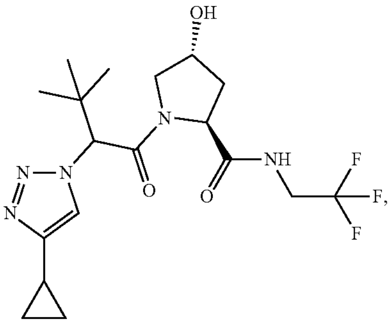

-continued

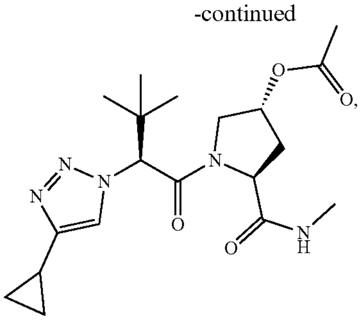

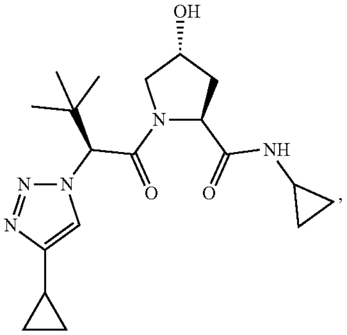

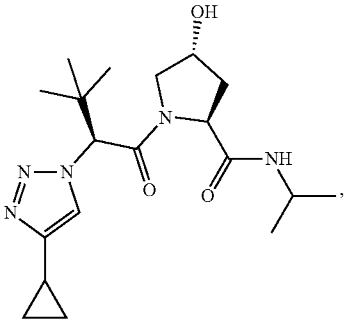

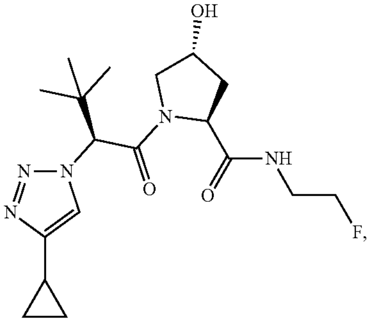

and

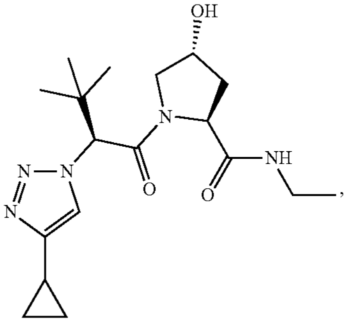

or a stereoisomer or tautomer thereof, or a pharmaceutically acceptable salt of any of the foregoing.

Embodiment 22: The compound of embodiment 1, or a stereoisomer or tautomer thereof, or a pharmaceutically acceptable salt of any of the foregoing, wherein the compound of formula (I) is a compound of formula (IB):

(IB)

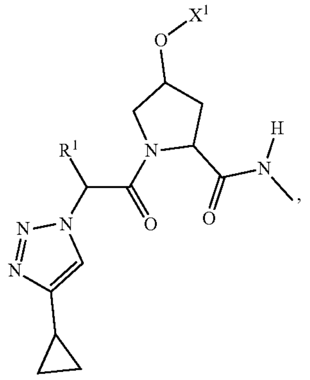

or a stereoisomer or tautomer thereof, or a pharmaceutically acceptable salt of any of the foregoing.

Embodiment 23: The compound of embodiment 22, or a stereoisomer or tautomer thereof, or a pharmaceutically acceptable salt of any of the foregoing, wherein the compound is selected from the group consisting of

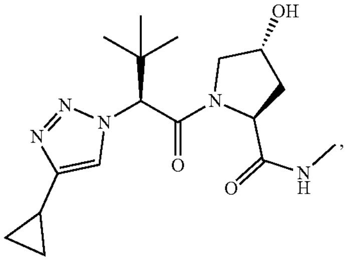

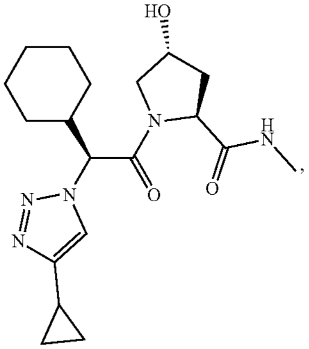

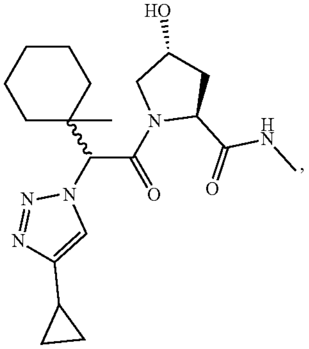

-continued

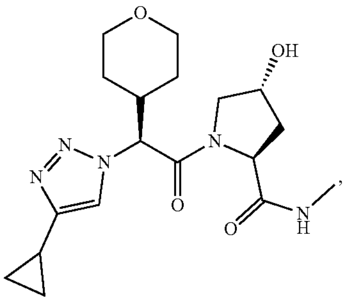

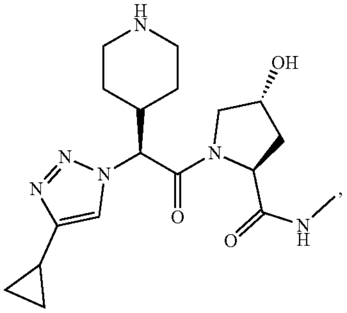

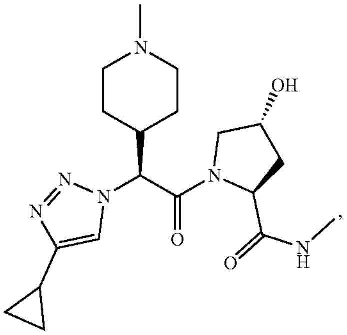

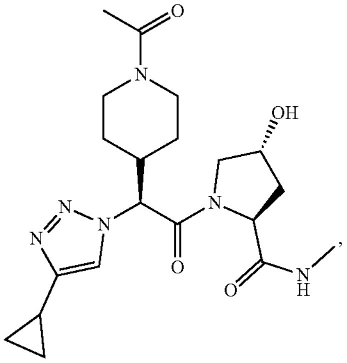

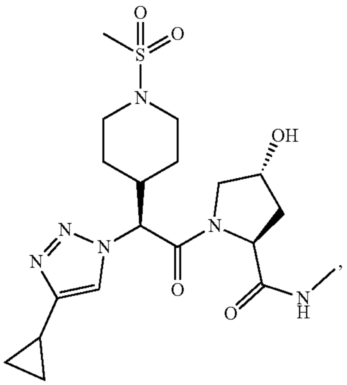

-continued

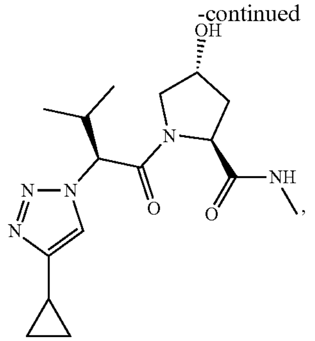

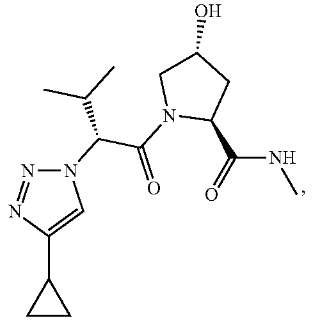

, and

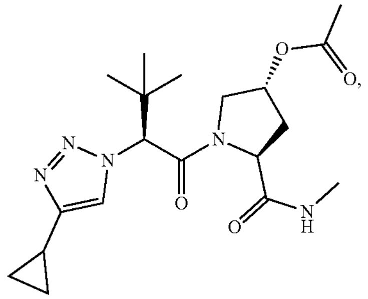

or a stereoisomer or tautomer thereof, or a pharmaceutically acceptable salt of any of the foregoing.

Embodiment 24: The compound of embodiment 1, or a stereoisomer or tautomer thereof, or a pharmaceutically acceptable salt of any of the foregoing, wherein the compound of formula (I) is a compound of formula (IC):

(IC)

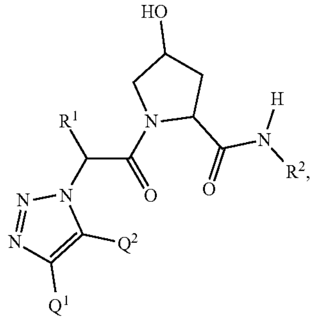

wherein:

$R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl;

$R^2$ is H or $C_{1-12}$alkyl;

$Q^1$ is H or $C_{3-15}$cycloalkyl; and $Q^2$ is, independently at each occurrence, H or C3-15cycloalkyl.

Embodiment 25: The compound of embodiment 24, or a stereoisomer or tautomer thereof, or a pharmaceutically acceptable salt of any of the foregoing, wherein the compound is selected from the group consisting of

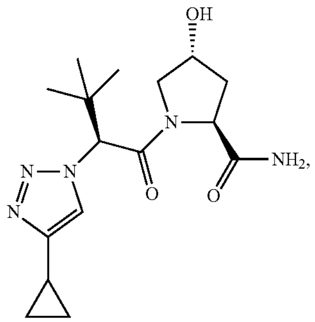

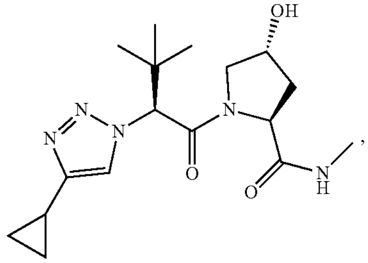

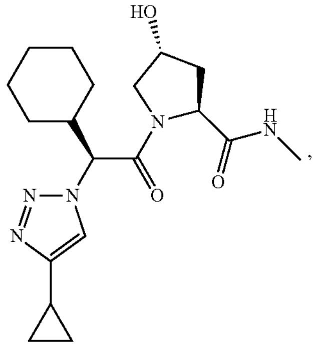

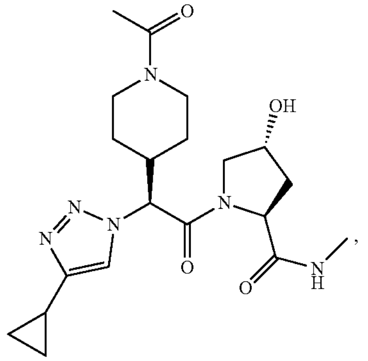

-continued
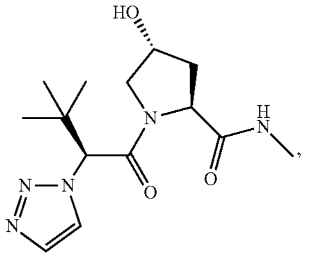
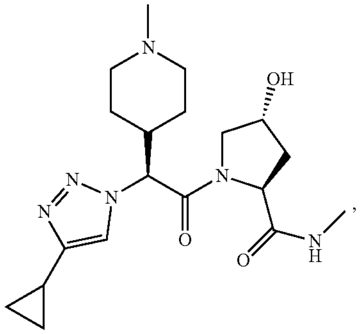
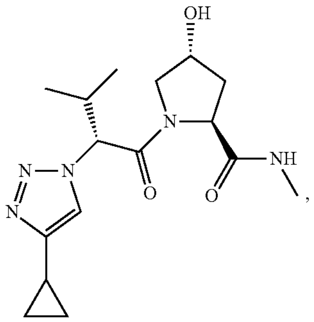
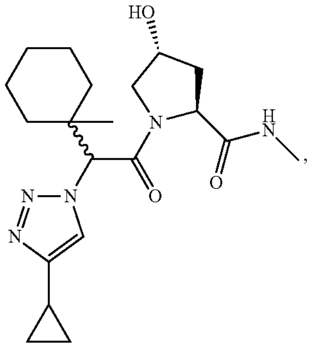
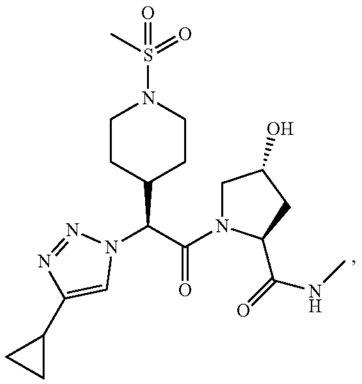
-continued
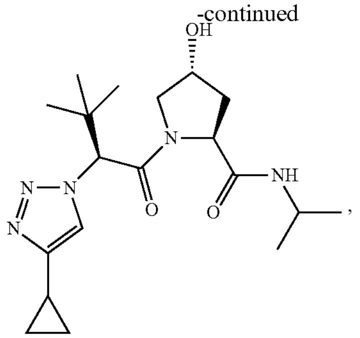
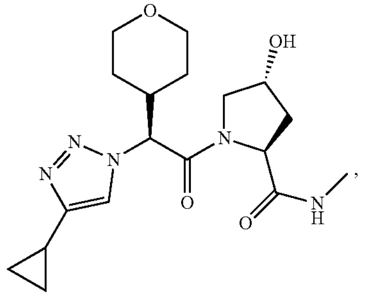
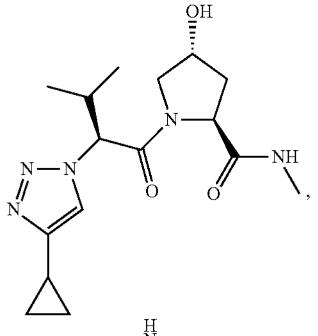
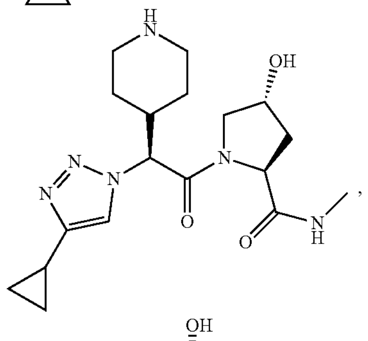
and
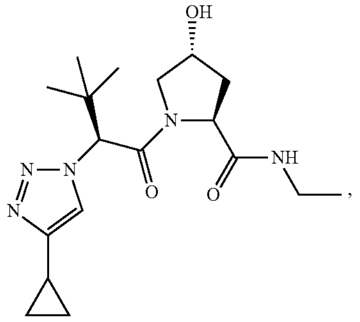
or a stereoisomer or tautomer thereof, or a pharmaceutically acceptable salt of any of the foregoing.
Embodiment 26: The compound of embodiment 1, or a stereoisomer or tautomer thereof, or a pharmaceutically acceptable salt of any of the foregoing, wherein the compound of formula (I) is a compound of formula (ID):

(ID)

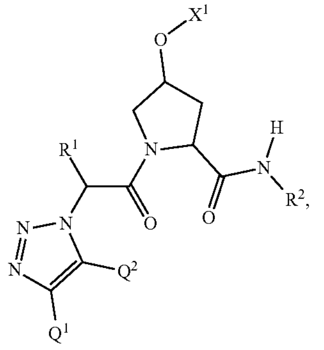

wherein:

$X^1$ is, independently at each occurrence, H or —C(O)—$C_{1-12}$alkyl;

$R^1$ is, independently at each occurrence, $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo;

$Q^1$ is H or $C_{3-5}$cycloalkyl; and $Q^2$ is, independently at each occurrence, H or $C_{3-5}$cycloalkyl.

Embodiment 27: The compound of any one of embodiments 1-26, or a stereoisomer or tautomer thereof, or a pharmaceutically acceptable salt of any of the foregoing, wherein the chiral carbon atom to which $R^1$ is attached is in the S stereochemical configuration.

Embodiment 28: The compound of embodiment 1, or a stereoisomer or tautomer thereof, or a pharmaceutically acceptable salt of any of the foregoing, wherein the compound is selected from the group consisting of

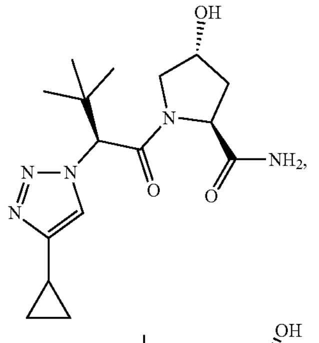

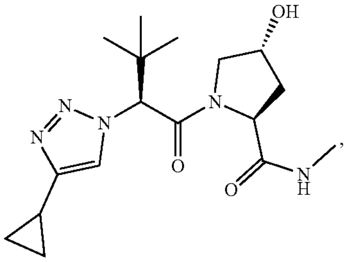

-continued

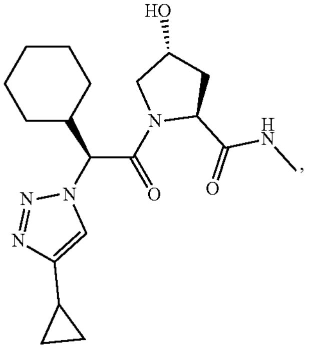

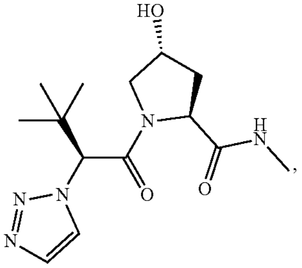

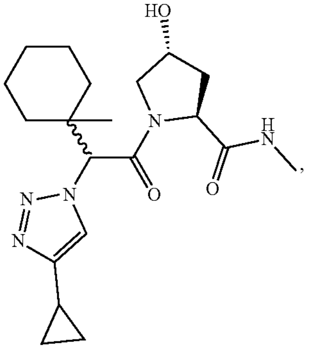

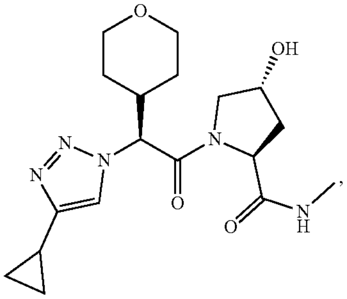

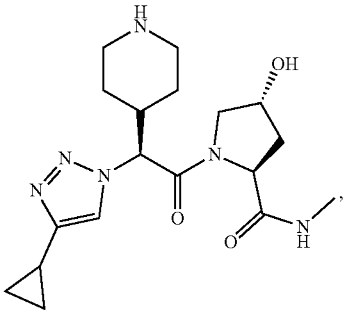

-continued
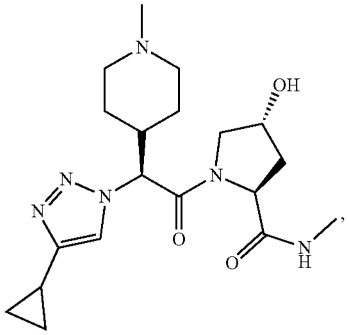
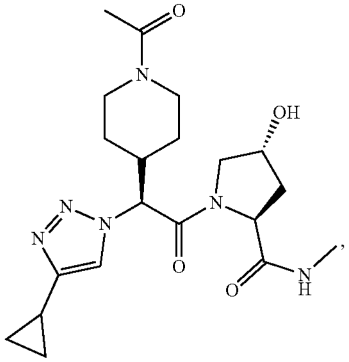
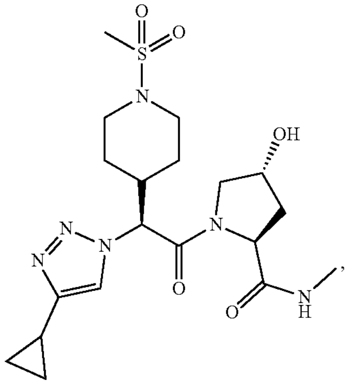
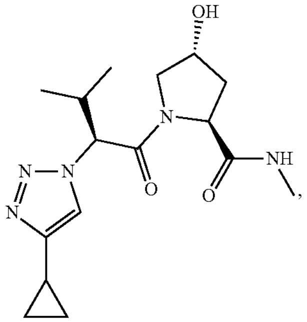
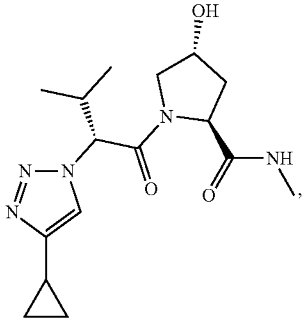
-continued
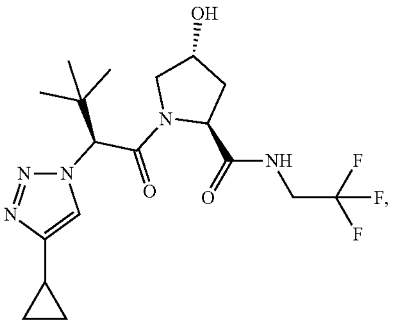
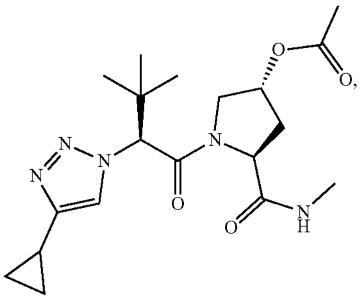 [SMILES: CNC(=O)[C@@H]1C[C@@H](OC(C)=O)CN1C(=O)[C@@H](n1cc(C2CC2)nn1)C(C)(C)C]
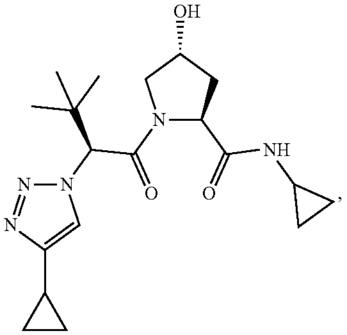
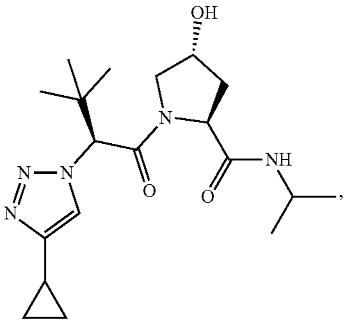
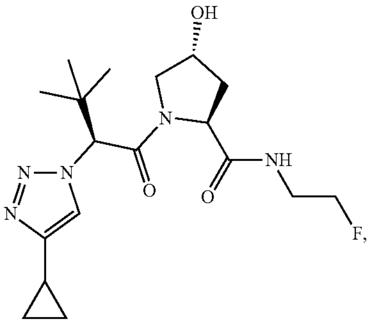
and -continued
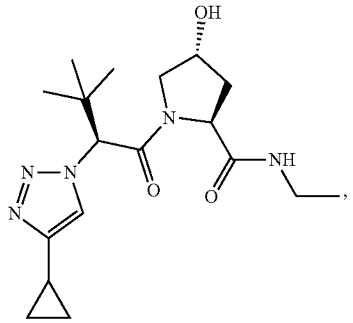
or a stereoisomer or tautomer thereof, or a pharmaceutically acceptable salt of any of the foregoing.
Embodiment 29: The compound of embodiment 1, or a stereoisomer or tautomer thereof, or a pharmaceutically acceptable salt of any of the foregoing, wherein the compound is selected from the group consisting of
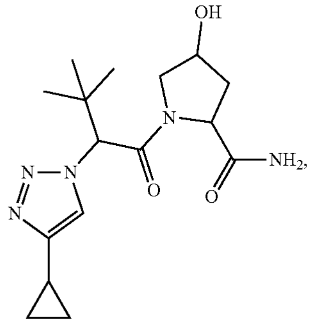
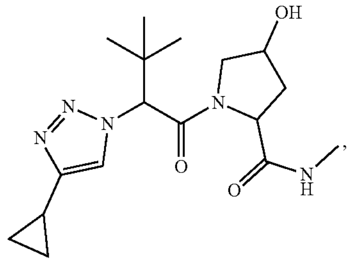
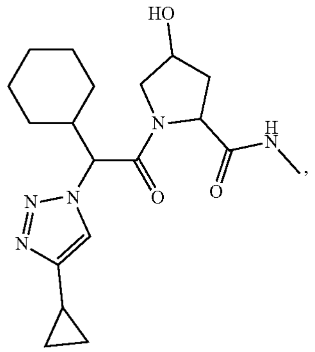
-continued
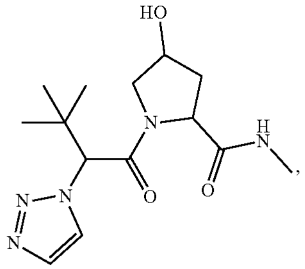
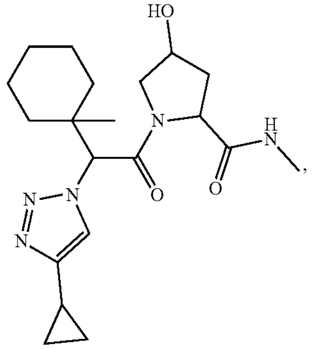
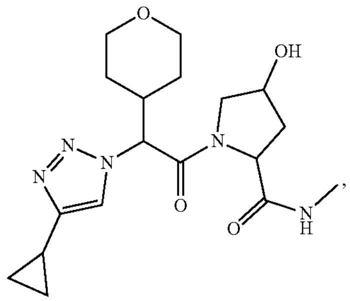
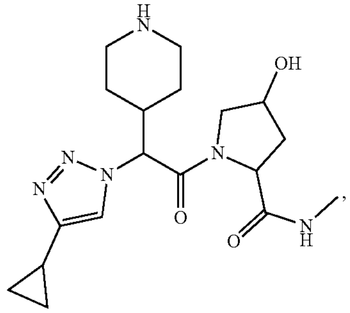
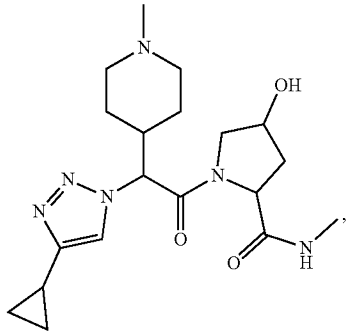

-continued
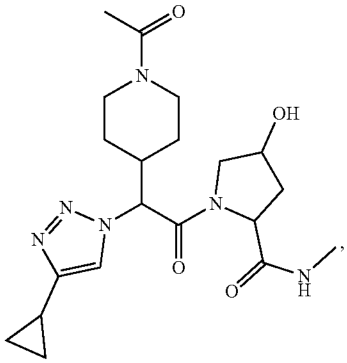
,
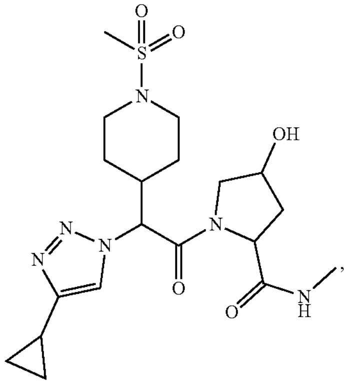
,
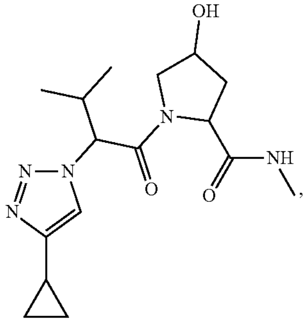
,
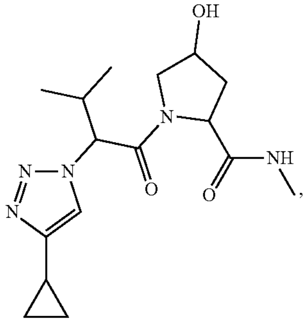
,
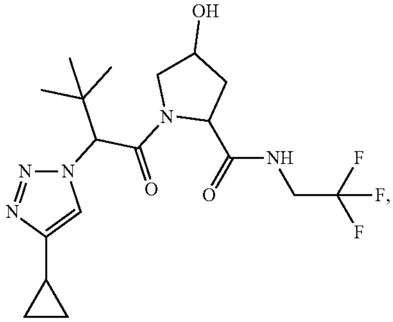
,
-continued
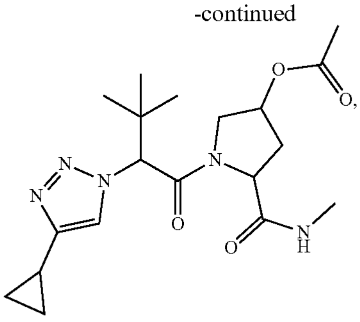
,
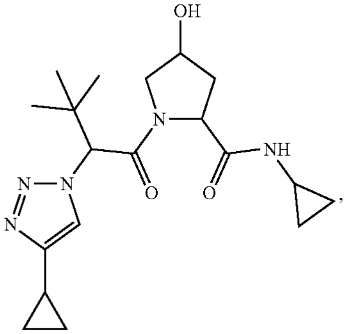
,
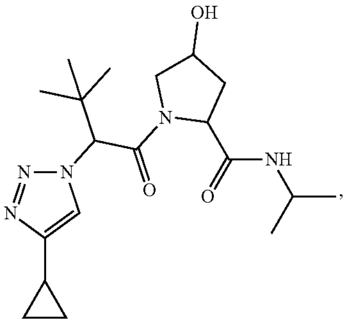
,
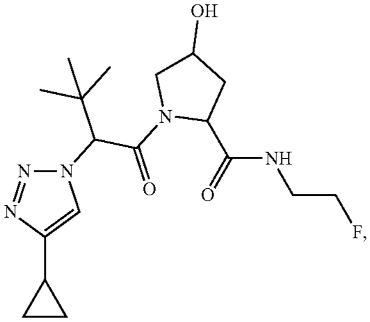
, and
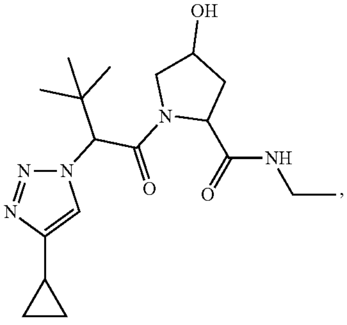
,
or a stereoisomer or tautomer thereof, or a pharmaceutically acceptable salt of any of the foregoing.
Embodiment 30: A pharmaceutical composition comprising a compound of any one of embodiments 1-29, or a stereoisomer or tautomer thereof, or a pharmaceutically acceptable salt of any of the foregoing, and one or more pharmaceutically acceptable excipients.

Embodiment 31: The pharmaceutical composition of embodiment 30, further comprising an additional bioactive agent.

Embodiment 32: A method of modulating VHL in a cell comprising exposing the cell to a composition comprising an effective amount of a compound according to any of embodiments 1-29, or a stereoisomer or tautomer thereof, or a pharmaceutically acceptable salt of any of the foregoing, or a composition of embodiment 30 or embodiment 31.

Embodiment 33: A method of inhibiting VHL in a cell comprising exposing the cell to a composition comprising an effective amount of a compound according to any of embodiments 1-29, or a stereoisomer or tautomer thereof, or a pharmaceutically acceptable salt of any of the foregoing, or a composition of embodiment 30 or embodiment 31.

Embodiment 34: A method of treating a disease, disorder, or condition in a human in need thereof, comprising administering to the human an effective amount of a compound of any one of embodiments 1-29, or stereoisomer or tautomer thereof, or a pharmaceutically acceptable salt of any of the foregoing, or a composition of embodiment 30 or embodiment 31.

Embodiment 35: The method of embodiment 34, wherein the disease, disorder, or condition is anemia.

Embodiment 36: The method of embodiment 35, wherein the anemia is chronic anemia or anemia associated with chronic kidney disease, dialysis, or cancer chemotherapy, or any combination thereof.

Embodiment 37: The method of embodiment 34, wherein the disease, disorder, or condition is ischemia, stroke, or damage to the cardiovascular system during ischemia, or any combination thereof.

Embodiment 38: A method of enhancing wound healing in a human in need thereof, comprising administering to the human an effective amount of a compound of any one of embodiments 1-29, or stereoisomer or tautomer thereof, or a pharmaceutically acceptable salt of any of the foregoing, or a composition of embodiment 30 or embodiment 31.

Embodiment 39: A method of reducing scarring secondary to wound healing in a human in need thereof, comprising administering to the human an effective amount of a compound of any one of embodiments 1-29, or stereoisomer or tautomer thereof, or a pharmaceutically acceptable salt of any of the foregoing, or a composition of embodiment 30 or embodiment 31.

Embodiment 40: A method of enhancing angiogenesis or arteriogenesis, or both, in a human in need thereof, comprising administering to the human an effective amount of a compound of any one of embodiments 1-29, or stereoisomer or tautomer thereof, or a pharmaceutically acceptable salt of any of the foregoing, or a composition of embodiment 30 or embodiment 31.

Embodiment 41: The method of embodiment 40, wherein the enhancement of angiogenesis or arteriogenesis, or both, occurs locally in the human.

Embodiment 42: A method of reducing the likelihood of stent occlusion in a human, comprising administering to the human an effective amount of a compound of any one of embodiments 1-29, or stereoisomer or tautomer thereof, or a pharmaceutically acceptable salt of any of the foregoing, or a composition of embodiment 30 or embodiment 31.

Embodiment 43: Use of a compound of any one of embodiments 1-29, or a stereoisomer or tautomer thereof, or a pharmaceutically acceptable salt of any of the foregoing, or a composition of embodiment 30 or embodiment 31, in the manufacture of a medicament for use in the treatment of anemia.

Embodiment 44: The use of embodiment 43, wherein the anemia is chronic anemia or anemia associated with chronic kidney disease, dialysis, or cancer chemotherapy, or any combination thereof.

Embodiment 45: Use of a compound of any one of embodiments 1-29, or a stereoisomer or tautomer thereof, or a pharmaceutically acceptable salt of any of the foregoing, or a composition of embodiment 30 or embodiment 31, in the manufacture of a medicament for use in the treatment of ischemia, stroke, or damage to the cardiovascular system during ischemia, or any combination thereof.

Embodiment 46: Use of a compound of any one of embodiments 1-29, or a stereoisomer or tautomer thereof, or a pharmaceutically acceptable salt of any of the foregoing, or a composition of embodiment 30 or embodiment 31, in the manufacture of a medicament for use in the enhancement of wound healing in a human in need thereof.

Embodiment 47: Use of a compound of any one of embodiments 1-29, or a stereoisomer or tautomer thereof, or a pharmaceutically acceptable salt of any of the foregoing, or a composition of embodiment 30 or embodiment 31, in the manufacture of a medicament for use in the reduction of scarring secondary to wound healing in a human in need thereof.

Embodiment 48: Use of a compound of any one of embodiments 1-29, or a stereoisomer or tautomer thereof, or a pharmaceutically acceptable salt of any of the foregoing, or a composition of embodiment 30 or embodiment 31, in the manufacture of a medicament for use in the enhancement of angiogenesis or arteriogenesis, or both, in a human in need thereof.

Embodiment 49: The use of embodiment 48, wherein the enhancement of angiogenesis or arteriogenesis, or both, occurs locally in the human.

Embodiment 50: Use of a compound of any one of embodiments 1-29, or a stereoisomer or tautomer thereof, or a pharmaceutically acceptable salt of any of the foregoing, or a composition of embodiment 30 or embodiment 31, in the manufacture of a medicament for use in reducing the likelihood of stent occlusion in a human in need thereof.

Embodiment 51: A compound of any one of embodiments 1-29, or a stereoisomer or tautomer thereof, or a pharmaceutically acceptable salt of any of the foregoing, or a composition of embodiment 30 or embodiment 31, for use in the treatment of anemia.

Embodiment 52: A compound of any one of embodiments 1-29, or a stereoisomer or tautomer thereof, or a pharmaceutically acceptable salt of any of the foregoing, or a composition of embodiment 30 or embodiment 31, for use in the treatment of chronic anemia or anemia associated with chronic kidney disease, dialysis, or cancer chemotherapy, or any combination thereof.

Embodiment 53: A compound of any one of embodiments 1-29, or a stereoisomer or tautomer thereof, or a pharmaceutically acceptable salt of any of the foregoing, or a composition of embodiment 30 or embodiment 31, for use in the treatment of ischemia, stroke, or damage to the cardiovascular system during ischemia, or any combination thereof.

Embodiment 54: A compound of any one of embodiments 1-29, or a stereoisomer or tautomer thereof, or a pharmaceutically acceptable salt of any of the foregoing, or a composition of embodiment 30 or embodiment 31, for use in the enhancement of wound healing in a human in need thereof.

Embodiment 55: A compound of any one of embodiments 1-29, or a stereoisomer or tautomer thereof, or a pharmaceutically acceptable salt of any of the foregoing, or a composition of embodiment 30 or embodiment 31, for use in the reduction of scarring secondary to wound healing in a human in need thereof.

Embodiment 56: A compound of any one of embodiments 1-29, or a stereoisomer or tautomer thereof, or a pharmaceutically acceptable salt of any of the foregoing, or a composition of embodiment 30 or embodiment 31, for use in the enhancement of angiogenesis or arteriogenesis, or both, in a human in need thereof.

Embodiment 57: A compound of any one of embodiments 1-29, or a stereoisomer or tautomer thereof, or a pharmaceutically acceptable salt of any of the foregoing, or a composition of embodiment 30 or embodiment 31, for use in the enhancement of angiogenesis or arteriogenesis, or both, in a human, wherein the enhancement of angiogenesis or arteriogenesis, or both, occurs locally in the human.

Embodiment 58: A compound of any one of embodiments 1-29, or a stereoisomer or tautomer thereof, or a pharmaceutically acceptable salt of any of the foregoing, or a composition of embodiment 30 or embodiment 31, for use in reducing the likelihood of stent occlusion in a human in need thereof.

Embodiment 59: A process for preparing a compound of formula (I):

(I)

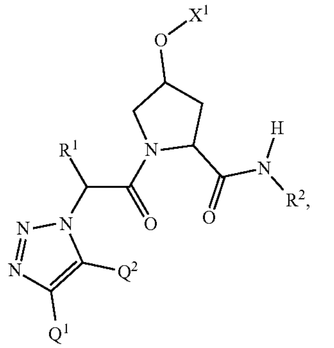

or a stereoisomer or tautomer thereof, or a pharmaceutically acceptable salt of any of the foregoing, wherein:

$X^1$ is, independently at each occurrence, H, $C_{1-12}$alkyl, or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; and $Q^1$ is H, halo, cyano, $C_{1-12}$alkyl, $C_{3-5}$cycloalkyl, $C_{6-20}$aryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

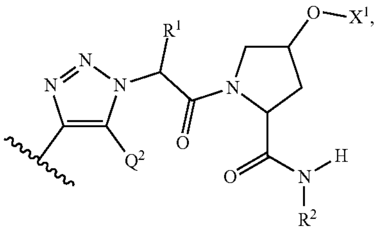

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-5}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

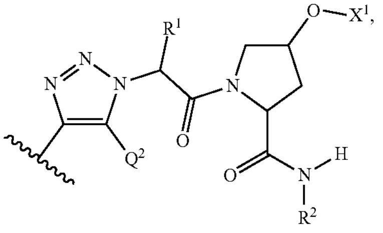

wherein the $C_{1-12}$alkyl of $R^q$ is independently further optionally substituted with one or more halo or —NHC(O)—$C_{1-12}$alkyl, and $Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

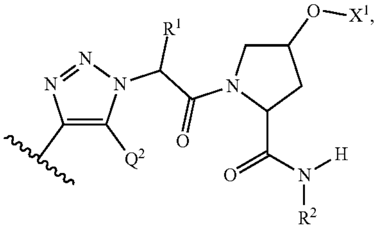

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, or $C_{1-12}$alkyl, wherein the $C_{1-12}$alkyl of $R^s$ is independently further optionally substituted with one or more halo, cyano, or OH.

Embodiment 60: A compound, or a stereoisomer or tautomer thereof, or a pharmaceutically acceptable salt of any of the foregoing, prepared by the process of embodiment 59.

Embodiment 61: A heterobifunctional compound of formula (II):

[A]-[B]—[C] (II), wherein:

[A] is a moiety of a VHL ligand of embodiment 1;

[B] is a linker moiety; and

[C] is a protein-binding moiety.

Embodiment 62: A method of using the heterobifunctional compound of embodiment 61 to degrade a target protein.

Embodiment 63: A compound of any one of embodiments 1-29, or a stereoisomer or tautomer thereof, or a pharmaceutically acceptable salt of any of the foregoing, or a composition of embodiment 30 or embodiment 31, for use in the treatment of a disease or condition modulated by VHL.

What is claimed is:

1. A compound of formula (I):

(I)

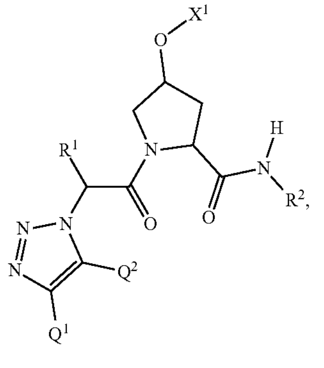

or a stereoisomer or tautomer thereof, or a pharmaceutically acceptable salt of any of the foregoing, wherein:

$X^1$ is H or —C(O)—$C_{1-12}$alkyl;

$R^1$ is $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN;

$Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

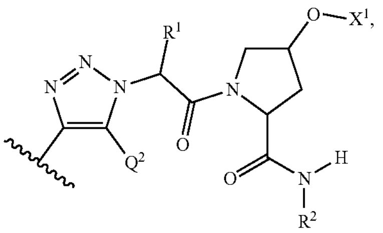

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

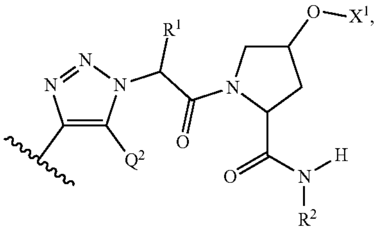

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

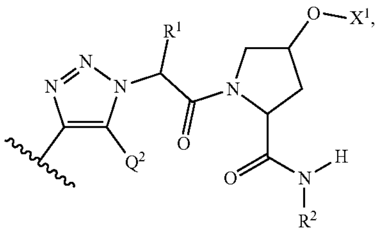

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH;

with the proviso that when $Q^1$ is cyclohexyl, biphenyl, or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

2. The compound of claim 1, or a stereoisomer or tautomer thereof, or a pharmaceutically acceptable salt of any of the foregoing, wherein:

$Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

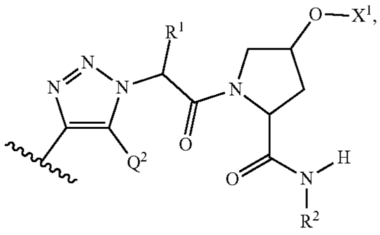

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

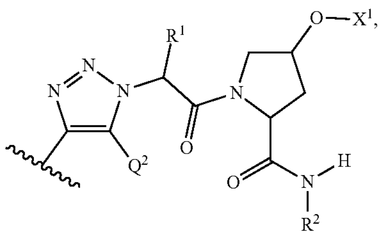

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN, or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

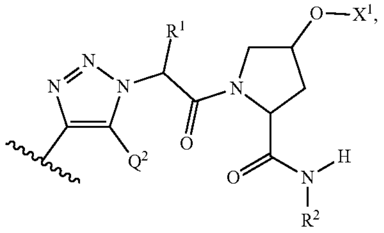

wherein the $C_{1-12}$alkyl or $C_{1-12}$alkoxy of $R^q$ is independently further optionally substituted with one or more halo or —NHC(O)—$C_{1-12}$alkyl.

3. The compound of claim 1, or a stereoisomer or tautomer thereof, or a pharmaceutically acceptable salt of any of the foregoing, wherein $R^1$ is, independently at each occurrence, $C_{1-12}$alkyl, wherein the $C_{1-12}$alkyl of $R^1$ is independently optionally substituted with one or more $C_{6-20}$aryl, —$S(O)_2$—$C_{1-12}$alkyl, or —C(O)—$C_{1-12}$alkyl.

4. The compound of claim 1, or a stereoisomer or tautomer thereof, or a pharmaceutically acceptable salt of any of the foregoing, wherein $R^1$ is, independently at each occurrence, $C_{3-15}$cycloalkyl, wherein the $C_{3-15}$cycloalkyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

5. The compound of claim 1, or a stereoisomer or tautomer thereof, or a pharmaceutically acceptable salt of any of the foregoing, wherein $R^1$ is, independently at each occurrence, 3-15 membered heterocyclyl, wherein the 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl.

6. The compound of claim 1, or a pharmaceutically acceptable salt thereof, wherein the compound of formula (I) is a compound of formula (I')

(I')

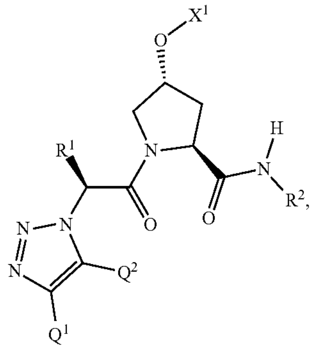

or a pharmaceutically acceptable salt thereof.

7. The compound of claim 1, or a stereoisomer or tautomer thereof, or a pharmaceutically acceptable salt of any of the foregoing, wherein the compound of formula (I) is a compound of formula (IA):

(IA)

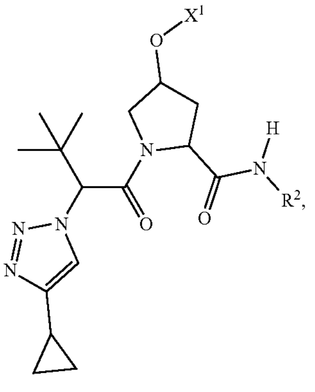

or a stereoisomer or tautomer thereof, or a pharmaceutically acceptable salt of any of the foregoing.

8. The compound of claim 1, or a stereoisomer or tautomer thereof, or a pharmaceutically acceptable salt of any of the foregoing, wherein the compound of formula (I) is a compound of formula (IB):

(IB)

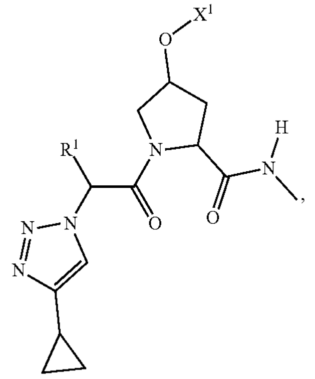

or a stereoisomer or tautomer thereof, or a pharmaceutically acceptable salt of any of the foregoing.

9. The compound of claim 1, or a stereoisomer or tautomer thereof, or a pharmaceutically acceptable salt of any of the foregoing, wherein the compound of formula (I) is a compound of formula (IC):

(IC)

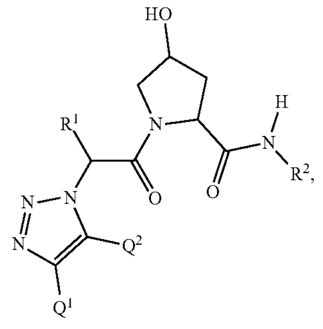

wherein:

$R^1$ is $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —$S(O)_2$—$C_{1-12}$alkyl, or —C(O)—$C_{1-12}$alkyl;

$R^2$ is H or $C_{1-12}$alkyl;

$Q^1$ is H or $C_{3-15}$cycloalkyl; and $Q^2$ is, independently at each occurrence, H or $C_{3-15}$cycloalkyl.

10. The compound of claim 1, or a stereoisomer or tautomer thereof, or a pharmaceutically acceptable salt of any of the foregoing, wherein the compound of formula (I) is a compound of formula (ID):

(ID)

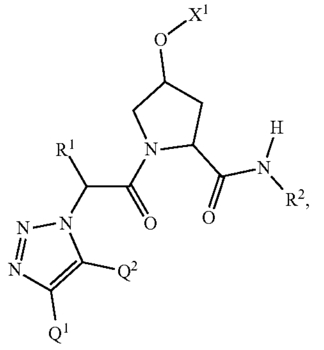

wherein:

$X^1$ is, independently at each occurrence, H or —C(O)—$C_{1-12}$alkyl;

$R^1$ is, independently at each occurrence, $C_{1-12}$alkyl, $C_{3-15}$cycloalkyl, or 3-15 membered heterocyclyl, wherein the $C_{1-12}$alkyl, $C_{3-15}$cycloalkyl, or 3-15 membered heterocyclyl of $R^1$ is independently optionally substituted with one or more $C_{1-12}$alkyl, —S(O)$_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo;

$Q^1$ is H, $C_{6-20}$aryl, 5-6 membered heteroaryl, or $C_{3-5}$cycloalkyl, wherein the 5-6 membered heteroaryl of $Q^1$ is independently optionally substituted with one or more $R^q$, wherein each $R^q$ is independently halo;

$Q^2$ is, independently at each occurrence, H or $C_{3-5}$cycloalkyl;

or $Q^1$ and $Q^2$ are taken, together with the atoms to which they are attached, to form a $C_{6-20}$aryl, wherein the $C_{6-20}$aryl formed by $Q^1$ and $Q^2$ is independently optionally substituted with one or more $R^s$, wherein $R^s$ is, independently at each occurrence, halo or $C_{1-6}$alkoxy;

with the proviso that when $Q^1$ is $C_{6-20}$aryl or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —S(O)$_2$—$C_{1-12}$alkyl, or —C(O)—$C_{1-12}$alkyl.

11. The compound of claim 1, or a stereoisomer or tautomer thereof, or a pharmaceutically acceptable salt of any of the foregoing, wherein the compound of formula (I) is a compound of formula (IE):

(IE)

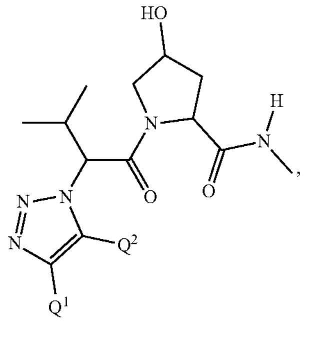

or a stereoisomer or tautomer thereof, or a pharmaceutically acceptable salt of any of the foregoing.

12. The compound of claim 1, or a stereoisomer or tautomer thereof, or a pharmaceutically acceptable salt of any of the foregoing, wherein the compound of formula (I) is a compound of formula (IF):

(IF)

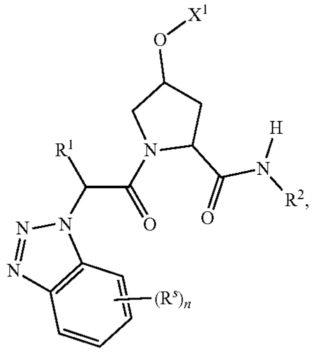

or a stereoisomer or tautomer thereof, or a pharmaceutically acceptable salt of any of the foregoing, wherein n is 0, 1, 2, 3, or 4; and $R^s$ is OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH.

13. The compound of claim 1, or a pharmaceutically acceptable salt thereof, wherein the compound is selected from the group consisting of

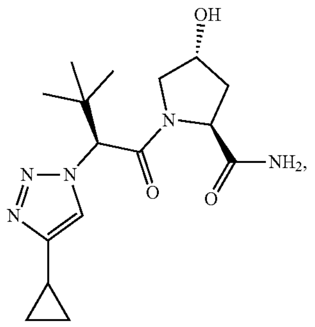

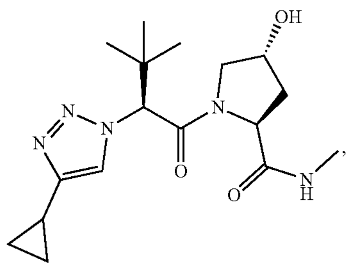

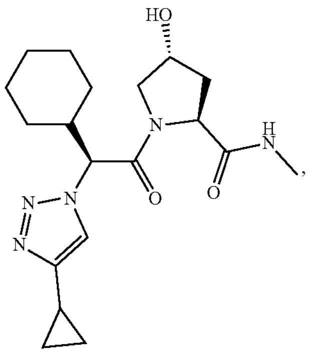
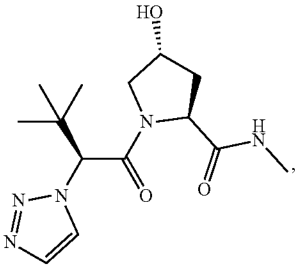
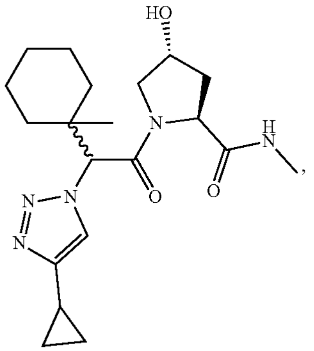
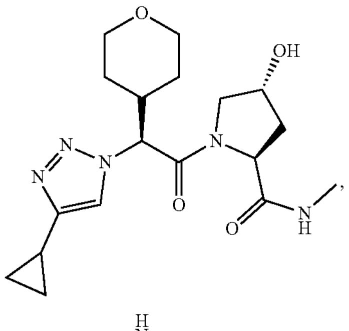
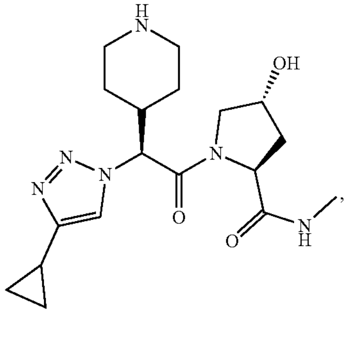
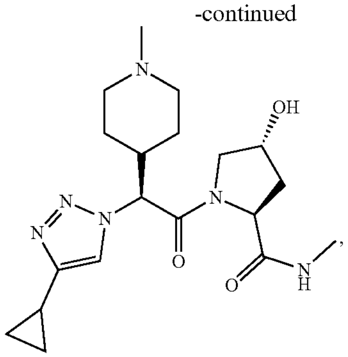
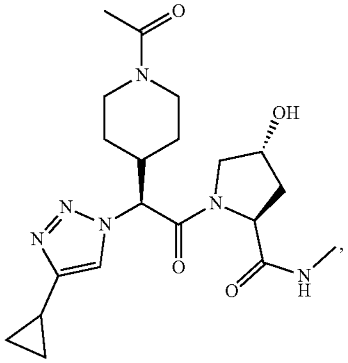
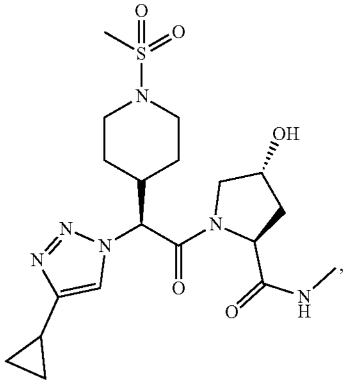
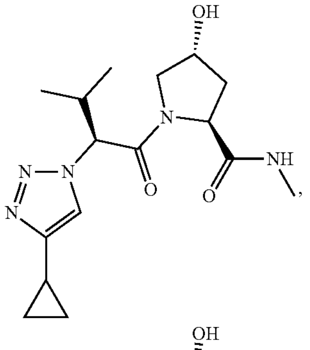
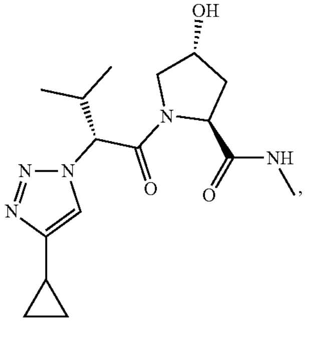

-continued
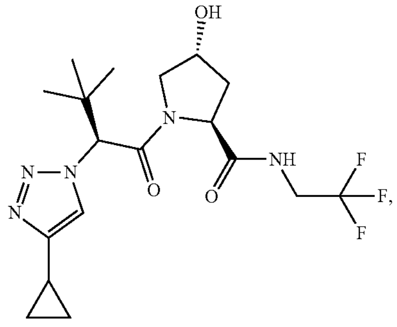
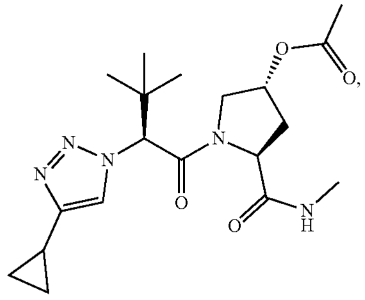
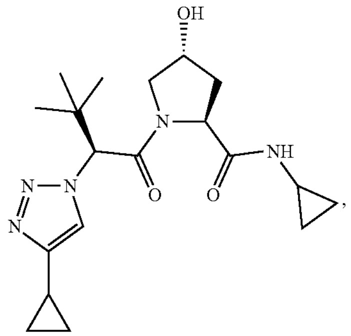
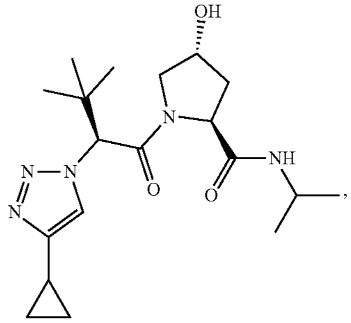
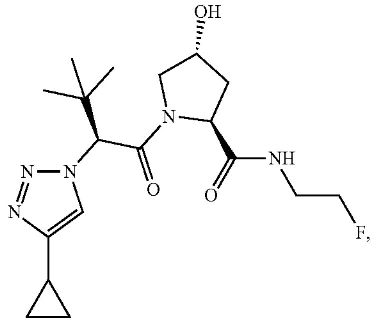
-continued
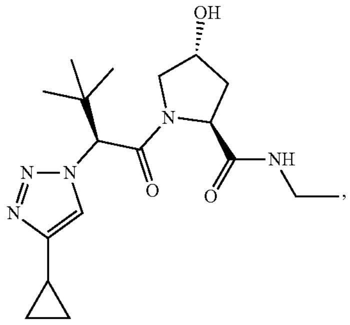
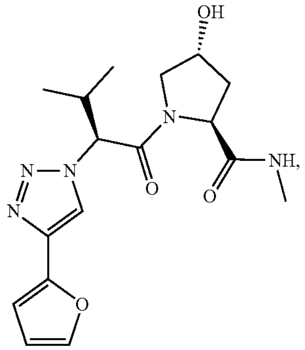
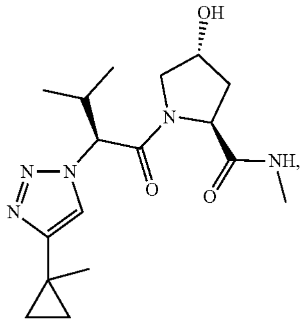
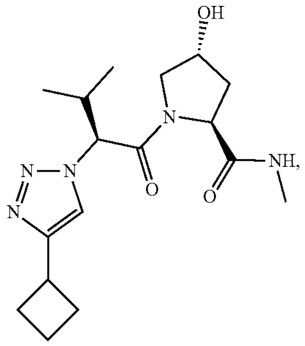
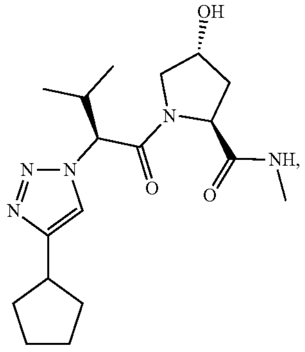

-continued
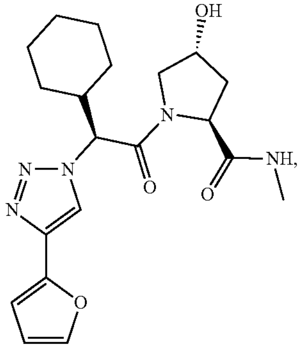,
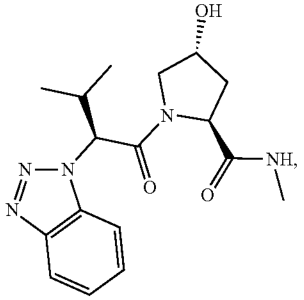,
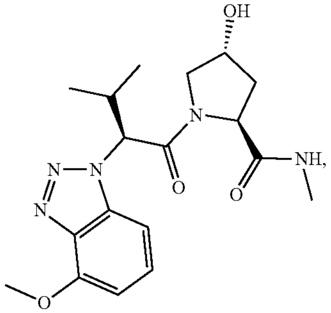,
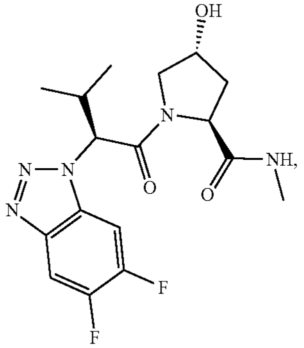,
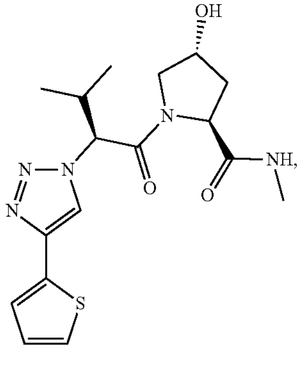,
-continued
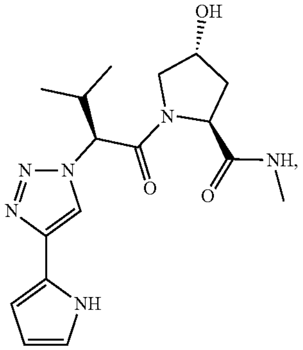,
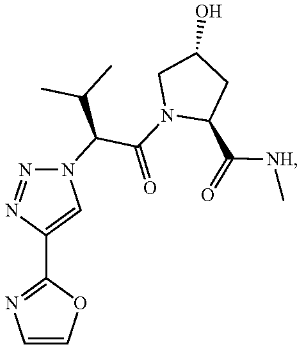,
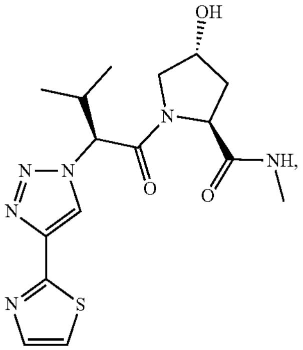,
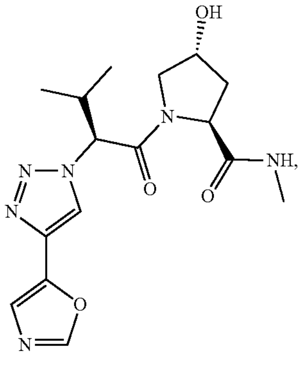, -continued
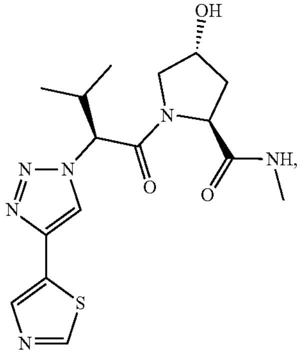
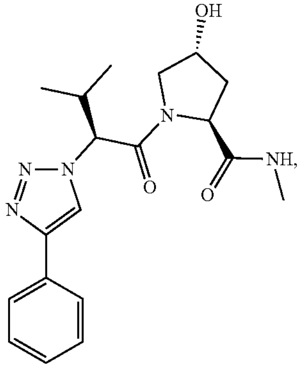
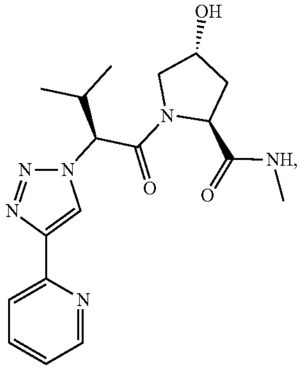
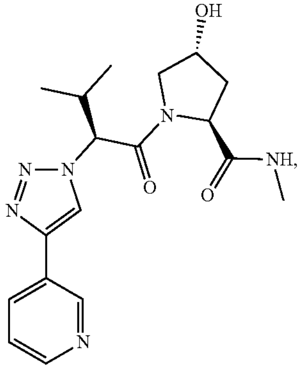
-continued
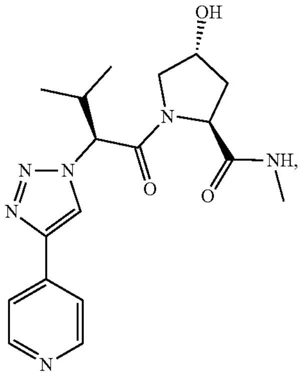
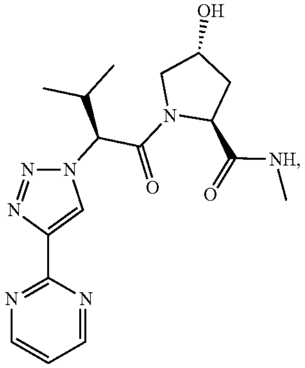
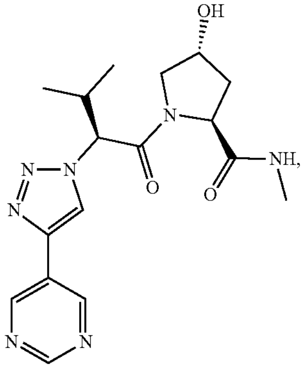
and
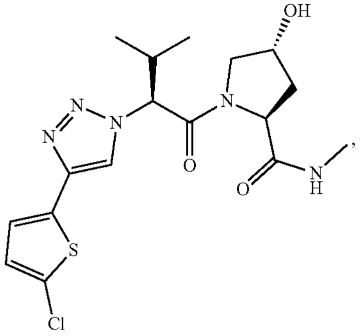
or a pharmaceutically acceptable salt thereof.
14. The compound of claim 1, or a stereoisomer or tautomer thereof, or a pharmaceutically acceptable salt of any of the foregoing, wherein the compound is selected from the group consisting of

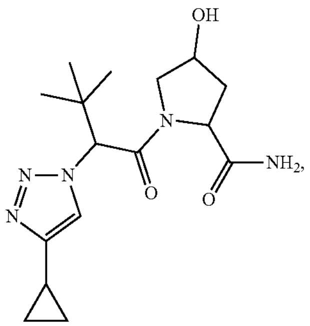
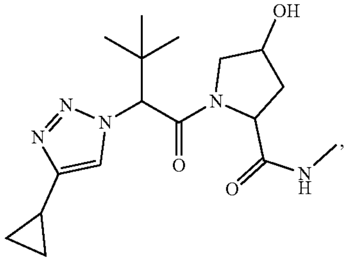
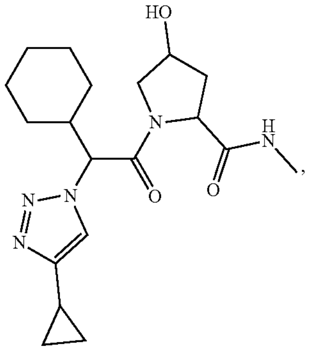
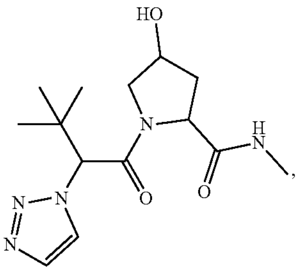
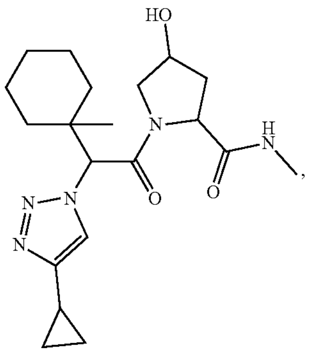
-continued
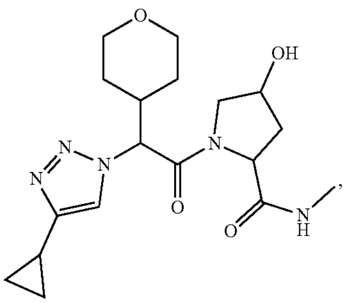
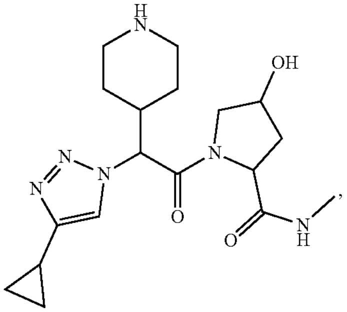
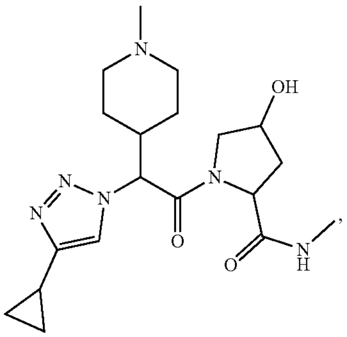
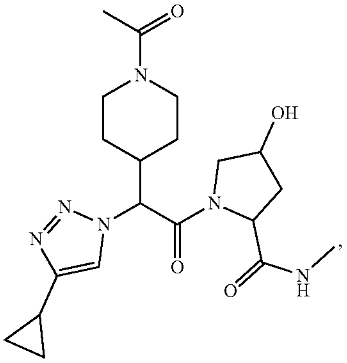
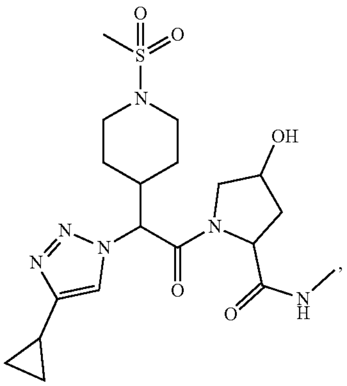

-continued
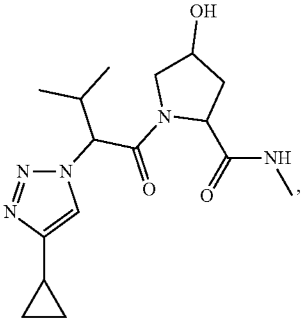
,
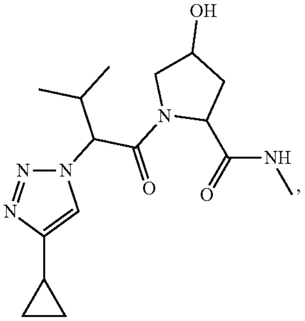
,
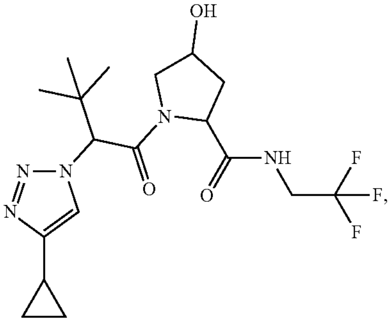
,
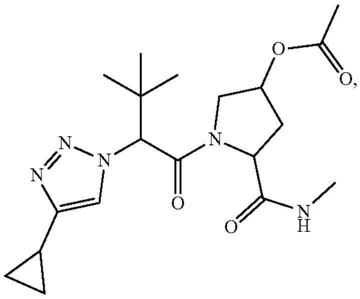
,
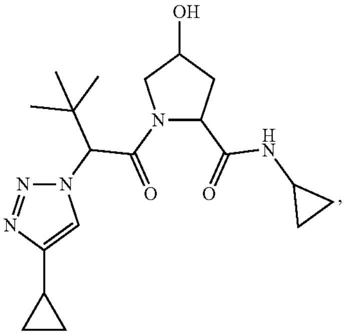
,
-continued
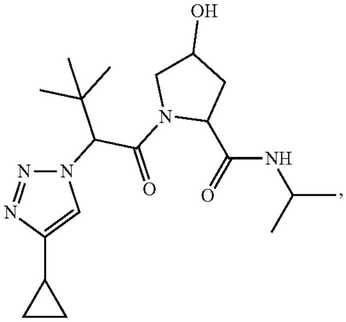
,
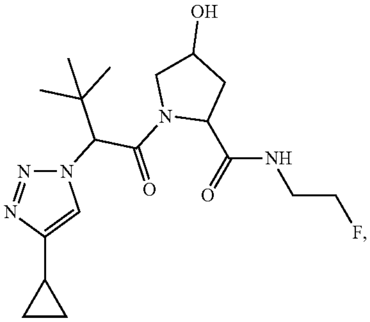
,
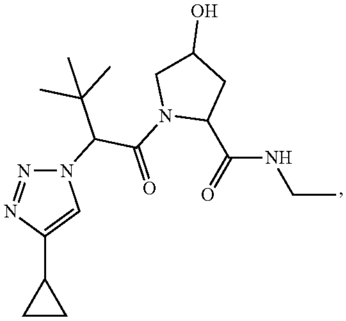
,
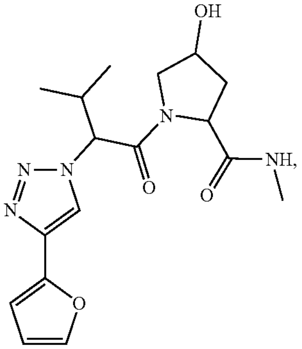
,
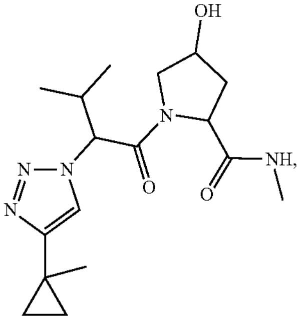
, -continued
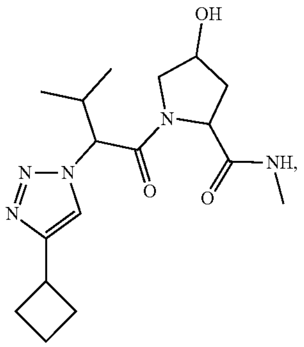
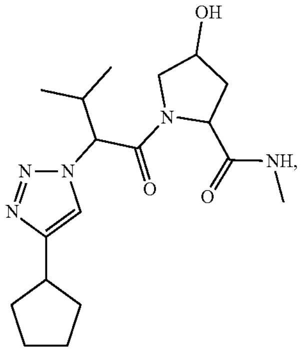
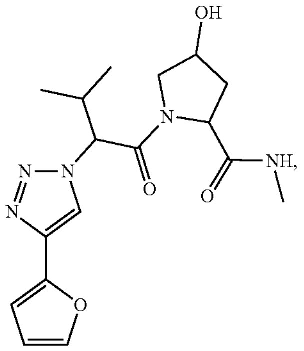
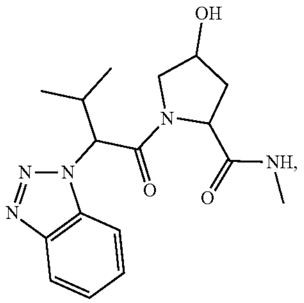
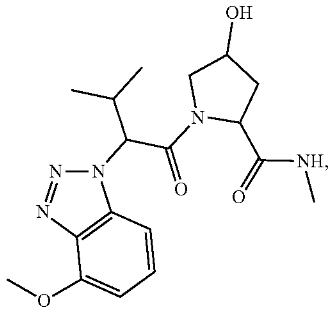
-continued
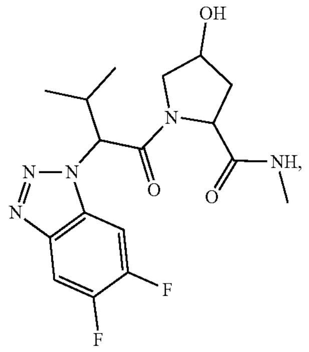
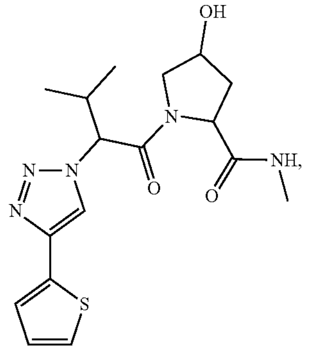
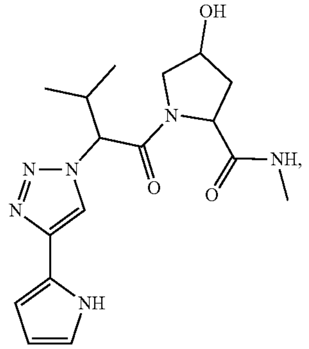
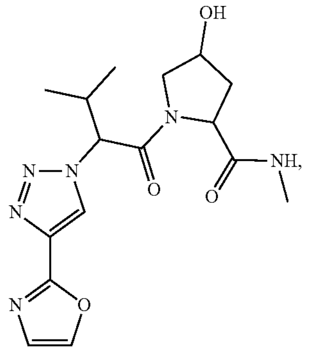

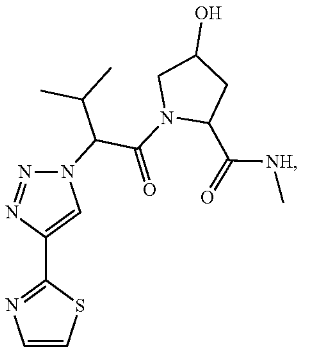
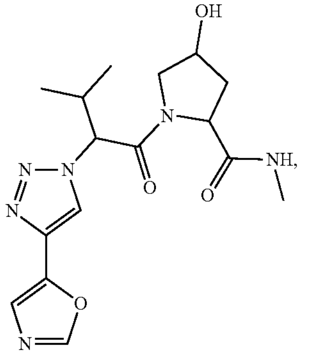
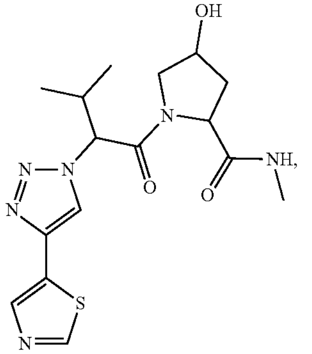
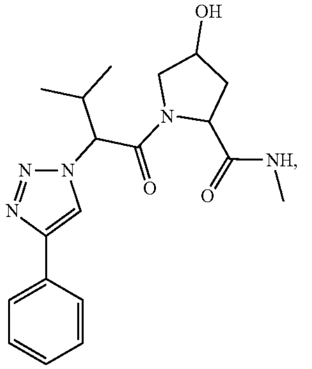
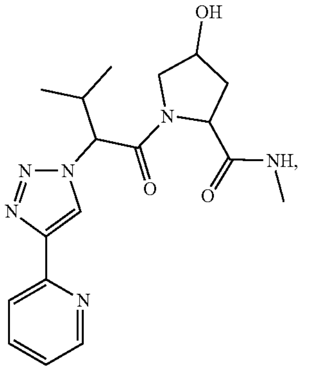
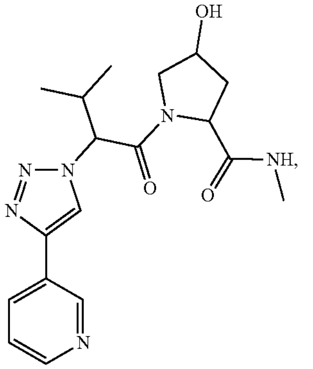
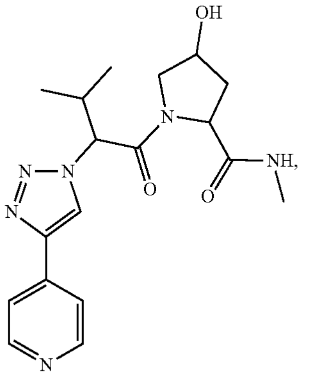
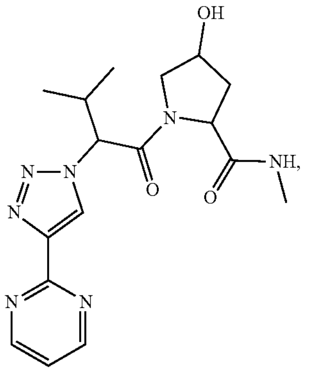

-continued

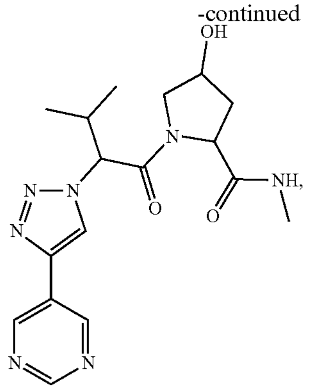

and

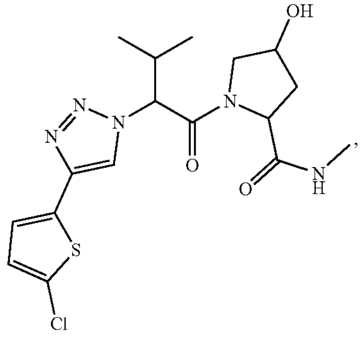

, or a stereoisomer or tautomer thereof, or a pharmaceutically acceptable salt of any of the foregoing.

15. A pharmaceutical composition comprising a compound or a stereoisomer or tautomer thereof, or a pharmaceutically acceptable salt of claim 1, and one or more pharmaceutically acceptable excipients.

16. A method of modulating VHL in a cell comprising exposing the cell to a composition comprising an effective amount of a compound or a stereoisomer or tautomer thereof, or a pharmaceutically acceptable salt of claim 1.

17. A method of inhibiting VHL in a cell comprising exposing the cell to a composition comprising an effective amount of a compound or a stereoisomer or tautomer thereof, or a pharmaceutically acceptable salt of claim 1.

18. A method of treating a disease, disorder, or condition in a human in need thereof, comprising administering to the human an effective amount of a compound or stereoisomer or tautomer thereof, or a pharmaceutically acceptable salt of claim 1.

19. A process for preparing a compound of formula (I):

(I)

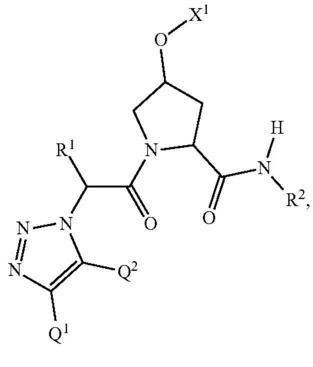

, or a stereoisomer or tautomer thereof, or a pharmaceutically acceptable salt of any of the foregoing, wherein:

$X^1$ is, independently at each occurrence, H or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; and $Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

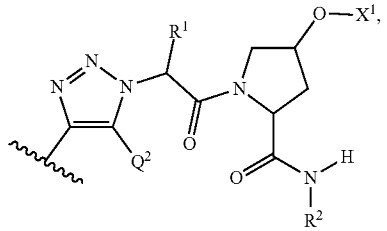

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

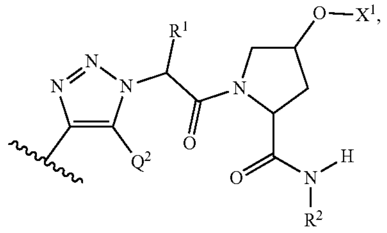

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

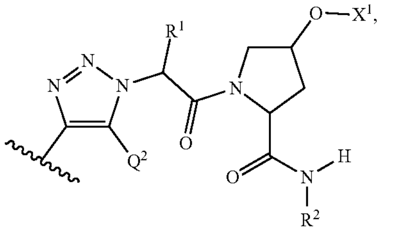

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH;

with the proviso that when Q1 is cyclohexyl, biphenyl, or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

wherein the process comprises reacting

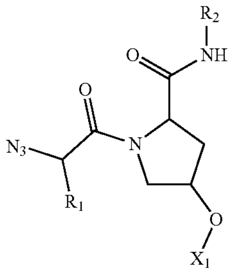

with

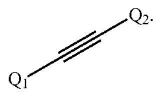

20. A heterobifunctional compound of formula (II):

[A]-[B]—[C] (II), wherein:

[A] is a moiety of a VHL ligand of claim 1;

[B] is a linker moiety; and

[C] is a protein-binding moiety.

21. A process for preparing a compound of formula (I):

(I)

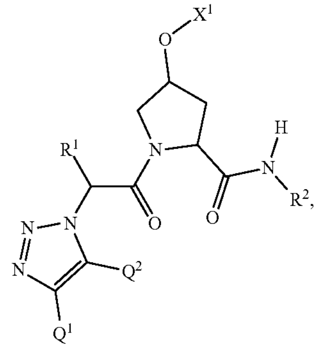

or a stereoisomer or tautomer thereof, or a pharmaceutically acceptable salt of any of the foregoing, wherein:

$X^1$ is, independently at each occurrence, H or —C(O)—$C_{1-12}$alkyl;

$R^1$ is, independently at each occurrence, $C_{1-12}$alkyl, $C_{2-12}$alkenyl, $C_{2-12}$alkynyl, $C_{3-15}$cycloalkyl, or 3-15 membered heterocyclyl, wherein the $C_{1-12}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

$R^2$ is, independently at each occurrence, H, $C_{1-12}$alkyl, or $C_{3-5}$cycloalkyl, wherein the $C_{1-12}$alkyl or $C_{3-5}$cycloalkyl of $R^2$ is independently optionally substituted with one or more halo or —CN; and $Q^1$ is H, halo, cyano, $C_{1-12}$alkyl, $C_{3-6}$cycloalkyl, $C_{6-20}$aryl, 5-6 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl of $Q^1$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

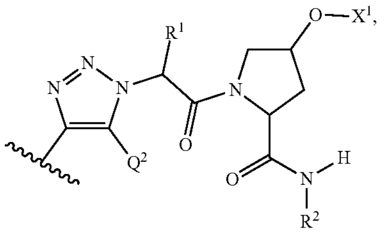

wherein the $C_{1-12}$alkyl or $C_{1-12}$alkoxy of $R^q$ is independently further optionally substituted with one or more halo or —NHC(O)—$C_{1-12}$alkyl, and wherein the $C_{3-6}$cycloalkyl of $Q^1$ is independently optionally substituted with one or more $R^q$, wherein each $R^q$ is independently $C_{1-12}$alkyl, $C_{2-12}$alkenyl, $C_{2-12}$alkynyl, or

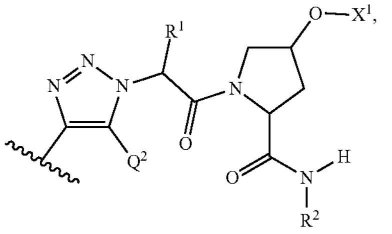

wherein the $C_{1-12}$alkyl of $R^q$ is independently further optionally substituted with one or more halo or —NHC(O)—$C_{1-12}$alkyl, and wherein the 5-6 membered heteroaryl of $Q^1$ is independently optionally substituted with one or more $R^q$, wherein each $R^q$ is independently halo, $C_{1-6}$alkoxy, —NHC(O)—$C_{1-12}$alkyl, —CN or —$NO_2$;

$Q^2$ is, independently at each occurrence, H, halo, cyano, $C_{1-12}$alkyl, $C_{3-15}$cycloalkyl, 3-15 membered heterocyclyl, $C_{6-20}$aryl, 5-20 membered heteroaryl, —C(O)—O($R^a$), or —C(O)—N($R^b$)($R^c$), wherein $R^a$, $R^b$, and $R^c$ are, independently of each other and independently at each occurrence, H or $C_{1-12}$alkyl, wherein the $C_{1-12}$alkyl or $C_{3-15}$cycloalkyl of $Q^2$ is independently optionally substituted with one or more $R^q$, wherein each $R^q$ is independently $C_{1-12}$alkyl, $C_{2-12}$alkenyl, $C_{2-12}$alkynyl, $C_{6-20}$aryl, $C_{1-12}$alkoxy, or

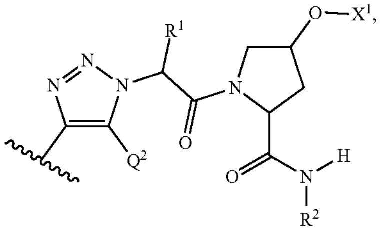

wherein the $C_{1-12}$alkyl or $C_{1-12}$alkoxy of $R^q$ is independently further optionally substituted with one or more halo or —NHC(O)—$C_{1-12}$alkyl, or $Q^1$ and $Q^2$ are taken, together with the atoms to which they are attached, to form a $C_{3-15}$cycloalkyl, 3-15 membered heterocyclyl, $C_{6-20}$aryl, or 5-20 membered heteroaryl, wherein the $C_{3-15}$cycloalkyl, 3-15 membered heterocyclyl, $C_{6-20}$aryl, or 5-20 membered heteroaryl formed by $Q^1$ and $Q^2$ is independently optionally substituted with one or more $R^s$, wherein $R^s$ is, independently at each occurrence, OH, cyano, halogen, oxo, —$NH_2$, —$NO_2$, —CHO, —C(O)OH, —C(O)$NH_2$, —SH, —$SO_2C_{1-12}$alkyl, —$SO_2NH_2$, $C_{1-6}$alkoxy, or $C_{1-12}$alkyl, wherein the $C_{1-12}$alkyl of $R^s$ is independently further optionally substituted with one or more halo, cyano, or OH;

with the proviso that when Q1 is cyclohexyl, biphenyl, or 5-6 membered heteroaryl, $R^1$ is $C_{1-3}$alkyl, $C_{2-12}$alkenyl, $C_{2-12}$alkynyl, $C_{3-15}$cycloalkyl, or 3-15 membered heterocyclyl, wherein the $C_{1-3}$alkyl, $C_{2-12}$alkenyl, $C_{2-12}$alkynyl, $C_{3-15}$cycloalkyl, or 3-15 membered heterocyclyl of $R^1$ is independently optionally substituted with one or more $C_{1-12}$alkyl, $C_{6-20}$aryl, —$S(O)_2$—$C_{1-12}$alkyl, or —C(O)—$C_{1-12}$alkyl;

wherein the process comprises reacting

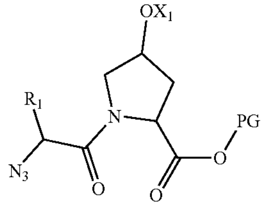

with

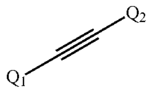

to form

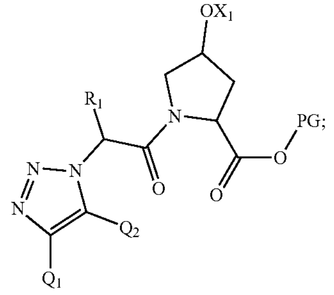

wherein PG is $C_{1-12}$alkyl.

* * * * *